US010174045B2

(12) United States Patent
Hermanson et al.

(10) Patent No.: US 10,174,045 B2
(45) Date of Patent: *Jan. 8, 2019

(54) BENZOPYRYLIUM COMPOUNDS

(71) Applicants: Pierce Biotechnology, Inc., Rockford, IL (US); Dyomics GmbH, Jena (DE)

(72) Inventors: Greg Hermanson, Loves Park, IL (US); Peter T. Czerney, Weimar (DE); Surbhi Desai, Rockford, IL (US); Matthias S. Wenzel, Jena (DE); Frank G. Lehmann, Jena (DE); Marie Christine Nlend, Rockford, IL (US)

(73) Assignees: Pierce Biotechnology, Inc., Rockford, IL (US); Dyomics GmbH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/493,208

(22) Filed: Apr. 21, 2017

(65) Prior Publication Data

US 2018/0002340 A1 Jan. 4, 2018

Related U.S. Application Data

(62) Division of application No. 14/411,447, filed as application No. PCT/US2013/055639 on Aug. 20, 2013, now Pat. No. 9,676,787.

(60) Provisional application No. 61/719,676, filed on Oct. 29, 2012, provisional application No. 61/693,918, filed on Aug. 28, 2012.

(51) Int. Cl.
C07D 491/147 (2006.01)
A61K 49/00 (2006.01)
G01N 33/58 (2006.01)
C07D 405/14 (2006.01)
C07D 405/06 (2006.01)
C07D 491/052 (2006.01)
C07D 491/16 (2006.01)
C09B 23/06 (2006.01)
C09B 23/04 (2006.01)
C09B 23/08 (2006.01)
C09B 69/00 (2006.01)

(52) U.S. Cl.
CPC ...... *C07D 491/147* (2013.01); *A61K 49/0021* (2013.01); *A61K 49/0032* (2013.01); *A61K 49/0054* (2013.01); *A61K 49/0058* (2013.01); *C07D 405/06* (2013.01); *C07D 405/14* (2013.01); *C07D 491/052* (2013.01); *C07D 491/16* (2013.01); *C09B 23/04* (2013.01); *C09B 23/06* (2013.01); *C09B 23/083* (2013.01); *C09B 23/086* (2013.01); *C09B 69/00* (2013.01); *G01N 33/582* (2013.01)

(58) Field of Classification Search
CPC ... A61K 49/00; C07D 403/06; C07D 491/147
See application file for complete search history.

(56) References Cited

U.S. PATENT DOCUMENTS

| | | |
|---|---|---|
| 1,524,791 A | 2/1925 | Konig |
| 3,996,345 A | 12/1976 | Ullman et al. |
| 4,351,760 A | 9/1982 | Khanna et al. |
| 4,839,265 A | 6/1989 | Ohno et al. |
| 4,966,983 A | 10/1990 | Guentner et al. |
| 4,981,977 A | 1/1991 | Southwick et al. |
| 5,268,486 A | 12/1993 | Waggoner et al. |
| 5,312,728 A | 5/1994 | Lizardi et al. |
| 5,486,616 A | 1/1996 | Waggoner et al. |
| 5,556,959 A | 9/1996 | Brush et al. |
| 5,569,587 A | 10/1996 | Waggoner |
| 5,569,766 A | 10/1996 | Waggoner et al. |
| 5,627,027 A | 5/1997 | Waggoner |
| 5,846,737 A | 12/1998 | Kang |
| 5,972,838 A | 10/1999 | Pearce et al. |
| 5,986,086 A | 11/1999 | Brush et al. |
| 6,048,982 A | 4/2000 | Waggoner |
| 6,083,485 A | 7/2000 | Licha et al. |
| 6,136,612 A | 10/2000 | Della Ciana et al. |
| 6,225,050 B1 | 5/2001 | Waggoner |
| 6,258,340 B1 | 7/2001 | Licha et al. |
| 6,342,326 B1 | 1/2002 | Milton |
| 6,534,041 B1 | 3/2003 | Licha et al. |
| 6,641,093 B2 | 11/2003 | Coudrais |
| 6,924,372 B2 * | 8/2005 | Czerney ............... C09B 23/02 546/101 |

(Continued)

FOREIGN PATENT DOCUMENTS

AU 2006200511 A1 2/2006
DE 4445065 A1 6/1996

(Continued)

OTHER PUBLICATIONS

Notification of the Second Office Action with English translation issued in Chinese Patent Application No. 201380040246.5 (dated Nov. 8, 2016, 10 pages).
Written Opinion of the International Searching Authority PCT/US2013/055639, dated Dec. 5, 2013, 4 pages.
International Search Report PCT/US2013/055639, dated Dec. 5, 2013, 4 pages.
Holland et al. Detection of specific polymerase chain reaction product by utilizing the 5' → 3' exonuclease activity of *Thermus aquaticus* DNA polymerase. Proc Natl Acad Sci USA 88(1991) 7276-7280.

(Continued)

*Primary Examiner* — Michael G Hartley
*Assistant Examiner* — Jagadishwar R Samala
(74) *Attorney, Agent, or Firm* — McNeill Baur PLLC

(57) ABSTRACT

Compounds used as labels with properties comparable to known fluorescent compounds. The compounds are conjugated to proteins and nucleic acids for biological imaging and analysis. Synthesis of the compounds, formation and use of the conjugated compounds, and specific non-limiting examples of each are provided.

15 Claims, 25 Drawing Sheets
(16 of 25 Drawing Sheet(s) Filed in Color)

(56) References Cited

U.S. PATENT DOCUMENTS

| | | |
|---|---|---|
| 6,939,532 B2 | 9/2005 | Achilefu et al. |
| 6,974,873 B2 | 12/2005 | Leung et al. |
| 6,977,305 B2 | 12/2005 | Leung et al. |
| 7,172,907 B2 | 2/2007 | Chen et al. |
| 7,566,790 B2 | 7/2009 | Leung et al. |
| 7,671,214 B2 | 3/2010 | Leung et al. |
| 7,745,640 B2 | 6/2010 | Czerney et al. |
| 7,750,163 B2 | 7/2010 | West et al. |
| 7,790,893 B2 | 9/2010 | Leung et al. |
| 7,820,824 B2 | 10/2010 | Leung et al. |
| 7,855,293 B2 | 12/2010 | Haalck et al. |
| 7,927,830 B2 | 4/2011 | Cheung et al. |
| 7,951,959 B2 | 5/2011 | Brush et al. |
| 8,431,111 B2 | 4/2013 | Nairne et al. |
| 2001/0055567 A1 | 12/2001 | Licha et al. |
| 2002/0064794 A1 | 5/2002 | Leung et al. |
| 2002/0077487 A1 | 6/2002 | Leung et al. |
| 2004/0230057 A1 | 11/2004 | Kuo et al. |
| 2004/0241095 A1 | 12/2004 | Achilefu et al. |
| 2006/0004188 A1 | 1/2006 | Leung et al. |
| 2006/0099638 A1 | 5/2006 | Leung et al. |
| 2007/0128659 A1 | 6/2007 | Czerney et al. |
| 2007/0020334 A1 | 8/2007 | West et al. |
| 2007/0178512 A1 | 8/2007 | Leung et al. |
| 2008/0233050 A1 | 9/2008 | Achilefu et al. |
| 2009/0035809 A1 | 2/2009 | Leung et al. |
| 2009/0305410 A1 | 12/2009 | Mao et al. |
| 2010/0040547 A1 | 2/2010 | Frangioni |
| 2010/0196282 A1 | 8/2010 | Nairne et al. |
| 2010/0215585 A1 | 8/2010 | Frangioni |
| 2010/0267937 A1 | 10/2010 | West et al. |
| 2010/0303732 A1 | 12/2010 | Bahner |
| 2011/0065876 A1 | 3/2011 | Okamoto et al. |
| 2011/0065896 A1 | 3/2011 | Licha et al. |
| 2011/0171678 A1 | 7/2011 | Leung et al. |
| 2011/0178397 A1 | 7/2011 | Bahner |
| 2012/0114563 A1 | 5/2012 | Carter et al. |
| 2014/0106349 A1 | 4/2014 | Mao et al. |

FOREIGN PATENT DOCUMENTS

| | | |
|---|---|---|
| DE | 19717904 A1 | 10/1998 |
| DE | 00/00802 | 3/1999 |
| DE | 19926460 A1 | 12/1999 |
| DE | 01/01946 | 5/2000 |
| DE | 10046215 B4 | 4/2004 |
| EP | 1152008 A2 | 11/2001 |
| EP | 1181940 A2 | 2/2002 |
| EP | 1322710 B1 | 1/2007 |
| EP | 1770129 A2 | 4/2007 |
| EP | 1792949 A2 | 6/2007 |
| EP | 1801165 A2 | 6/2007 |
| EP | 2325263 A1 | 5/2011 |
| GB | 434875 | 9/1935 |
| JP | 03217837 | 9/1991 |
| JP | Hei 5-313304 | 11/1993 |
| WO | 96/17628 A1 | 6/1996 |
| WO | 98/48838 A1 | 11/1998 |
| WO | 00/075329 A2 | 12/2000 |
| WO | 02/26891 A1 | 4/2002 |
| WO | 02/32466 A1 | 4/2002 |
| WO | 2004/065491 | 8/2004 |
| WO | 2004/072232 | 8/2004 |
| WO | 2005/044923 A1 | 5/2005 |
| WO | 2005/103162 A1 | 11/2005 |
| WO | 2006/020947 A2 | 2/2006 |
| WO | 2008/015415 | 2/2008 |
| WO | 2009/016180 | 2/2009 |
| WO | 2009/016181 | 2/2009 |
| WO | 2009/078970 A1 | 6/2009 |
| WO | 2010/091126 A1 | 8/2010 |
| WO | 2010/106169 | 9/2010 |
| WO | 2012/088007 A1 | 6/2012 |
| WO | 2012/129128 A1 | 9/2012 |

OTHER PUBLICATIONS

Lee et al. Allelic discrimination by nick-translation PCR with fluorogenic probes. Nucleic Acids Res. 21(1993) 3761-3766.

Tyagi et al. Molecular beacons: Probes that fluoresce upon hybridization. Nature Biotech. 14 (1996) 303-308.

Hermanson (2013) Bioconjugate Techniques, Third Edition, Chapter 1, Section 3.1, Elsevier pp. 1-125.

Search Report issued by the German Patent Office for App #10 2006 029 454.8 dated Oct. 10, 2006 (with English language summary), 5 pages.

Search Report issued by the German Patent Office for App #10 2006 057 345.5 dated May 21, 2007 (with English language summary), 5 pages.

International Search Report and Written Opinion for PCT/US2011/065975, dated Mar. 15, 2012 (8 pages).

United Kingdom Search and Examination Report GB1214580.1, dated Nov. 22, 2012, 4 pages.

Alvarez-Maubecin et al. Functional Coupling Between Neurons and Glia. The Journal of Neuroscience. Jun. 1, 2000, 20(11):4091-4098.

Bharaj et al. Rapid sequencing of the p53 gene with a new automated DNA sequencer. Clinical Chemistry. 44:7 1397-1403 (1998).

Biotium. Product brochure titled CF™ Dyes The next-generation dyes for protein labeling. Apr. 6, 2009.

Burns et al. An Integrated Nanoliter DNA Analysis Device. Science. vol. 282, pp. 484-487, Oct. 16, 1998.

DeRisi et al. Exploring the Metabolic and Genetic Control of Gene Expression on a Genomic Scale. Science. vol. 278, ppl. 680-686, Oct. 24, 1997.

Fradelizi et al. Quantitative Measurement of Proteins by Western Blotting with Cy5™-Coupled Secondary Antibodies. BioTechniques. 26:484-494 Mar. 1999.

Gragg. Synthesis of Near-Infrared Heptamethine Cyanine Dyes. Chemistry Theses. Paper 28 (Apr. 26, 2010.). http://digitalarchive.gsu.edu/chemistry_theses/28.

MacBeath and Schreiber. Printing Proteins as Microarrays for High-Throughput Function Determination. Science. vol. 289, pp. 1760-1763, Sep. 8, 2000.

Manders et al. Direct Imaging of DNA in Living Cells Reveals the Dynamics of Chromosome Formation. The Journal of Cell Biology. vol. 144, No. 5, Mar. 8, 1999 813-821.

Mank et al., Visible Diode Laser-Induced Fluorescence Detection in Liquid Chromatography after Precolumn Derivatization of Amines. Anal. Chem. vol. 67, pp. 1742-1748, 1995.

Mujumdar et al. Cyanine Dye Labeling Reagents: Sulfoindocyanine Succinimidyl Esters. Bioconjug Chem. vol. 4, No. 2, pp. 105-111, Mar./Apr. 1993.

Patonay et al. Noncovalent Labeling of Biomolecules with Red and Near-Infrared Dyes. Molecules. 9, 40-49, 2004.

Pharmacia Biotech. Table of Contents p. 294 and p. 295 of the Pharmacia Biotech Catalogue. 1994.

Roman et al. Non-Radioisotopic AFLP Method Using PCR Primers Fluorescently Labeled with Cy™5. BioTechniques. vol. 26, No. 2, pp. 236-238, Feb. 1999.

Schena et al. Parallel human genome analysis: Microarray-based expression monitoring of 1000 genes. Proc. Natl. Acad. Sci. USA. vol. 93, pp. 10614-10619, Oct. 1996.

Shao et al. Monofunctional Carbocyanine Dyes for Bio- and Bioorthogonal Conjugation. Bioconjugate Chemistry. 19(12): 2487-2491, Dec. 2008.

Voss et al. Automated Cycle Sequencing with Taquenase ™: Protocols for Internal Labeling, Dye Primer and "Doublex" Simultaneous Sequencing. BioTechniques. vol. 23, No. 2, pp. 312-318, Aug. 1997.

Wilchek and Miron. Activation of Sepharose with N, N'-disuccinimidyl carbonate. Applied Biochemistry and Biotechnology, vol. 11, pp. 191-193 (1985).

International Search Report and Written Opinion for PCT App #US2013/028252, issued by the European Patent Office, and dated Apr. 25, 2013, 12 pages.

Examination Report, Great Britain Application No. 1214580.1, dated May 31, 2013 (4 pages).

(56) References Cited

OTHER PUBLICATIONS

International Preliminary Report on Patentability, PCT/US/2011/065975, dated Jul. 4, 2013 (8 pages).
Licha et al. Synthesis and Characterization of Cyanine Dye—Poly(ethylene Glycol) Conjugates as Contrast Agents for In Vivo Fluorescence Imaging. SPIE 3196 (1998) 98-102.
Riefke et al. Tumor Detection with Cyanine Dye-Poly(ethylene Glycol) Conjugates as Contrast Agents for Near-Infrared Imaging. SPIE 3196 (1998) 103-110.
International Preliminary Report on Patentability, PCT/US2013/055639, dated Mar. 3, 2015 (8 pages).
Extended European Search Report, European Application No. 13833348.9, dated Jan. 4, 2016, 10 pages.
Paull et al: "Suitable Labels for Molecular Imaging—Influence of Dye Structure and Hydrophilicity on the Spectroscopic Properties of IgG Conjugates",Bioconjugate Chemistry 22 (2011) 1298-1308, XP55234730,US ISSN: 1043-1802, DOI: 10.1021 /bc1 004763.
Fishbum: "The pharmacology of PEGylation: Balancing PO with PK to generate novel therapeutics", Journal of Pharmaceutical Sciences, American Pharmaceutical Association, Washington, US 97 (2008) 4167-4183, XP002725227,1SSN: 0022-3549, DOI: 10.1 002/JPS.21278Retrieved from the Internet: URL:http://onlinelibrary.wiley.com/doi/1 0.1 002/jps.21278/abstract [retrieved on Jan. 15, 2008].
Paull et al: "Novel Fluorophores as Building Blocks for Optical Probes for in Vivo Near Infrared Fluorescence (NIRF) Imaging", Journal of Fluorescence, Kluwer Academic Publishersplenum Publishers, NE 20 (2010) 681-693, XP019822873,1SSN: 1573-4994.
Extended European Search Report, European Patent Application No. 15198169.3 (dated Mar. 29, 2016, 8 pages).
Second Office Action with English translation issued in Chinese Patent Application No. 201380005497.X (dated Apr. 28, 2016, 21 pages).
Extended European Search Report and Written Opinion issued in European Patent Application No. 16169172.0 (dated Jul. 14, 2016, 7 pages).
Rejection Decision with English translation issued in Chinese Patent Application No. 201380005497.X (dated Nov. 2, 2016, 11 pages).

\* cited by examiner

Heart

Kidney

Liver

Lung

Spleen

Heart

Kidney

Liver

Lung

Spleen

BENZOPYRYLIUM COMPOUNDS

This application is a division of co-pending U.S. patent application Ser. No. 14/411,447 filed Dec. 26, 2014, which is a National Phase entry of International Patent Application No. PCT/US2013/055639 filed Aug. 20, 2013, which claims the benefit of provisional U.S. Patent Application Nos. 61/719,676 filed Oct. 29, 2012, and 61/693,918 filed Aug. 28, 2012, each of which is expressly incorporated by reference in its entirety.

Compounds useful as labels with properties comparable to known fluorescent compounds are disclosed. The compounds can be conjugated to proteins and nucleic acids for biological imaging and analysis. Synthesis of the compounds, formation and use of the conjugated compounds, and specific non-limiting examples of each are disclosed. The compounds are benzopyrylo-polymethine based compounds, abbreviated as benzopyrylium compounds, that contain at least one ethylene glycol.

Organic fluorescent compounds, also referred to as dyes, are used as sensitive detection reagents in biological assays. Benzopyrylo-polymethine based dyes are commercially available as research reagents.

Compounds that contain at least one ethylene glycol, diethylene glycol, or polyethylene glycol (i.e., (poly)ethylene glycol, PEG, or pegylated benzopyrylium derivatives), specifically sulfonamide derivatives and aryl sulfonamide derivatives of compounds containing a benzopyrylo-polymethine ring structure are disclosed. These are referred to as fluorescent pegylated benzopyrylo-polymethine compounds or dyes. Adding one or more aryl sulfonamide derivatives, as well as adding ethylene glycol and/or polyethylene glycol (PEG) moieties to the benzopyrylo-polymethine compound, e.g., at the sulfonamide nitrogen, results in enhanced hydrophilicity and other properties over those of unsubstituted compounds. In one embodiment, the compounds optionally contain a reactive group that may be used for covalent coupling to biomolecules.

These compounds have enhanced fluorescence, water solubility, and biocompatibility, and are used in compositions and methods as fluorescent probes in biological and other types of assays. Their properties compare favorably with negatively charged sulfonate derivatives.

Compounds that react with biomolecules (e.g., antigens, antibodies, DNA-segments with the corresponding complimentary species for measuring enzyme kinetics, receptor-ligand interactions, nucleic acid hybridization kinetics in vitro as well as in vivo, etc.), termed labels or dyes, are useful for, e.g., pharmacological characterization of receptors and drugs, binding data, etc. Compounds such as xanthylium salts (U.S. Pat. No. 5,846,737) and/or cyanines (U.S. Pat. No. 5,627,027) are used for such applications, but aggregate and form dimers, especially in aqueous solution, due to planarity of their π-system. Compounds that have insufficient hydrophilicity undergo non-specific interactions with various surfaces, resulting in problems when attempting purify the corresponding conjugate, and an unsatisfactory signal to noise ratio.

Efforts are directed to reducing undesirable properties by introducing substituents that increase the hydrophilicity of the compounds. The challenge was to create highly hydrophilic content polymethine-based fluorescent markers with high extinction coefficients and a high degree of photo and storage stability. These can be excited simply to emit fluorescent light by monochromatic (laser/laser diodes) or polychromatic light (white light sources) in the ultraviolet (UV), visual, or near infrared (NIR) spectrum range, or can function as quenchers.

Symmetrical xanthylium salt (fluorescein and rhodamine) or polymethine (indocyanine) as claimed in, for example, U.S. Pat. No. 5,627,027 are normally used. All these markers have the disadvantage that they tend towards aggregation and dimerization owing to the planarity of the pi-electron system, especially in aqueous systems. Moreover, insufficiently hydrophilic markers show non-specific interactions with different surfaces, resulting in problems with clearing the corresponding conjugates and in an unsatisfactory signal/noise ratio. To circumvent these disadvantages, corresponding asymmetrical polymethines on the basis of benzopyran-2-ylide or benzo[b]pyran-4-ylide-compounds were described in PCT/DE00/00802, PCT/DE01/01946, and U.S. Pat. No. 6,924,372.

The inventive compounds and methods are improved by introducing additional substituents that increased hydrophilicity of the compounds. Compounds that contain at least one ethylene glycol, diethylene glycol, or polyethylene glycol (i.e., (poly)ethylene glycol, PEG), or pegylated benzopyrylo-polymethine-based compounds for use in optical, and in particular optical-fluorescent, determination and detection procedures, e.g., in medicine, the pharmaceutical industry and in bioscience, materials science, and environmental science, are disclosed. The disclosed compounds are useful as labels in optical, especially fluorescence optical, determination and detection methods. The compounds have high hydrophilicity, high molar absorbance, high photostability, and high storage stability. These compounds can be excited by monochromatic (e.g., lasers, laser diodes) or polychromatic (e.g., white light sources) light in the UV, visible, and NIR spectral region to generate emission of fluorescence light.

Typical application methods are based on the reaction of the compounds with biomolecules such as proteins (e.g., antigens, antibodies, etc.), DNA and/or RNA segments, etc. with the corresponding complimentary species. Thus, among other embodiments, the compounds are useful to measure enzyme kinetics, receptor-ligand interactions, and nucleic acid hybridization kinetics in vitro and/or in vivo. The compounds are useful for the pharmacological characterization of receptors and/or drugs. Applications include, but are not limited to, uses in medicine, pharmacy, biological sciences, materials sciences, environmental control, detection of organic and inorganic micro samples occurring in nature, etc.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
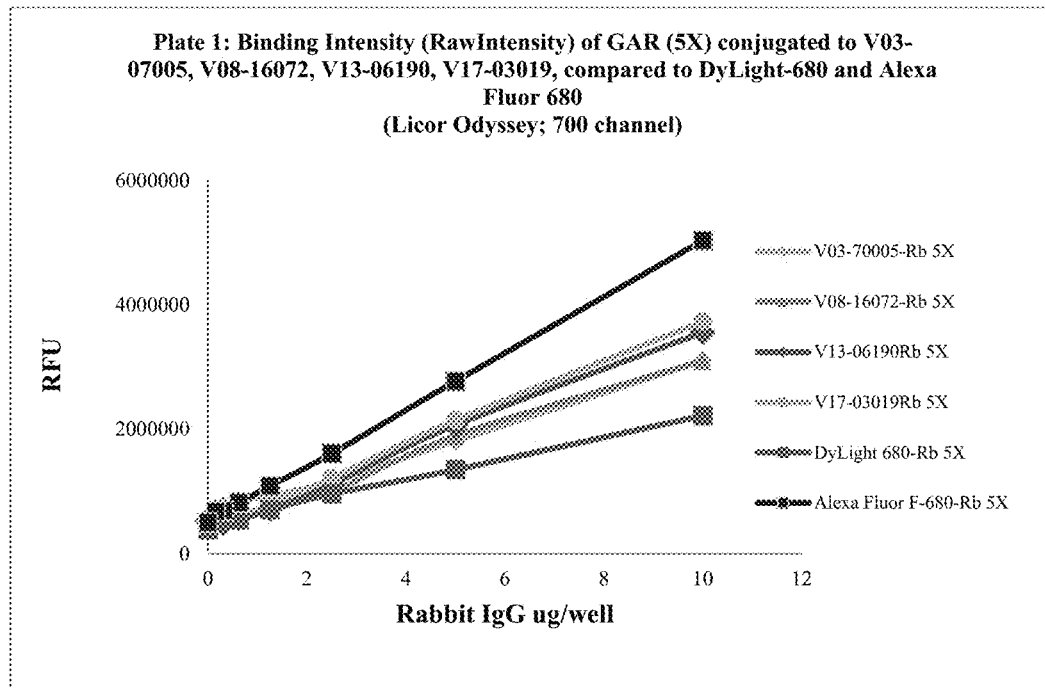
FIG. 1 shows functional assay results with commercial dyes and the inventive compounds in one embodiment.

The following nomenclature is used to describe various embodiments: 682 Compound X, where X indicates position(s) on general formula I or II which contains PEG group(s). For example, in one embodiment, 682 Compound 2/3 contains at least ethylene glycol, diethylene glycol, or (poly)ethylene glycol at each of R2 and R3.

In one embodiment, the compounds have at least one ethylene glycol group, diethylene glycol group, or ethylene glycol polymer (i.e., poly(ethylene) glycol, abbreviated as PEG) in any position of the compound, and a function for conjugating the compound to a biomolecule in any position of the compound. In one embodiment, the compound has, in any position of the compound, at least one sulfo and/or sulfoalkyl. In one embodiment, the compound has, in any position of the compound, a sulfonamide and/or carboxamide group comprising an ethylene glycol group or an ethylene glycol polymer (i.e., poly(ethylene) glycol, abbreviated as PEG), either directly or indirectly attached to the compound. Indirect attachment indicates use of a linker, direct attachment indicates lack of such a linker. A linker can be any moiety.

In one embodiment, the compound is general formula I

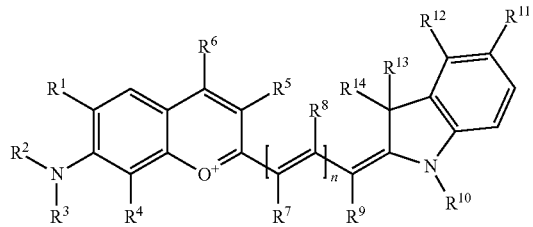

or general formula II

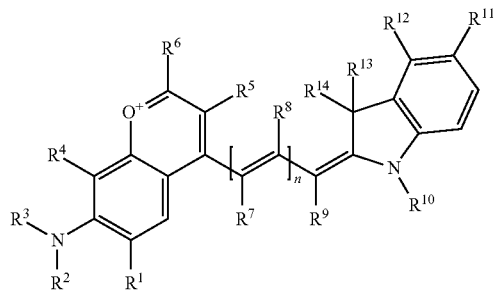

where each of $R^1$, $R^2$, $R^3$, $R^4$, $R^5$, $R^6$, $R^{11}$, and $R^{12}$ is the same or different and is independently selected from H, $SO_3$, Z, L-Z, a PEG group P-L-Z where P is an ethylene glycol group, a diethylene glycol group, or a polyethylene glycol group, where the polyethylene glycol group is $(CH_2CH_2O)_s$, where s is an integer from 3-6 inclusive, a sulfonamide group -L-$SO_2$NH—P-L-Z, a carboxamide group -L-CONH—P-L-Z, hydrogen, alkyl-, tert-alkyl, aryl-, carboxyaryl-, dicarboxyaryl, heteroaryl-, cycloalkyl-, heterocycloalkyl-, alkyloxy-, alkylmercapto- with alkyl and cycloalkyl including olefin linkage residues, aryloxy-, arylmercapto-, heteroaryloxy-, heteroarylmercapto-, hydroxy-, nitro-, a carboxylic acid, an amino group, or cyano residues; where L is a divalent linear (—$(CH_2)_t$—, t=0 to 15), branched, or cyclic alkane group that can be substituted by at least one atom of oxygen, nitrogen, substituted nitrogen, and/or sulfur; where Z is H, $CH_3$, alkyl group, sulfoalkyl, heteroalkyl group, $NH_2$, —$COO^-$, —COOH, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-biomolecule, —CONR'-L-$COO^-$, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR'-L-CO—NH—$NH_2$, —CONR'-L-OH, —CONR'-L-O-phosphoramidite, —CONR'-L-CHO, —CONR'-L-maleimide, or —CONR'-L-NH—CO—$CH_2$—I; each of R' and R" is selected from H, aliphatic group, or heteroaliphatic group, and the biomolecule is a protein, peptide, antibody, nucleotide, oligonucleotide, biotin, or hapten;

each of $R^{10}$, $R^{13}$, and $R^{14}$ is the same or different and is independently selected from aliphatic, heteroaliphatic, sulfoalkyl group, carboxyalkyl group, heteroaliphatic with terminal $SO_3$, Z, L-Z, PEG group P-L-Z where P is an ethylene glycol group, a diethylene glycol group, or a polyethylene glycol group where the polyethylene glycol group is $(CH_2CH_2O)_s$, where s is an integer from 3-6 inclusive, a sulfonamide group -L-SO$_2$NH—P-L-Z, or a carboxamide group -L-CONH—P-L-Z;

each of $R^7$ and $R^9$ is the same or different and is independently hydrogen, aliphatic group, heteroaliphatic group, or PEG group P-L-Z where P is selected from an ethylene glycol group, a diethylene glycol group, or a polyethylene glycol group where the polyethylene glycol group is $(CH_2CH_2O)_s$, where s is an integer from 3-6 inclusive; or $R^7$ and $R^9$ together form a cyclic structure where $R^3$ and $R^4$ are joined using a divalent structural element selected from —$(CH_2)_q$—, —$(CH_2)_qO(CH_2)_{q'}$—, —$(CH_2)_qS(CH_2)_{q'}$—, —$(CH_2)_q$CH=CH—, —OCH=CH— where each of q and q' is the same or different and is a integer from 1 to 6 inclusive; and $R^8$ is selected from hydrogen, alkyl, sulfoalkyl, fluorine, chlorine, bromine, and PEG group P-L-Z where P is selected from an ethylene glycol group, a diethylene glycol group, or a polyethylene glycol group, where the polyethylene glycol group is $(CH_2CH_2O)_s$, where s is an integer from 3-6 inclusive;

each of $R^1$ and $R^2$, $R^2$ and $R^3$, $R^3$ and $R^4$, $R^5$ and $R^6$, $R^5$ and $R^8$, $R^9$ and $R^{10}$, $R^{11}$ and $R^{12}$, or $R^{12}$ and $R^{13}$ may form one or more aliphatic, heteroaliphatic, or aromatic rings, and where the resultant ring(s) is optionally substituted by at least one alkyl-, sulfoalkyl, tert-alkyl, carboxyaryl-, dicarboxyaryl, heteroaryl-, cycloalkyl-, heterocycloalkyl-, alkyloxy-, alkylmercapto- with alkyl and cycloalkyl including olefin linkage residues, aryloxy-, arylmercapto-, heteroaryloxy-, heteroarylmercapto-, hydroxy-, nitro-, sulfonic acid, a carboxylic acid, an amino group, or cyano residues;

at least one of $R^1$-$R^{14}$ may constitute an additional solubilizing agent, or ionizing or ionized substituent, besides PEG, such as $SO_3^-$, $PO_3^{2-}$, $CO_2H$, OH, $NR_3^+$, cyclodextrins or sugars, which provide hydrophilic characteristics of dyes; these substituents may also be linked to the actual basic chromophore by an aliphatic or heteroaliphatic or cyclical spacer group, with the proviso that at least one of $R^1$-$R^{14}$ contains a PEG group; and n is 0, 1, 2, or 3.

In one embodiment, PEG group P is selected from —$CH_2$—$CH_2$—O—$CH_3$ (ethylene glycol with terminal methyl), —$CH_2$—$CH_2$—O—$CH_2$—$CH_2$—O—$CH_3$ (diethylene glycol with terminal methyl), —$CH_2$—$CH_2$—O—$CH_2$—$CH_2$—O—$CH_2$—$CH_2$—O—$CH_3$ (polyethylene glycol (3) with terminal methyl), —$CH_2$—$CH_2$—O—$CH_2$—$CH_2$—O—$CH_2$—$CH_2$—O—$CH_2$—$CH_2$—O—$CH_3$ (polyethylene glycol (4) with terminal methyl), —$CH_2$—$CH_2$—O—$CH_2$—$CH_2$—O—$CH_2$—$CH_2$—O—$CH_2$—$CH_2$—O—$CH_2$—$CH_2$—O—$CH_3$ (polyethylene glycol (5) with terminal methyl), and $CH_2$—$CH_2$—O—$CH_2$—$CH_2$—O—$CH_2$—$CH_2$—O—$CH_2$—$CH_2$—O—$CH_2$—$CH_2$—O—$CH_2$—$CH_2$—O—$CH_3$ (polyethylene glycol (6) with terminal methyl). In one embodiment, PEG group P may be either uncapped, e.g., lack a terminal methyl, or may be capped with an atom or group other than methyl. In one embodiment, PEG group P terminates with a Z group, where Z is defined above and includes H, $CH_3$, a $CH_3$ group, an alkyl group, or a heteroalkyl group.

In one embodiment, the compound is general formula Ia, Ib, Ic, Id, Ie, If, Ig, Ih or general formula IIa, IIb, IIc, IId, IIe, IIf, IIg, IIh, as shown below:

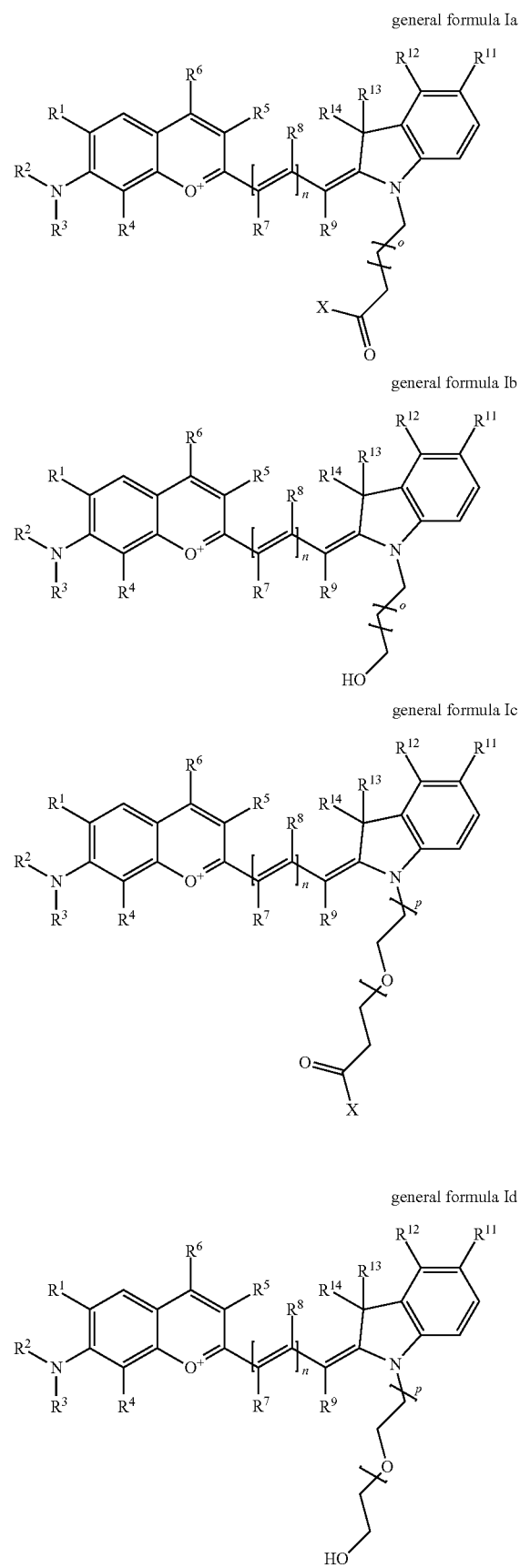

general formula Ia general formula Ib general formula Ic general formula Id general formula Ie
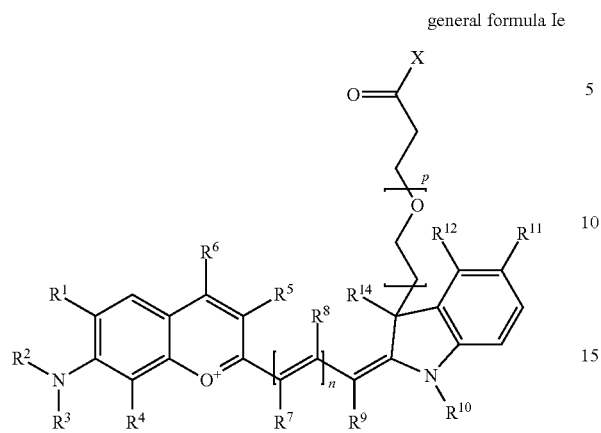
general formula IIa
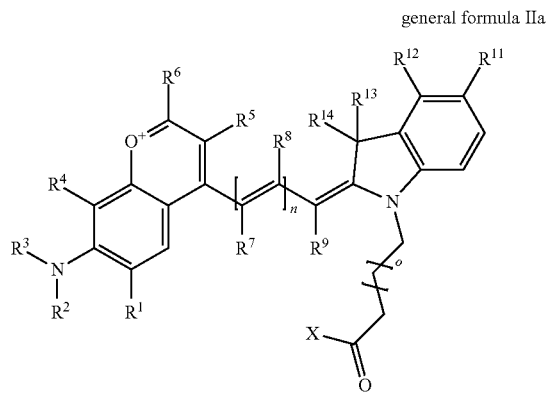
general formula If
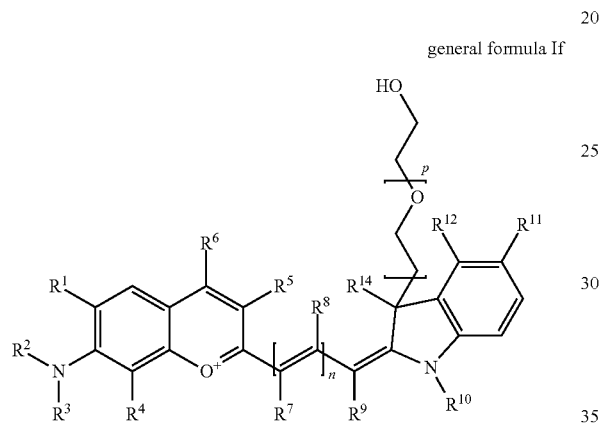
general formula IIb
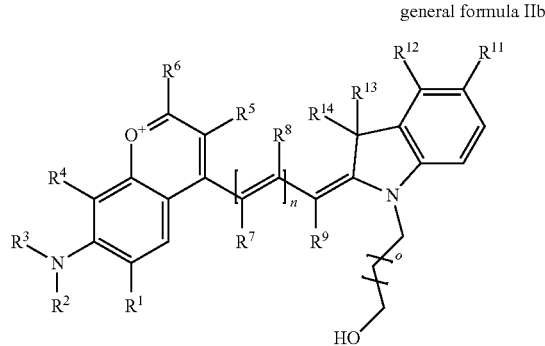
general formula Ig
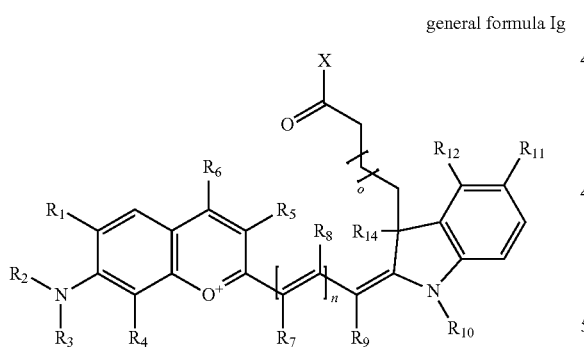
general formula IIc
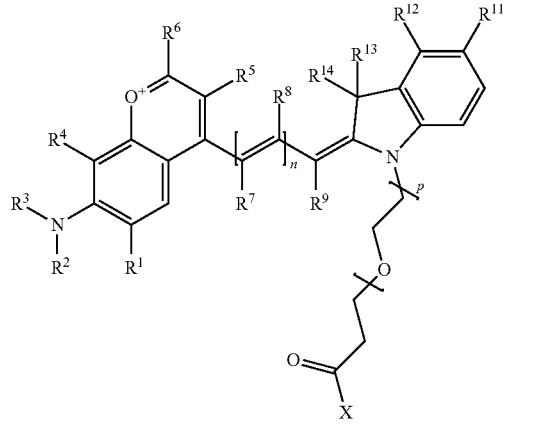
general formula Ih
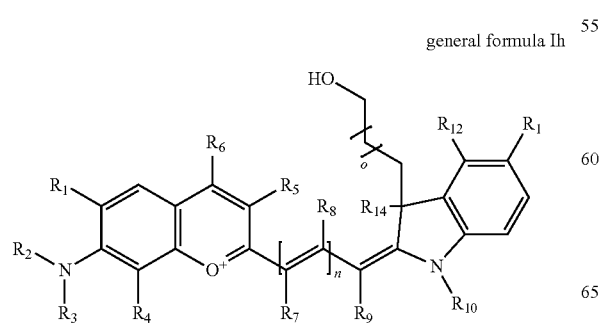
general formula IId
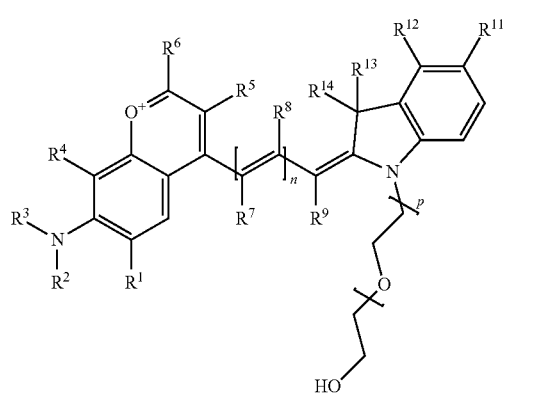

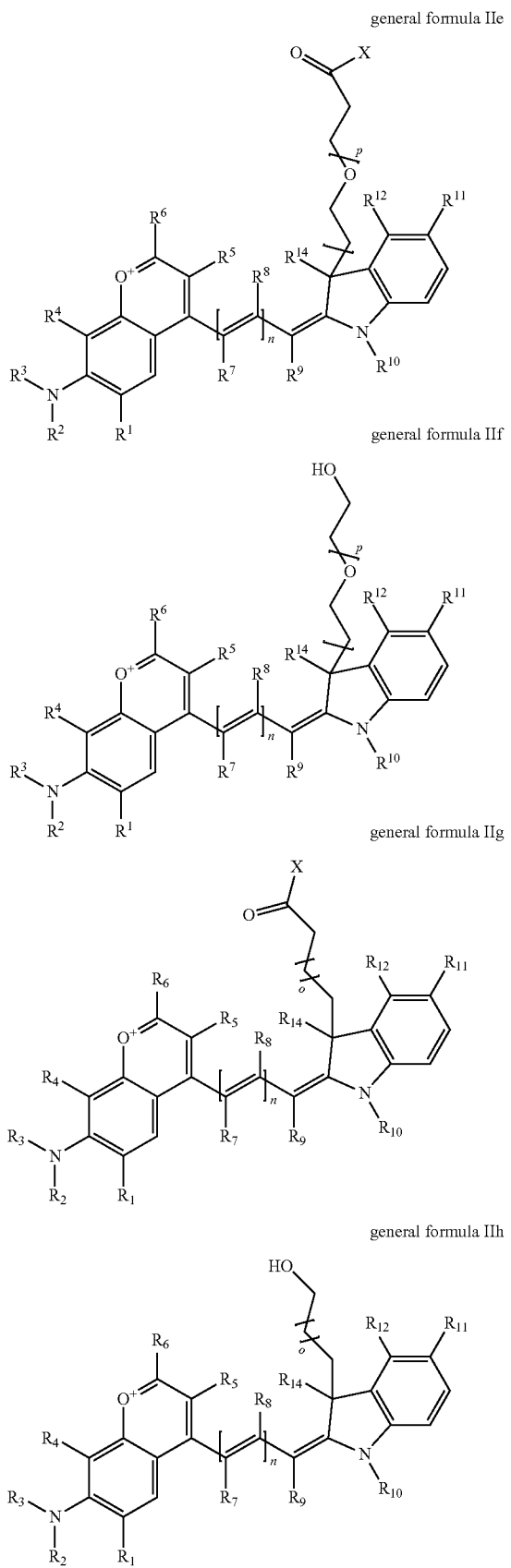

where each of $R^1$-$R^{14}$ is as defined above, X is selected from —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O-STP (4-sulfo-2, 3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, or —NR-L-NH—CO—CH$_2$—I, where R is —H or an aliphatic or heteroaliphatic group; Kat is a number of Na$^+$, K$^+$, Ca$^{2+}$, ammonia, or other cation(s) needed to compensate the negative charge(s); o is an integer from 0 to 12 inclusive; p is an integer from 1 to 6 inclusive; and n is 0, 1, 2, or 3.

In one embodiment, the compound is general formula Ia where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R13 and R14 are independently selected from alkyl, sulfoalkyl, or a PEG group P-L-Z, where P, L, and Z are defined above; and R1, R4, R7, R8, R9, and R12 are H. In one embodiment, R2 and/or R3 is sulfopropyl. In one embodiment, R5 is methyl. In one embodiment, R13 and/or R14 is sulfopropyl.

In one embodiment, the compound is general formula Ib where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R13 and R14 are independently selected from alkyl, sulfoalkyl, or a PEG group P-L-Z, where P, L, and Z are defined above; and R1, R4, R7, R8, R9, and R12 are H. In one embodiment, R2 and/or R3 is sulfopropyl. In one embodiment, R5 is methyl. In one embodiment, R13 and/or R14 is sulfopropyl.

In one embodiment, the compound is general formula Ic where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R13 and R14 are independently selected from alkyl, sulfoalkyl, or a PEG group P-L-Z, where P, L, and Z are defined above; and R1, R4, R7, R8, R9, and R12 are H. In one embodiment, R2 and/or R3 is sulfopropyl. In one embodiment, R5 is methyl. In one embodiment, R13 and/or R14 is sulfopropyl.

In one embodiment, the compound is general formula Id where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R13 and R14 are independently selected from alkyl, sulfoalkyl, or a PEG group P-L-Z, where P, L, and Z are defined above; and R1, R4, R7, R8, R9, and R12 are H. In one embodiment, R2 and/or R3 is sulfopropyl. In one embodiment, R5 is methyl. In one embodiment, R13 and/or R14 is sulfopropyl.

In one embodiment, the compound is general formula Ie where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R10 is alkyl, sulfoalkyl, or a PEG group P-L-Z, where P, L, and Z are defined above; R14 is alkyl; and R1, R4, R7, R8, R9, and R12 are H. In one embodiment, R2 and/or R3 is sulfopropyl. In one embodiment, R5 is methyl. In one embodiment, R10 is sulfopropyl. In one embodiment, R14 is methyl.

In one embodiment, the compound is general formula If where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R10 is alkyl, sulfoalkyl, or a PEG group P-L-Z, where P, L, and Z are defined above; R14 is alkyl; and R1, R4, R7, R8, R9, and R12 are H. In one embodiment, R2 and/or R3 is sulfopropyl. In one embodiment, R5 is methyl. In one embodiment, R10 is sulfopropyl. In one embodiment, R14 is methyl.

In one embodiment, the compound is general formula Ig where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R10 is alkyl, sulfoalkyl, or a PEG group P-L-Z, where P, L, and Z are defined above; R14 is alkyl; and R1, R4, R7, R8, R9, and R12 are H. In one embodiment, R2 and/or R3 is sulfopropyl. In one embodiment, R5 is methyl. In one embodiment, R10 is sulfopropyl. In one embodiment, R14 is methyl.

In one embodiment, the compound is general formula Ih where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R10 is alkyl, sulfoalkyl, or a PEG group P-L-Z, where P, L, and Z are defined above; R14 is alkyl; and R1, R4, R7, R8, R9, and R12 are H. In one embodiment, R2 and/or R3 is sulfopropyl. In one embodiment, R5 is methyl. In one embodiment, R10 is sulfopropyl. In one embodiment, R14 is methyl.

In one embodiment, the compound is general formula IIa where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R13 and R14 are independently selected from alkyl, sulfoalkyl, or a PEG group P-L-Z, where P, L, and Z are defined above; and R1, R4, R7, R8, R9, and R12 are H. In one embodiment, R2 and/or R3 is sulfopropyl. In one embodiment, R5 is methyl. In one embodiment, R13 and/or R14 is sulfopropyl.

In one embodiment, the compound is general formula IIb where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R13 and R14 are independently selected from alkyl, sulfoalkyl, or a PEG group P-L-Z, where P, L, and Z are defined above; and R1, R4, R7, R8, R9, and R12 are H. In one embodiment, R2 and/or R3 is sulfopropyl. In one embodiment, R5 is methyl. In one embodiment, R13 and/or R14 is sulfopropyl.

In one embodiment, the compound is general formula IIc where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R13 and R14 are independently selected from alkyl, sulfoalkyl, or a PEG group P-L-Z, where P, L, and Z are defined above; and R1, R4, R7, R8, R9, and R12 are H. In one embodiment, R2 and/or R3 is sulfopropyl. In one embodiment, R5 is methyl. In one embodiment, R13 and/or R14 is sulfopropyl.

In one embodiment, the compound is general formula IId where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R13 and R14 are independently selected from alkyl, sulfoalkyl, or a PEG group P-L-Z, where P, L, and Z are defined above; and R1, R4, R7, R8, R9, and R12 are H. In one embodiment, R2 and/or R3 is sulfopropyl. In one embodiment, R5 is methyl. In one embodiment, R13 and/or R14 is sulfopropyl.

In one embodiment, the compound is general formula IIe where R2 and R3 are independently selected from sulfoalkyl or a PEG group P-L-Z, where P, L, and Z are defined above; R5 is alkyl; R6 is either t-butyl or an unsubstituted or substituted phenyl; R11 is either sulfonic acid, carboxylic acid, or an amino group; R10 is alkyl, sulfoalkyl, or a PEG group P-L-Z, where P, L, and Z are defined above; R14 is alkyl; and R1, R4, R7, R8, R9, and R12 are H. In one embodiment, R2 and/or R3 is sulfopropyl. In one embodiment, R5 is methyl. In one embodiment, R10 is sulfopropyl. In one embodiment, R14 is methyl.

In one embodiment, the compound is general formula IIf where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R10 is alkyl, sulfoalkyl, or a PEG group P-L-Z, where P, L, and Z are defined above; R14 is alkyl; and R1, R4, R7, R8, R9, and R12 are H. In one embodiment, R2 and/or R3 is sulfopropyl. In one embodiment, R5 is methyl. In one embodiment, R10 is sulfopropyl. In one embodiment, R14 is methyl.

In one embodiment, the compound is general formula IIg where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R10 is alkyl, sulfoalkyl, or a PEG group P-L-Z, where P, L, and Z are defined above; R14 is alkyl; and R1, R4, R7, R8, R9, and R12 are H. In one embodiment, R2 and/or R3 is sulfopropyl. In one embodiment, R5 is methyl. In one embodiment, R10 is sulfopropyl. In one embodiment, R14 is methyl.

In one embodiment, the compound is general formula IIh where R2 and R3 are independently selected from sulfoalkyl or a PEG group P-L-Z, where P, L, and Z are defined above; R5 is alkyl; R6 is either t-butyl or an unsubstituted or substituted phenyl; R11 is sulfonic acid, carboxylic acid, or an amino group; R10 is alkyl, sulfoalkyl, or a PEG group P-L-Z, where P, L, and Z are defined above; R14 is alkyl; and R1, R4, R7, R8, R9, and R12 are H. In one embodiment, R2 and/or R3 is sulfopropyl. In one embodiment, R5 is methyl. In one embodiment, R10 is sulfopropyl. In one embodiment, R14 is methyl.

In embodiments, and as described above, R2 and/or R3, in conjunction with other position(s), may form additional ring(s). In one embodiment, the benzopyrylium group of the described compound comprises additional ring(s). For example, in one embodiment, as shown in the benzopyrylium portion of general formula II below, R2 and R3 each form an additional 6-membered ring, forming an N-bridged compound. In one embodiment, the compound is an N-bridged compound where R5 is alkyl; R6 is either t-butyl or an unsubstituted or substituted phenyl; and R7, R8, and R9 are H. In one embodiment, R5 is methyl. In one embodiment, the N-bridged compound is according to general formula I.

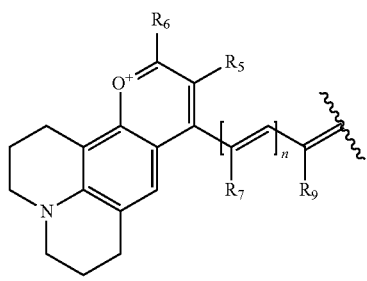

In one embodiment, as shown in the benzopyrylium portion of general formula II below, R3 forms an additional, substituted 6-membered ring, forming an N-bridged compound. In one embodiment, the compound is an N-bridged compound where R2 is sulfoalkyl or a PEG group P-L-Z, where P, L, and Z are defined above; R3' is sulfonic acid, carboxylic acid, or an amino group; R5 is alkyl; R6 is either t-butyl or an unsubstituted or substituted phenyl; and R7, R8, and R9 are H. In one embodiment, R2 is sulfopropyl. In one embodiment, R3' is sulfonic acid. In one embodiment, R5 is methyl. In one embodiment, the N-bridged compound is according to general formula I.

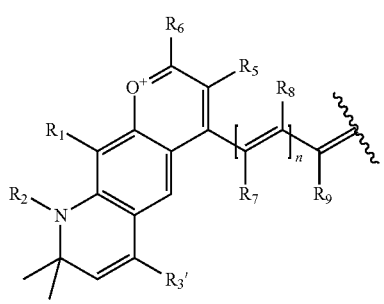

In one embodiment, the compound is 682 Compound 2 ((E)-2-((E)-3-(4-tert-butyl-7-((2-methoxyethyl)(3-sulfonatopropyl)amino)chromenylium-2-yl)allylidene)-3-(3-carboxypropyl)-3-methyl-1-(3-sulfonatopropyl)indoline-5-sulfonate), shown below, which contains an ethylene glycol (PEG$_1$) bound to the benzopyrylium by N, i.e., a methylated ethylene glycol, and —COOH at R13. The methyl group on the ethylene glycol/PEG prevents the terminal —OH from oxidation. Oxidation is known to occur, over time, on an unprotected PEG terminus. Adding a methyl ether provides this protection, and prevents reaction with electrophilic reactive groups.

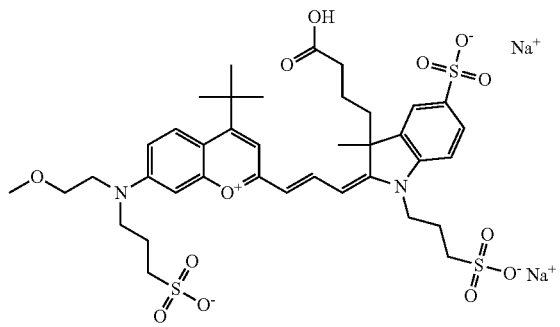 [SMILES: COCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)O)[o+]c2c1 ; [Na+] ; [Na+]]

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 682 Compound 2 (PEG$_1$), but one skilled in the art appreciates that activation is not limited to these examples. One non-limiting example of an activated compound is an NHS-ester of 682 Compound 2 (PEG$_1$), shown below:

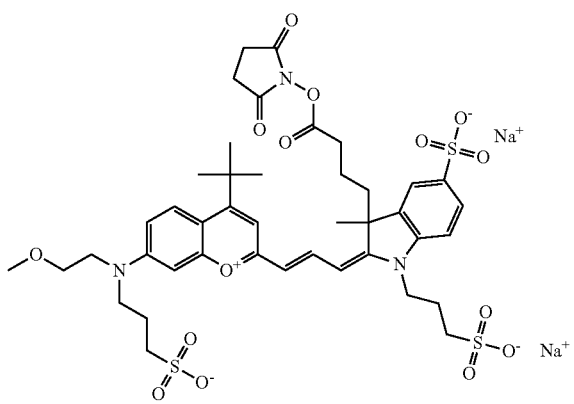 [SMILES: COCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)ON3C(=O)CCC3=O)[o+]c2c1 ; [Na+] ; [Na+]]

One non-limiting example of an activated 682 Compound 2 (PEG$_1$) is a tetrafluorophenyl (TFP)-ester form of 682 Compound 2, shown below:

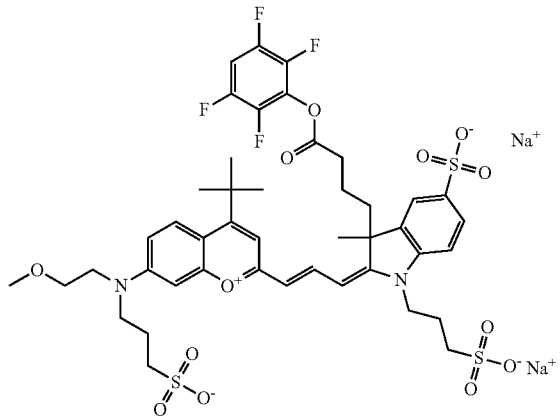 [SMILES: COCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)Oc3c(F)c(F)cc(F)c3F)[o+]c2c1 ; [Na+] ; [Na+]]

One non-limiting example of an activated 682 Compound 2 (PEG$_1$) is a sulfotetrafluorophenyl (STP)-ester form of 682 Compound 2, shown below:

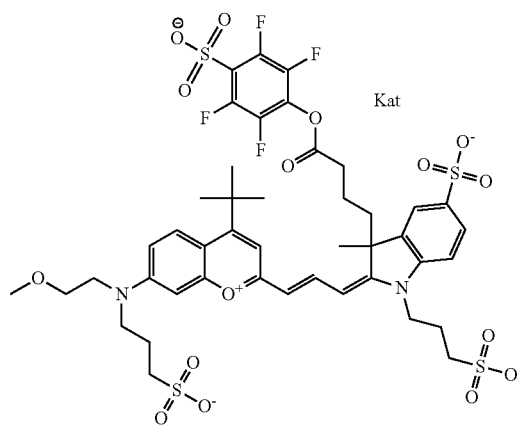 [SMILES: COCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)Oc3c(F)c(F)c(S(=O)(=O)[O-])c(F)c3F)[o+]c2c1]

One non-limiting example of an activated 682 Compound 2 (PEG$_1$) is a hydrazide form of 682 Compound 2, shown below:

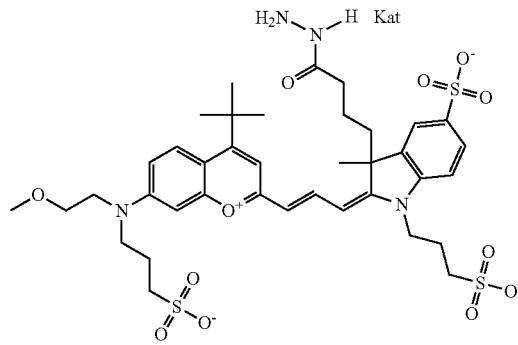 [SMILES: COCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)NN)[o+]c2c1]

One non-limiting example of an activated 682 Compound 2 (PEG$_1$) is a maleimide form of 682 Compound 2, shown below:

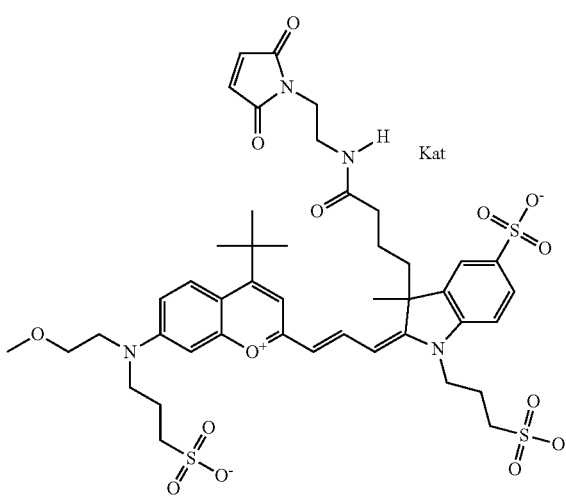

In one embodiment, the compound is 682 Compound 2 ((E)-2-((E)-3-(4-tert-butyl-7-((2-(2-methoxyethoxy)ethyl)(3-sulfonatopropyl)amino)chromenylium-2-yl)allylidene)-3-(3-carboxypropyl)-3-methyl-1-(3-sulfonatopropyl)indoline-5-sulfonate), shown below, which contains an diethylene glycol (PEG$_2$) bound to the benzopyrylium by N, i.e., a methylated diethylene glycol, and —COOH at R13.

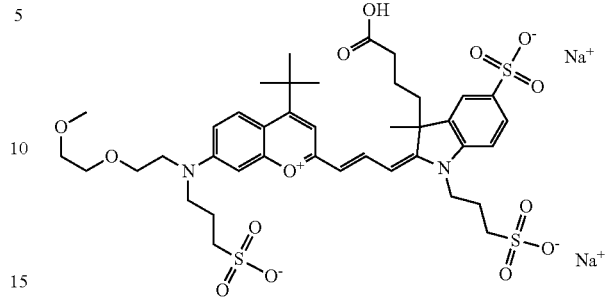

One non-limiting example of an activated compound is an NHS-ester of 682 Compound 2 (PEG$_2$), shown below:

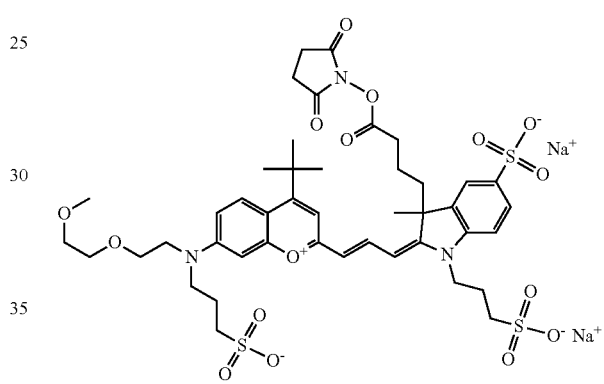

In one embodiment, the compound is 682 Compound 2 ((E)-2-((E)-3-(4-tert-butyl-7-((2-(2-(2-methoxyethoxy)ethoxy)ethyl)(3-sulfonatopropyl)amino)chromenylium-2-yl)allylidene)-3-(3-carboxypropyl)-3-methyl-1-(3-sulfonatopropyl)indoline-5-sulfonate), shown below, which contains a polyethylene glycol (PEG$_3$) bound to the benzopyrylium by N, i.e., a methylated polyethylene glycol, and —COOH at R13.

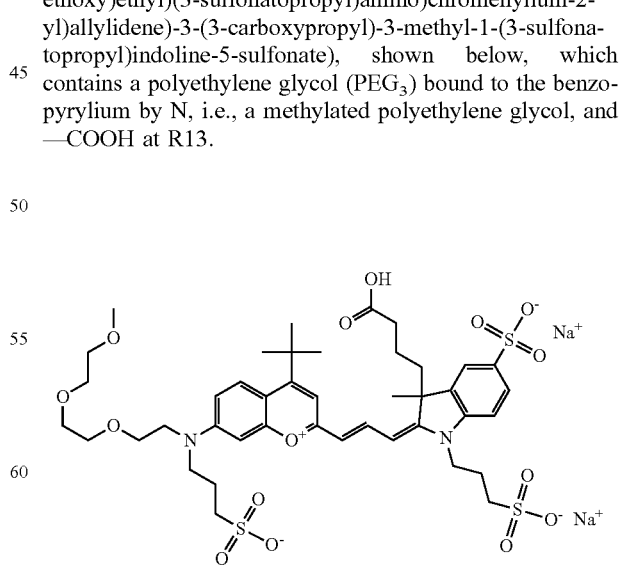

One non-limiting example of an activated compound is an NHS-ester of 682 Compound 2 (PEG$_3$), shown below:

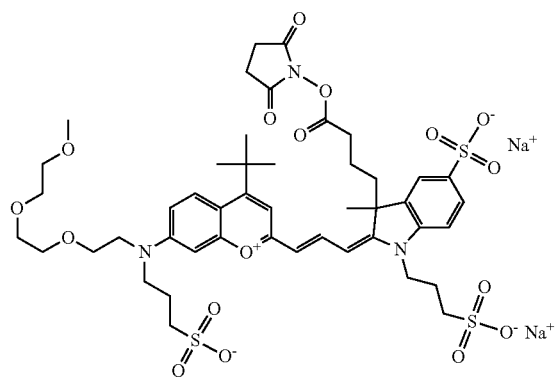 [SMILES: COCCOCCOCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)ON3C(=O)CCC3=O)[o+]c2c1 ; [Na+] ; [Na+]]

In one embodiment, the compound is 682 Compound 2 (V17-03019) ((E)-2-((E)-3-(4-tert-butyl-7-((3-sulfonatopropyl)(2,5,8,11-tetraoxatridecan-13-yl)amino)chromenylium-2-yl)allylidene)-3-(3-carboxypropyl)-3-methyl-1-(3-sulfonatopropyl)indoline-5-sulfonate), shown below, which contains a polyethylene glycol (PEG$_4$) bound to the benzopyrylium by N, i.e., a methylated polyethylene glycol, and —COOH at R13.

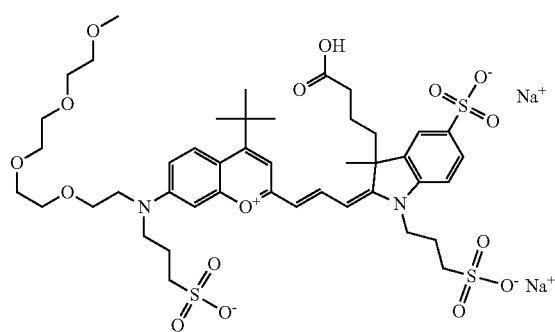 [SMILES: COCCOCCOCCOCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)O)[o+]c2c1 ; [Na+] ; [Na+]]

One non-limiting example of an activated compound is an NHS-ester of 682 Compound 2 (PEG$_4$), shown below:

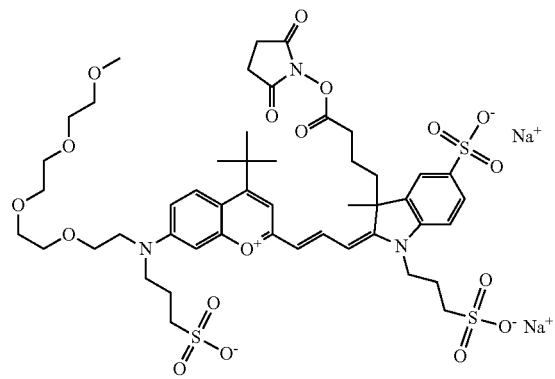 [SMILES: COCCOCCOCCOCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)ON3C(=O)CCC3=O)[o+]c2c1 ; [Na+] ; [Na+]]

In one embodiment, the compound is 682 Compound 2 ((E)-2-((E)-3-(7-(2,5,8,11,14-pentaoxahexadecan-16-yl(3-sulfonatopropyl)amino)-4-tert-butylchromenylium-2-yl)allylidene)-3-(3-carboxypropyl)-3-methyl-1-(3-sulfonatopropyl)indoline-5-sulfonate), shown below, which contains a polyethylene glycol (PEG$_5$) bound to the benzopyrylium by N, i.e., a methylated polyethylene glycol, and —COOH at R13.

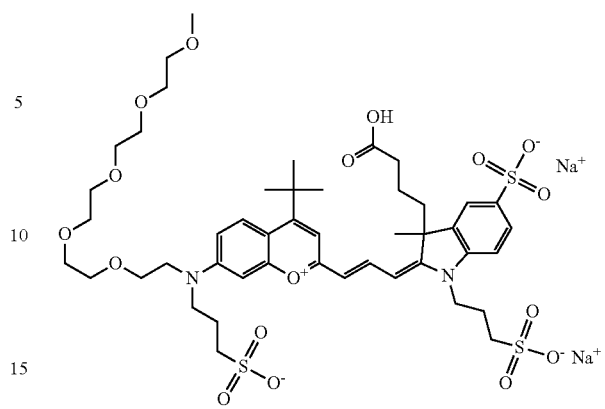

One non-limiting example of an activated compound is an NHS-ester of 682 Compound 2 (PEG$_5$), shown below:

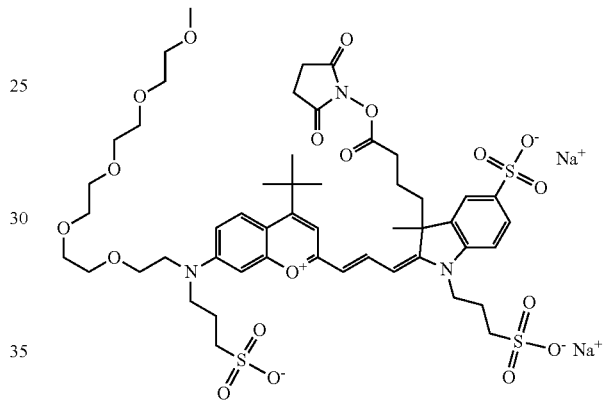

In one embodiment, the compound is 682 Compound 2 ((E)-2-((E)-3-(7-(2,5,8,11,14,17-hexaoxanonadecan-19-yl(3-sulfonatopropyl)amino)-4-tert-butylchromenylium-2-yl)allylidene)-3-(3-carboxypropyl)-3-methyl-1-(3-sulfonatopropyl)indoline-5-sulfonate), shown below, which contains a polyethylene glycol (PEG$_6$) bound to the benzopyrylium by N, i.e., a methylated polyethylene glycol, and —COOH at R13.

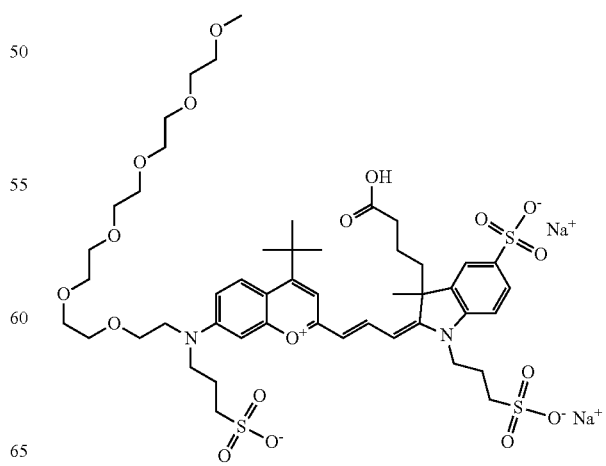

One non-limiting example of an activated compound is an NHS-ester of 682 Compound 2 (PEG$_6$), shown below:

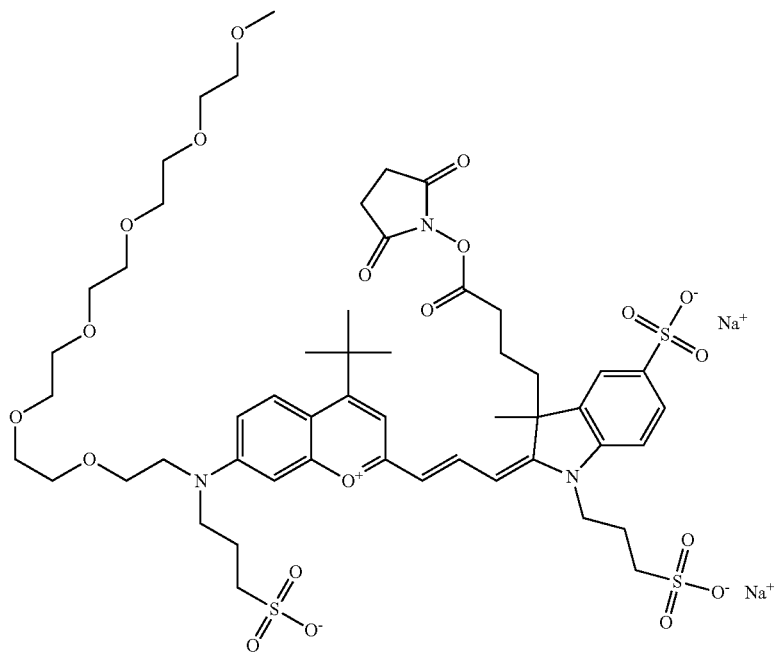 [SMILES: COCCOCCOCCOCCOCCOCCN(CCCS(=O)(=O)[O-])c1ccc2c(C(C)(C)C)cc(/C=C/C=C3/N(CCCS(=O)(=O)[O-])c4ccc(S(=O)(=O)[O-])cc4C3(C)CCCC(=O)ON3C(=O)CCC3=O)[o+]c2c1 ; [Na+] ; [Na+]]

In one embodiment, the compound is 682 Compound 2 ((E)-2-((E)-3-(4-tert-butyl-7-((2-(2-methoxyethoxy)ethyl)(3-sulfonatopropyl)amino)chromenylium-2-yl)allylidene)-1-(5-carboxypentyl)-3-methyl-3-(3-sulfonatopropyl)indoline-5-sulfonate), according to general formula I and shown below, which contains an ethylene glycol (PEG$_1$) bound to the benzopyrylium by N, i.e., a methylated ethylene glycol, and —COOH at R10:

or according to general formula II shown below

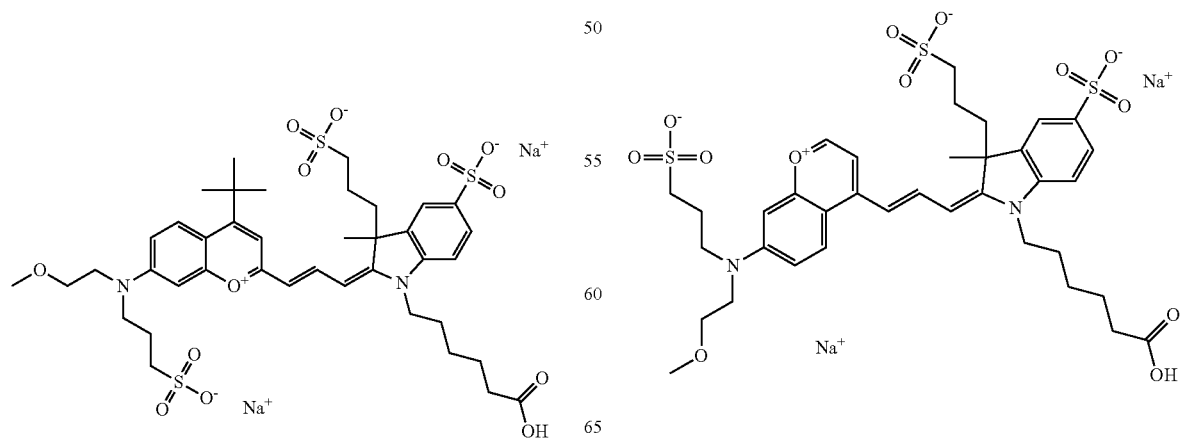

One non-limiting example of an activated compound according to general formula I is an NHS-ester of 682 Compound 2 (PEG$_1$), shown below:

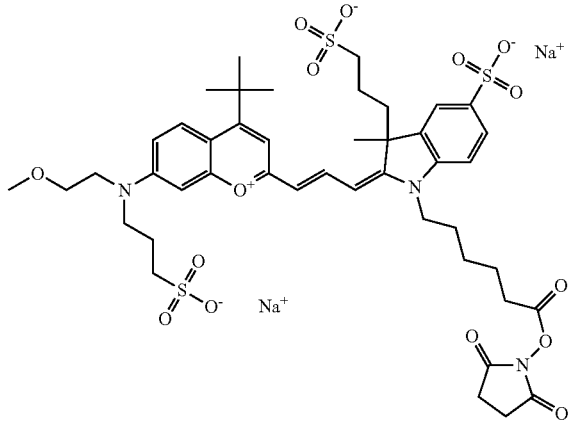

or according to general formula II shown below

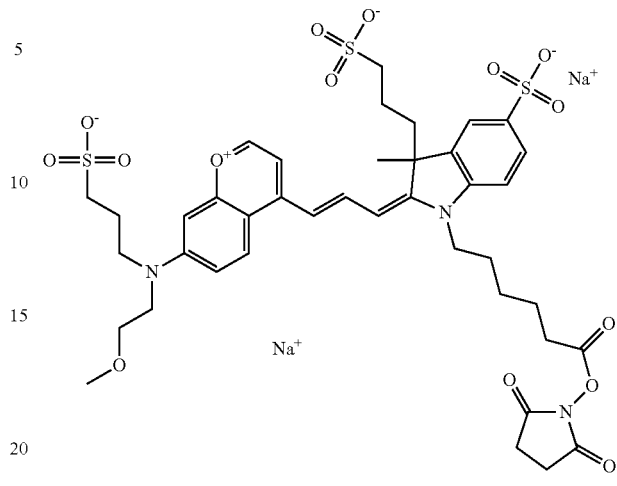

In one embodiment, the compound is 682 Compound 2 ((E)-2-((E)-3-(4-tert-butyl-7-((2-(2-methoxyethoxy)ethyl) (3-sulfonatopropyl)amino)chromenylium-2-yl)allylidene)-1-(5-carboxypentyl)-3-methyl-3-(3-sulfonatopropyl)indoline-5-sulfonate), according to general formula I and shown below, which contains a diethylene glycol (PEG$_2$) bound to the benzopyrylium by N, i.e., a methylated diethylene glycol, and —COOH at R10:

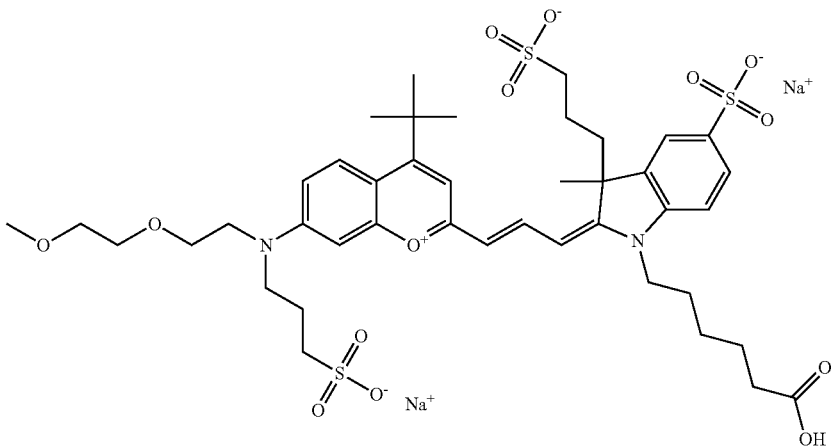

or according to general formula II shown below

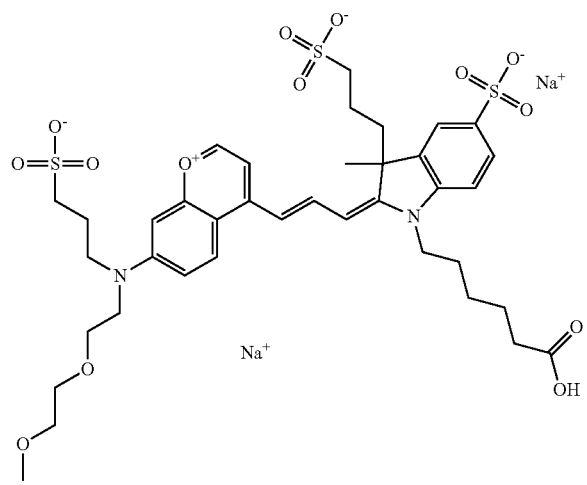

One non-limiting example of an activated compound according to general formula I is an NHS-ester of 682 Compound 2 (PEG$_2$), shown below:

or according to general formula II shown below

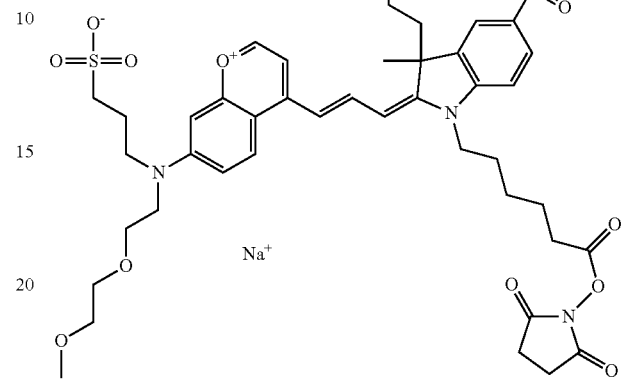

In one embodiment, the compound is 682 Compound 2 ((E)-2-((E)-3-(4-tert-butyl-7-((2-(2-(2-methoxyethoxy)ethoxy)ethyl)(3-sulfonatopropyl)amino)chromenylium-2-yl)allylidene)-1-(5-carboxypentyl)-3-methyl-3-(3-sulfonatopropyl)indoline-5-sulfonate), according to general formula I and shown below, which contains a polyethylene glycol (PEG$_3$) bound to the benzopyrylium by N, i.e., a methylated polyethylene glycol, and —COOH at R10:

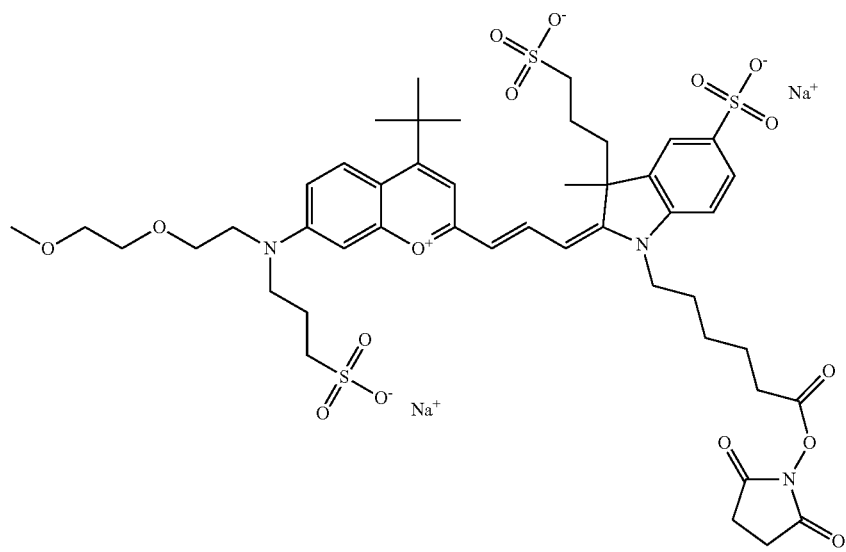

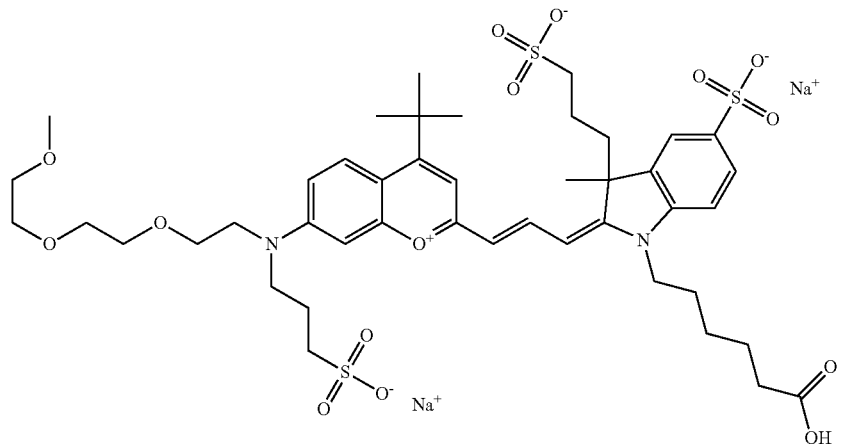

or according to general formula II shown below

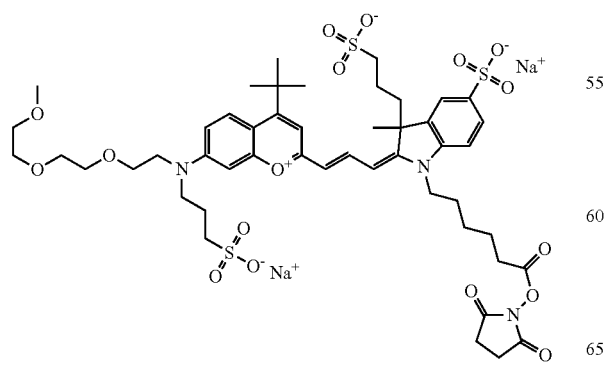

One non-limiting example of an activated compound according to general formula I is an NHS-ester of 682 Compound 2 (PEG₃), shown below:

or according to general formula II shown below

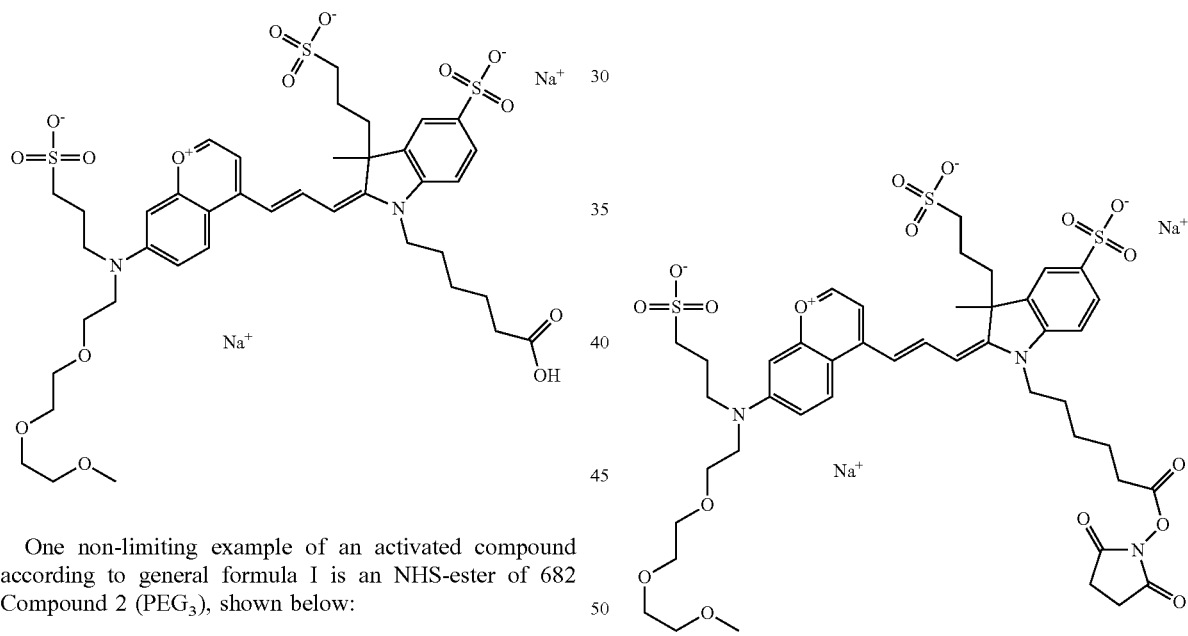

In one embodiment, the compound is 682 Compound 2 (V08-16072) ((E)-2-((E)-3-(4-tert-butyl-7-((3-sulfonatopropyl)(2,5,8,11-tetraoxatridecan-13-yl)amino)chromenylium-2-yl)allylidene)-1-(5-carboxypentyl)-3-methyl-3-(3-sulfonatopropyl)indoline-5-sulfonate), according to general formula I and shown below, which contains a polyethylene glycol (PEG₄) bound to the benzopyrylium by N, i.e., a methylated polyethylene glycol, and —COOH at R10:

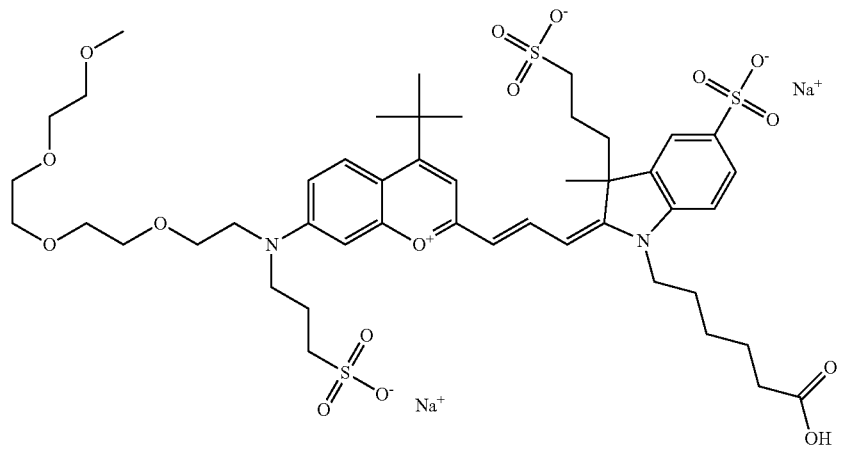

or according to general formula II shown below

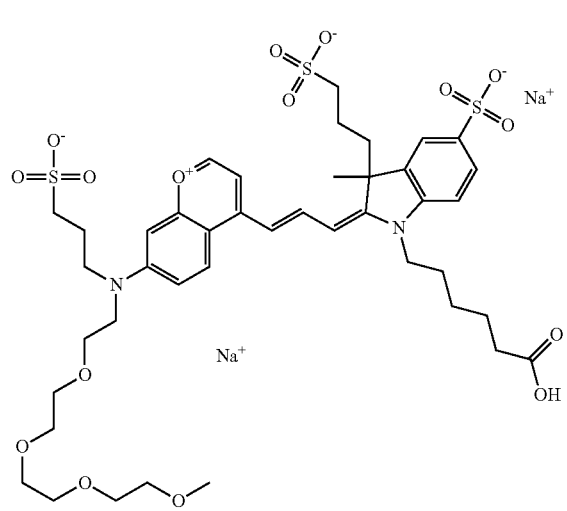

One non-limiting example of an activated compound according to general formula I is an NHS-ester of 682 Compound 2 (PEG₄), shown below:

or according to general formula II shown below

In one embodiment, the compound is 682 Compound 2 ((E)-2-((E)-3-(7-(2,5,8,11,14-pentaoxahexadecan-16-yl(3-sulfonatopropyl)amino)-4-tert-butylchromenylium-2-yl)allylidene)-1-(5-carboxypentyl)-3-methyl-3-(3-sulfonatopropyl)indoline-5-sulfonate), according to general formula I and shown below, which contains a polyethylene glycol (PEG₅) bound to the benzopyrylium by N, i.e., a methylated polyethylene glycol, and —COOH at R10:

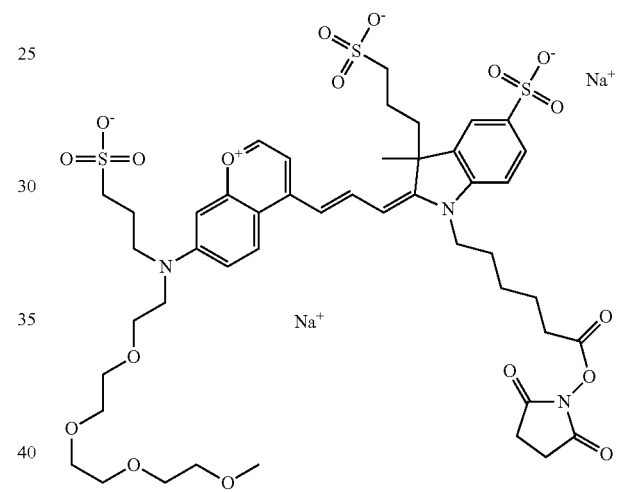

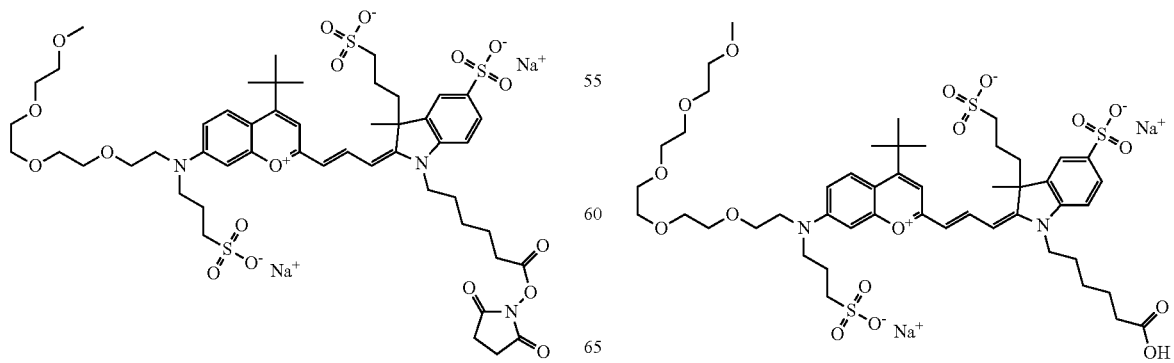

or according to general formula II shown below

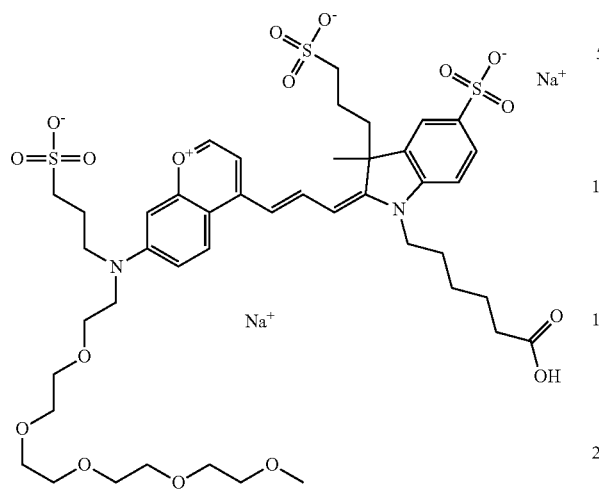

One non-limiting example of an activated compound according to general formula I is an NHS-ester of 682 Compound 2 (PEG₅), shown below:

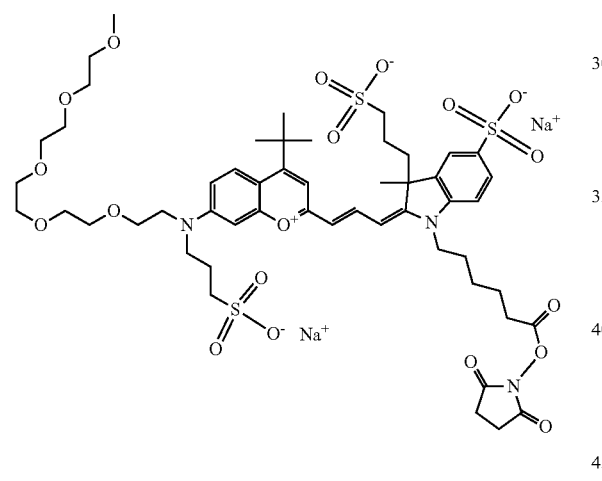

or according to general formula II shown below

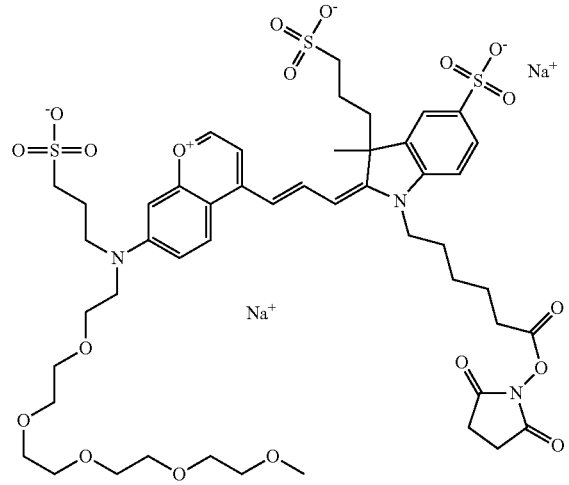

In one embodiment, the compound is 682 Compound 2 ((E)-2-((E)-3-(7-(2,5,8,11,14,17-hexaoxanonadecan-19-yl (3-sulfonatopropyl)amino)-4-tert-butylchromenylium-2-yl) allylidene)-1-(5-carboxypentyl)-3-methyl-3-(3-sulfonatopropyl)indoline-5-sulfonate), according to general formula I and shown below, which contains a polyethylene glycol (PEG₆) bound to the benzopyrylium by N, i.e., a methylated polyethylene glycol, and —COOH at R10:

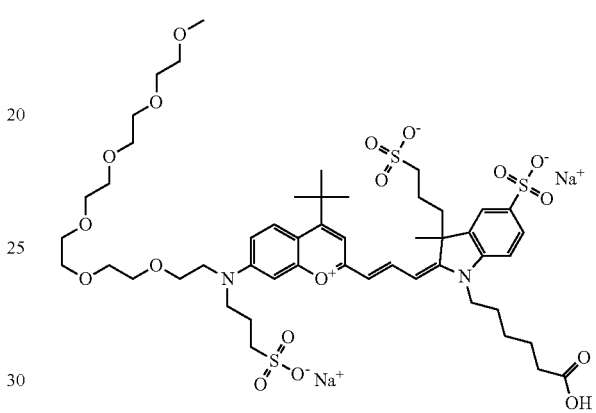

or according to general formula II shown below

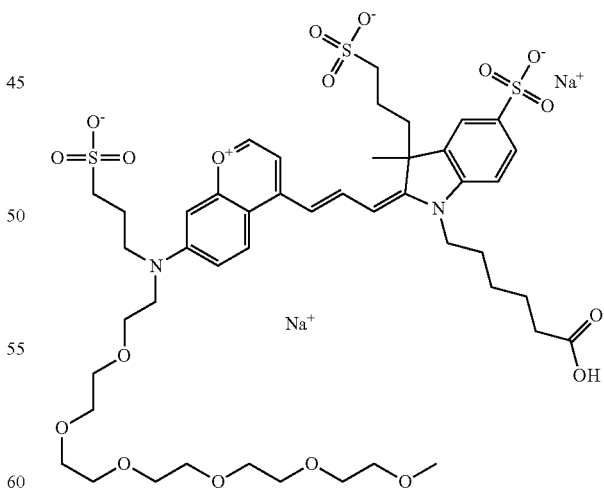

One non-limiting example of an activated compound according to general formula I is an NHS-ester of 682 Compound 2 (PEG₆), shown below

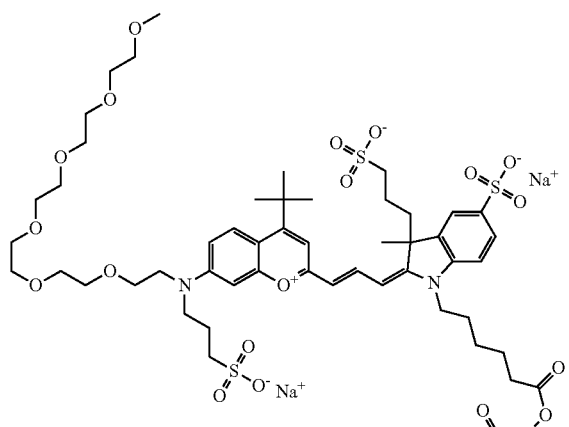

or according to general formula II shown below

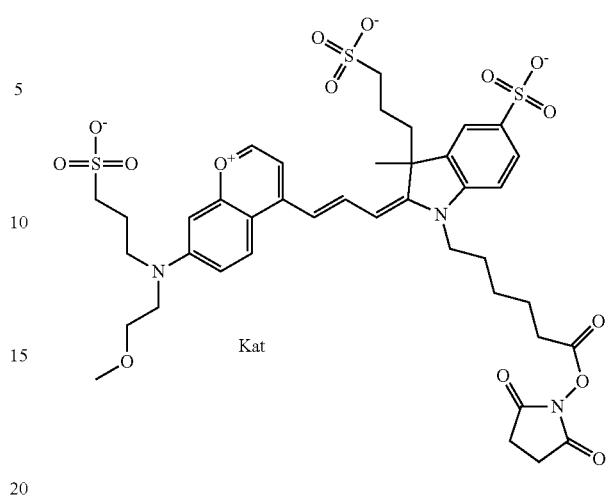

One non-limiting example of an activated 682 Compound 2 (PEG$_1$) according to general formula I is a tetrafluorophenyl (TFP)-ester form of 682 Compound 2, shown below:

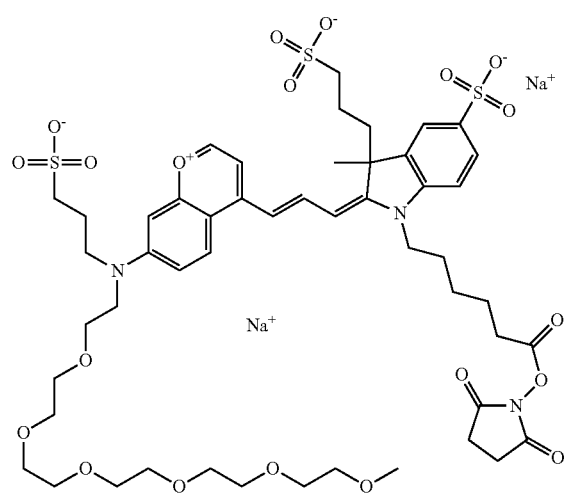

One non-limiting example of an activated compound according to general formula I is the NHS-ester of 682 Compound 2 (PEG$_1$), shown below:

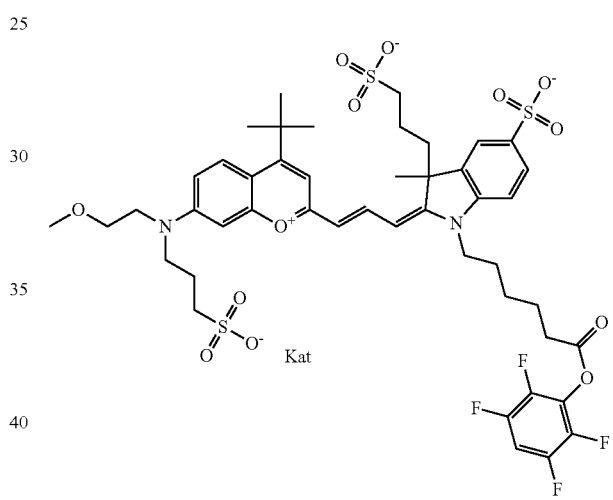

or according to general formula II shown below

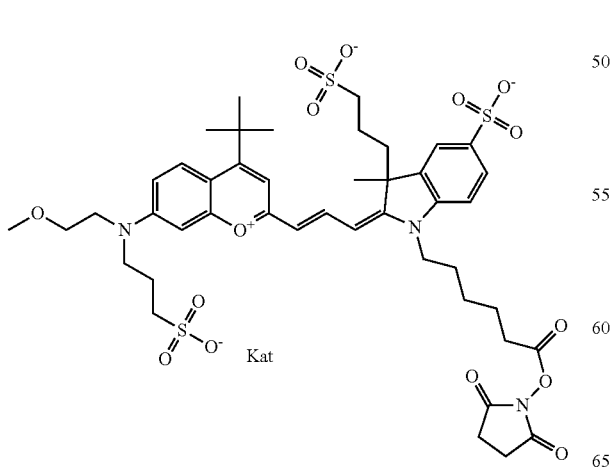

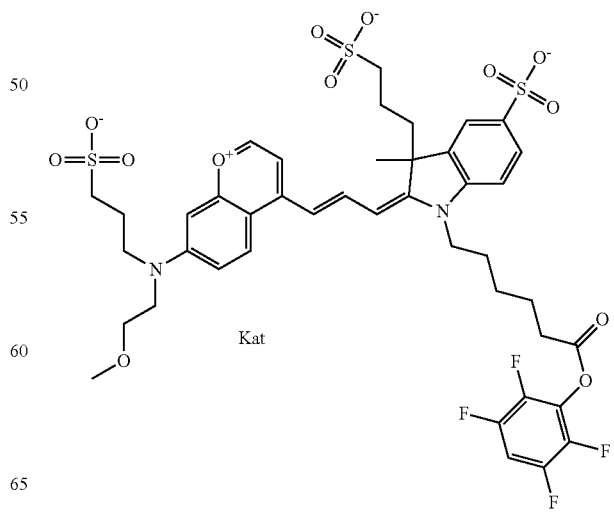

One non-limiting example of an activated 682 Compound 2 (PEG$_1$) according to general formula I is a sulfotetrafluorophenyl (STP)-ester form of 682 Compound 2, shown below:

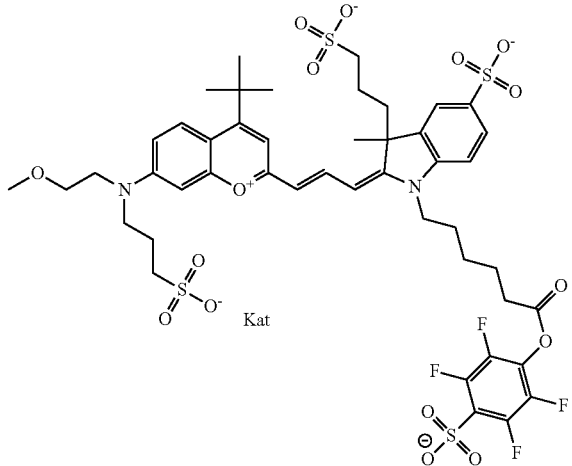

or according to general formula II shown below

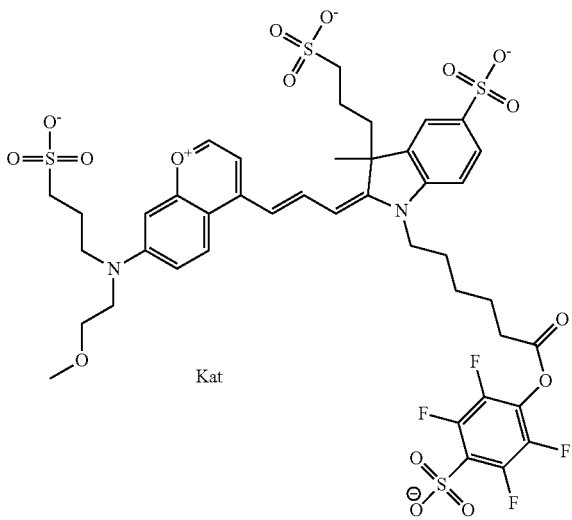

One non-limiting example of an activated 682 Compound 2 (PEG$_1$) according to general formula I is a hydrazide form of 682 Compound 2, shown below:

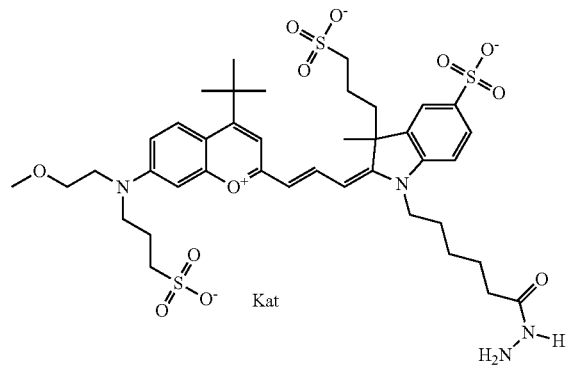

or according to general formula II shown below

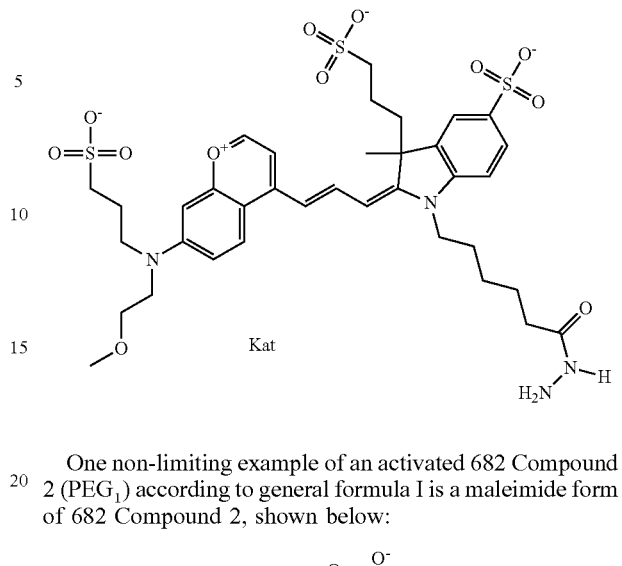

One non-limiting example of an activated 682 Compound 2 (PEG$_1$) according to general formula I is a maleimide form of 682 Compound 2, shown below:

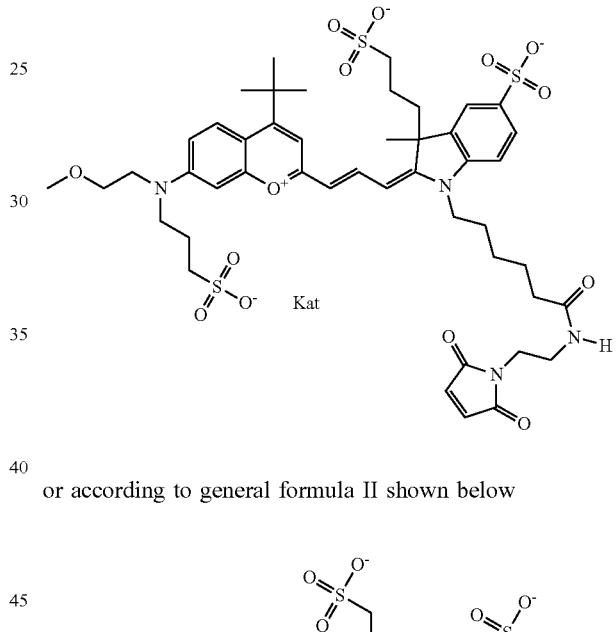

or according to general formula II shown below

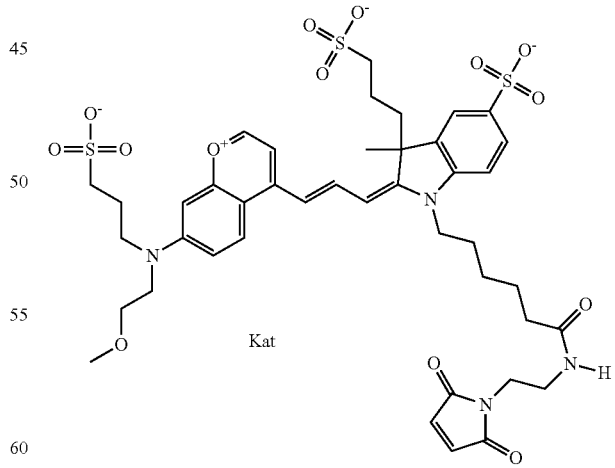

In one embodiment, the compound is 682 Compound 10 ((E)-2-((E)-3-(4-tert-butyl-7-(ethyl(3-sulfonatopropyl) amino)chromenylium-2-yl)allylidene)-1-(2-(2-carboxyethoxy)ethyl)-3-methyl-3-(3-sulfonatopropyl)indoline-5-sulfonate), according to general formula I and shown below, which contains an ethylene glycol (PEG$_1$) on the indole N, terminating with —COOH, at R10:

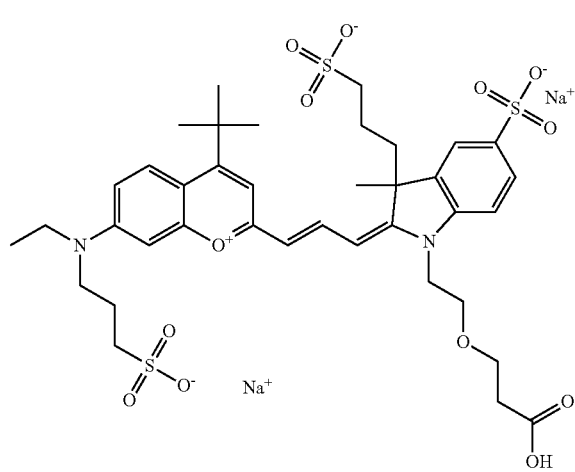

or according to general formula II shown below:

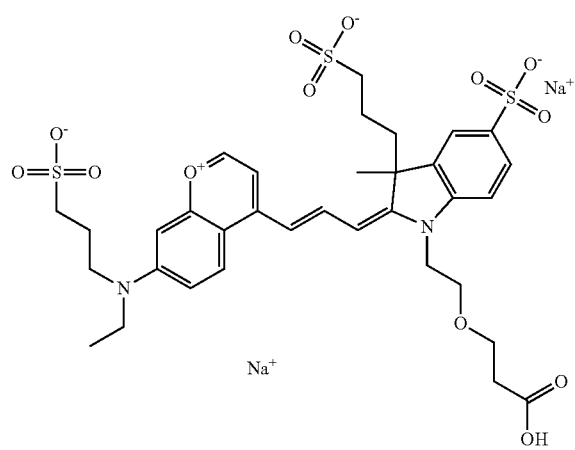

In one embodiment, the compound is 682 Compound 10, according to general formula I and shown below, which contains an ethylene glycol (PEG$_1$) on the indole N, terminating with —OH, at R10:

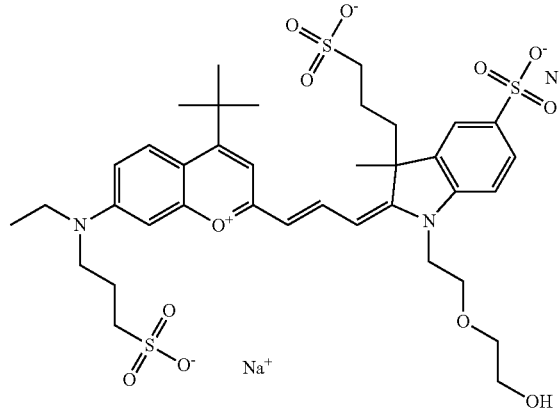

or according to general formula II shown below

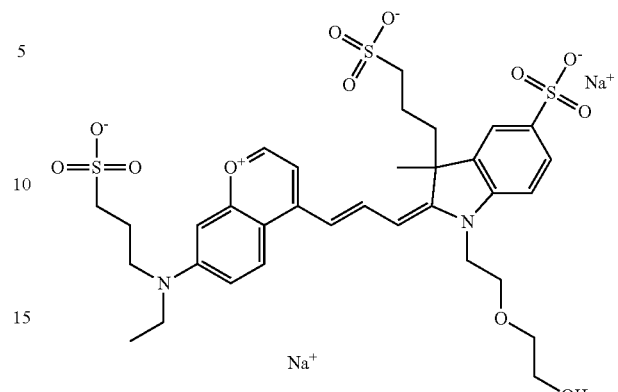

One non-limiting example of an activated compound according to general formula I is the NHS-ester of 682 Compound 10 (PEG$_1$), shown below:

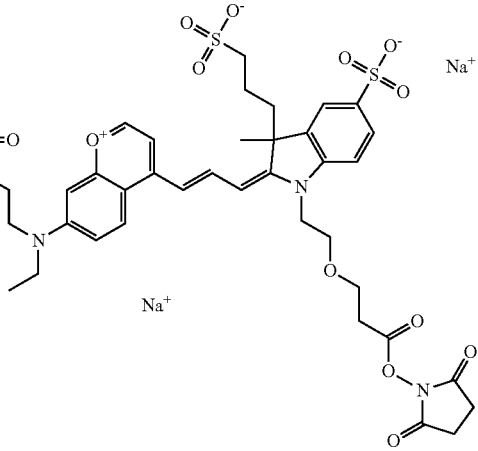

or according to general formula II shown below

In one embodiment, the compound is 682 Compound 10 ((E)-2-((E)-3-(4-tert-butyl-7-(ethyl(3-sulfonatopropyl)amino)chromenylium-2-yl)allylidene)-1-(2-(2-(2-carboxyethoxy)ethoxy)ethyl)-3-methyl-3-(3-sulfonatopropyl)indoline-5-sulfonate), according to general formula I and shown below, which contains an diethylene glycol (PEG$_2$) on the indole N, terminating with a —COOH, at R10:

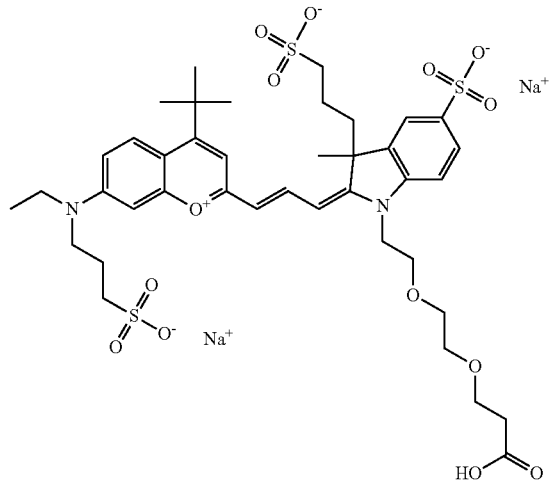

or according to general formula II shown below

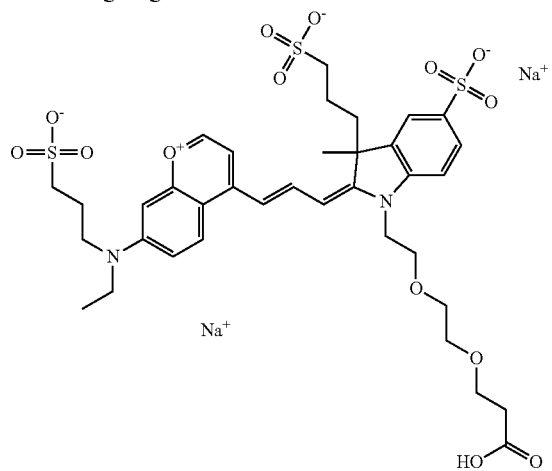

In one embodiment, the compound is 682 Compound 10, according to general formula I and shown below, which contains an diethylene glycol (PEG$_2$) on the indole N, terminating with a —OH, at R10:

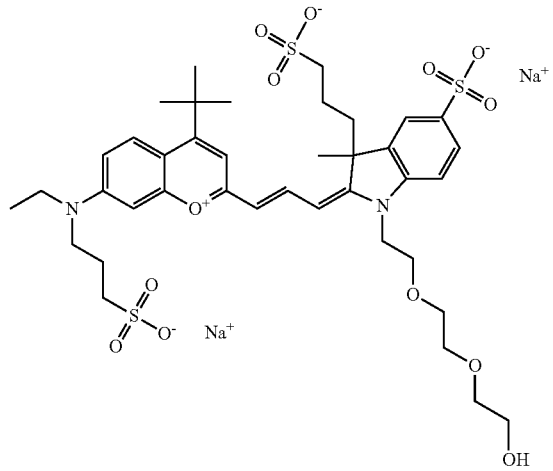

or according to general formula II shown below

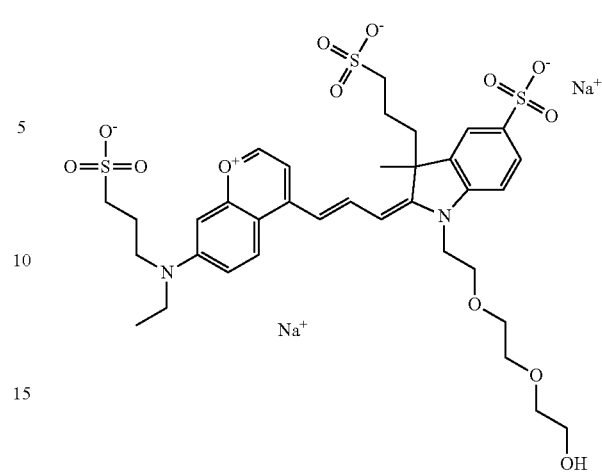

One non-limiting example of an activated compound according to general formula I is the NHS-ester of 682 Compound 10 (PEG$_2$), shown below:

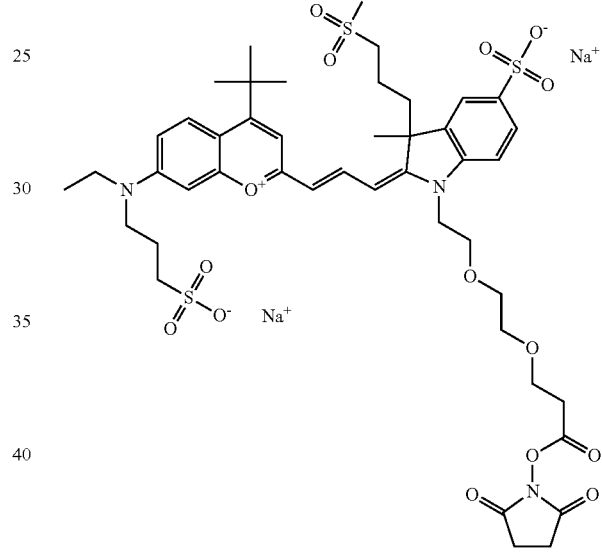

or according to general formula II shown below

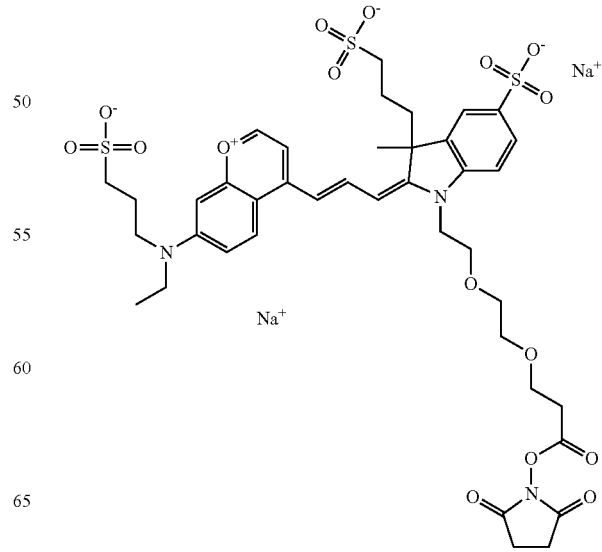

In one embodiment, the compound is 682 Compound 10 ((E)-2-((E)-3-(4-tert-butyl-7-(ethyl(3-sulfonatopropyl)amino)chromenylium-2-yl)allylidene)-1-(2-(2-(2-(2-carboxyethoxy)ethoxy)ethoxy)ethyl)-3-methyl-3-(3-sulfonatopropyl)indoline-5-sulfonate), according to general formula I and shown below, which contains an polyethylene glycol (PEG$_3$) on the indole N, terminating with a —COOH, at R10:

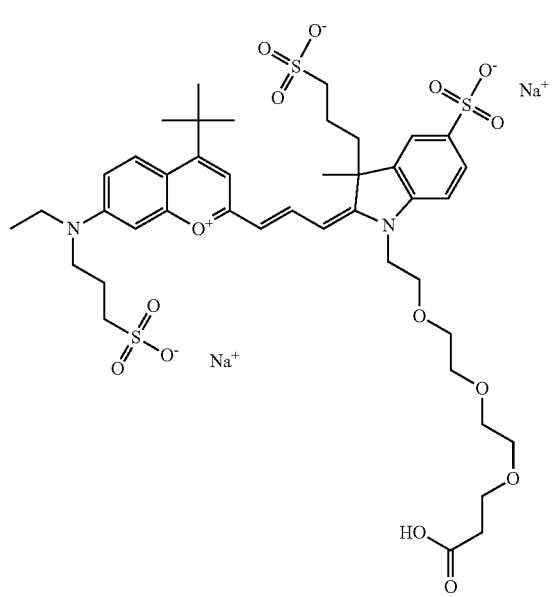

or according to general formula II shown below

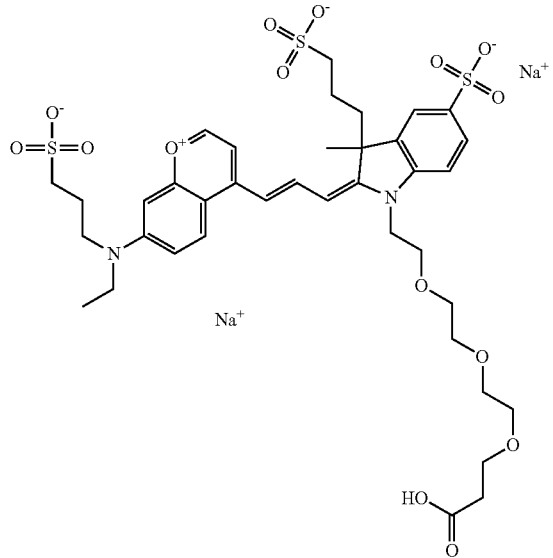

In one embodiment, the compound is 682 Compound 10, according to general formula I and shown below, which contains an polyethylene glycol (PEG$_3$) on the indole N, terminating with a —OH, at R10:

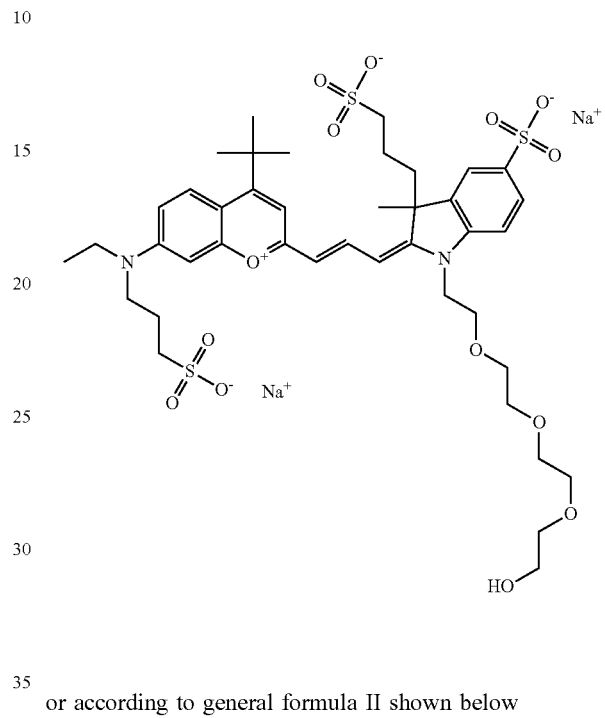

or according to general formula II shown below

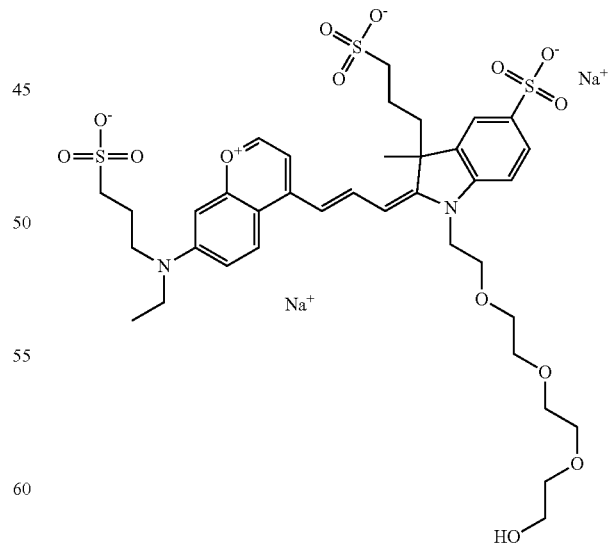

One non-limiting example of an activated compound according to general formula I is the NHS-ester of 682 Compound 10 (PEG$_3$), shown below:

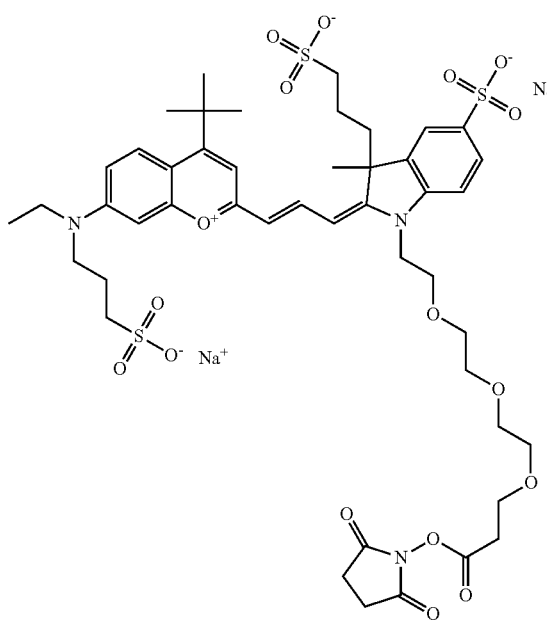

or according to general formula II shown below

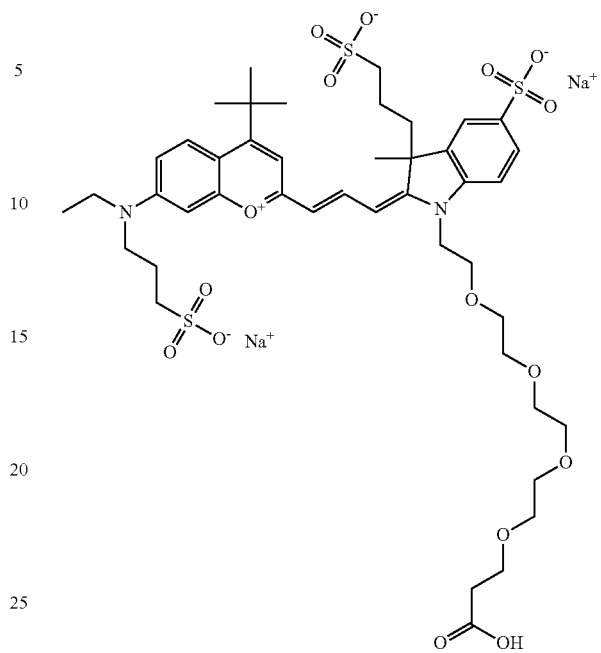

or according to general formula II shown below

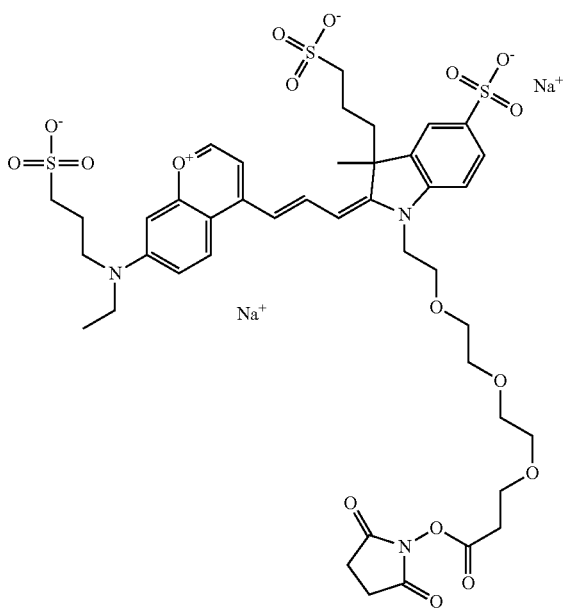

In one embodiment, the compound is 682 Compound 10 ((E)-2-((E)-3-(4-tert-butyl-7-(ethyl(3-sulfonatopropyl)amino)chromenylium-2-yl)allylidene)-1-(14-carboxy-3,6,9,12-tetraoxatetradecyl)-3-methyl-3-(3-sulfonatopropyl)indoline-5-sulfonate), according to general formula I and shown below, which contains an polyethylene glycol (PEG$_4$) on the indole N, terminating with a —COOH, at R10:

In one embodiment, the compound is 682 Compound 10, according to general formula I and shown below, which contains an polyethylene glycol (PEG$_4$) on the indole N, terminating with —OH, at R10:

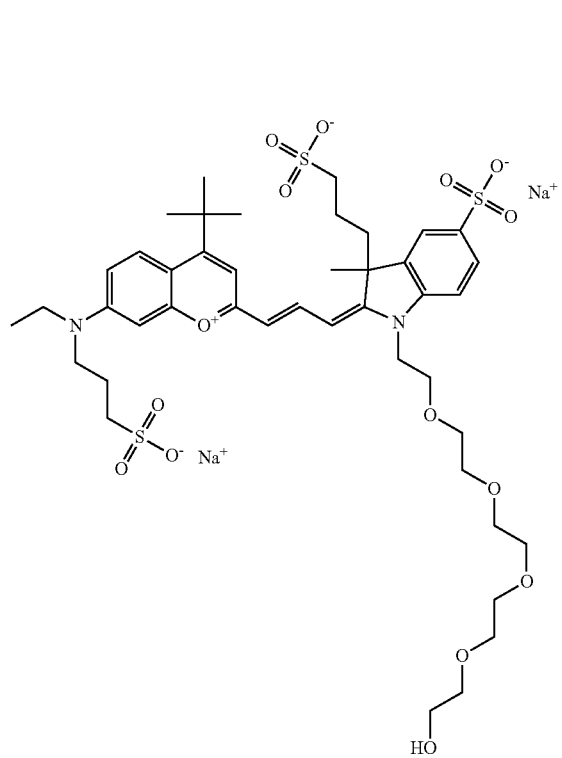

or according to general formula II shown below

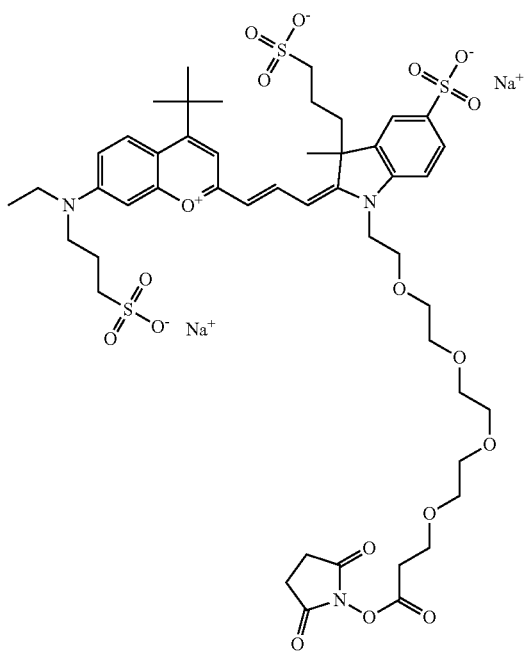

or according to general formula II shown below

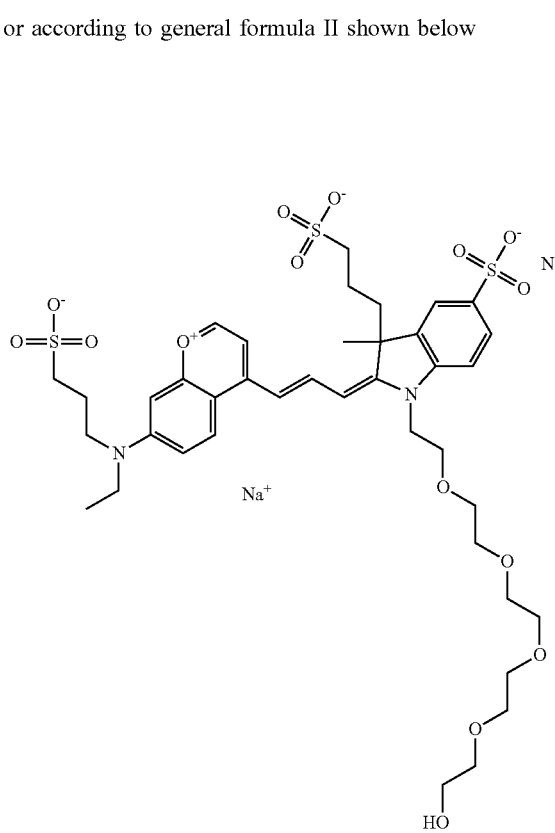

One non-limiting example of an activated compound according to general formula I is the NHS-ester of 682 Compound 10 (PEG$_4$), shown below:

In one embodiment, the compound is 682 Compound 10 ((E)-2-((E)-3-(4-tert-butyl-7-(ethyl(3-sulfonatopropyl) amino)chromenylium-2-yl)allylidene)-1-(17-carboxy-3,6,9, 12,15-pentaoxaheptadecyl)-3-methyl-3-(3-sulfonatopropyl) indoline-5-sulfonate), according to general formula I and shown below, which contains a polyethylene glycol (PEG$_5$) on the indole N, terminating with a —COOH, at R10:

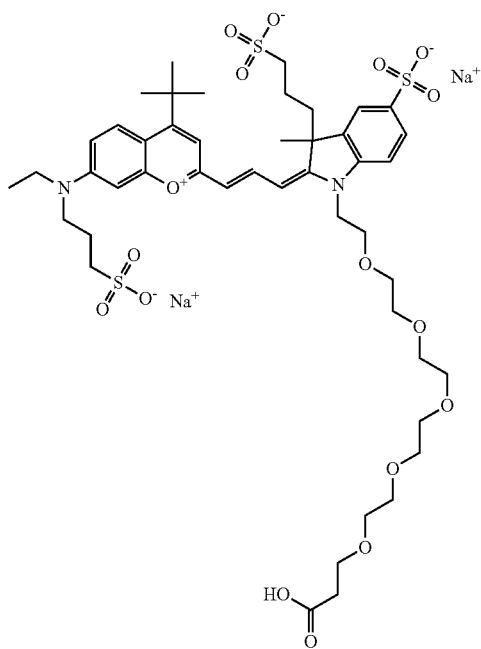

or according to general formula II shown below

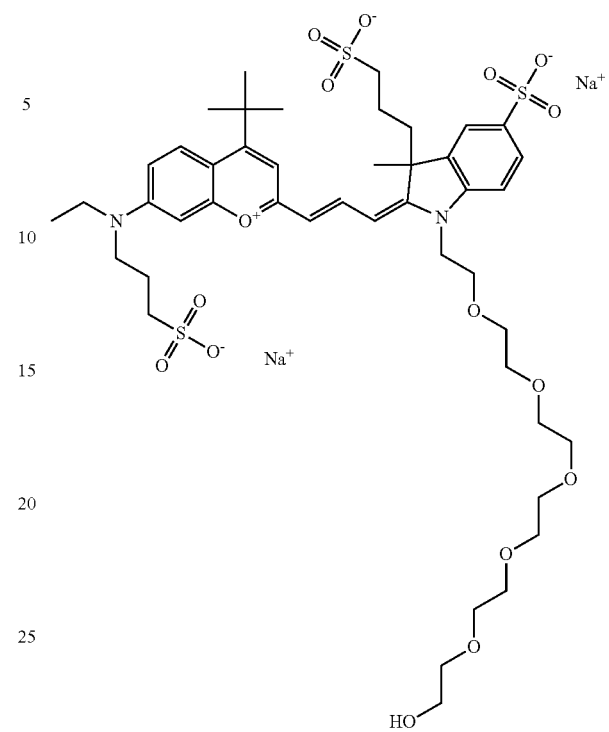

or according to general formula II shown below

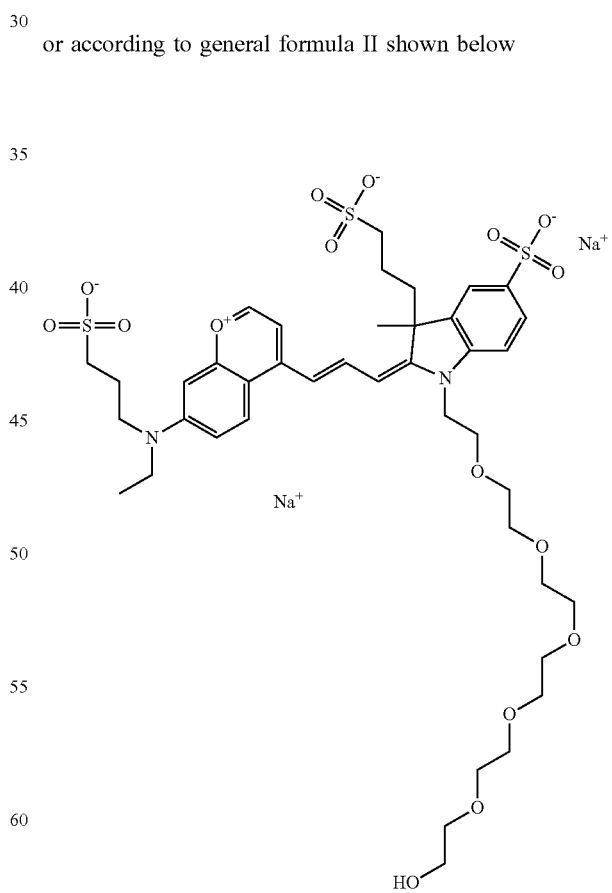

In one embodiment, the compound is 682 Compound 10, according to general formula I and shown below, which contains an polyethylene glycol (PEG$_5$) on the indole N, terminating with —OH, at R10:

One non-limiting example of an activated compound according to general formula I is the NHS-ester of 682 Compound 10 (PEG$_5$), shown below:

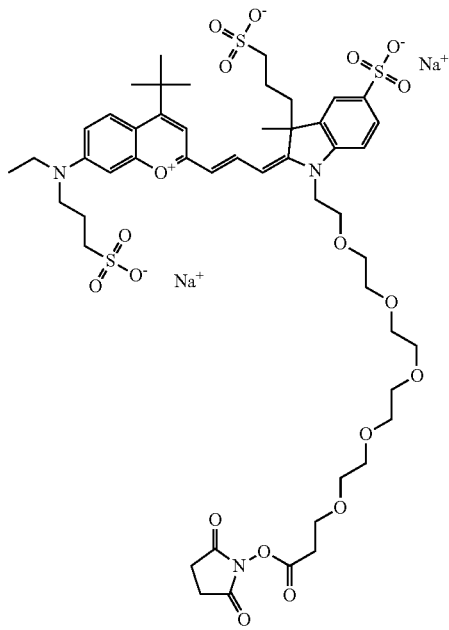

or according to general formula II shown below

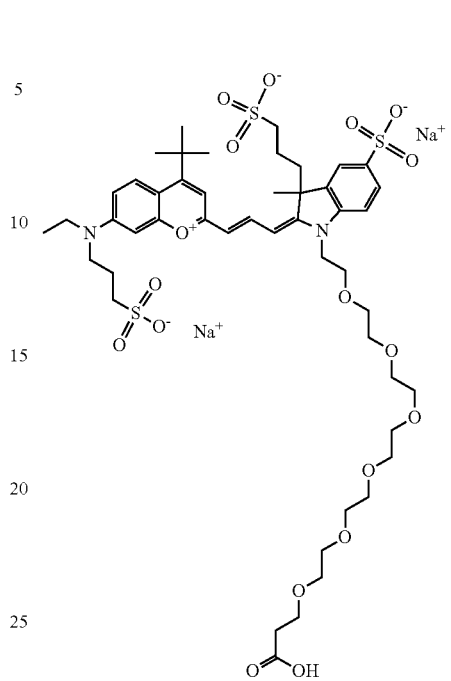

or according to general formula II shown below

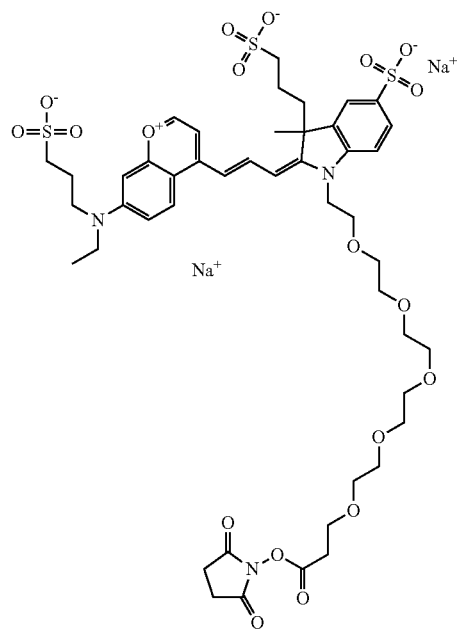

In one embodiment, the compound is 682 Compound 10 ((E)-2-((E)-3-(4-tert-butyl-7-(ethyl(3-sulfonatopropyl) amino)chromenylium-2-yl)allylidene)-1-(20-carboxy-3,6,9, 12,15,18-hexaoxaicosyl)-3-methyl-3-(3-sulfonatopropyl)indoline-5-sulfonate), according to general formula I and shown below, which contains an polyethylene glycol ($PEG_6$) on the indole N, terminating with —COOH, at R10:

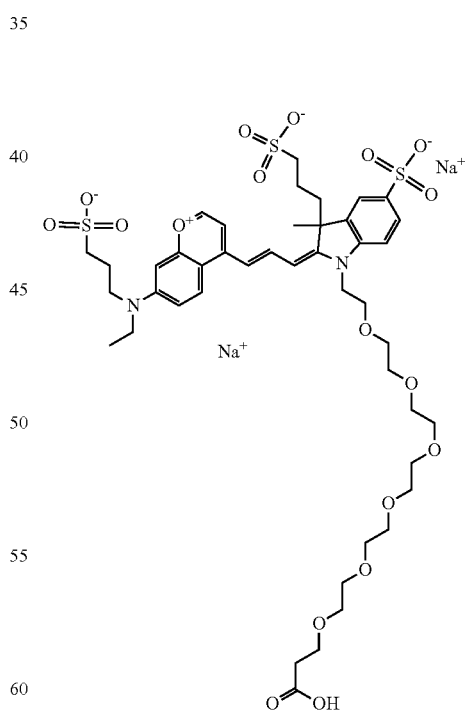

In one embodiment, the compound is 682 Compound 10, according to general formula I and shown below, which contains an polyethylene glycol ($PEG_6$) on the indole N, terminating with —OH, at R10:

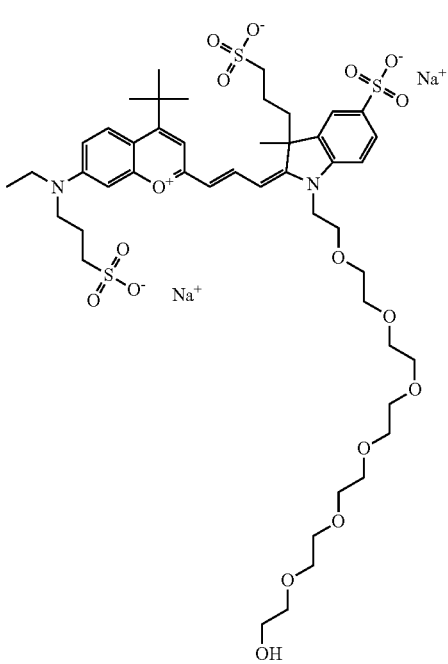

or according to general formula II shown below

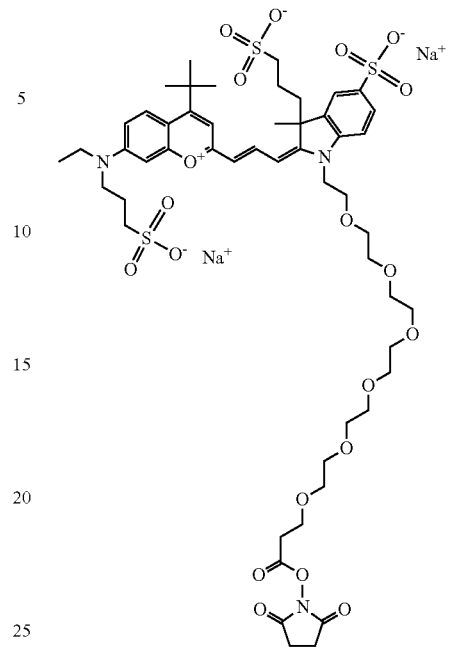

or according to general formula II shown below

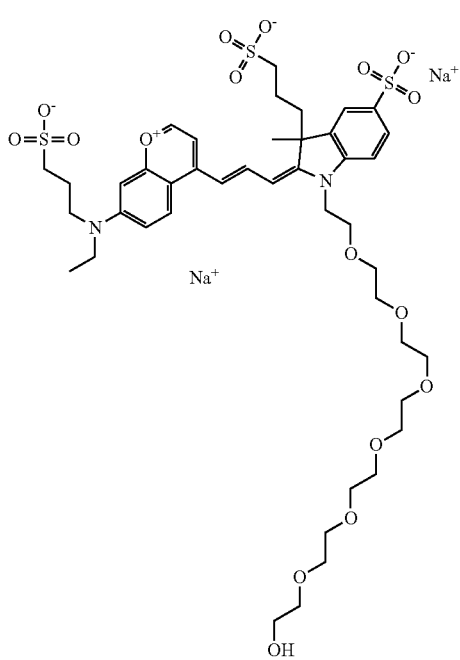

One non-limiting example of an activated compound according to general formula I is the NHS-ester of 682 Compound 10 (PEG$_6$), shown below:

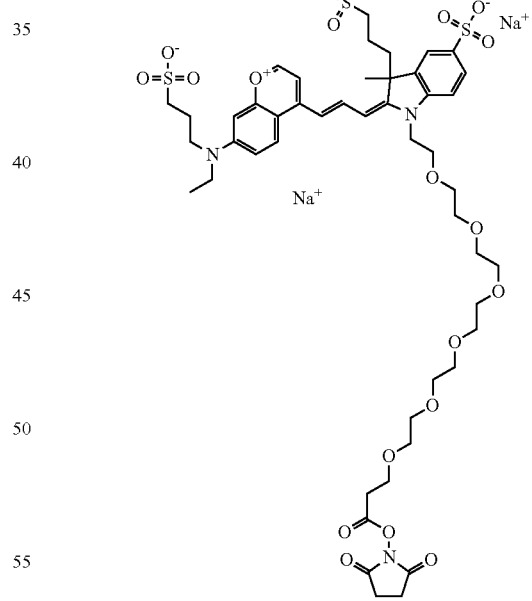

In one embodiment, the compound is 682 Compound 2/10 ((E)-2-((E)-3-(4-tert-butyl-7-((2-methoxyethyl)(3-sulfonatopropyl)amino)chromenylium-2-yl)allylidene)-1-(2-(2-carboxyethoxy)ethyl)-3-methyl-3-(3-sulfonatopropyl)indoline-5-sulfonate), according to general formula I and shown below, which contains an ethylene glycol (PEG$_1$) bound to the benzopyrylium by N, i.e., a methylated ethylene glycol, an ethylene glycol (PEG$_1$) on the indole N, and —COOH at R10:

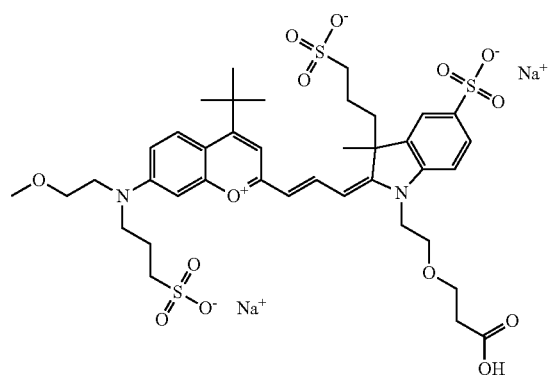

or according to general formula II shown below

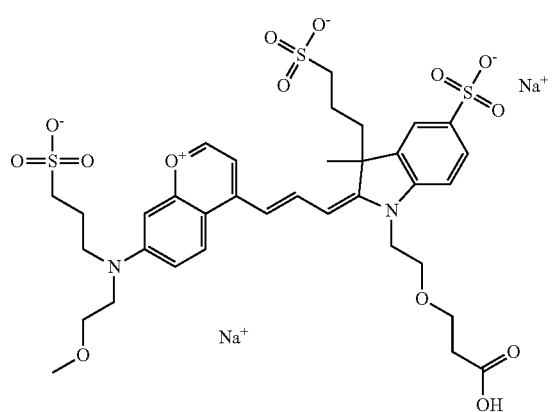

One non-limiting example of an activated compound according to general formula I is the NHS-ester of 682 Compound 2/10 (PEG₁), shown below:

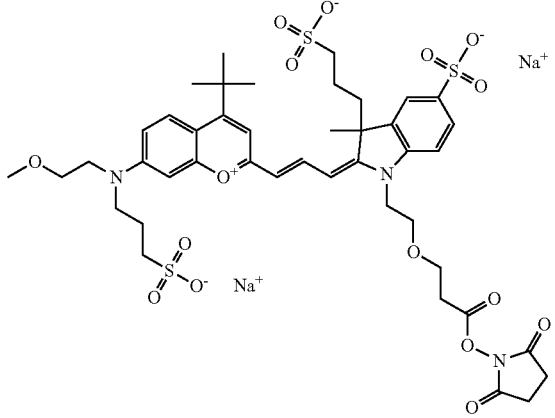

or according to general formula II shown below

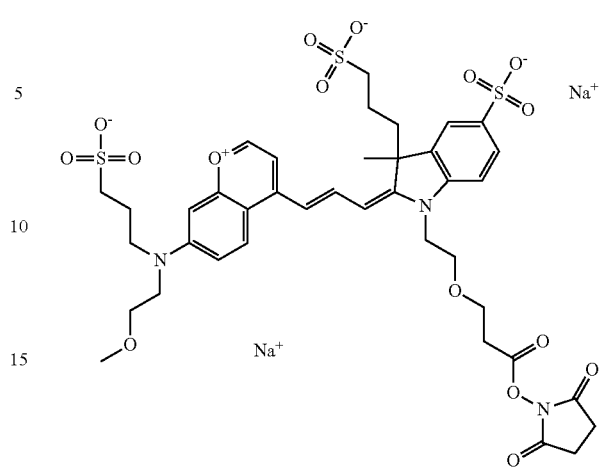

In one embodiment, the compound is 682 Compound 2/10 ((E)-2-((E)-3-(4-tert-butyl-7-((2-(2-methoxyethoxy)ethyl)(3-sulfonatopropyl)amino)chromenylium-2-yl)allylidene)-1-(2-(2-(2-carboxyethoxy)ethoxy)ethyl)-3-methyl-3-(3-sulfonatopropyl)indoline-5-sulfonate), according to general formula I and shown below, which contains a diethylene glycol (PEG₂) bound to the benzopyrylium by N, i.e., a methylated diethylene glycol, a diethylene glycol (PEG₂) on the indole N, and —COOH at R10:

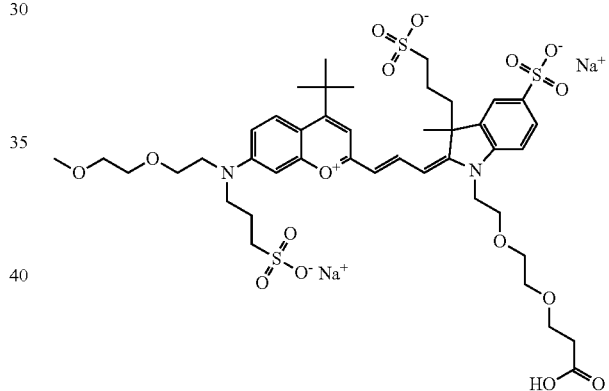

or according to general formula II shown below

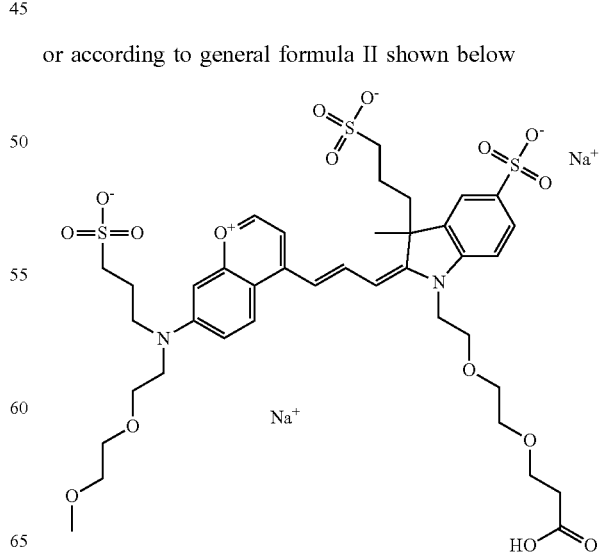

One non-limiting example of an activated compound according to general formula I is the NHS-ester of 682 Compound 2/10 (PEG₂), shown below:

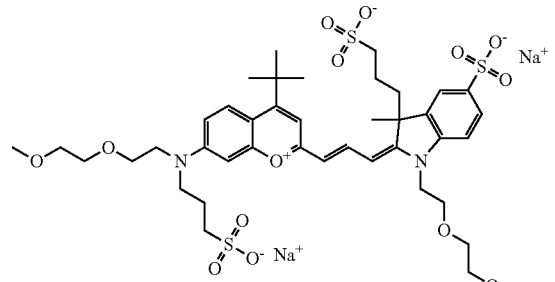

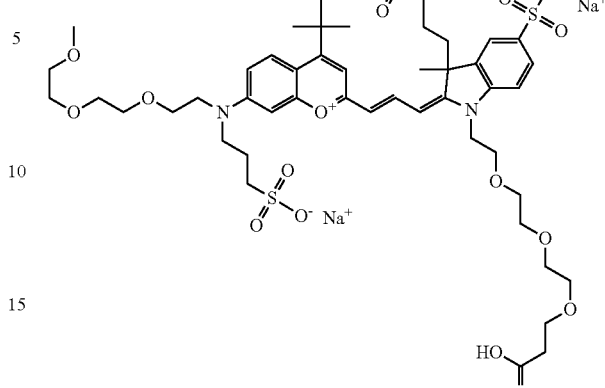

or according to general formula II shown below

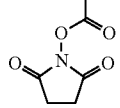

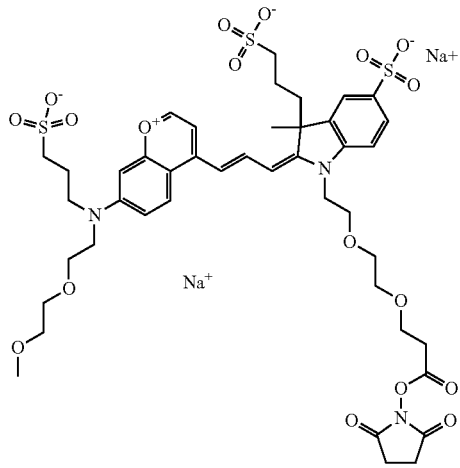

In one embodiment, the compound is 682 Compound 2/10 ((E)-2-((E)-3-(4-tert-butyl-7-((2-(2-(2-methoxyethoxy)ethoxy)ethyl)(3-sulfonatopropyl)amino)chromenylium-2-yl)allylidene)-1-(2-(2-(2-(2-carboxyethoxy)ethoxy)ethoxy)ethyl)-3-methyl-3-(3-sulfonatopropyl)indoline-5-sulfonate), according to general formula I and shown below, which contains a polyethylene glycol (PEG₃) bound to the benzopyrylium by N, i.e., a methylated polyethylene glycol, a polyethylene glycol (PEG₃) on the indole N, and —COOH at R10:

or according to general formula II shown below

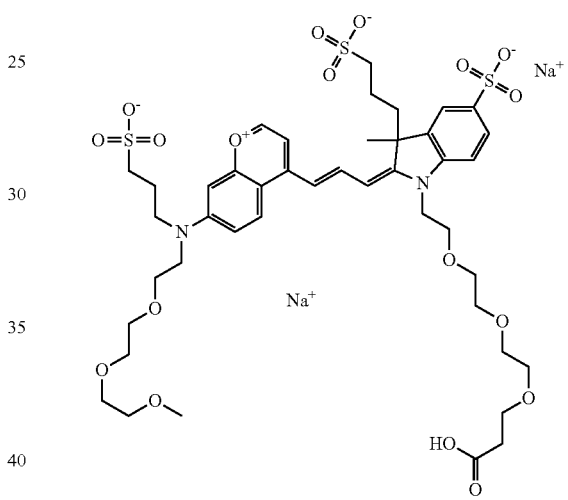

One non-limiting example of an activated compound according to general formula I is the NHS-ester of 682 Compound 2/10 (PEG₃), shown below:

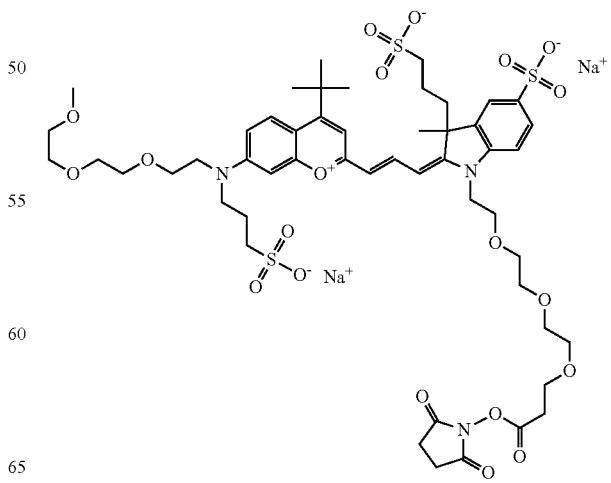

or according to general formula II shown below or according to general formula II shown below

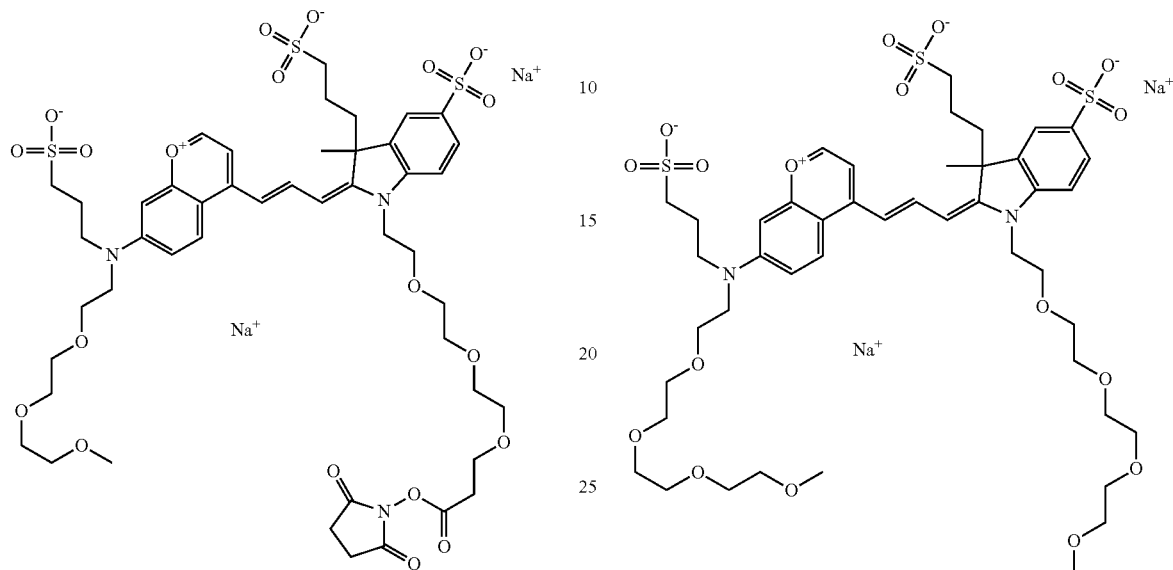

In one embodiment, the compound is 682 Compound 2/10 (V13-06190) ((E)-2-((E)-3-(4-tert-butyl-7-((3-sulfonatopropyl)(2,5,8,11-tetraoxatridecan-13-yl)amino)chromenylium-2-yl)allylidene)-1-(14-carboxy-3,6,9,12-tetraoxatetradecyl)-3-methyl-3-(3-sulfonatopropyl)indoline-5-sulfonate), according to general formula I and shown below, which contains a polyethylene glycol (PEG$_4$) bound to the benzopyrylium by N, i.e., a methylated polyethylene glycol, a polyethylene glycol (PEG$_4$) on the indole N, and —COOH at R10:

One non-limiting example of an activated compound according to general formula I is the NHS-ester of 682 Compound 2/10 (PEG$_4$), shown below:

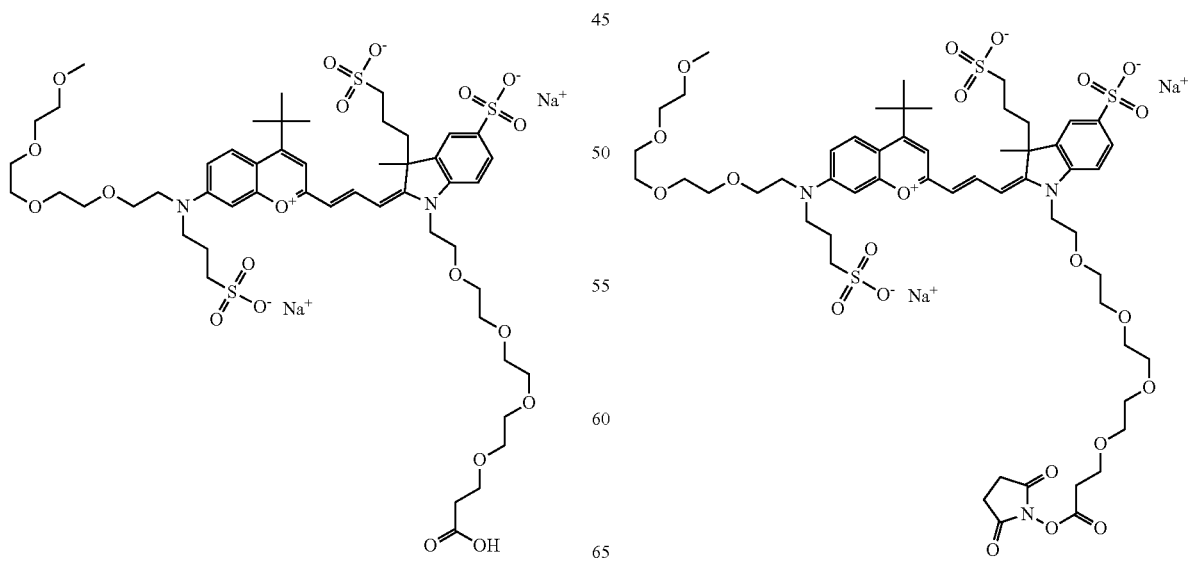

or according to general formula II shown below

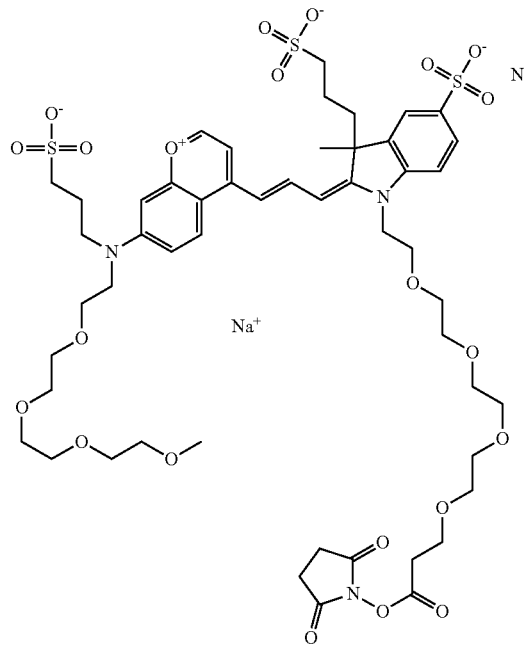

In one embodiment, the compound is 682 Compound 2/10 ((E)-2-((E)-3-(7-(2,5,8,11,14-pentaoxahexadecan-16-yl(3-sulfonatopropyl)amino)-4-tert-butylchromenylium-2-yl)allylidene)-1-(17-carboxy-3,6,9,12,15-pentaoxaheptadecyl)-3-methyl-3-(3-sulfonatopropyl)indoline-5-sulfonate), according to general formula I and shown below, which contains a polyethylene glycol (PEG$_5$) bound to the benzopyrylium by N, i.e., a methylated polyethylene glycol, a polyethylene glycol (PEG$_5$) on the indole N, and —COOH at R10:

or according to general formula II shown below

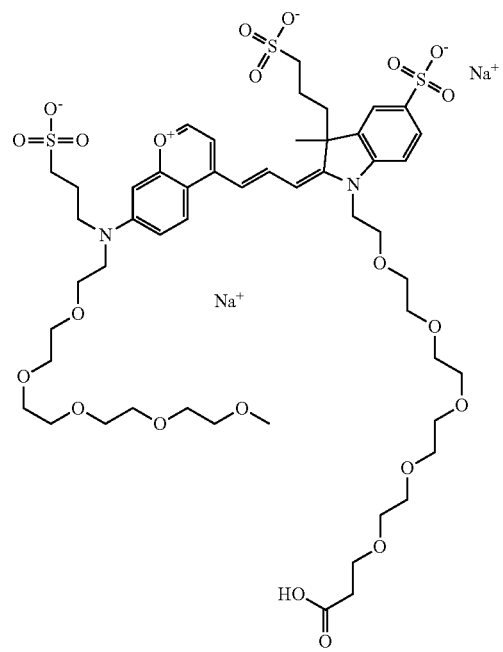

One non-limiting example of an activated compound according to general formula I is the NHS-ester of 682 Compound 2/10 (PEG$_5$), shown below:

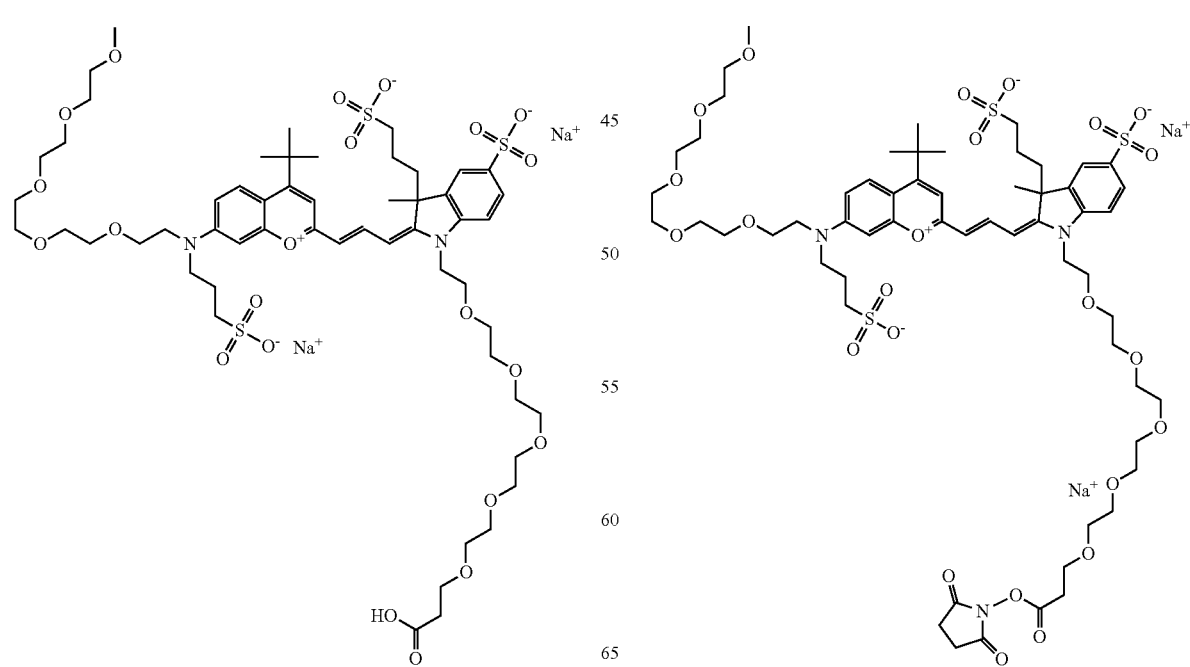

or according to general formula II shown below or according to general formula II shown below

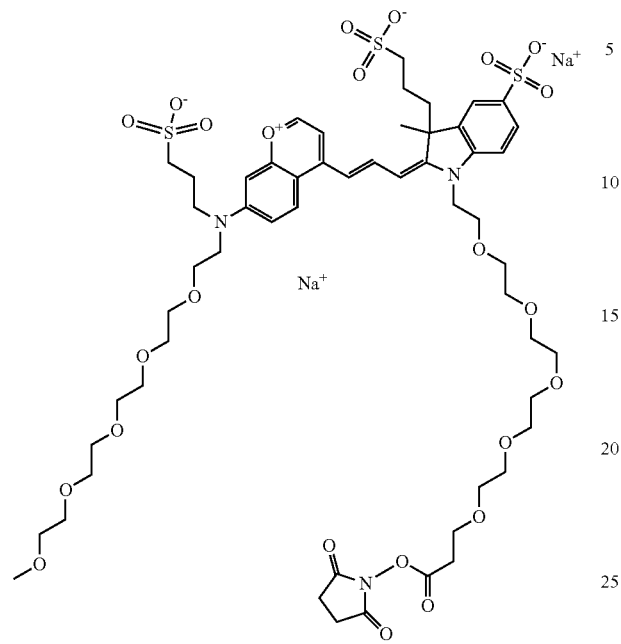

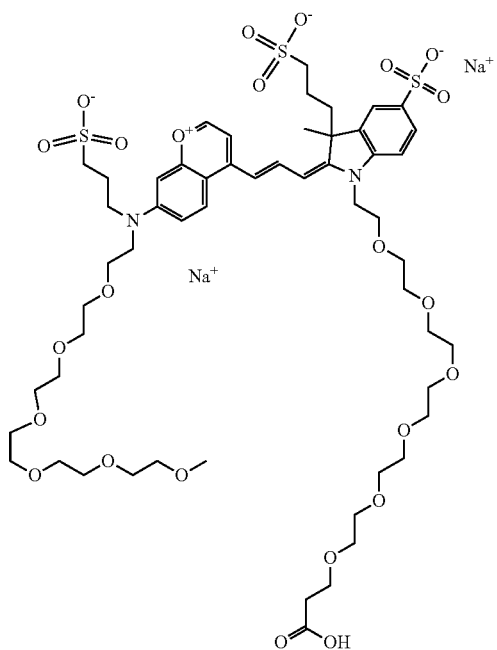

In one embodiment, the compound is 682 Compound 2/10 ((E)-2-((E)-3-(7-(2,5,8,11,14,17-hexaoxanonadecan-19-yl (3-sulfonatopropyl)amino)-4-tert-butylchromenylium-2-yl) allylidene)-1-(20-carboxy-3,6,9,12,15,18-hexaoxaicosyl)-3-methyl-3-(3-sulfonatopropyl)indoline-5-sulfonate), according to general formula I and shown below, which contains a polyethylene glycol (PEG$_6$) bound to the benzopyrylium by N, i.e., a methylated polyethylene glycol, and a polyethylene glycol (PEG$_6$) on the indole N, and —COOH at R10:

One non-limiting example of an activated compound according to general formula I is the NHS-ester of 682 Compound 2/10 (PEG$_6$), shown below:

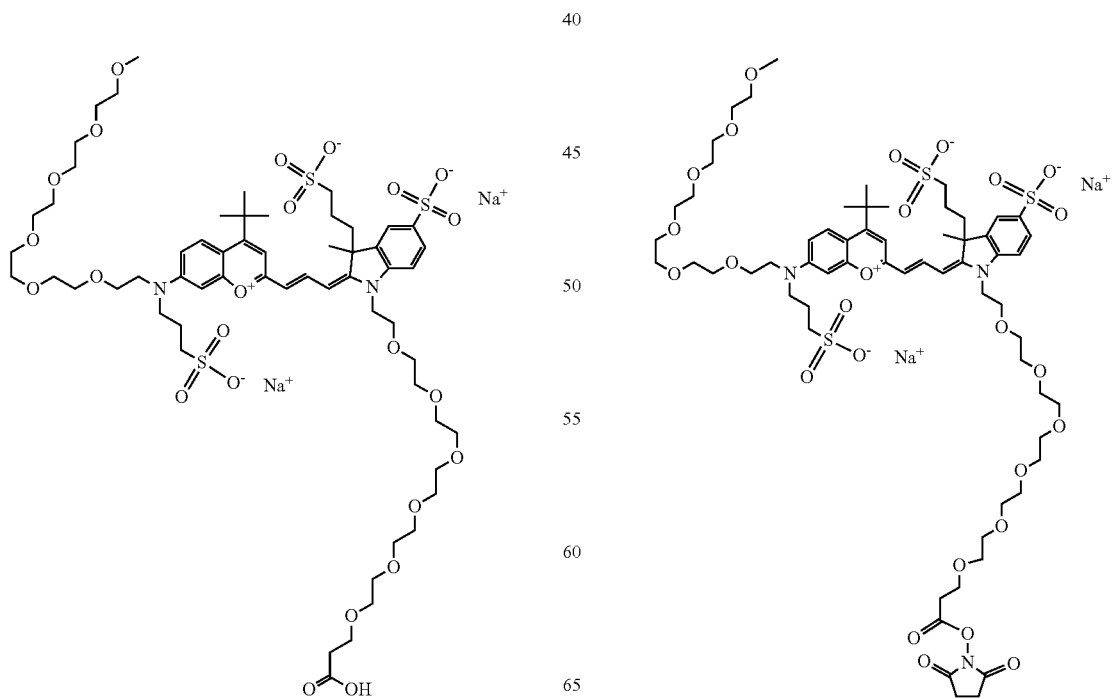

61 or according to general formula II shown below

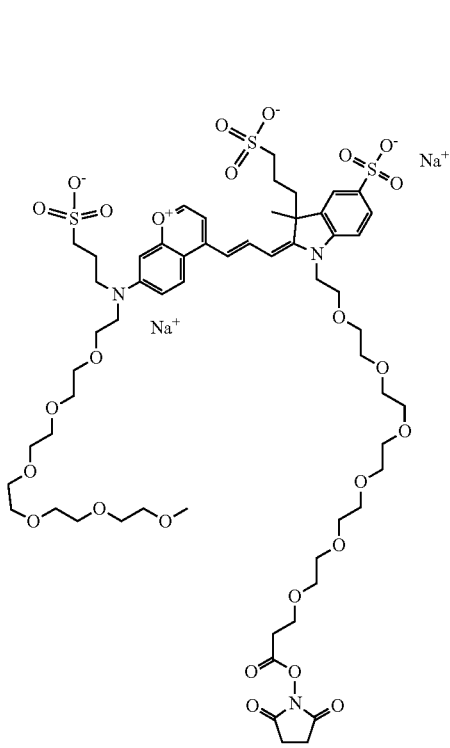

In one embodiment, the compound is 682 Compound 2/3 ((E)-2-((7-(bis(2-methoxyethyl)amino)-4-tert-butylchromenylium-2-yl)methylene)-3-(3-carboxypropyl)-3-methyl-1-(3-sulfonatopropyl)indoline-5-sulfonate) according to general formula I, shown below, which contains two ethylene glycols (PEG$_1$) bound to the benzopyrylium by N, i.e., a methylated ethylene glycol, and —COOH at R13. The methyl group on the ethylene glycol/PEG prevents the terminal —OH from oxidation, with a monomethine linker connecting the benzopyrylium with the indole group. Oxidation is known to occur, over time, on an unprotected PEG terminus. Adding a methyl ether provides this protection, and prevents reaction with electrophilic reactive groups:

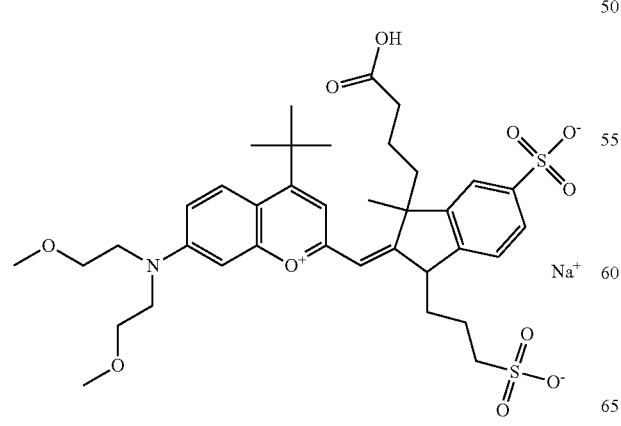

or according to general formula II shown below

62 or according to general formula II shown below

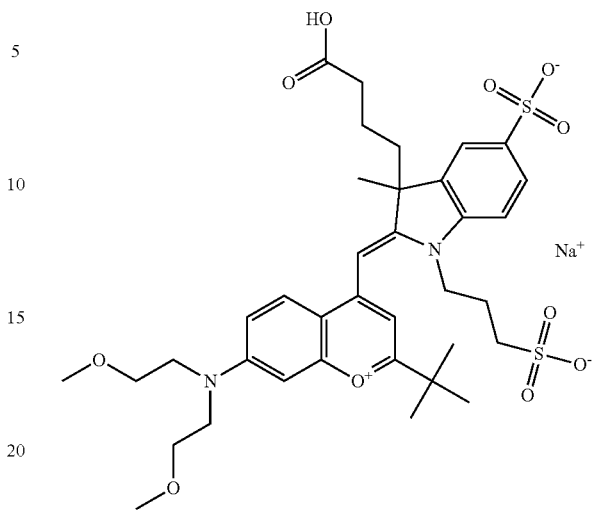

In one embodiment, the compound is 682 Compound 2/3 ((E)-2-((E)-3-(7-(bis(2-methoxyethyl)amino)-4-tert-butylchromenylium-2-yl)allylidene)-3-(3-carboxypropyl)-3-methyl-1-(3-sulfonatopropyl)indoline-5-sulfonate) according to general formula I, shown below, which contains two ethylene glycols (PEG$_1$) bound to the benzopyrylium by N, i.e., a methylated ethylene glycol, —COOH at R13, and with a trimethine linker connecting the benzopyrylium with the indole group:

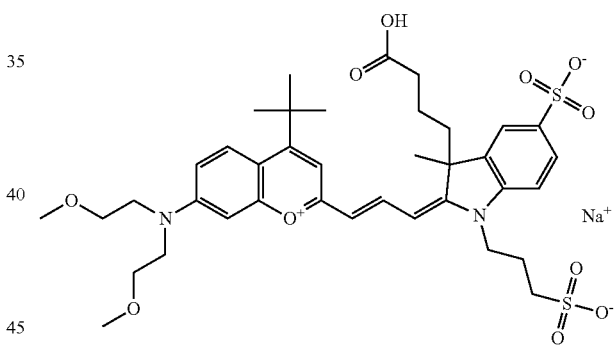

or according to general formula II shown below

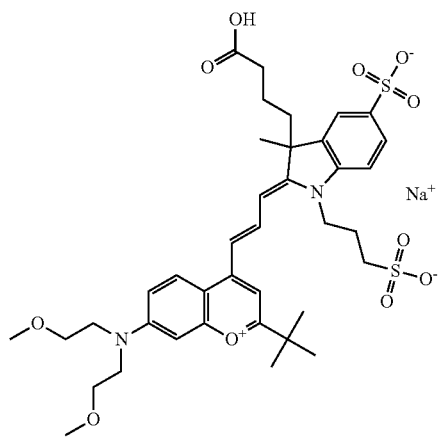

In one embodiment, the compound is 682 Compound 2/3 ((E)-2-((2E,4E)-5-(7-(bis(2-methoxyethyl)amino)-4-tert-butylchromenylium-2-yl)penta-2,4-dienylidene)-3-(3-carboxypropyl)-3-methyl-1-(3-sulfonatopropyl)indoline-5-sulfonate) according to general formula I, shown below, which contains two ethylene glycols (PEG$_1$) bound to the benzopyrylium by N, i.e., a methylated ethylene glycol, and —COOH at R13:

In one embodiment, the compound is 682 Compound 2/3 ((E)-2-((2E,4E,6E)-7-(7-(bis(2-methoxyethyl)amino)-4-tert-butylchromenylium-2-yl)hepta-2,4,6-trienylidene)-3-(3-carboxypropyl)-3-methyl-1-(3-sulfonatopropyl)indoline-5-sulfonate) according to general formula I, shown below, which contains two ethylene glycols (PEG$_1$) bound to the benzopyrylium by N, i.e., a methylated ethylene glycol, and —COOH at R13:

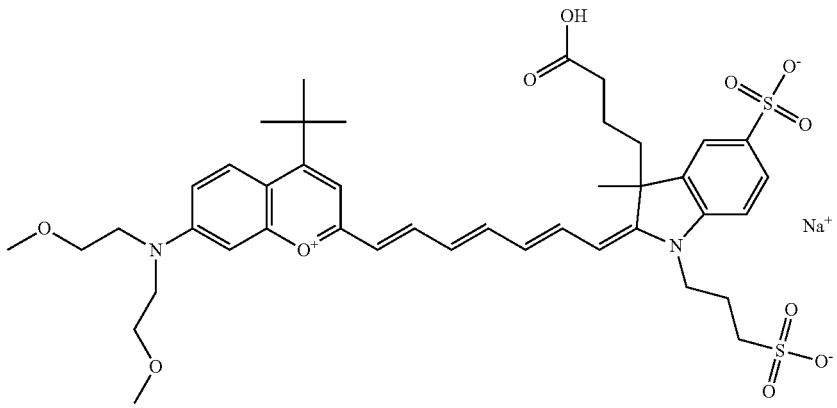

or according to general formula II shown below

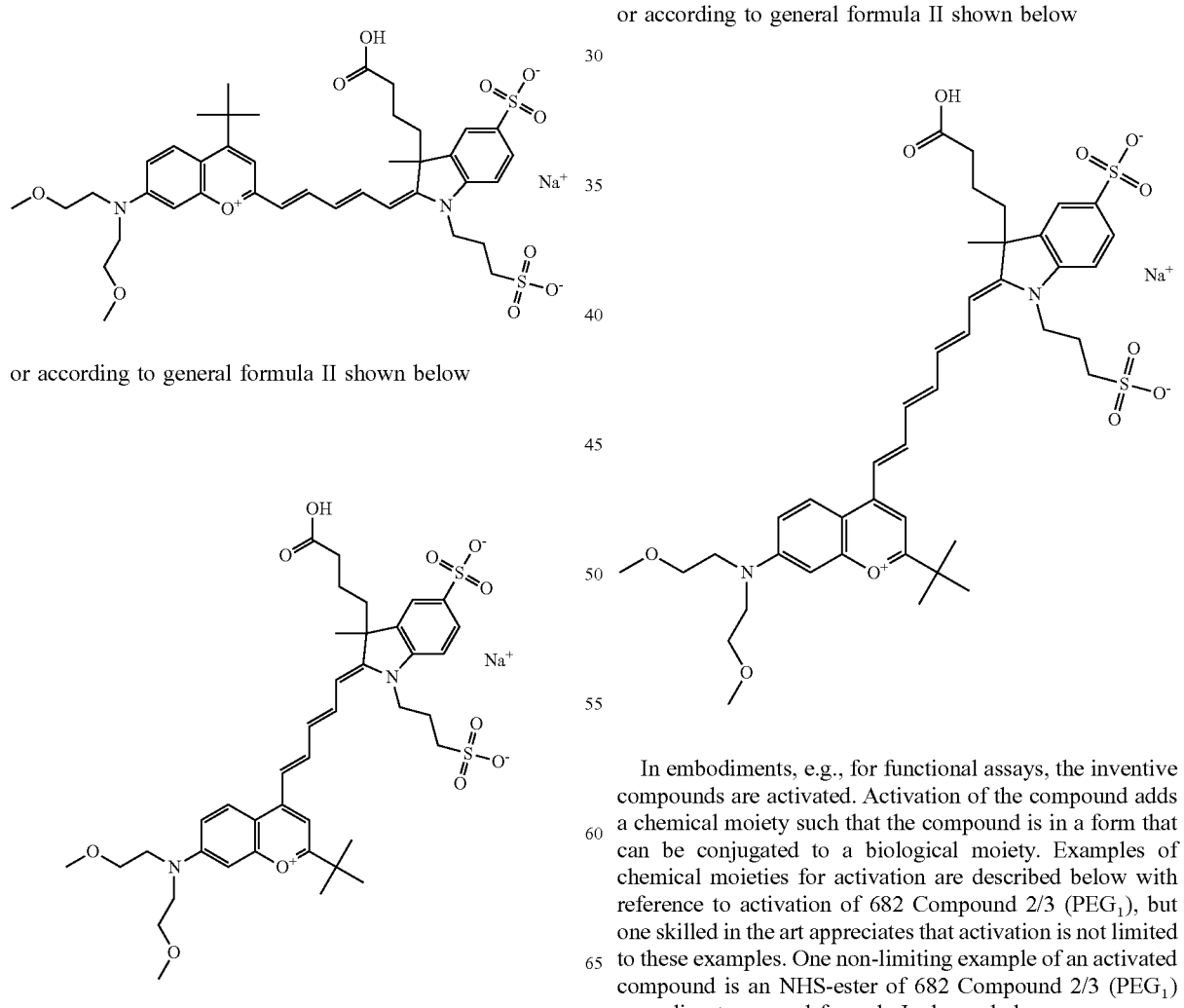

or according to general formula II shown below

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 682 Compound 2/3 (PEG$_1$), but one skilled in the art appreciates that activation is not limited to these examples. One non-limiting example of an activated compound is an NHS-ester of 682 Compound 2/3 (PEG$_1$) according to general formula I, shown below:

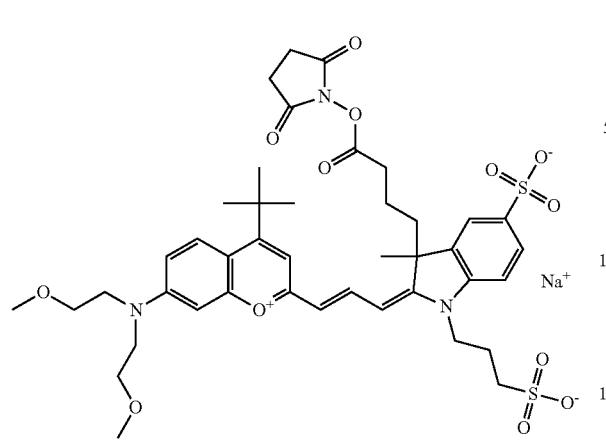

or according to general formula II shown below:

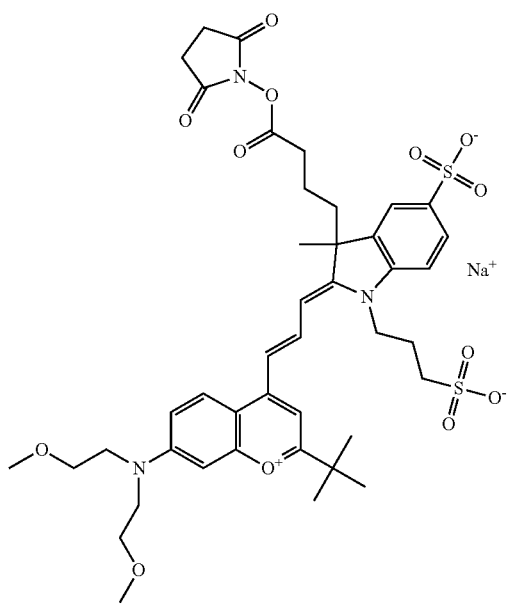

One non-limiting example of an activated 682 Compound 2/3 (PEG$_1$) is a tetrafluorophenyl (TFP)-ester form of 682 Compound 2/3, shown below:

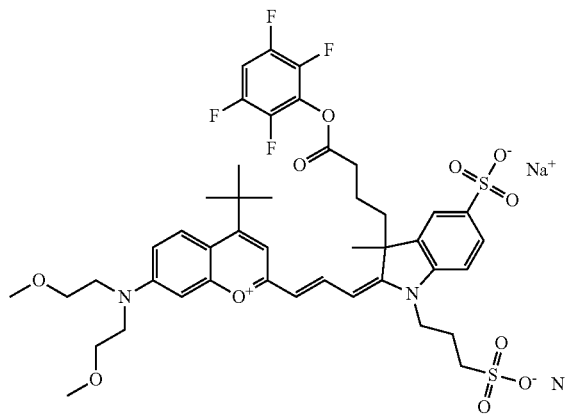

One non-limiting example of an activated 682 Compound 2/3 (PEG$_1$) is a sulfotetrafluorophenyl (STP)-ester form of 682 Compound 2/3, shown below

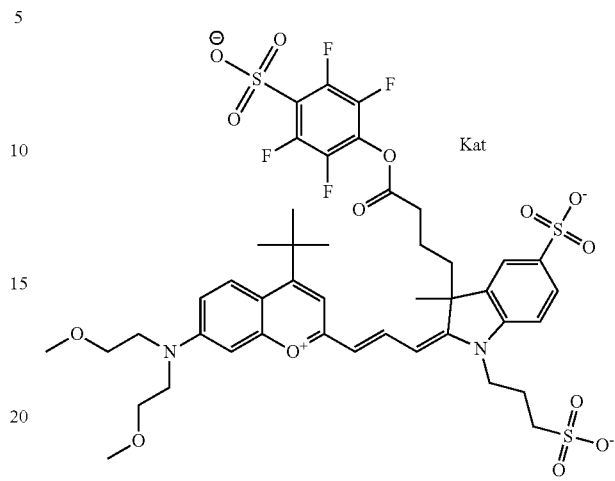

One non-limiting example of an activated 682 Compound 2/3 (PEG$_1$) is a hydrazide form of 682 Compound 2/3, shown below

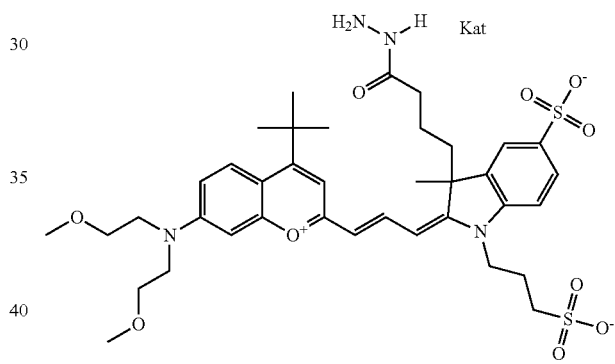

One non-limiting example of an activated 682 Compound 2/3 (PEG$_1$) is a maleimide form of 682 Compound 2/3, shown below

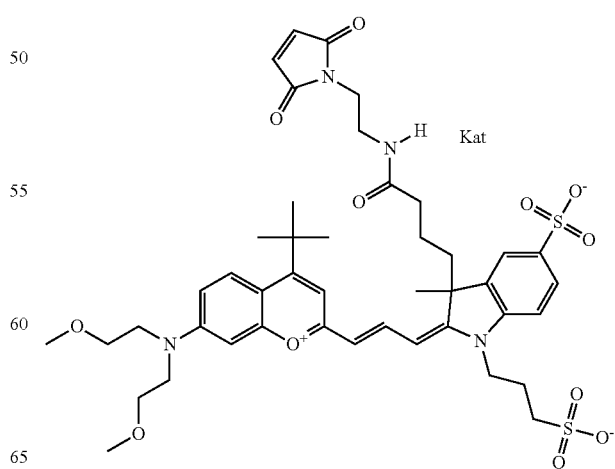

One non-limiting example of an activated compound is an NHS-ester of 682 Compound 2/3 (PEG$_1$), shown below

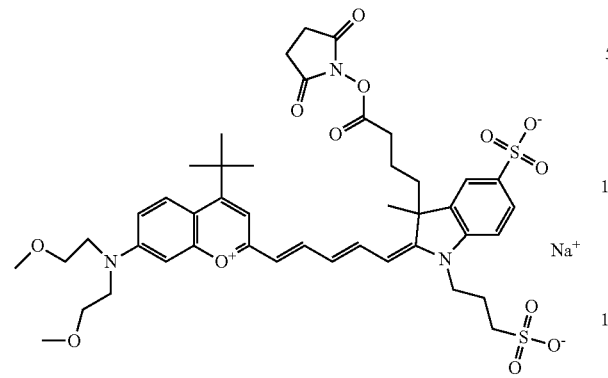

One non-limiting example of an activated compound is an NHS-ester of 682 Compound 2/3 (PEG$_1$), shown below

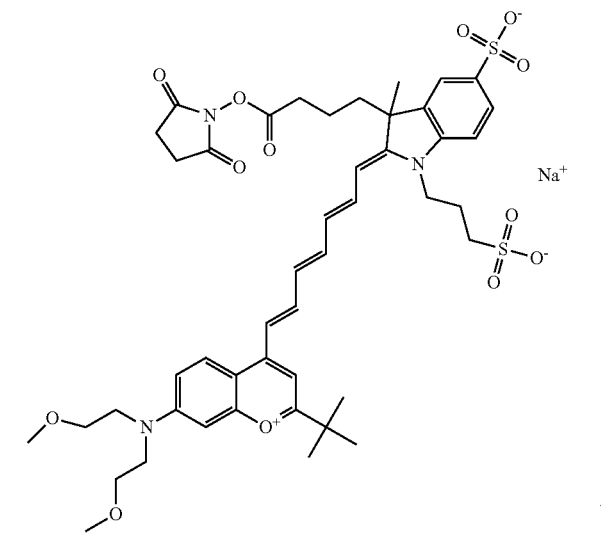

In one embodiment, the compound is 682 Compound 2/3 ((E)-2-((E)-3-(7-(bis(2-(2-methoxyethoxy)ethyl)amino)-4-tert-butylchromenylium-2-yl)allylidene)-3-(3-carboxypropyl)-3-methyl-1-(3-sulfonatopropyl)indoline-5-sulfonate) according to general formula I, shown below, which contains two diethylene glycols (PEG$_2$) bound to the benzopyrylium by N, positions R2 and R3, i.e., a methylated diethylene glycol, and —COOH at R13:

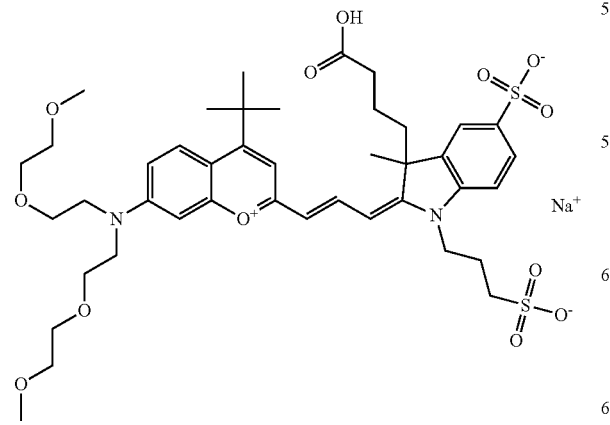

or according to general formula II shown below

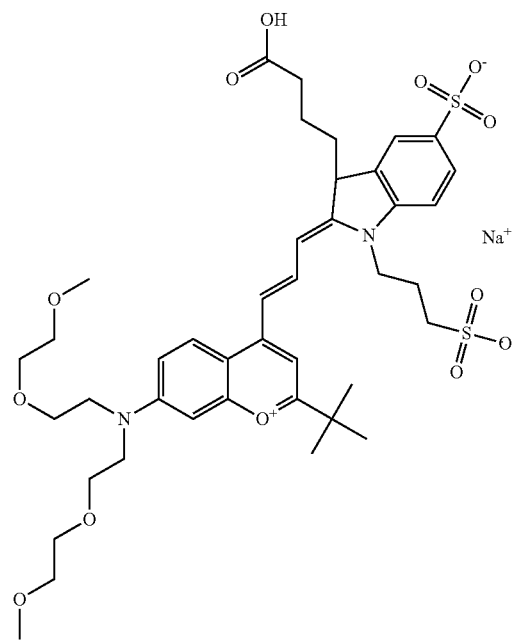

One non-limiting example of an activated compound is the NHS-ester of 682 Compound 2/3 (PEG$_2$) according to general formula I, shown below:

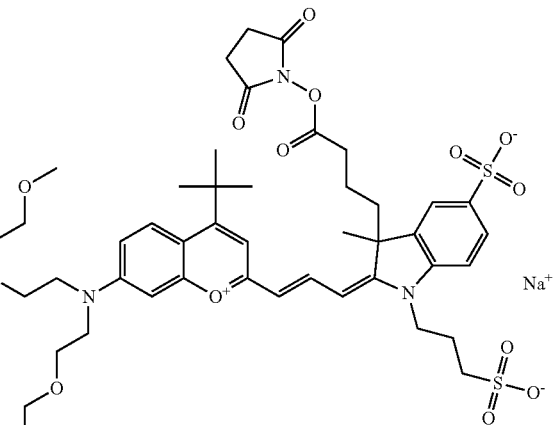

or according to general formula II shown below or according to general formula II shown below

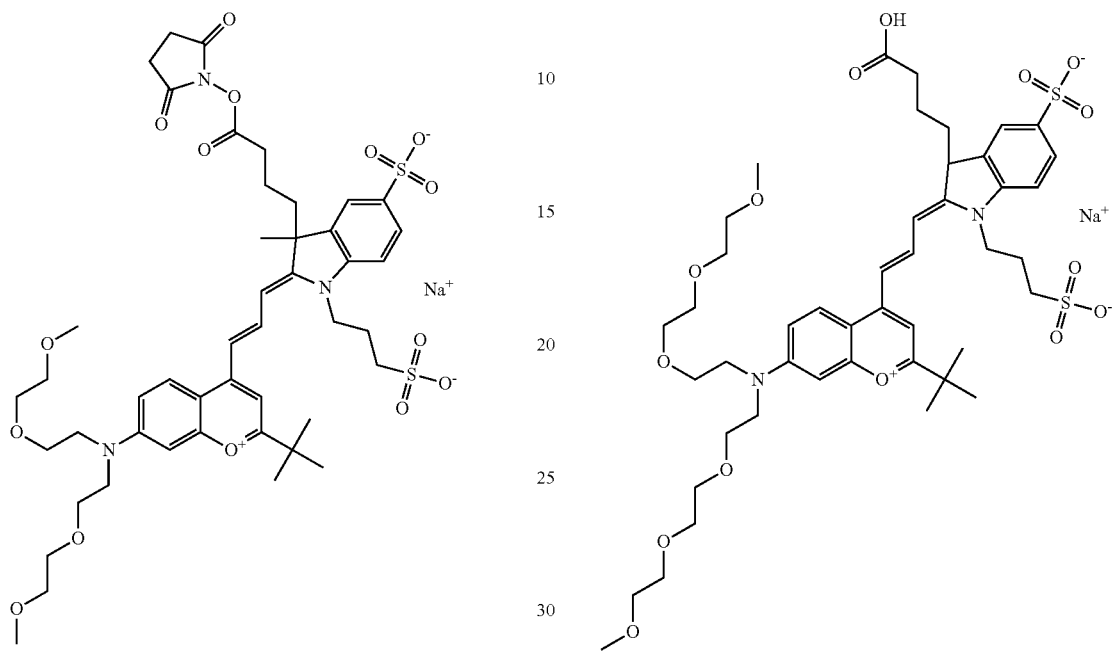

In one embodiment, the compound is 682 Compound 2/3 ((E)-2-((E)-3-(7-(bis(2-(2-(2-methoxyethoxy)ethoxy)ethyl)amino)-4-tert-butylchromenylium-2-yl)allylidene)-3-(3-carboxypropyl)-3-methyl-1-(3-sulfonatopropyl)indoline-5-sulfonate) according to general formula I, shown below, which contains two polyethylene glycols (PEG$_3$) bound to the benzopyrylium by N, positions R2 and R3, i.e., a methylated polyethylene glycol, and —COOH at R13:

One non-limiting example of an activated compound is the NHS-ester of 682 Compound 2/3 (PEG$_3$) according to general formula I, shown below:

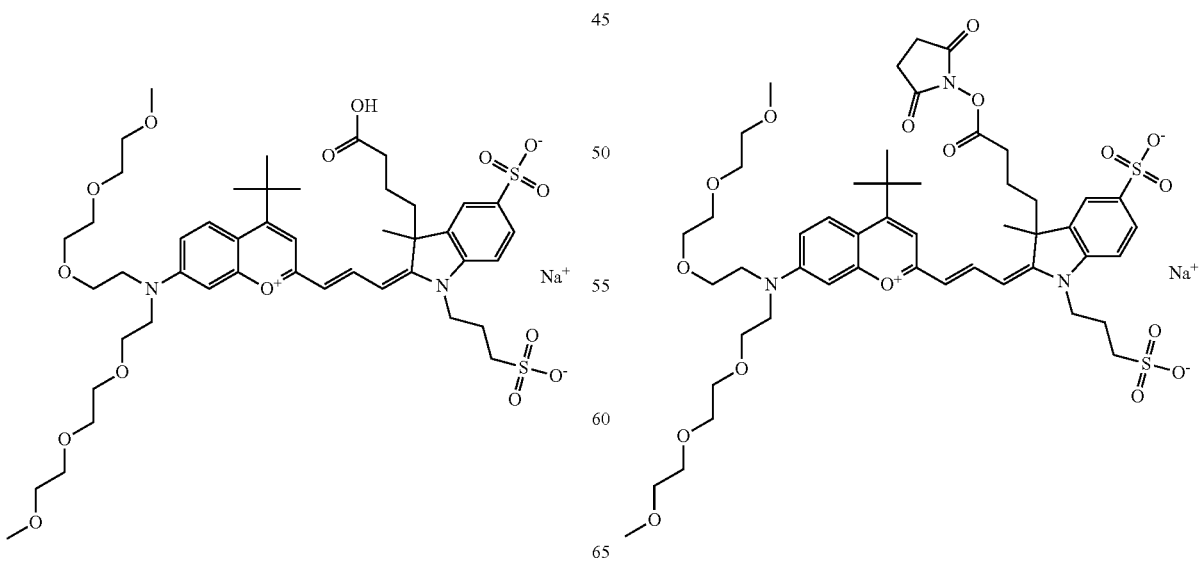

or according to general formula II shown below or according to general formula II shown below

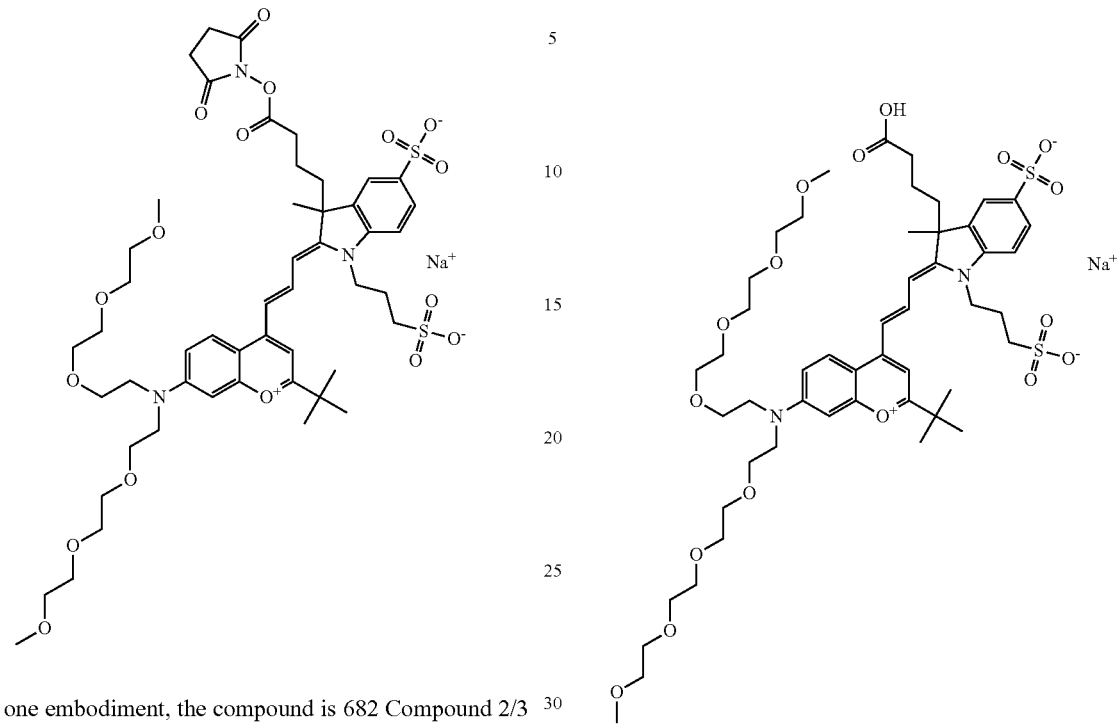

In one embodiment, the compound is 682 Compound 2/3 (V03-07005) ((E)-2-((E)-3-(4-tert-butyl-7-(di2,5,8,11-tetraoxatridecan-13-ylamino)chromenylium-2-yl)allylidene)-3-(3-carboxypropyl)-3-methyl-1-(3-sulfonatopropyl)indoline-5-sulfonate) according to general formula I, shown below, which contains two polyethylene glycols (PEG$_4$) bound to the benzopyrylium by N, positions R2 and R3, i.e., a methylated polyethylene glycol, and —COOH at R13:

One non-limiting example of an activated compound is the NHS-ester of 682 Compound 2/3 (PEG$_4$) according to general formula I, shown below:

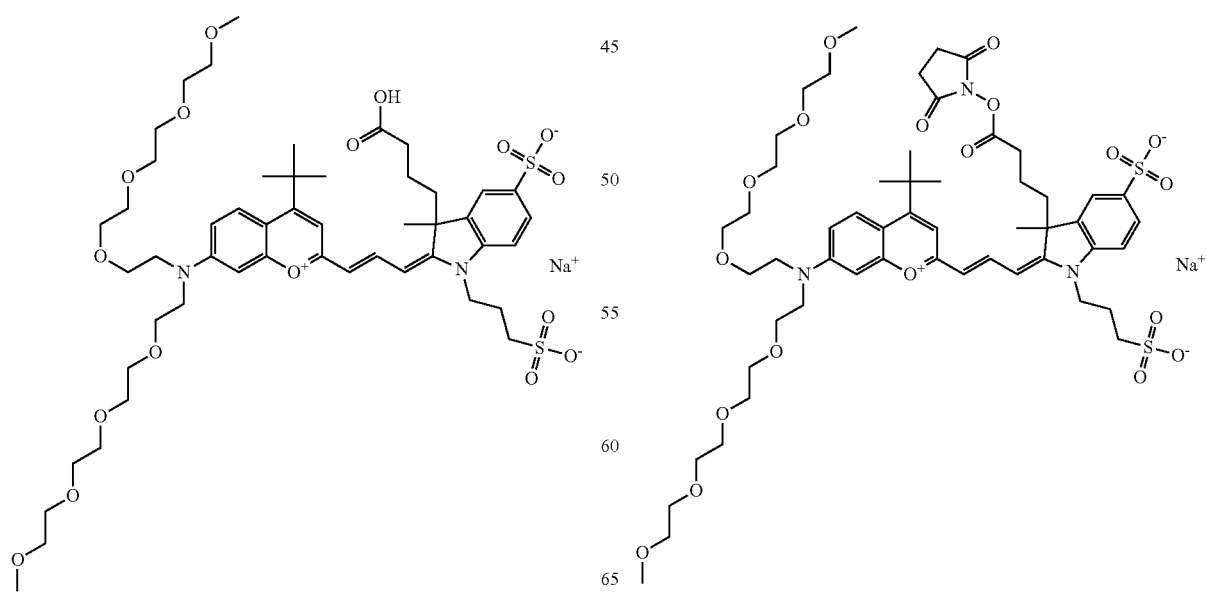

or according to general formula II shown below or according to general formula II shown below

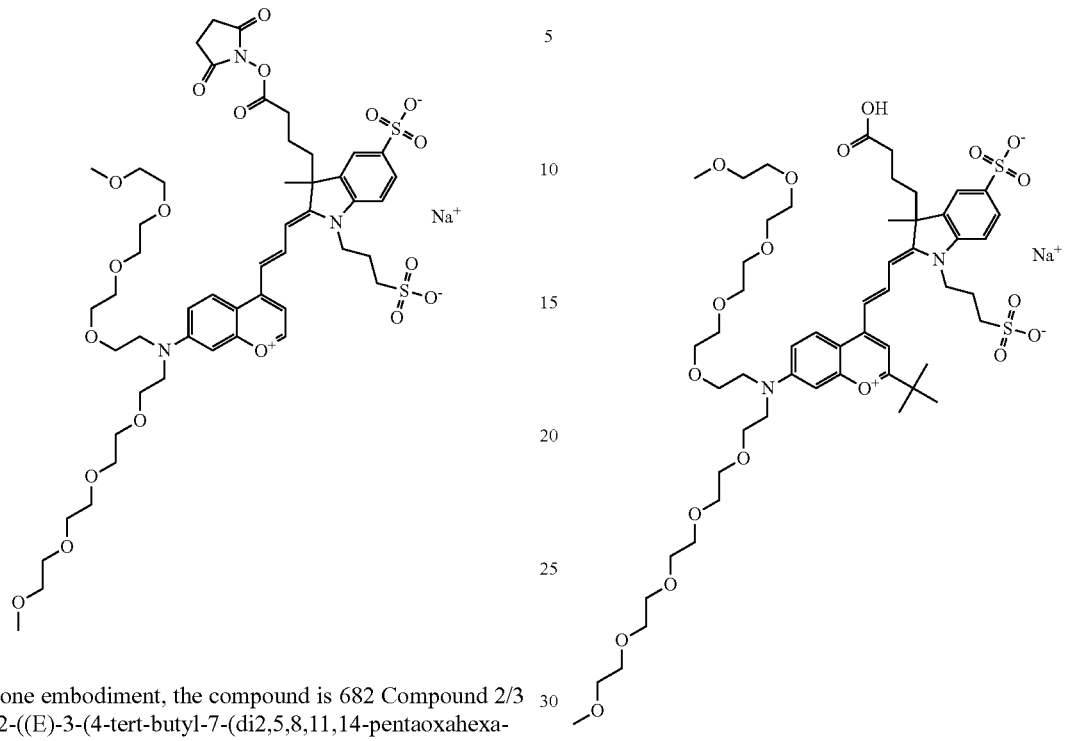

In one embodiment, the compound is 682 Compound 2/3 ((E)-2-((E)-3-(4-tert-butyl-7-(di2,5,8,11,14-pentaoxahexadecan-16-ylamino)chromenylium-2-yl)allylidene)-3-(3-carboxypropyl)-3-methyl-1-(3-sulfonatopropyl)indoline-5-sulfonate) according to general formula I, shown below, which contains two polyethylene glycols (PEG$_5$) bound to the benzopyrylium by N, positions R2 and R3, i.e., a methylated polyethylene glycol, and —COOH at R13:

One non-limiting example of an activated compound is the NHS-ester of 682 Compound 2/3 (PEG$_5$) according to general formula I, shown below:

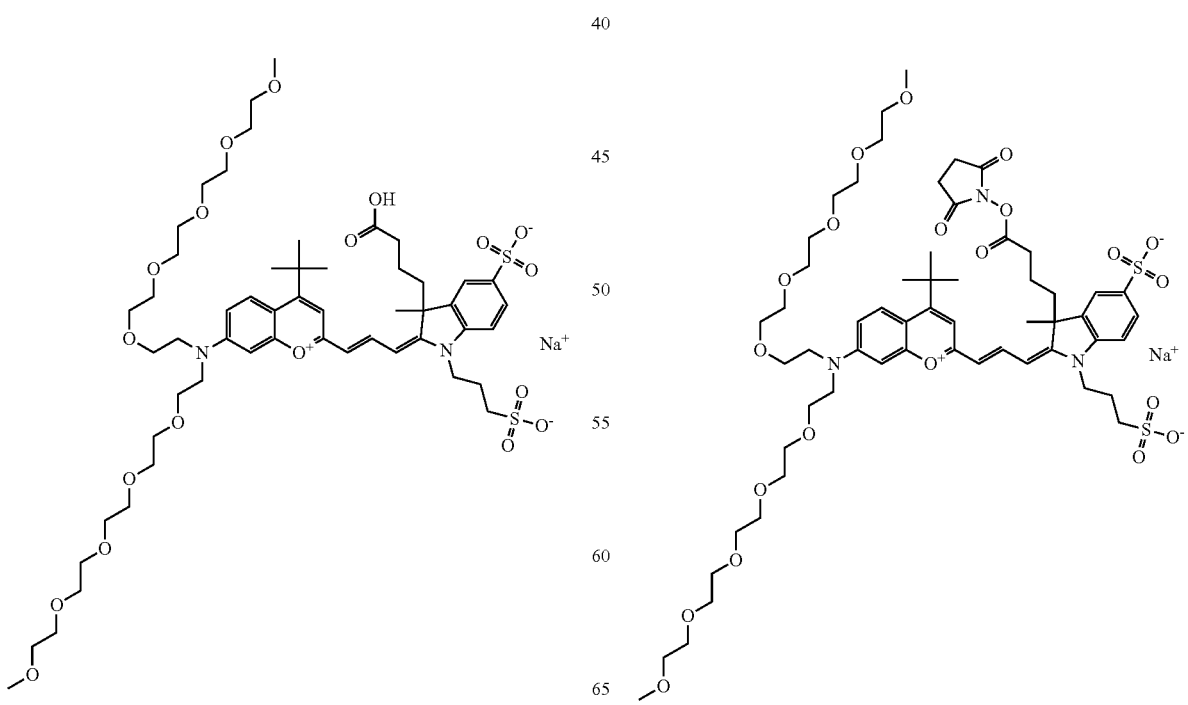

or according to general formula II shown below

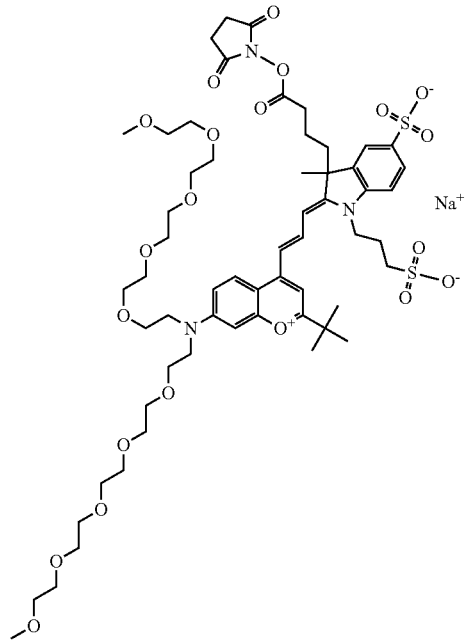

In one embodiment, the compound is 682 Compound 2/3 ((E)-2-((E)-3-(4-tert-butyl-7-(di2,5,8,11,14,17-hexaoxanonadecan-19-ylamino)chromenylium-2-yl)allylidene)-3-(3-carboxypropyl)-3-methyl-1-(3-sulfonatopropyl)indoline-5-sulfonate) according to general formula I, shown below, which contains two polyethylene glycols (PEG$_6$) bound to the benzopyrylium by N, positions R2 and R3, i.e., a methylated polyethylene glycol, and —COOH at R13:

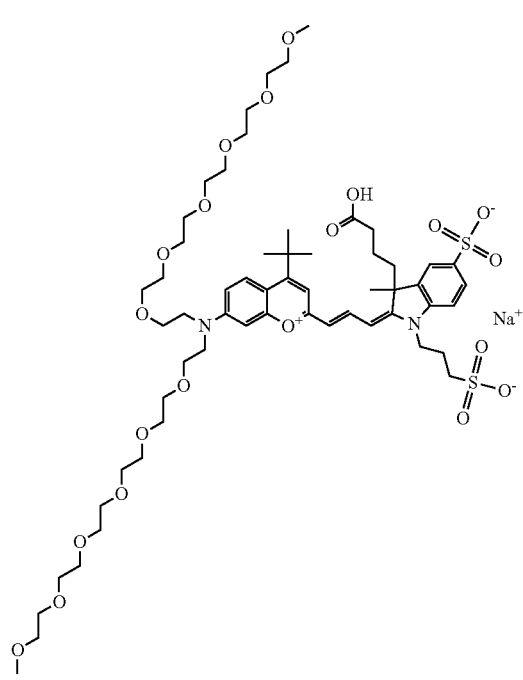

or according to general formula II shown below

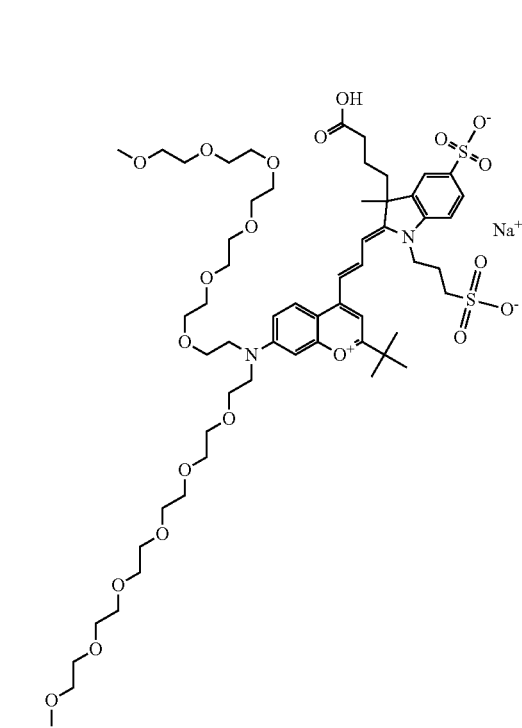

One non-limiting example of an activated compound is the NHS-ester of 682 Compound 2/3 (PEG$_6$) according to general formula I, shown below:

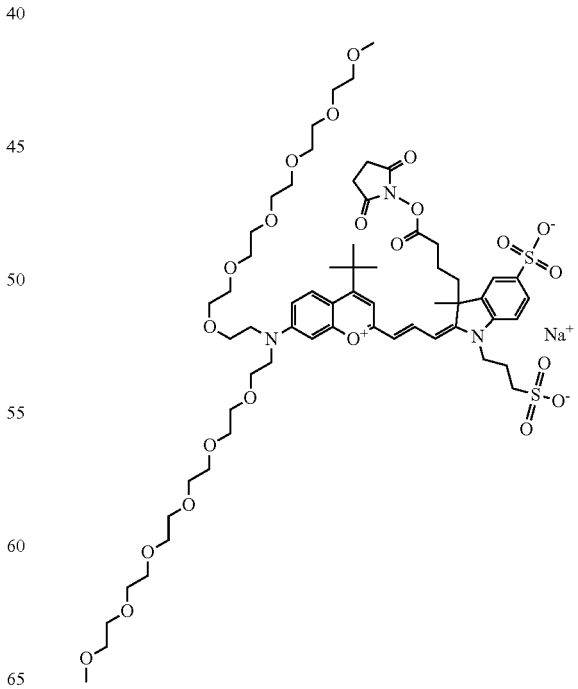

or according to general formula II shown below

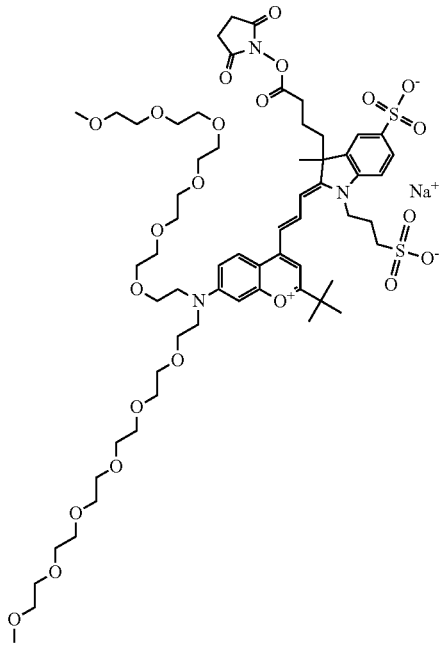

In one embodiment, the compound is 682 Compound 2/3 ((E)-2-((E)-3-(7-(bis(2-methoxyethyl)amino)-4-tert-butyl-chromenylium-2-yl)allylidene)-1-(5-carboxypentyl)-3-methyl-3-(3-sulfonatopropyl)indoline-5-sulfonate), according to general formula I and shown below, which contains two ethylene glycols (PEG$_1$) bound to the benzopyrylium by N, positions R2 and R3, i.e., a methylated ethylene glycol, and —COOH at R10:

or according to general formula II shown below

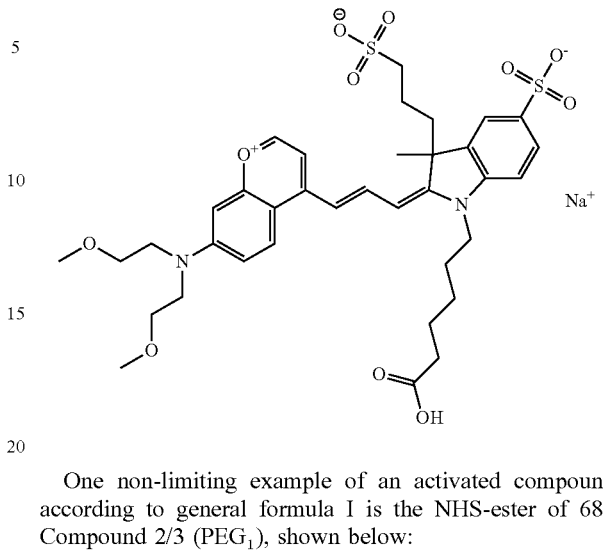

One non-limiting example of an activated compound according to general formula I is the NHS-ester of 682 Compound 2/3 (PEG$_1$), shown below:

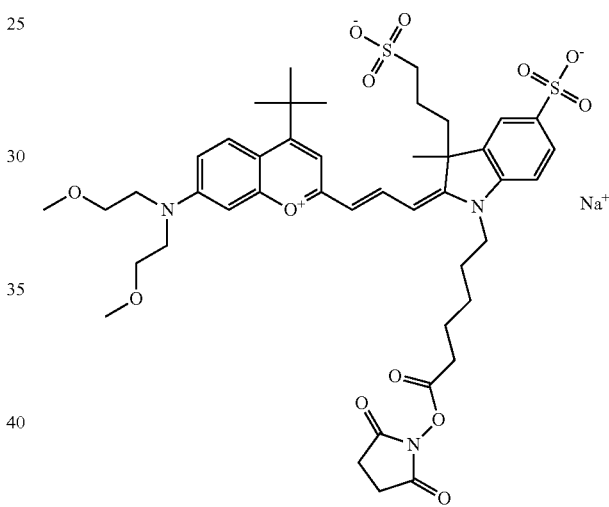

or according to general formula II shown below

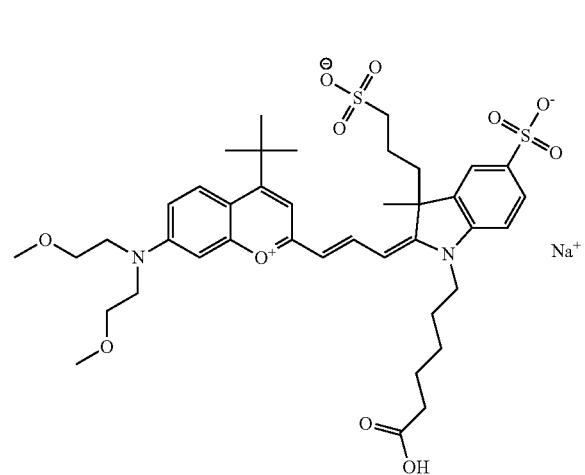

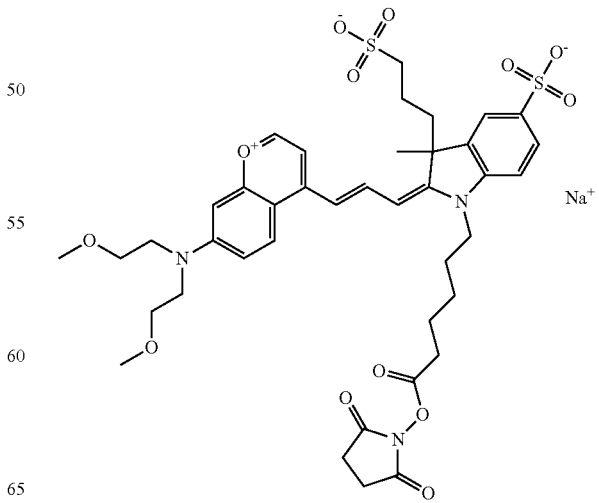

In one embodiment, the compound is 682 Compound 2/3 ((E)-2-((E)-3-(7-(bis(2-(2-methoxyethoxy)ethyl)amino)-4-tert-butylchromenylium-2-yl)allylidene)-1-(5-carboxypentyl)-3-methyl-3-(3-sulfonatopropyl)indoline-5-sulfonate), according to general formula I and shown below, which contains two diethylene glycols (PEG$_2$) bound to the benzopyrylium by N, positions R2 and R3, i.e., a methylated diethylene glycol, and —COOH at R10:

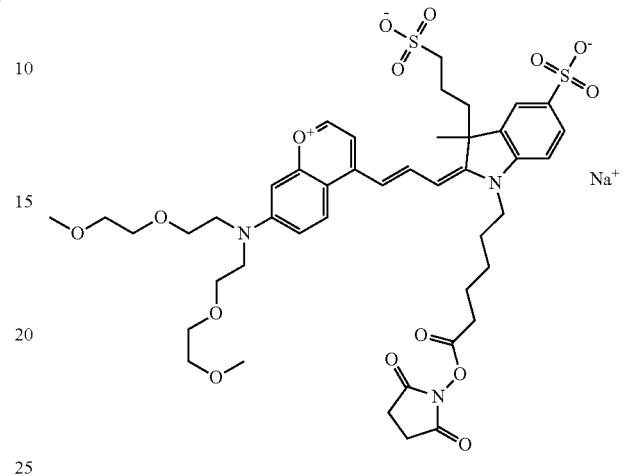

or according to general formula II shown below

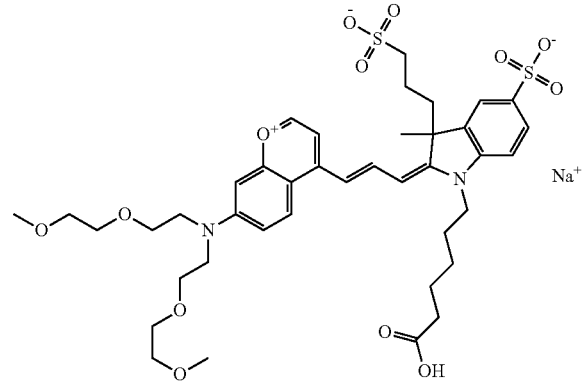

In one embodiment, the compound is 682 Compound 2/3 ((E)-2-((E)-3-(7-(bis(2-(2-(2-methoxyethoxy)ethoxy)ethyl)amino)-4-tert-butylchromenylium-2-yl)allylidene)-1-(5-carboxypentyl)-3-methyl-3-(3-sulfonatopropyl)indoline-5-sulfonate), according to general formula I and shown below, which contains two polyethylene glycols (PEG$_3$) bound to the benzopyrylium by N, positions R2 and R3, i.e., a methylated polyethylene glycol, and —COOH at R10:

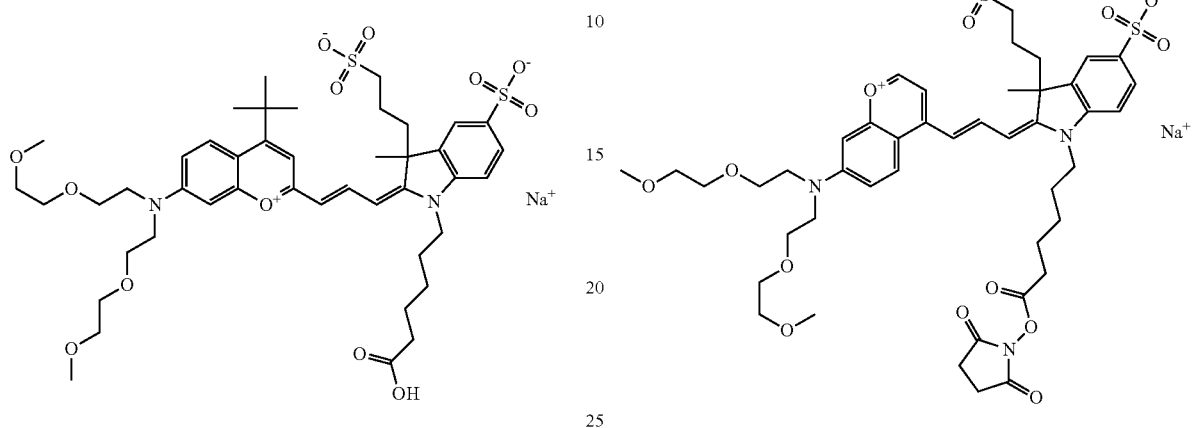

One non-limiting example of an activated compound according to general formula I is the NHS-ester of 682 Compound 2/3 (PEG$_2$), shown below:

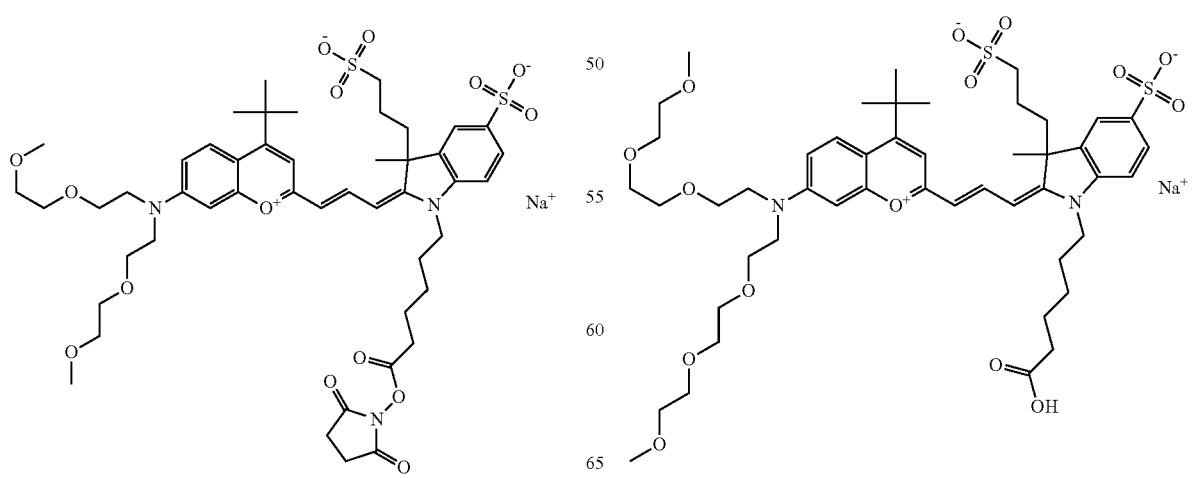

or according to general formula II shown below
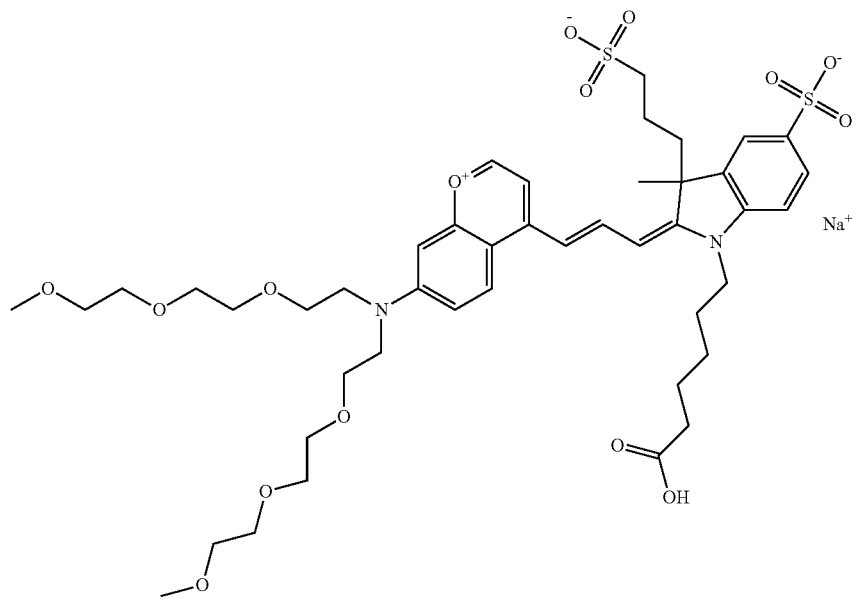
One non-limiting example of an activated compound according to general formula I is the NHS-ester of Compound 2/3 (PEG₃), shown below:
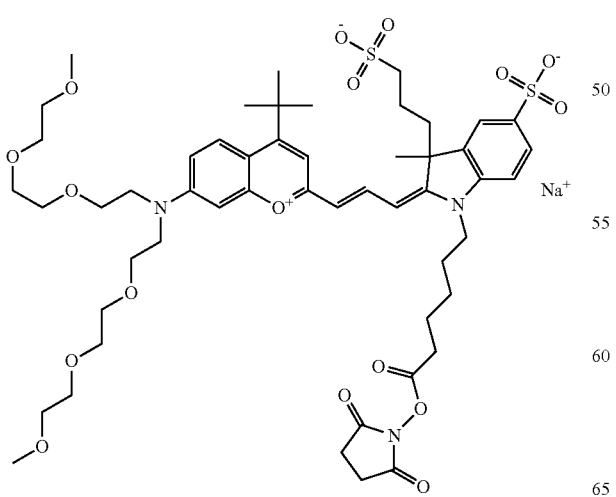

or according to general formula II shown below

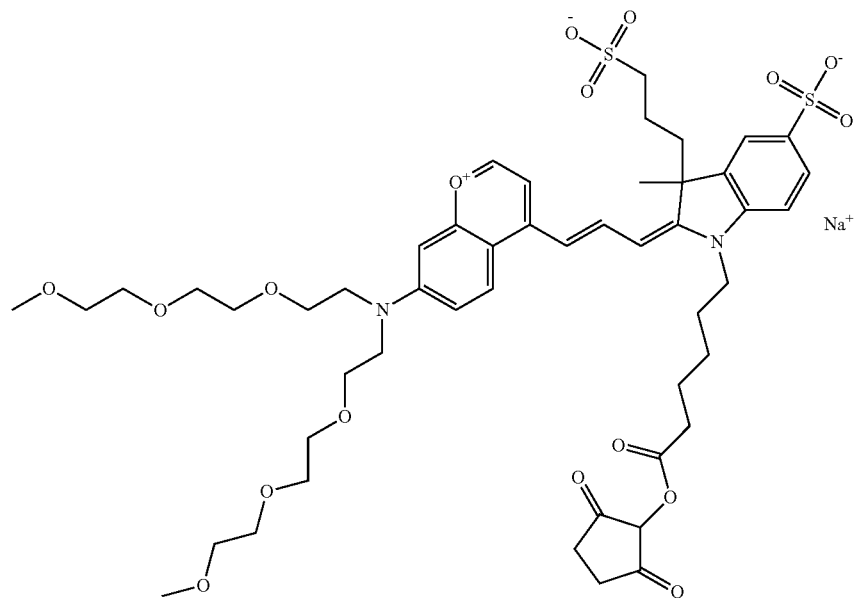

In one embodiment, the compound is 682 Compound 2/3 ((E)-2-((E)-3-(4-tert-butyl-7-(di2,5,8,11-tetraoxatridecan-13-ylamino)chromenylium-2-yl)allylidene)-1-(5-carboxypentyl)-3-methyl-3-(3-sulfonatopropyl)indoline-5-sulfonate), according to general formula I and shown below, which contains two polyethylene glycols (PEG$_4$) bound to the benzopyrylium by N, positions R2 and R3, i.e., a methylated polyethylene glycol, and —COOH at R10:

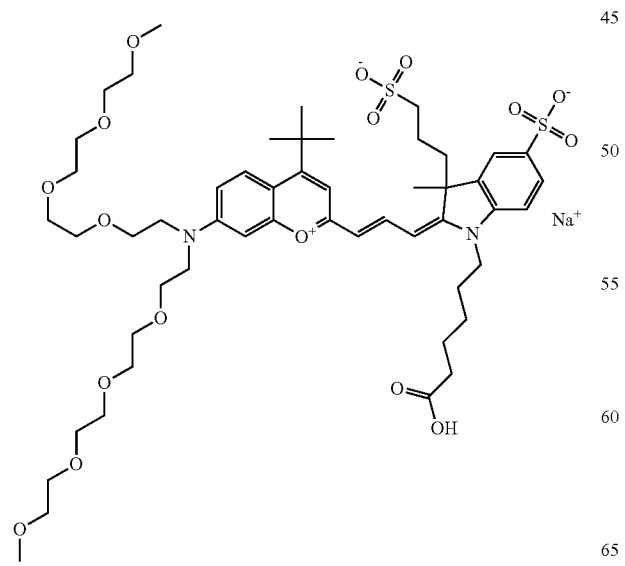

or according to general formula II shown below
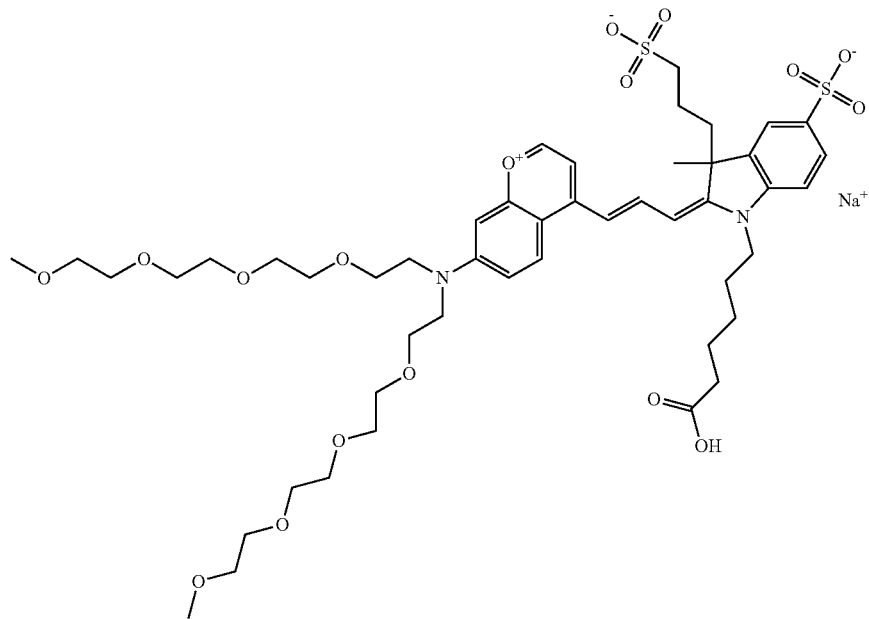
One non-limiting example of an activated compound according to general formula I is the NHS-ester of 682 Compound 2/3 (PEG$_4$), shown below:
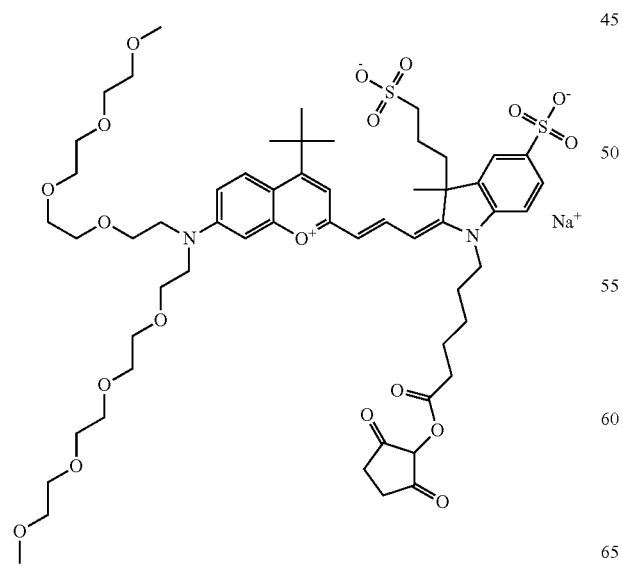

or according to general formula II shown below

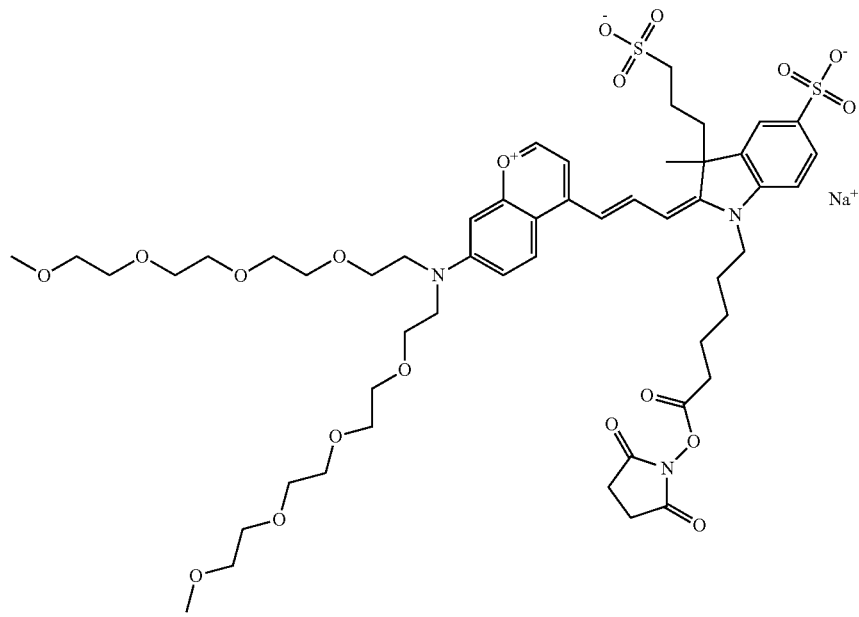

In one embodiment, the compound is 682 Compound 2/3 ((E)-2-((E)-3-(4-tert-butyl-7-(di2,5,8,11,14-pentaoxahexadecan-16-ylamino)chromenylium-2-yl)allylidene)-1-(5-carboxypentyl)-3-methyl-3-(3-sulfonatopropyl)indoline-5-sulfonate), according to general formula I and shown below, which contains two polyethylene glycols ($PEG_5$) bound to the benzopyrylium by N, positions R2 and R3, i.e., a methylated polyethylene glycol, and —COOH at R10:

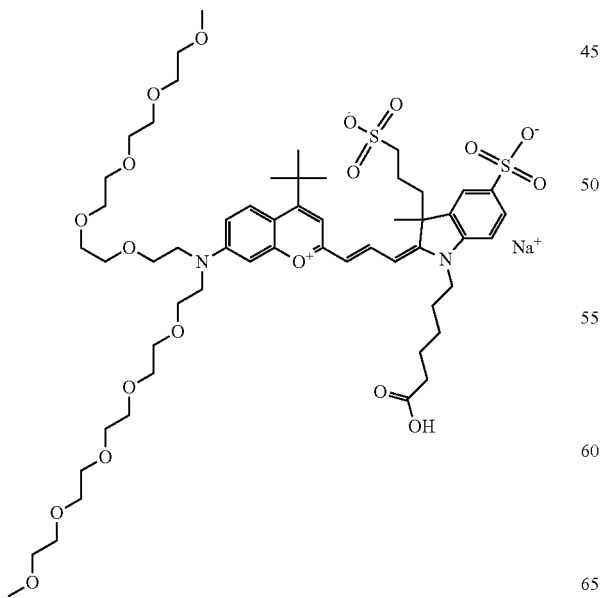

or according to general formula II shown below
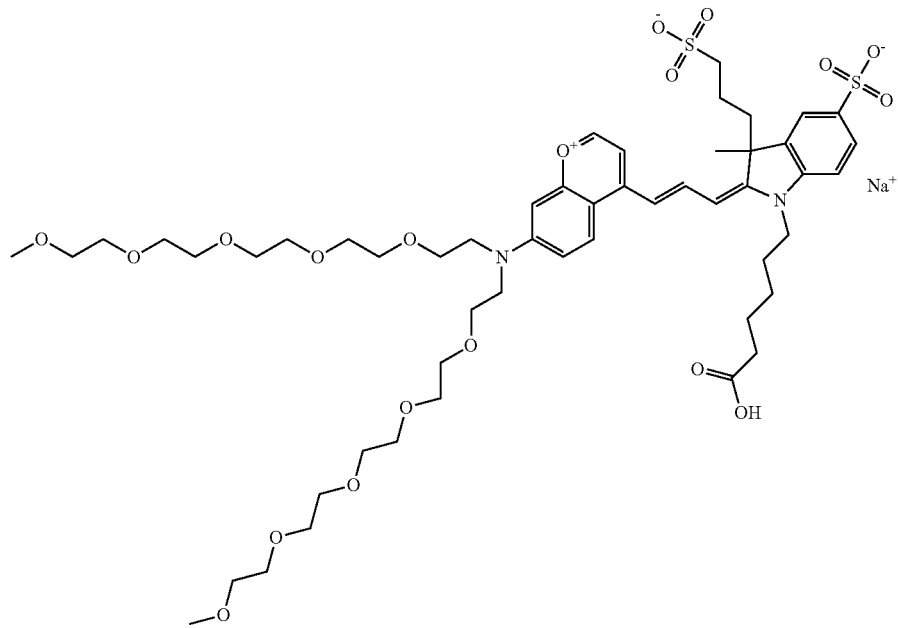
One non-limiting example of an activated compound according to general formula I is the NHS-ester of 682 Compound 2/3 (PEG$_5$), shown below:
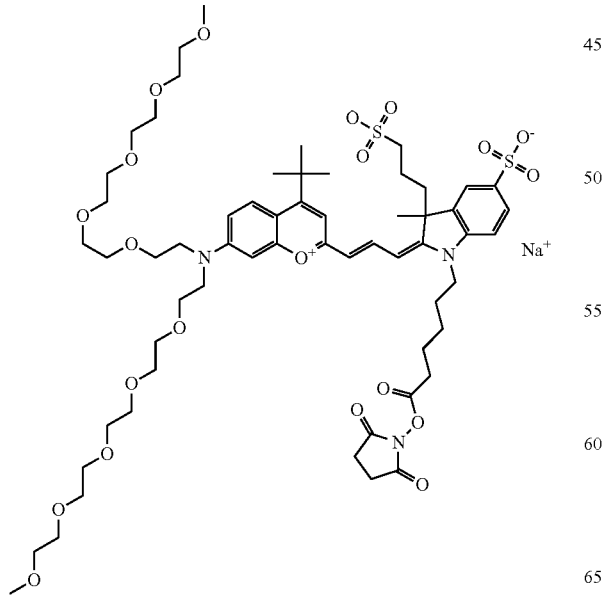

or according to general formula II shown below

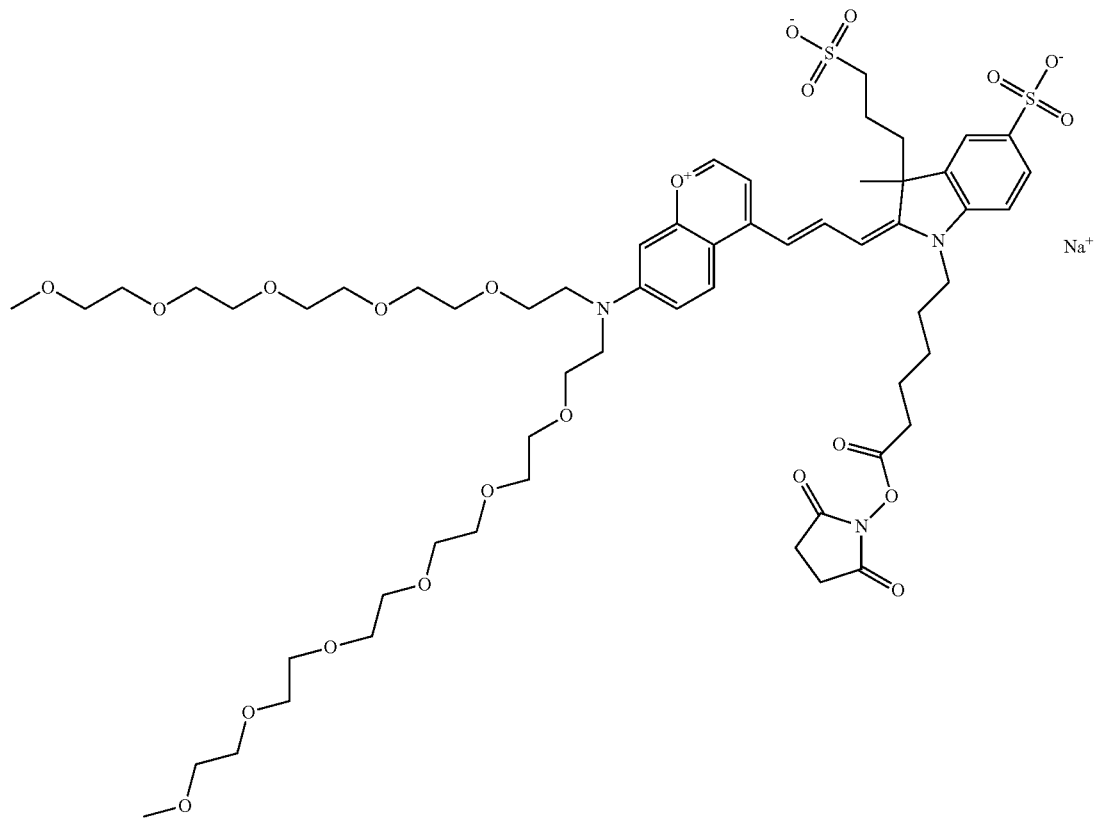

In one embodiment, the compound is 682 Compound 2/3 ((E)-2-((E)-3-(4-tert-butyl-7-(di2,5,8,11,14,17-hexaoxanonadecan-19-ylamino)chromenylium-2-yl)allylidene)-1-(5-carboxypentyl)-3-methyl-3-(3-sulfonatopropyl)indoline-5-sulfonate), according to general formula I and shown below, which contains two polyethylene glycols (PEG$_6$) bound to the benzopyrylium by N, positions R2 and R3, i.e., a methylated polyethylene glycol, and —COOH at R10:

or according to general formula II shown below

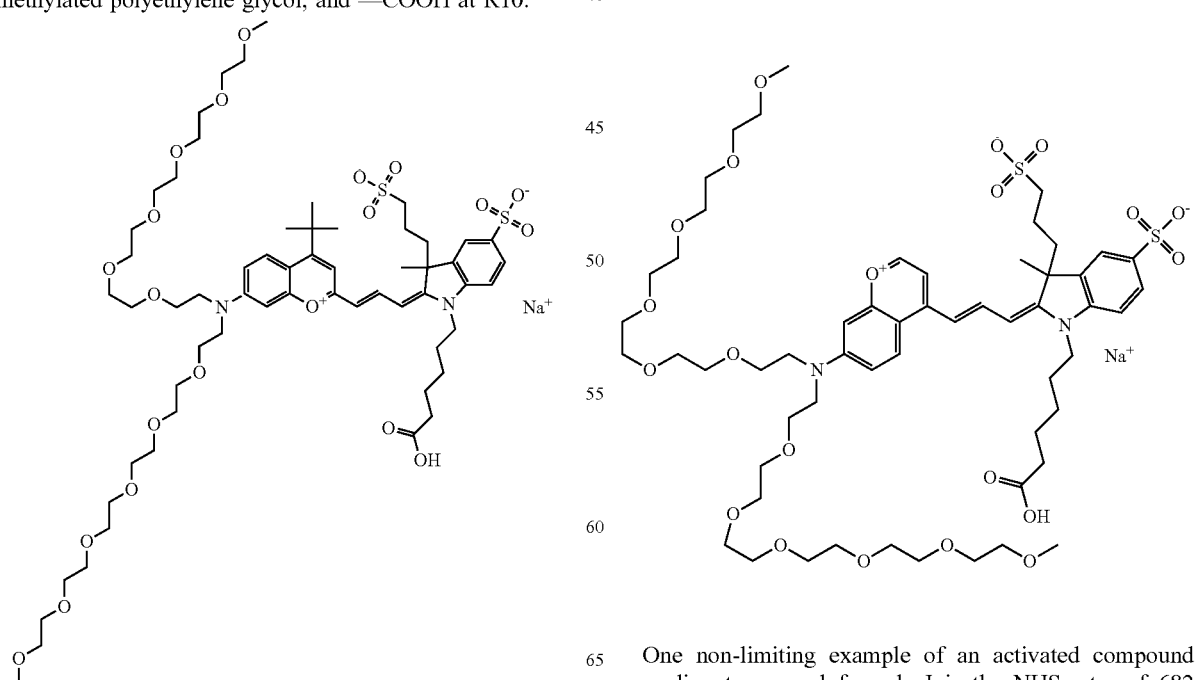

One non-limiting example of an activated compound according to general formula I is the NHS-ester of 682 Compound 2/3 (PEG$_6$), shown below:

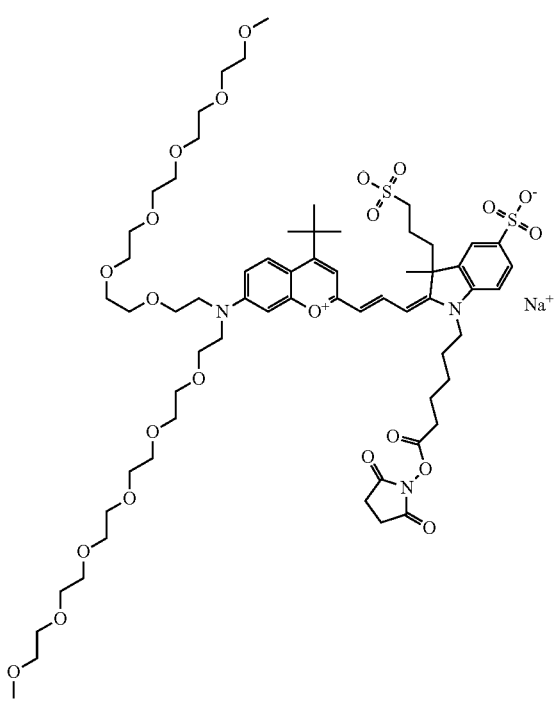

or according to general formula II shown below

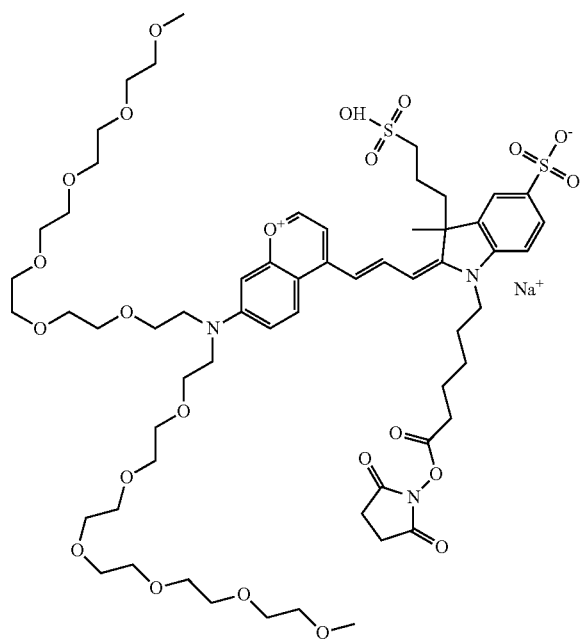

In one embodiment, the compound is 682 Compound 2/3 ((E)-2-((7-(bis(2-methoxyethyl)amino)-4-tert-butylchromenylium-2-yl)methylene)-1-(5-carboxypentyl)-3,3-dimethylindoline-5-sulfonate), according to general formula I and shown below, which contains an ethylene glycol (PEG₁) bound to the benzopyrylium by N, i.e., a methylated ethylene glycol, with a monomethine linker connecting the benzopyrylium with the indole group, and —COOH at R10:

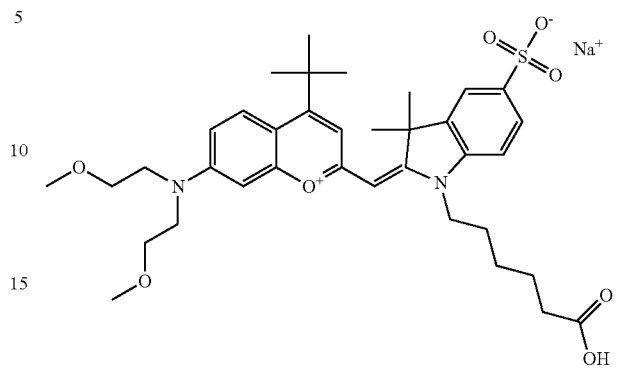

or according to general formula II shown below

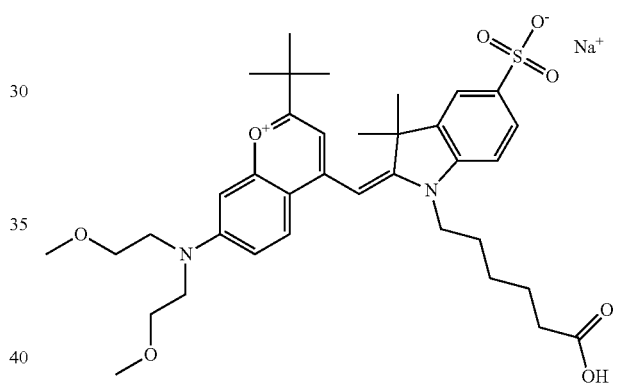

In one embodiment, the compound is 682 Compound 2/3 ((E)-2-((E)-3-(7-(bis(2-methoxyethyl)amino)-4-tert-butyl-chromenylium-2-yl)allylidene)-1-(5-carboxypentyl)-3,3-dimethylindoline-5-sulfonate), according to general formula I and shown below, which contains an ethylene glycol (PEG₁) bound to the benzopyrylium by N, i.e., a methylated ethylene glycol, with a trimethine linker connecting the benzopyrylium with the indole group, and —COOH at R10:

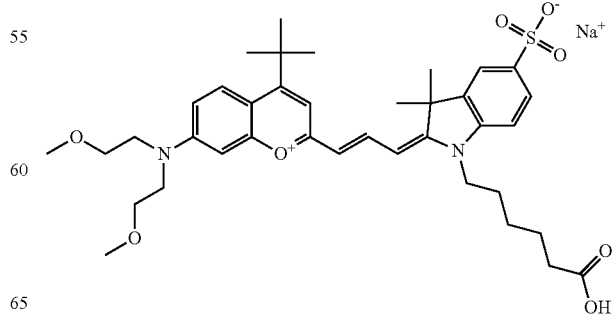

or according to general formula II shown below or according to general formula II shown below

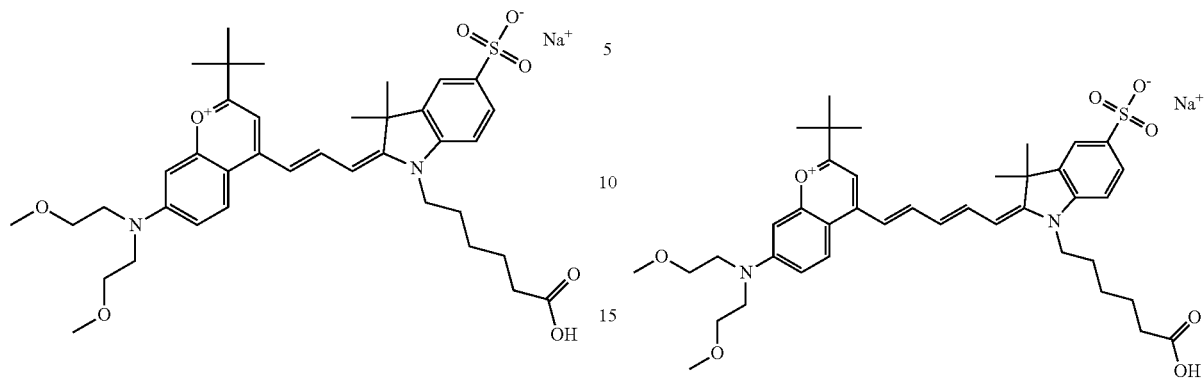

In one embodiment, the compound is 682 Compound 2/3 ((E)-2-((2E,4E)-5-(7-(bis(2-methoxyethyl)amino)-4-tert-butylchromenylium-2-yl)penta-2,4-dienylidene)-1-(5-carboxypentyl)-3,3-dimethylindoline-5-sulfonate), according to general formula I and shown below, which contains an ethylene glycol (PEG$_1$) bound to the benzopyrylium by N, i.e., a methylated ethylene glycol, with a pentamethine linker connecting the benzopyrylium with the indole group, and —COOH at R10:

In one embodiment, the compound is 682 Compound 2/3 ((E)-2-((2E,4E,6E)-7-(7-(bis(2-methoxyethyl)amino)-4-tert-butylchromenylium-2-yl)hepta-2,4,6-trienylidene)-1-(5-carboxypentyl)-3,3-dimethylindoline-5-sulfonate), according to general formula I and shown below, which contains an ethylene glycol (PEG$_1$) bound to the benzopy-

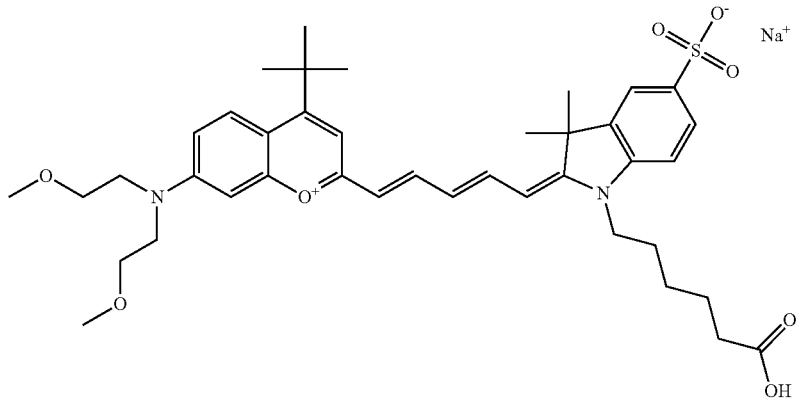

rylium by N, i.e., a methylated ethylene glycol, with a heptamethine linker connecting the benzopyrylium with the indole group, and —COOH at R10:

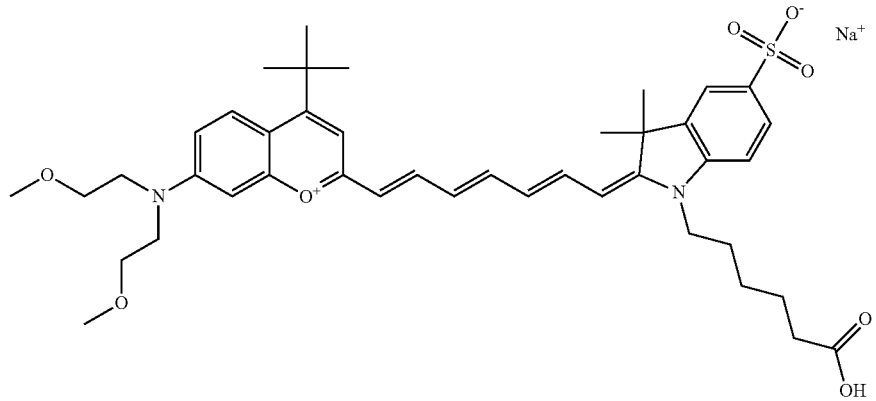 [SMILES: COCCN(CCOC)c1ccc2c(C(C)(C)C)cc(/C=C/C=C/C=C/C=C3/N(CCCCCC(=O)O)c4ccc(S(=O)(=O)[O-])cc4C3(C)C)[o+]c2c1 ; [Na+]]

or according to general formula II shown below

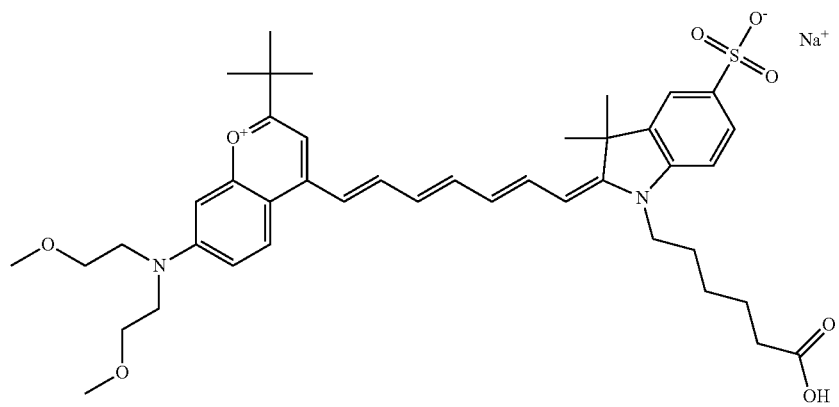

One non-limiting example of an activated compound according to general formula I is an NHS-ester of 682 Compound 2/3 (PEG$_1$), shown below:

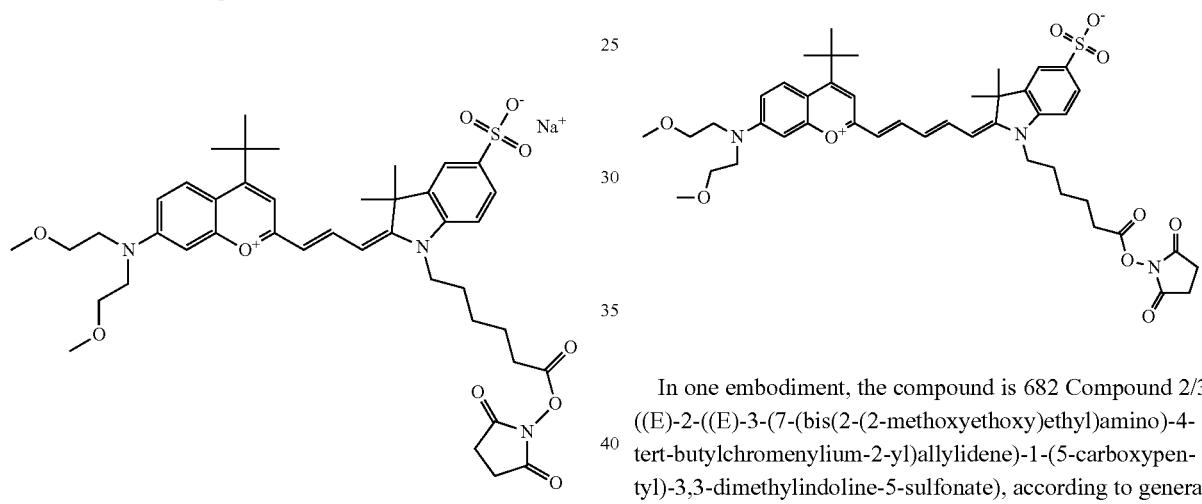

or according to general formula II shown below

In one embodiment, the compound is 682 Compound 2/3 ((E)-2-((E)-3-(7-(bis(2-(2-methoxyethoxy)ethyl)amino)-4-tert-butylchromenylium-2-yl)allylidene)-1-(5-carboxypentyl)-3,3-dimethylindoline-5-sulfonate), according to general formula I and shown below, which contains two diethylene glycols (PEG$_2$) bound to the benzopyrylium by N, positions R2 and R3, i.e., a methylated diethylene glycol and —COOH at R10:

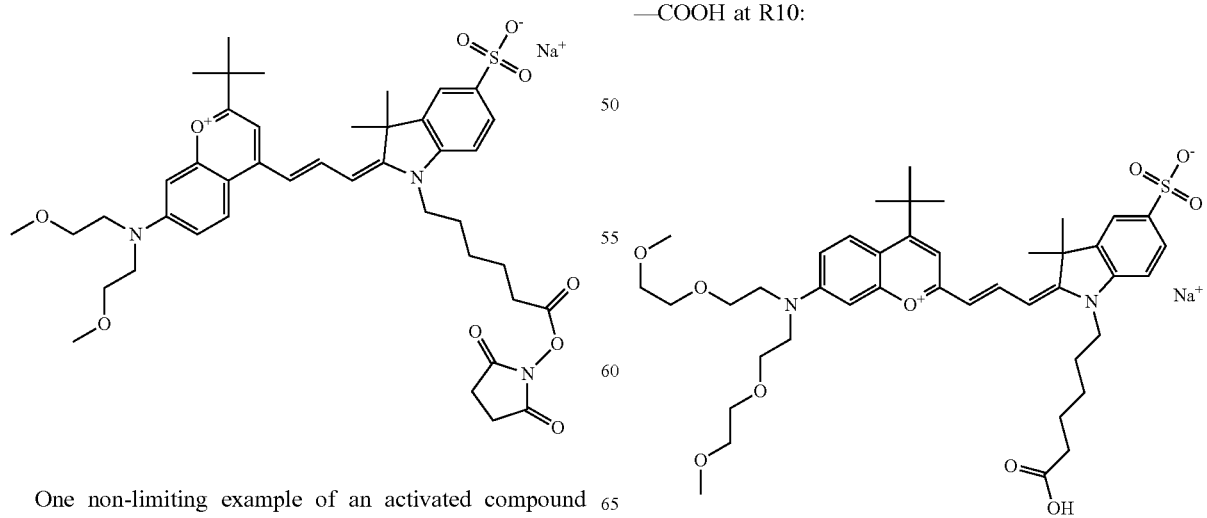

One non-limiting example of an activated compound according to general formula I is an NHS-ester of 682 Compound 2/3 (PEG$_1$), shown below:

99 or according to general formula II shown below

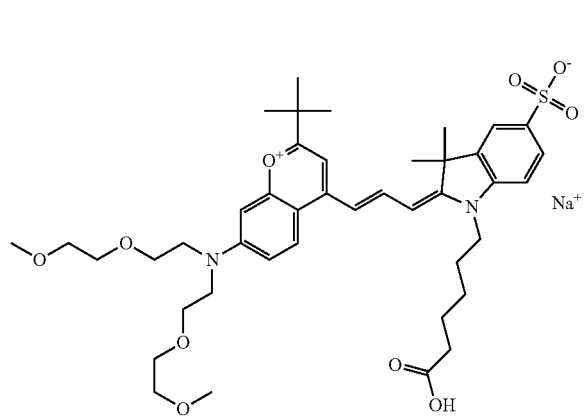

One non-limiting example of an activated compound according to general formula I is the NHS-ester of 682 Compound 2/3 (PEG₂), shown below:

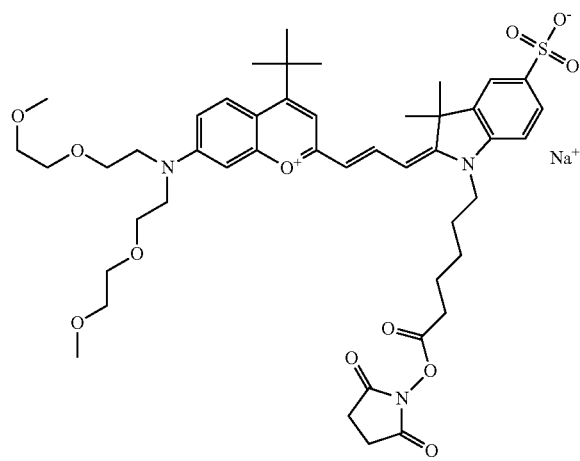

100 or according to general formula II shown below

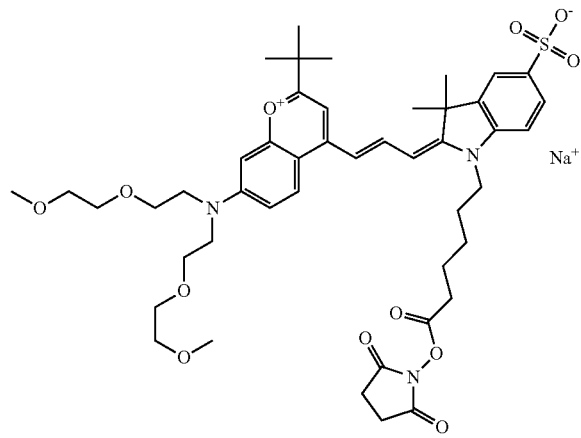

In one embodiment, the compound is 682 Compound 2/3 ((E)-2-((E)-3-(7-(bis(2-(2-(2-methoxyethoxy)ethoxy)ethyl)amino)-4-tert-butylchromenylium-2-yl)allylidene)-1-(5-carboxypentyl)-3-methyl-3-(3-sulfonatopropyl)indoline-5-sulfonate), according to general formula I and shown below, which contains two polyethylene glycols (PEG₃) bound to the benzopyrylium by N, positions R2 and R3, i.e., a methylated polyethylene glycol, and —COOH at R10:

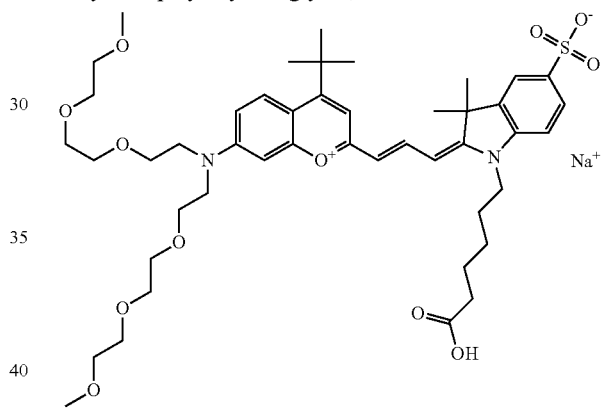

or according to general formula II shown below

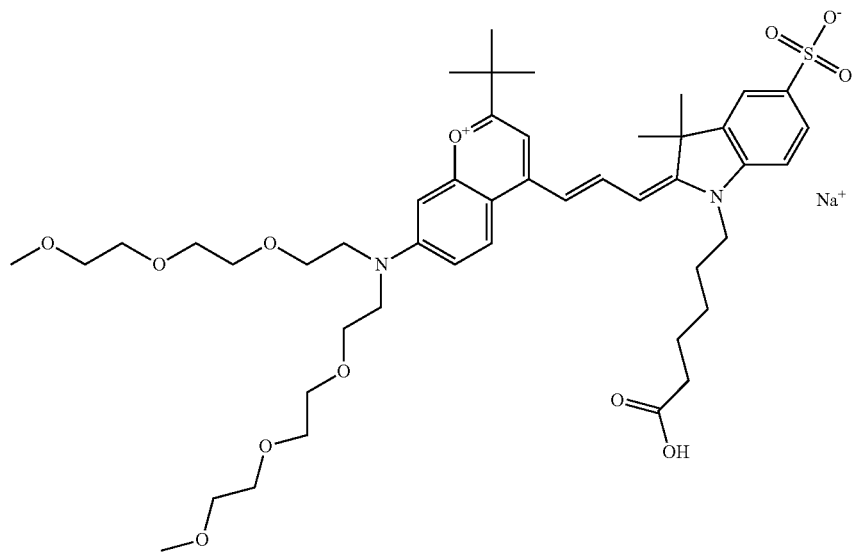

One non-limiting example of an activated compound according to general formula I is the NHS-ester of 682 Compound 2/3 (PEG₃), shown below:
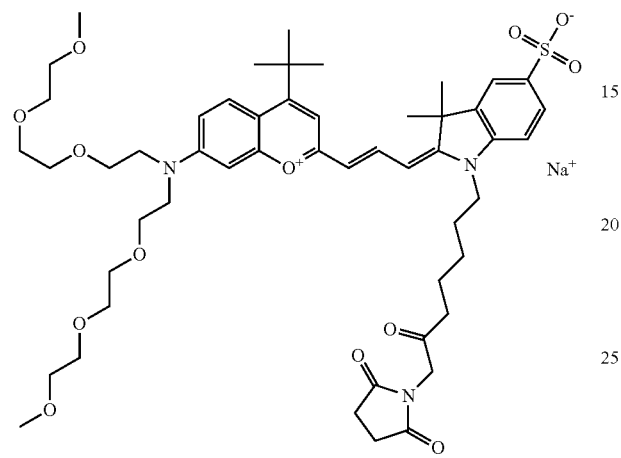
or according to general formula II shown below
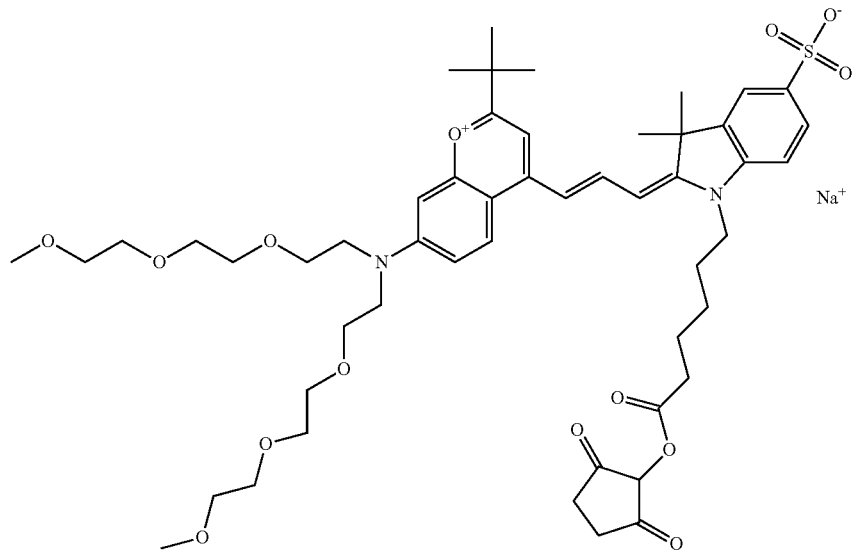

In one embodiment, the compound is 682 Compound 2/3 ((E)-2-((E)-3-(4-tert-butyl-7-(di2,5,8,11-tetraoxatridecan-13-ylamino)chromenylium-2-yl)allylidene)-1-(5-carboxypentyl)-3-methyl-3-(3-sulfonatopropyl)indoline-5-sulfonate), according to general formula I and shown below, which contains two polyethylene glycols (PEG$_4$) bound to the benzopyrylium by N, positions R2 and R3, i.e., a methylated polyethylene glycol, and —COOH at R10:

One non-limiting example of an activated compound according to general formula I is the NHS-ester of 682 Compound 2/3 (PEG$_4$), shown below:

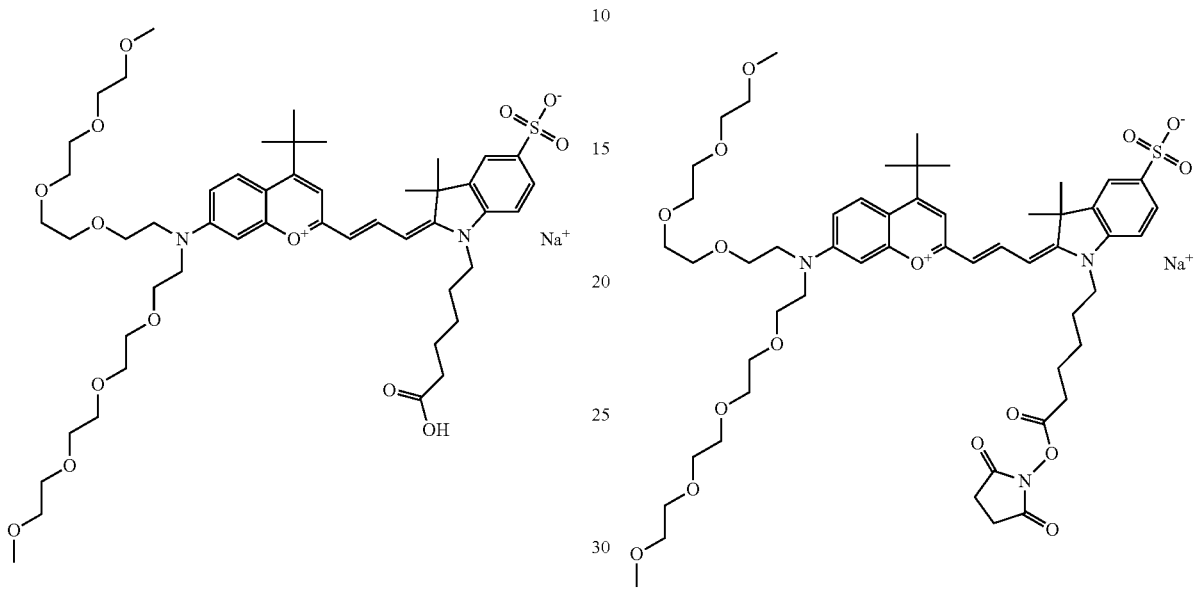

or according to general formula II shown below

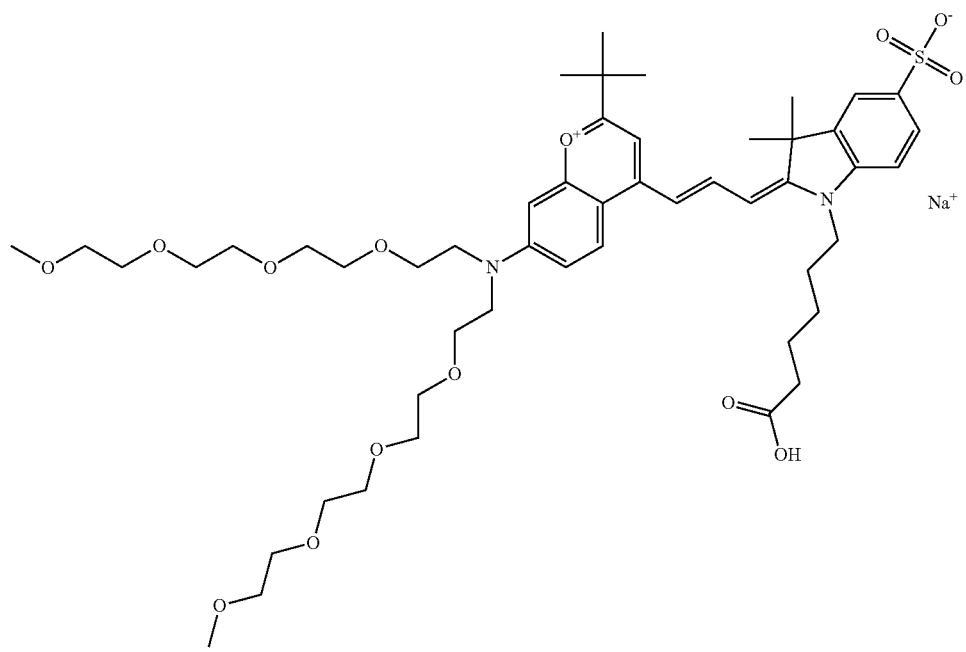

or according to general formula II shown below

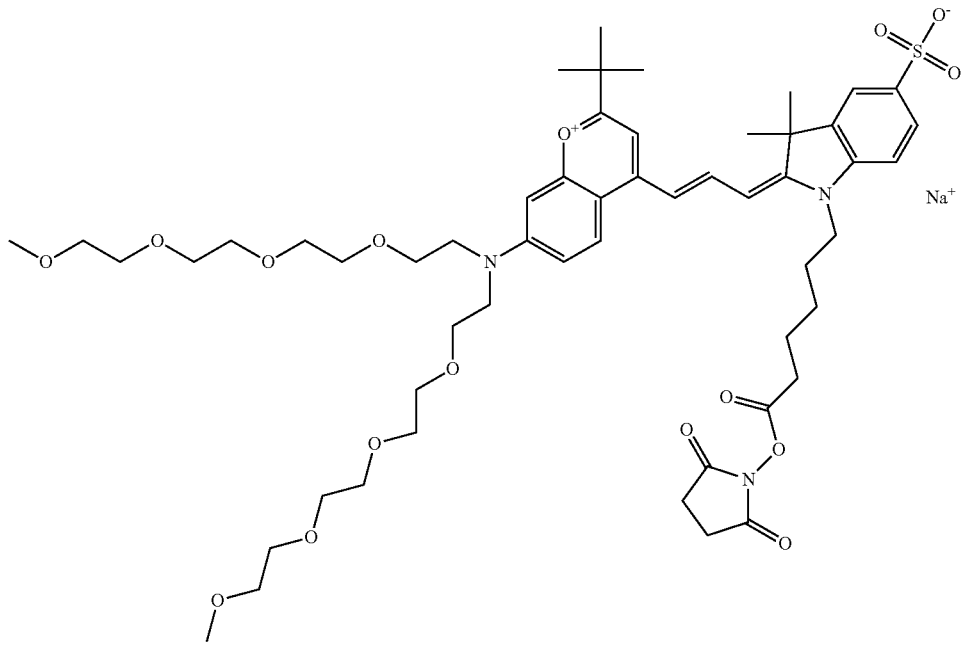

In one embodiment, the compound is 682 Compound 2/3 ((E)-2-((E)-3-(4-tert-butyl-7-(di2,5,8,11,14-pentaoxahexadecan-16-ylamino)chromenylium-2-yl)allylidene)-1-(5-carboxypentyl)-3-methyl-3-(3-sulfonatopropyl)indoline-5-sulfonate), according to general formula I and shown below, which contains two polyethylene glycols (PEG$_5$) bound to the benzopyrylium by N, positions R2 and R3, i.e., a methylated polyethylene glycol, and —COOH at R10:

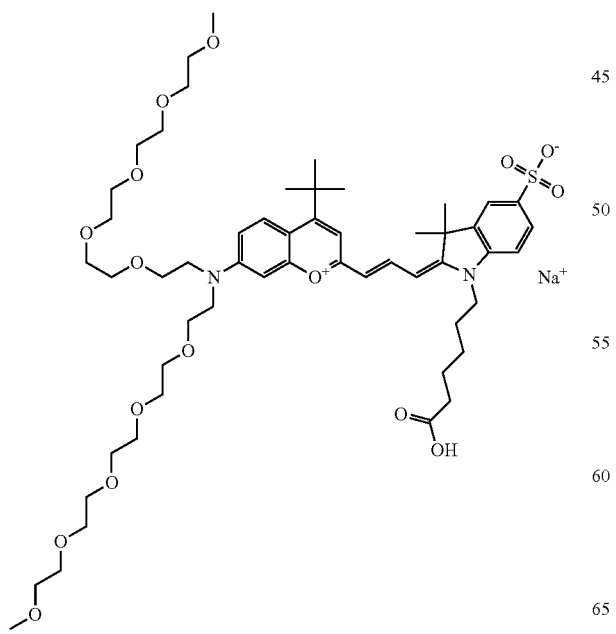

or according to general formula II shown below
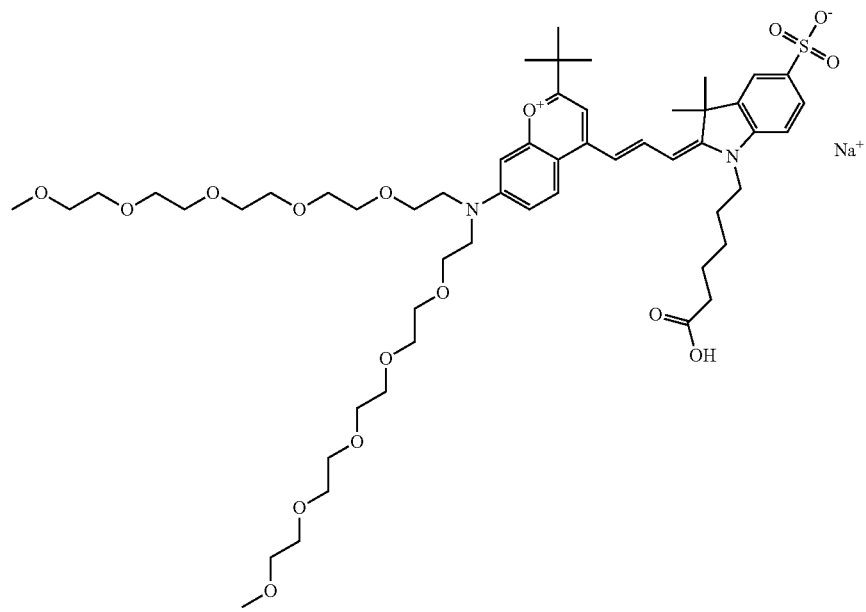
One non-limiting example of an activated compound according to general formula I is the NHS-ester of 682 Compound 2/3 (PEG$_5$), shown below:
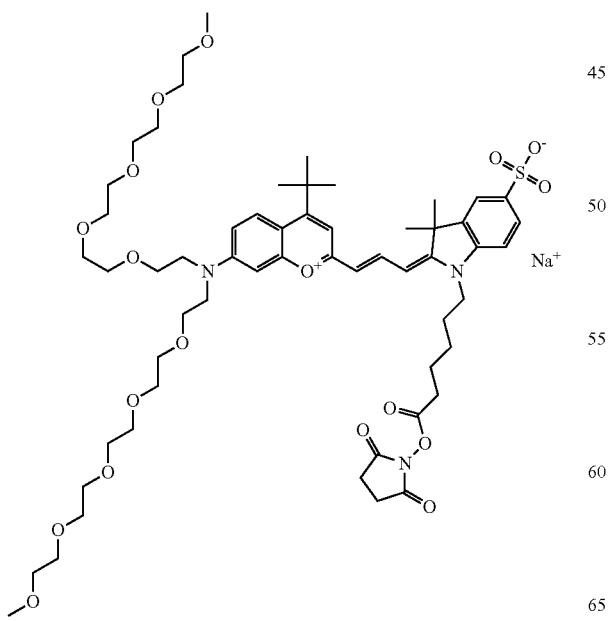

or according to general formula II shown below

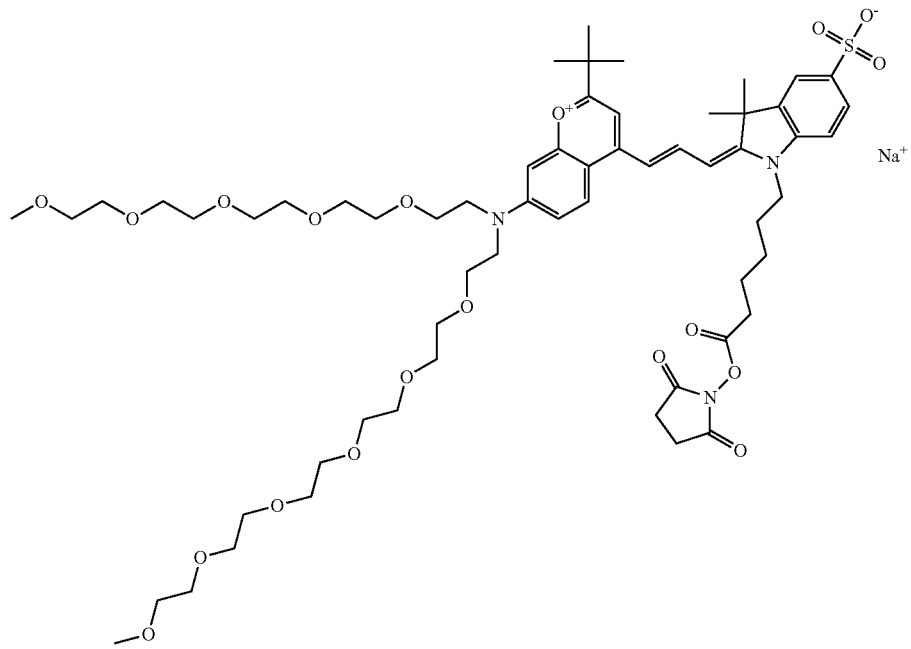

In one embodiment, the compound is 682 Compound 2/3 ((E)-2-((E)-3-(4-tert-butyl-7-(di2,5,8,11,14,17-hexaoxanonadecan-19-ylamino)chromenylium-2-yl)allylidene)-1-(5-carboxypentyl)-3-methyl-3-(3-sulfonatopropyl)indoline-5-sulfonate), according to general formula I and shown below, which contains two polyethylene glycols ($PEG_6$) bound to the benzopyrylium by N, positions R2 and R3, i.e., a methylated polyethylene glycol, and —COOH at R10:

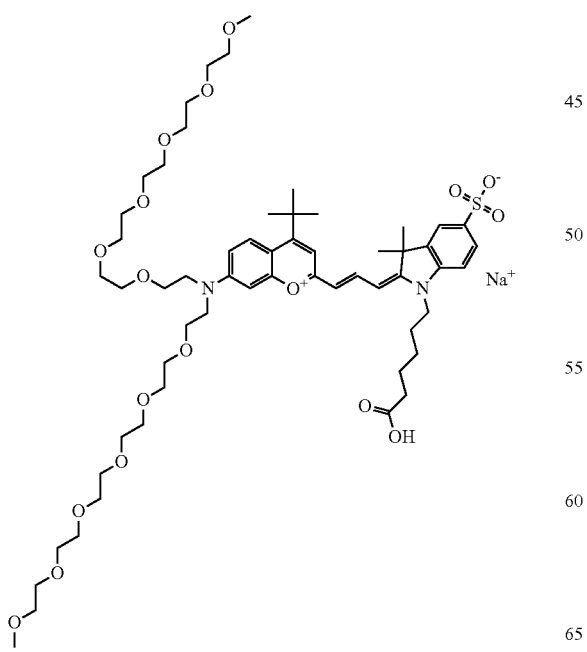

or according to general formula II shown below

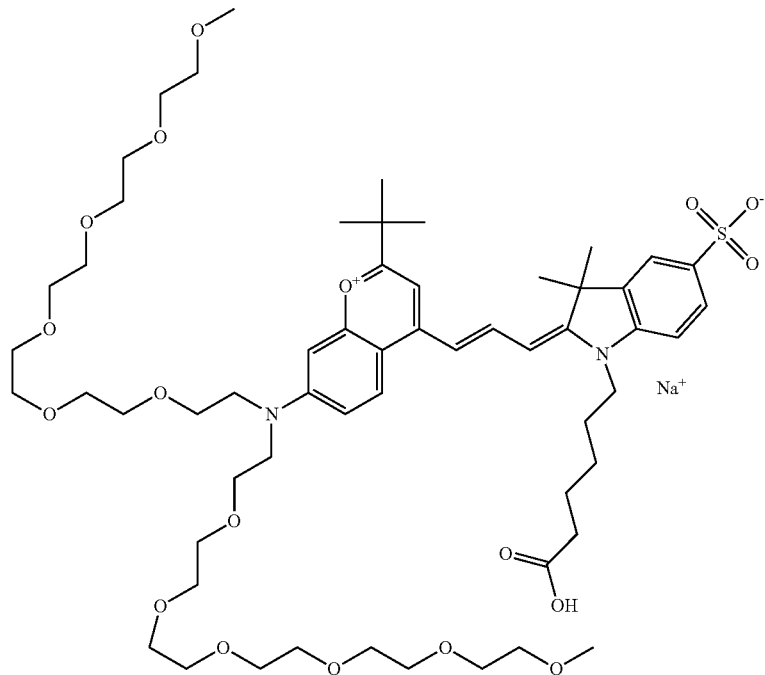

One non-limiting example of an activated compound according to general formula I is the NHS-ester of 682 Compound 2/3 (PEG$_6$), shown below:

or according to general formula II shown below

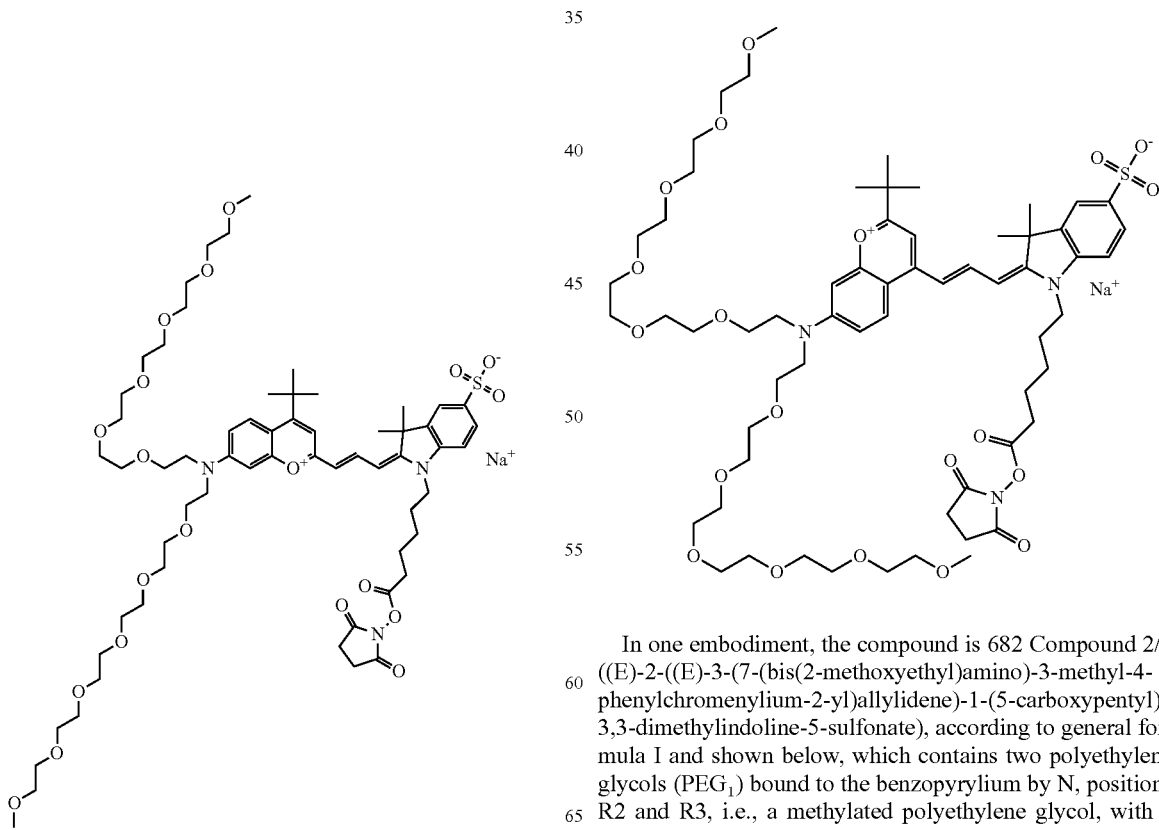

In one embodiment, the compound is 682 Compound 2/3 ((E)-2-((E)-3-(7-(bis(2-methoxyethyl)amino)-3-methyl-4-phenylchromenylium-2-yl)allylidene)-1-(5-carboxypentyl)-3,3-dimethylindoline-5-sulfonate), according to general formula I and shown below, which contains two polyethylene glycols (PEG$_1$) bound to the benzopyrylium by N, positions R2 and R3, i.e., a methylated polyethylene glycol, with a monomethine linker connecting the benzopyrylium with the indole group, and —COOH at R10:

113

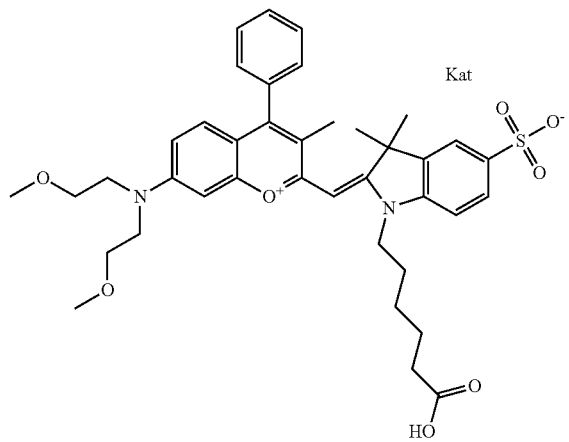 [SMILES: COCCN(CCOC)c1ccc2c(-c3ccccc3)c(C)c(/C=C3/N(CCCCCC(=O)O)c4ccc(S(=O)(=O)[O-])cc4C3(C)C)[o+]c2c1]

or according to general formula II shown below

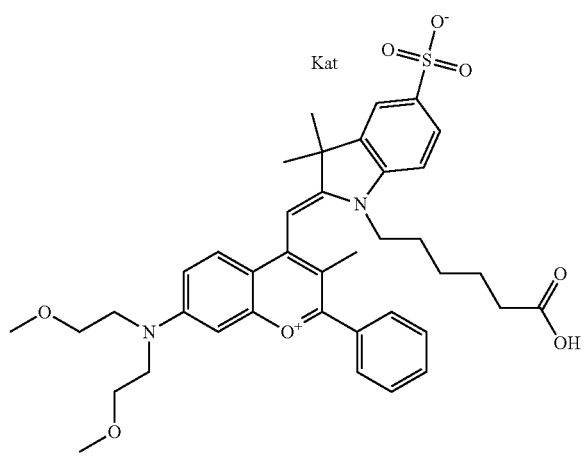

In one embodiment, the compound is 682 Compound 2/3 ((E)-2-((E)-3-(7-(bis(2-methoxyethyl)amino)-3-methyl-4-phenylchromenylium-2-yl)allylidene)-1-(5-carboxypentyl)-3,3-dimethylindoline-5-sulfonate), according to general formula I and shown below, which contains two polyethylene glycols (PEG$_1$) bound to the benzopyrylium by N, positions R2 and R3, i.e., a methylated polyethylene glycol, with a trimethine linker connecting the benzopyrylium with the indole group, and —COOH at R10:

114

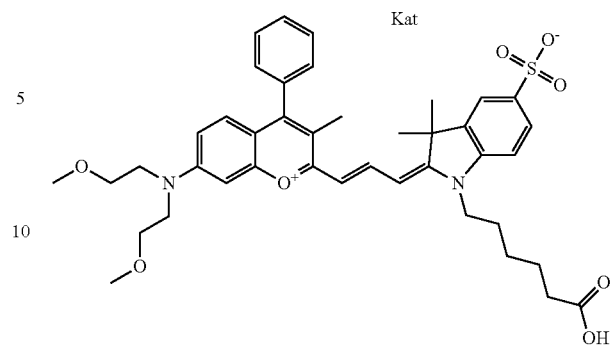

or according to general formula II shown below

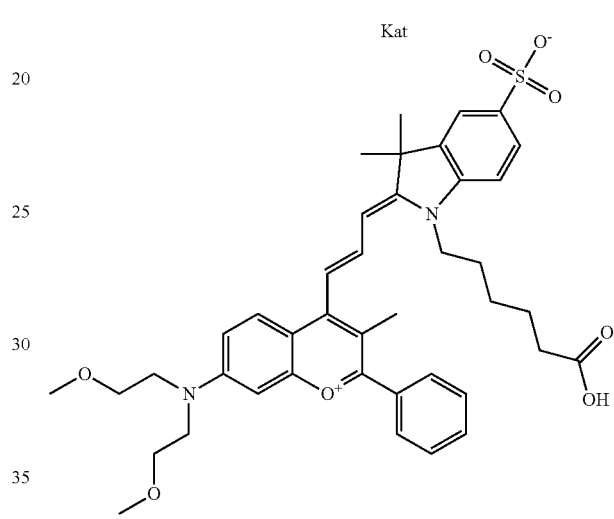

In one embodiment, the compound is 682 Compound 2/3 ((E)-2-((2E,4E)-5-(7-(bis(2-methoxyethyl)amino)-3-methyl-4-phenylchromenylium-2-yl)penta-2,4-dienylidene)-1-(5-carboxypentyl)-3,3-dimethylindoline-5-sulfonate), according to general formula I and shown below, which contains two polyethylene glycols (PEG$_1$) bound to the benzopyrylium by N, positions R2 and R3, i.e., a methylated polyethylene glycol, with a pentamethine linker connecting the benzopyrylium with the indole group, and —COOH at R10:

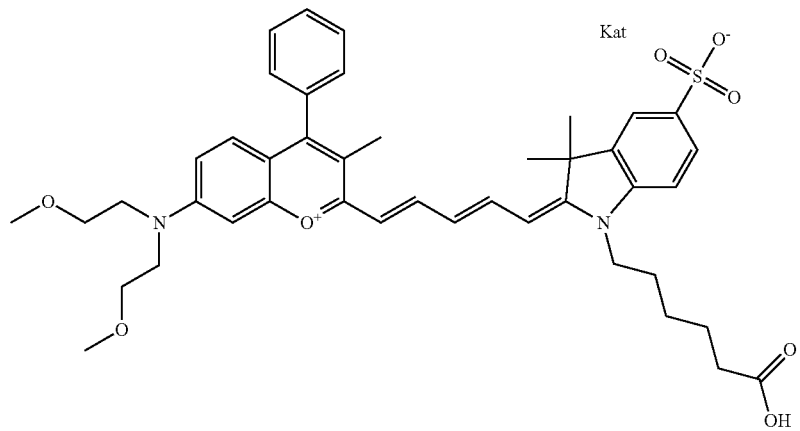

115 or according to general formula II shown below

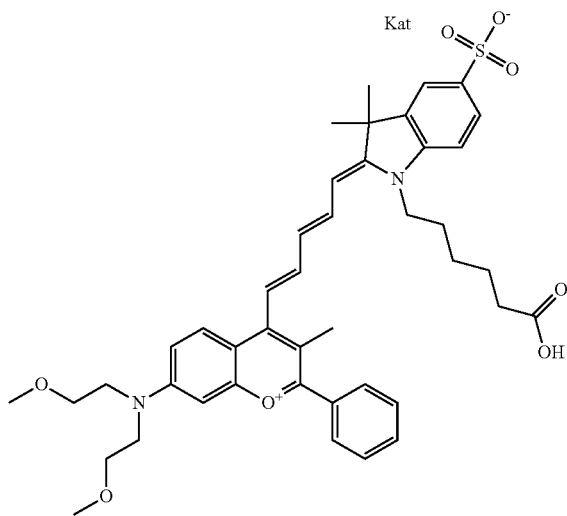

In one embodiment, the compound is 682 Compound 2/3 ((E)-2-((2E,4E,6E)-7-(7-(bis(2-methoxyethyl)amino)-3-methyl-4-phenylchromenylium-2-yl)hepta-2,4,6-trienylidene)-1-(5-carboxypentyl)-3,3-dimethylindoline-5-sulfonate), according to general formula I and shown below, which contains two polyethylene glycols (PEG$_1$) bound to the benzopyrylium by N, positions R2 and R3, i.e., a methylated polyethylene glycol, with a heptamethine linker connecting the benzopyrylium with the indole group, and —COOH at R10:

116 or according to general formula II shown below

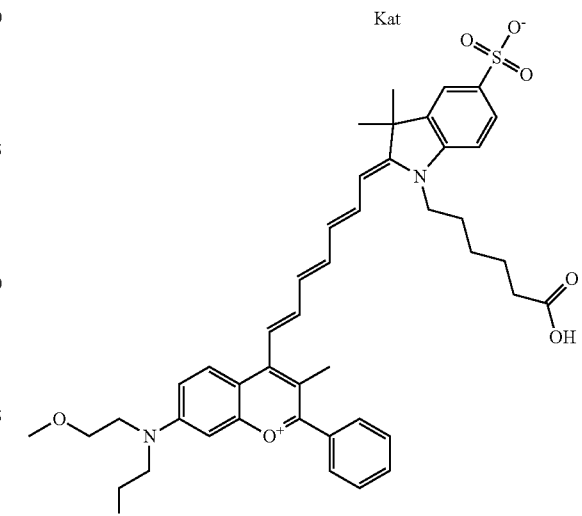

One non-limiting example of an activated compound according to general formula I is an NHS-ester of 682 Compound 2/3 (PEG$_1$), shown below:

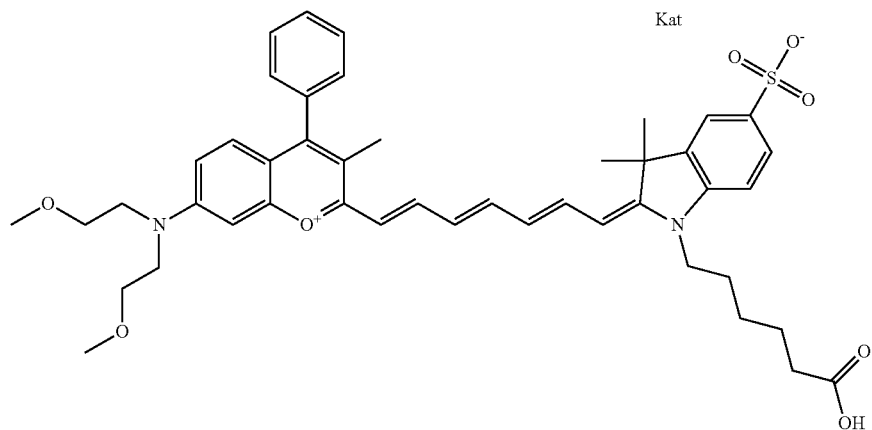

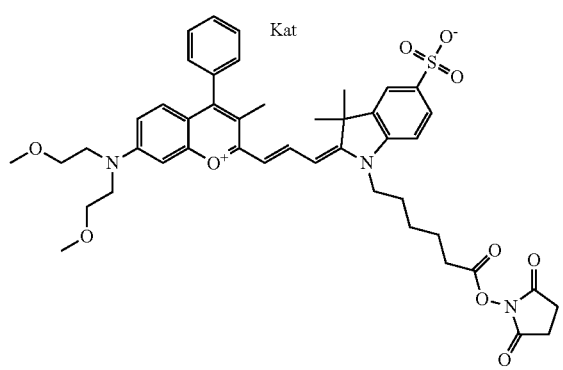

or according to general formula II shown below

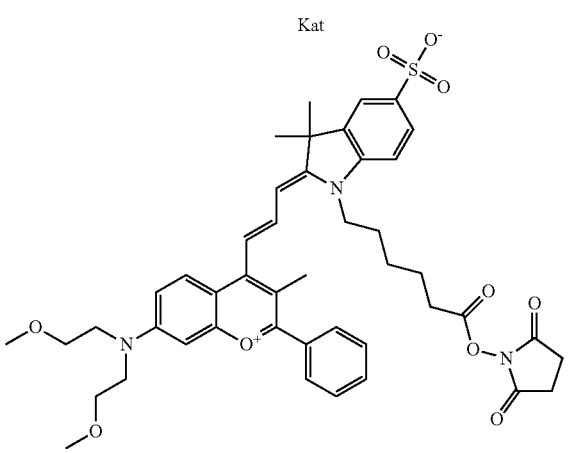

In one embodiment, the compound is 682 Compound 2/3 ((E)-2-((E)-3-(7-(bis(2-(2-methoxyethoxy)ethyl)amino)-3-methyl-4-phenylchromenylium-2-yl)allylidene)-1-(5-carboxypentyl)-3,3-dimethylindoline-5-sulfonate), according to general formula I and shown below, which contains two polyethylene glycols (PEG$_2$) bound to the benzopyrylium by N, positions R2 and R3, i.e., a methylated polyethylene glycol, and —COOH at R10:

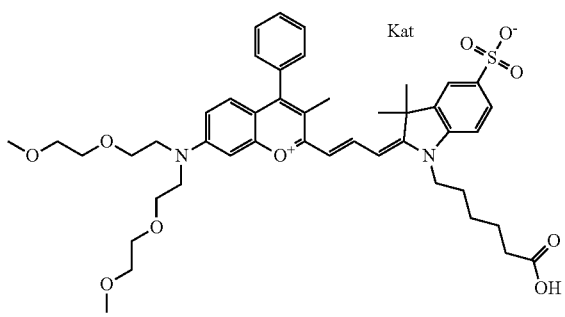

or according to general formula II shown below

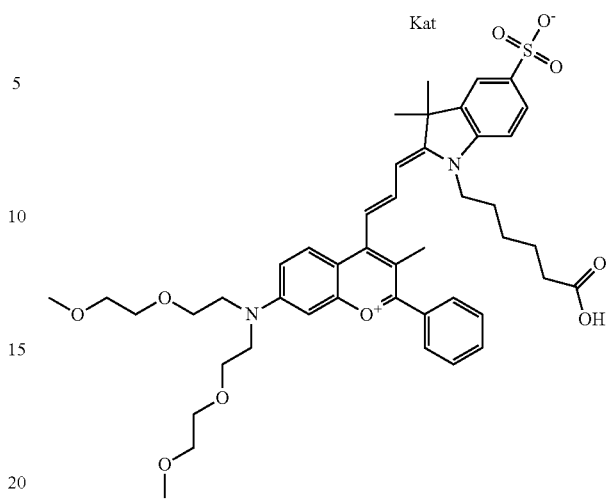

One non-limiting example of an activated compound according to general formula I is an NHS-ester of 682 Compound 2/3 (PEG$_2$), shown below:

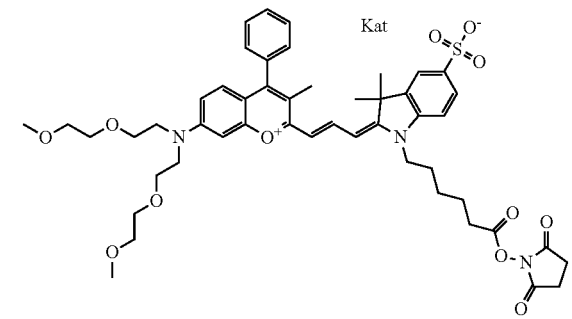

or according to general formula II shown below

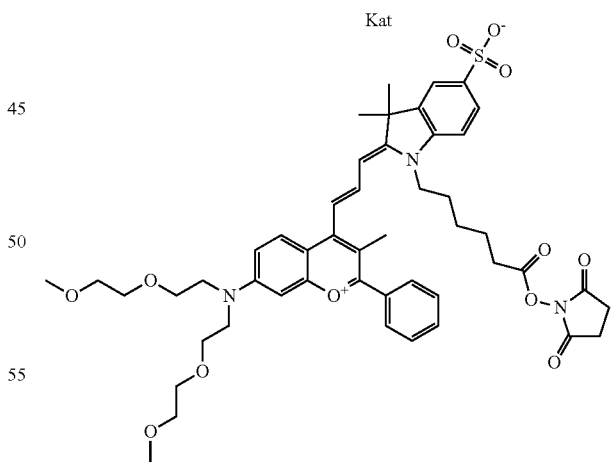

In one embodiment, the compound is 682 Compound 2/3 ((E)-2-((E)-3-(7-(bis(2-(2-(2-methoxyethoxy)ethoxy)ethyl)amino)-3-methyl-4-phenylchromenylium-2-yl)allylidene)-1-(5-carboxypentyl)-3,3-dimethylindoline-5-sulfonate), according to general formula I and shown below, which contains two polyethylene glycols (PEG$_3$) bound to the benzopyrylium by N, positions R2 and R3, i.e., a methylated polyethylene glycol, and —COOH at R10:

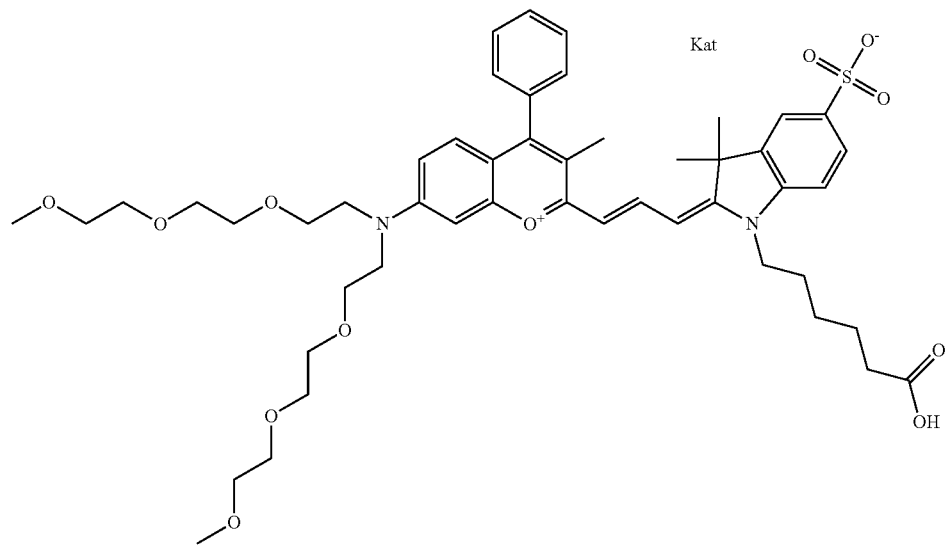
or according to general formula II shown below
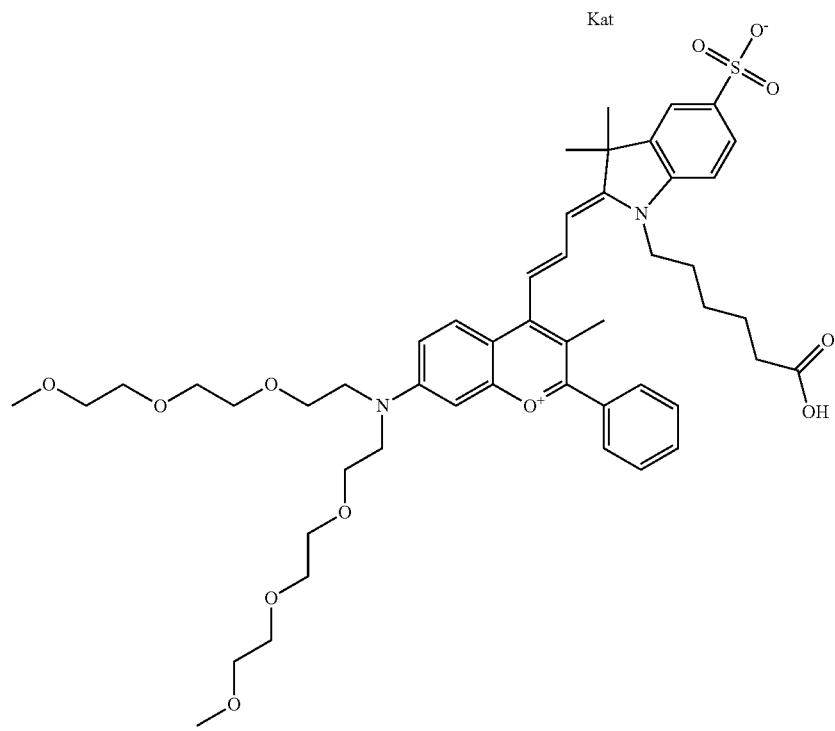

One non-limiting example of an activated compound according to general formula I is an NHS-ester of 682 Compound 2/3 (PEG₃), shown below:

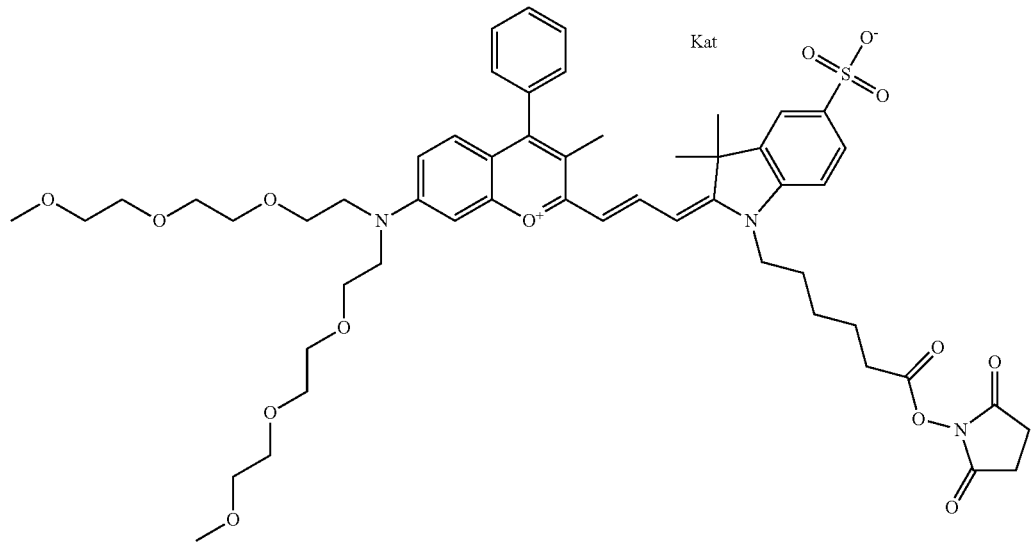

or according to general formula II shown below

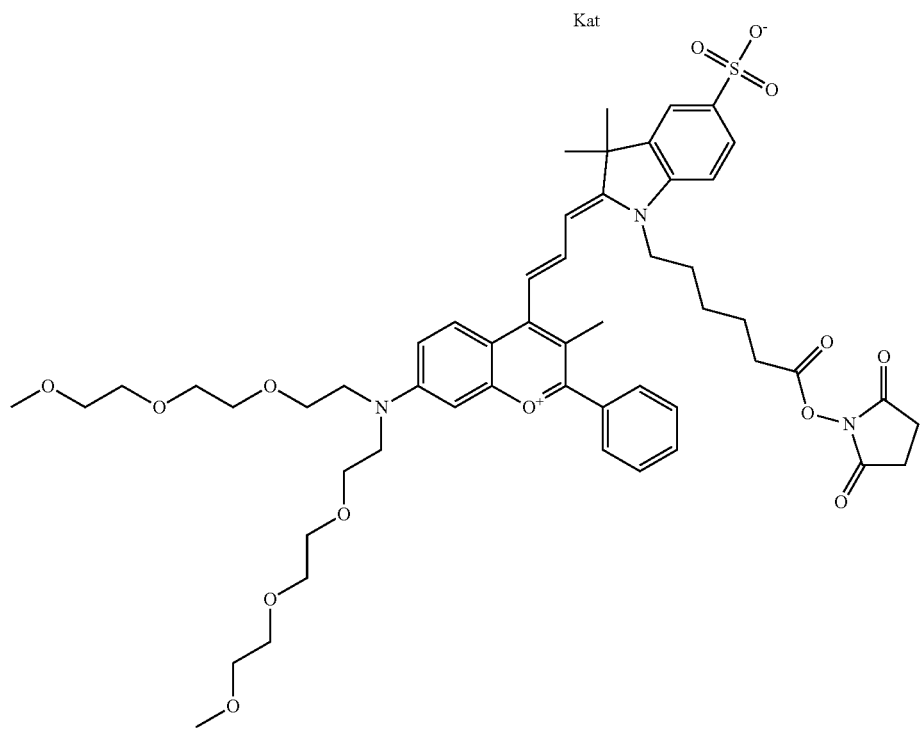

In one embodiment, the compound is 682 Compound 2/3 ((E)-1-(5-carboxypentyl)-2-((E)-3-(7-(di2,5,8,11-tetraoxatridecan-13-ylamino)-3-methyl-4-phenylchromenylium-2-yl)allylidene)-3,3-dimethylindoline-5-sulfonate), according to general formula I and shown below, which contains two polyethylene glycols (PEG₄) bound to the benzopyrylium by N, positions R2 and R3, i.e., a methylated polyethylene glycol, and —COOH at R10:

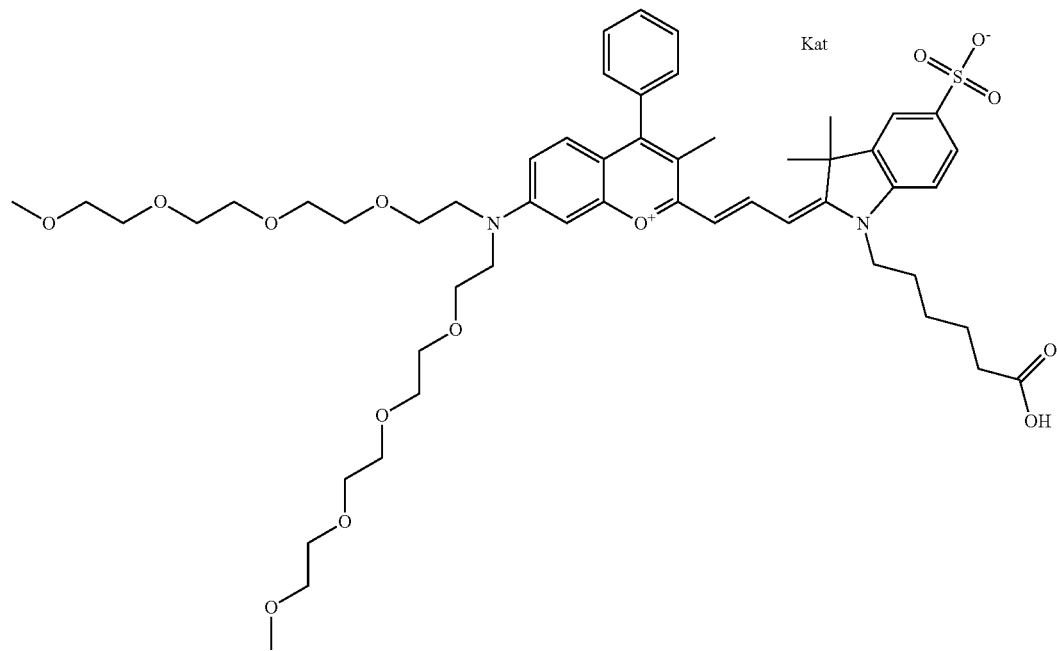
or according to general formula II shown below
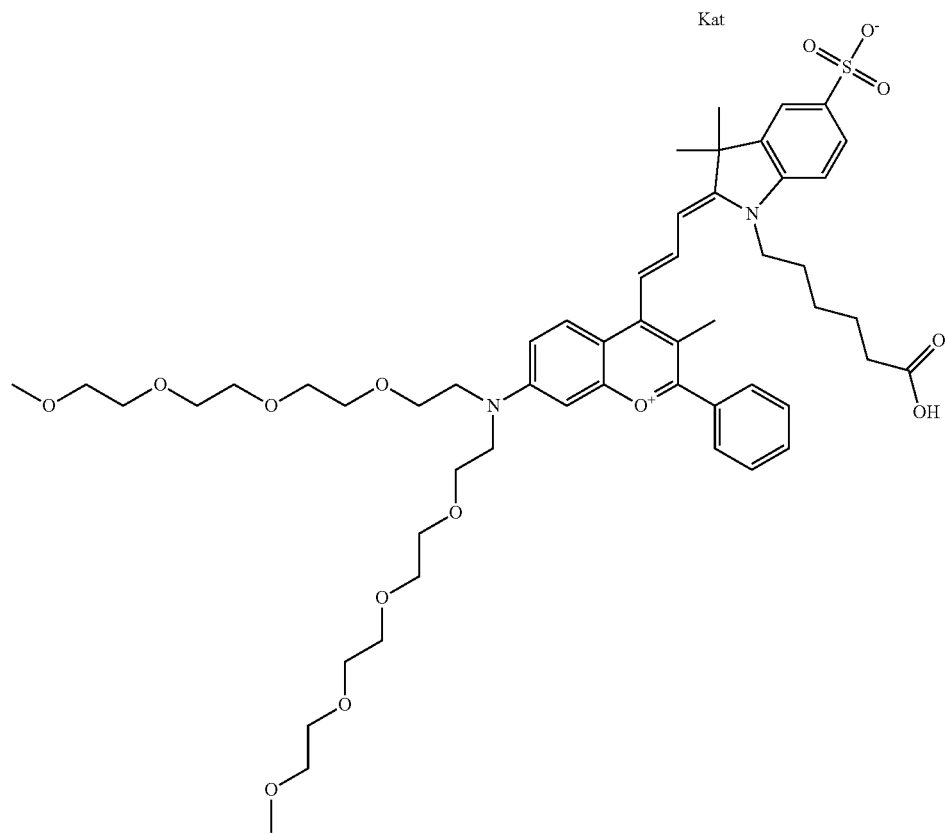

One non-limiting example of an activated compound according to general formula I is an NHS-ester of 682 Compound 2/3 (PEG$_4$), shown below:

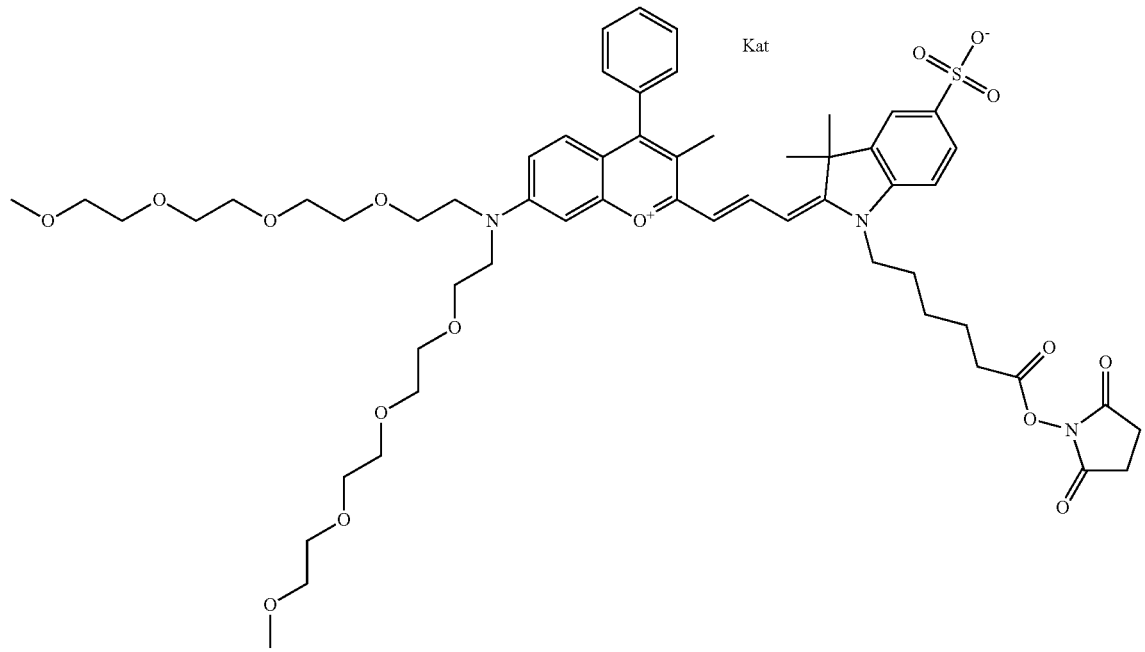

or according to general formula II shown below

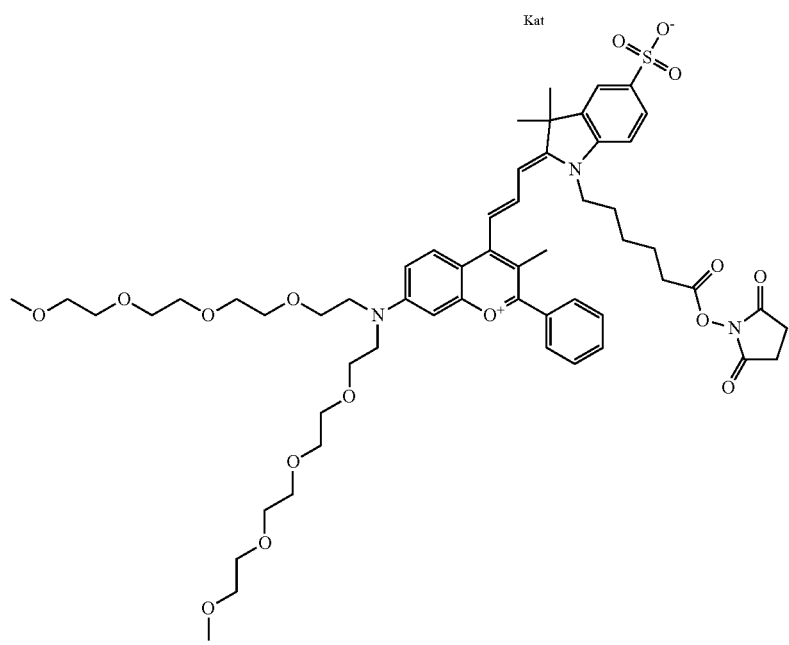

In one embodiment, the compound is 682 Compound 2/3 ((E)-1-(5-carboxypentyl)-2-((E)-3-(7-(di2,5,8,11,14-pentaoxahexadecan-16-ylamino)-3-methyl-4-phenylchromenylium-2-yl)allylidene)-3,3-dimethylindoline-5-sulfonate), according to general formula I and shown below, which contains two polyethylene glycols (PEG$_5$) bound to the benzopyrylium by N, positions R2 and R3, i.e., a methylated polyethylene glycol, and —COOH at R10:

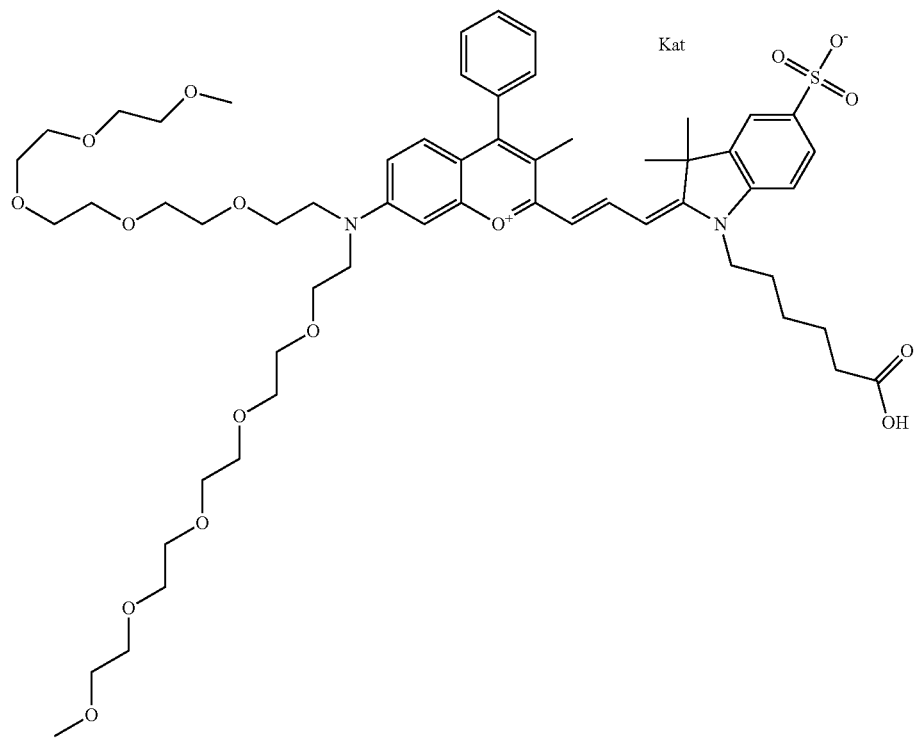
or according to general formula II shown below
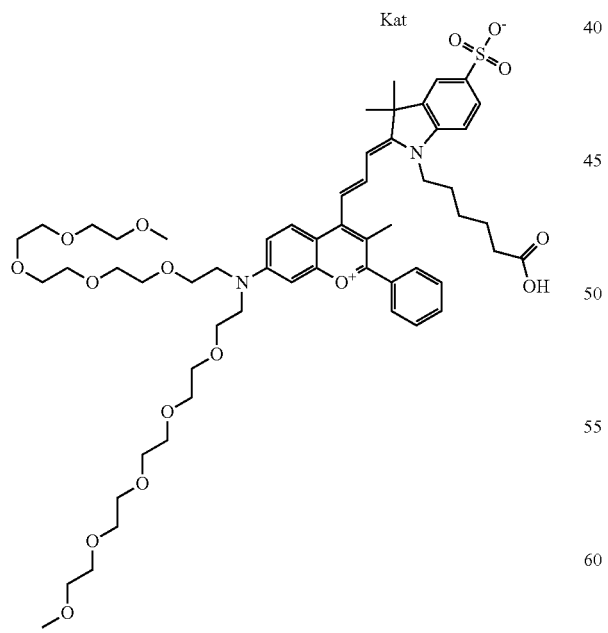
One non-limiting example of an activated compound according to general formula I is an NHS-ester of 682 Compound 2/3 (PEG$_5$), shown below:

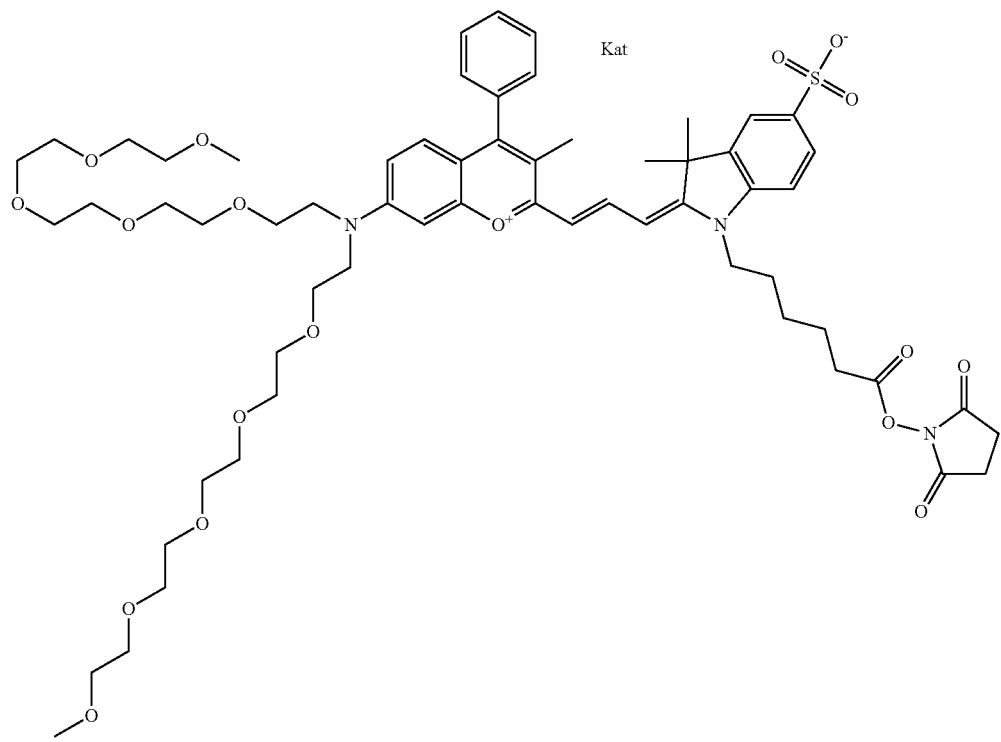

or according to general formula II shown below

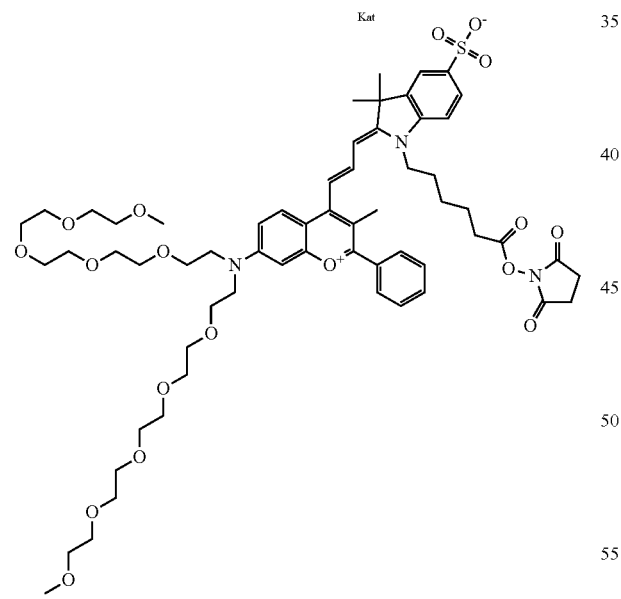

In one embodiment, the compound is 682 Compound 2/3 ((E)-1-(5-carboxypentyl)-2-((E)-3-(7-(di2,5,8,11,14,17-hexaoxanonadecan-19-ylamino)-3-methyl-4-phenyl-chromenylium-2-yl)allylidene)-3,3-dimethylindoline-5-sulfonate), according to general formula I and shown below, which contains two polyethylene glycols (PEG$_6$) bound to the benzopyrylium by N, positions R2 and R3, i.e., a methylated polyethylene glycol, and —COOH at R10:

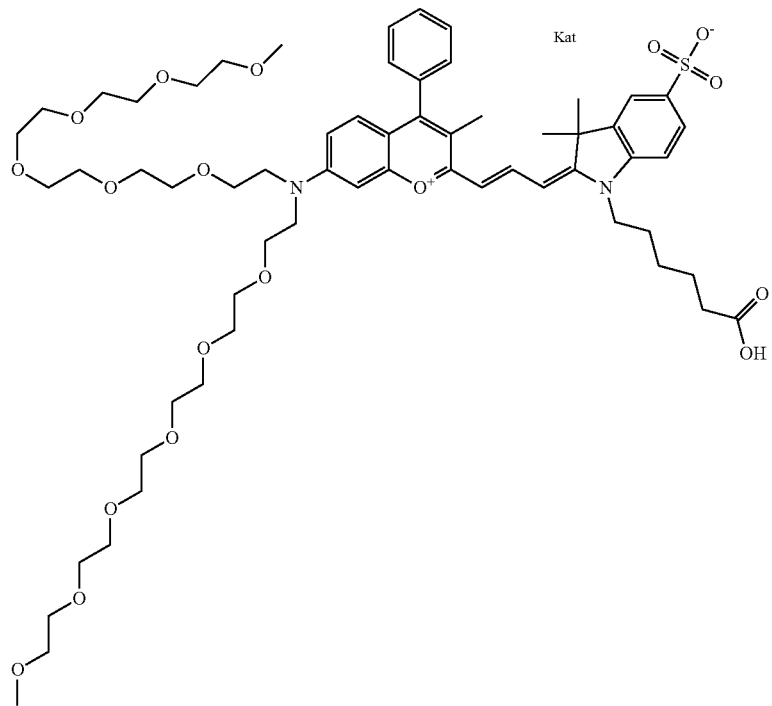
or according to general formula II shown below
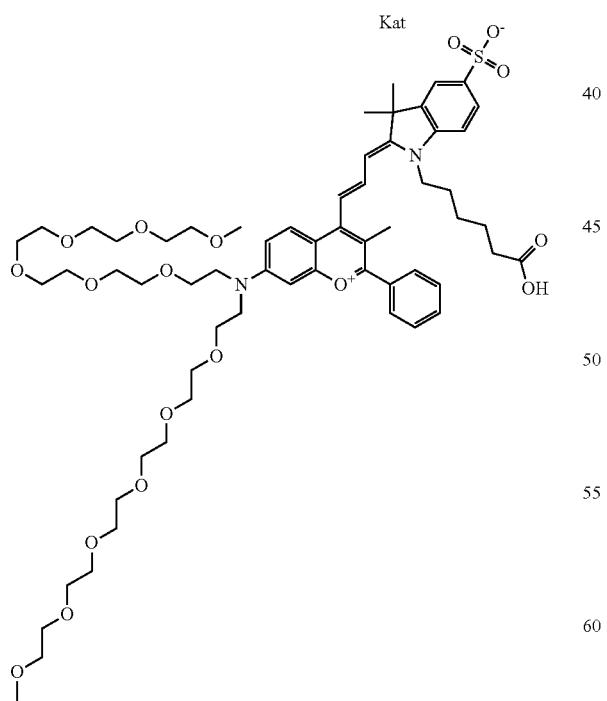
One non-limiting example of an activated compound according to general formula I is an NHS-ester of 682 Compound 2/3 (PEG$_6$), shown below:

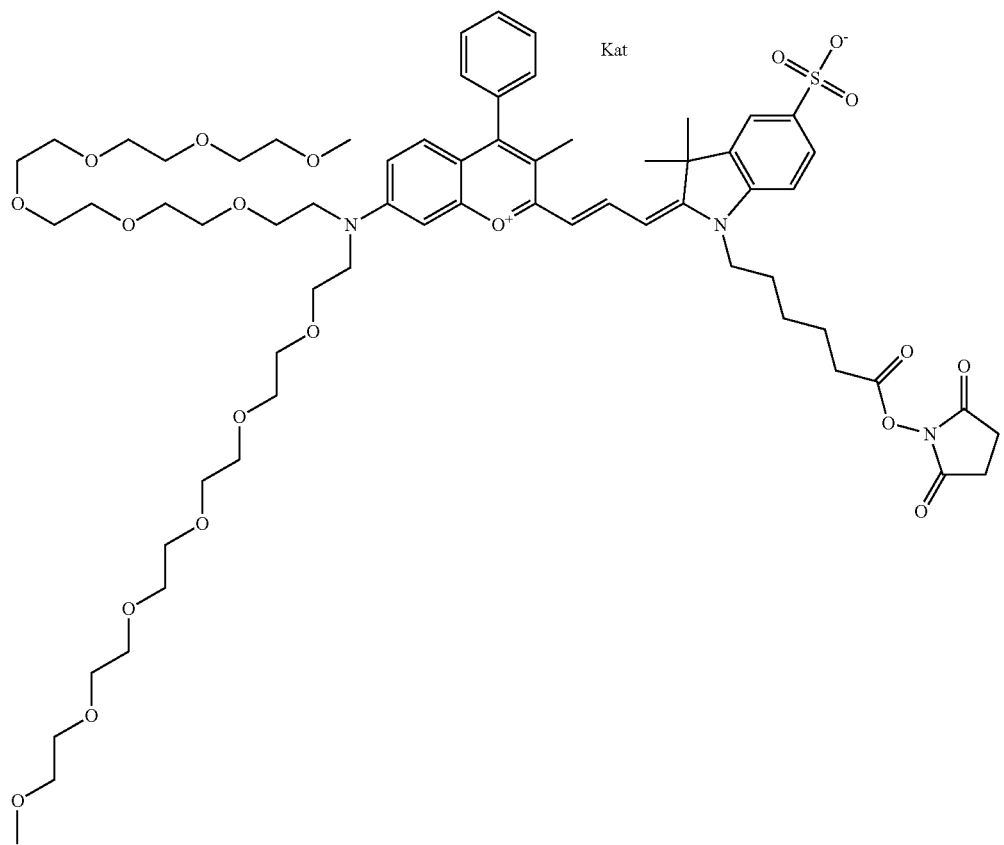

or according to general formula II shown below

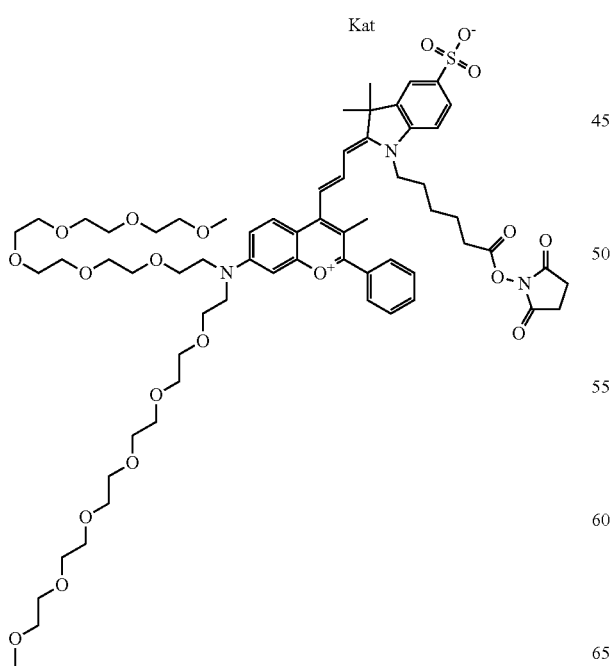

In one embodiment, the compound is 682 Compound 2/3 ((E)-2-((E)-3-(7-(bis(2-methoxyethyl)amino)-3-methyl-4-phenylchromenylium-2-yl)allylidene)-3-(3-carboxypropyl)-3-methyl-1-(3-sulfonatopropyl)indoline-5-sulfonate), according to general formula I and shown below, which contains two polyethylene glycols ($PEG_1$) bound to the benzopyrylium by N, positions R2 and R3, i.e., a methylated polyethylene glycol, with a monomethine linker connecting the benzopyrylium with the indole group, and —COOH at R13:

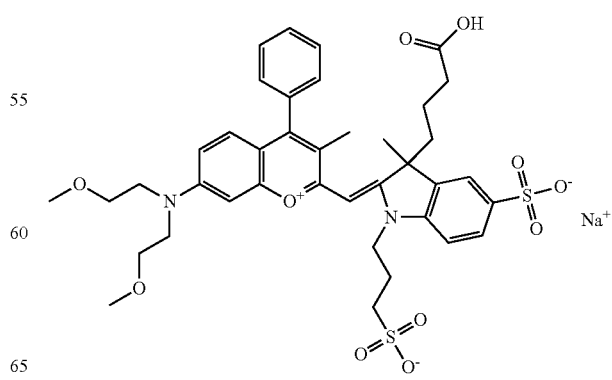

or according to general formula II shown below

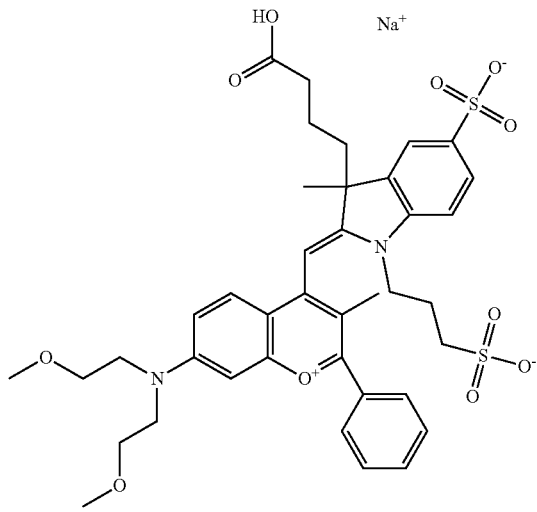

In one embodiment, the compound is 682 Compound 2/3 ((E)-2-((E)-3-(7-(bis(2-methoxyethyl)amino)-3-methyl-4-phenylchromenylium-2-yl)allylidene)-3-(3-carboxypropyl)-3-methyl-1-(3-sulfonatopropyl)indoline-5-sulfonate), according to general formula I and shown below, which contains two polyethylene glycols ($PEG_1$) bound to the benzopyrylium by N, positions R2 and R3, i.e., a methylated polyethylene glycol, with a trimethine linker connecting the benzopyrylium with the indole group, and —COOH at R13:

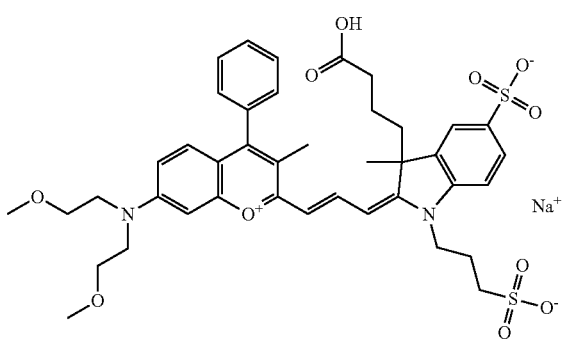

or according to general formula II shown below

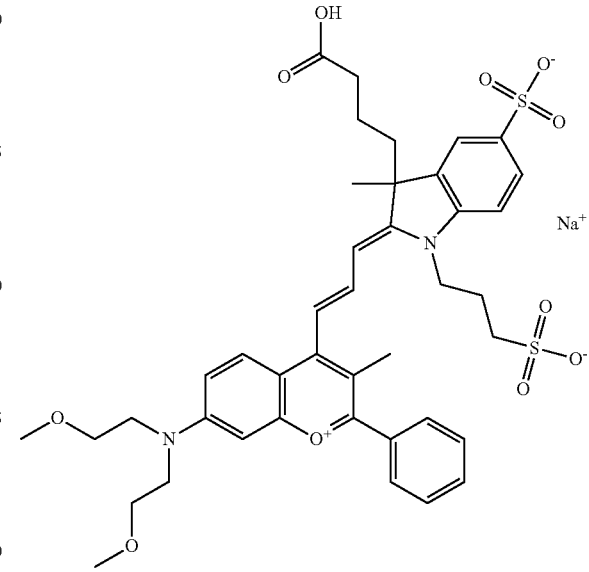

In one embodiment, the compound is 682 Compound 2/3 ((E)-2-((2E,4E)-5-(7-(bis(2-methoxyethyl)amino)-3-methyl-4-phenylchromenylium-2-yl)penta-2,4-dienylidene)-3-(3-carboxypropyl)-3-methyl-1-(3-sulfonatopropyl)indoline-5-sulfonate), according to general formula I and shown below, which contains two polyethylene glycols ($PEG_1$) bound to the benzopyrylium by N, positions R2 and R3, i.e., a methylated polyethylene glycol, with a pentamethine linker connecting the benzopyrylium with the indole group, and —COOH at R13:

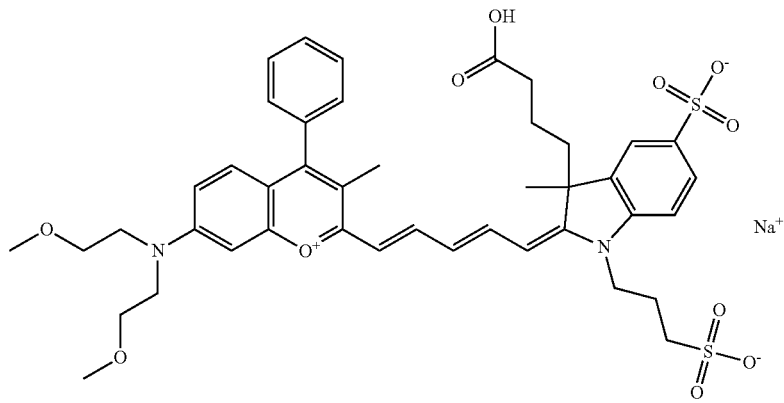

or according to general formula II shown below or according to general formula II shown below

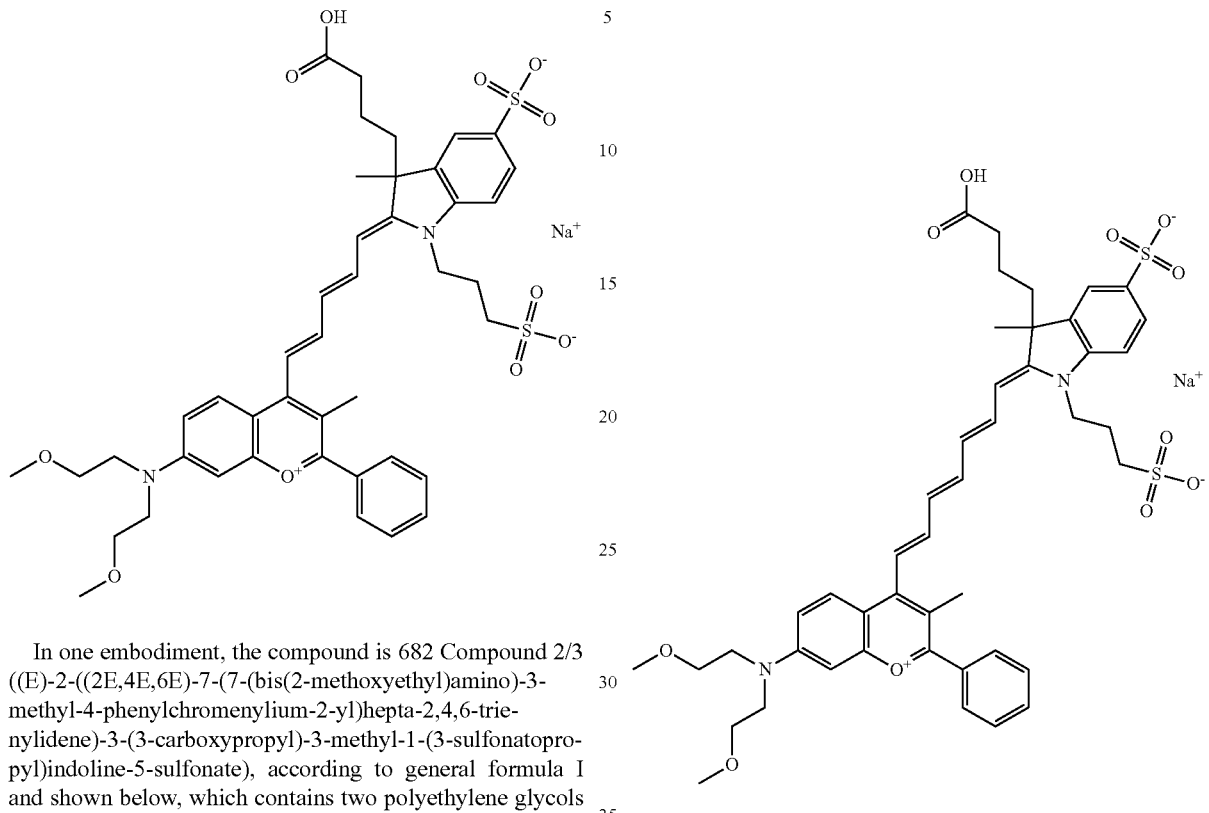

In one embodiment, the compound is 682 Compound 2/3 ((E)-2-((2E,4E,6E)-7-(7-(bis(2-methoxyethyl)amino)-3-methyl-4-phenylchromenylium-2-yl)hepta-2,4,6-trienylidene)-3-(3-carboxypropyl)-3-methyl-1-(3-sulfonatopropyl)indoline-5-sulfonate), according to general formula I and shown below, which contains two polyethylene glycols (PEG$_1$) bound to the benzopyrylium by N, positions R2 and R3, i.e., a methylated polyethylene glycol, with a heptamethine linker connecting the benzopyrylium with the indole group, and —COOH at R13:

One non-limiting example of an activated compound according to general formula I is an NHS-ester of 682 Compound 2/3 (PEG$_1$), shown below:

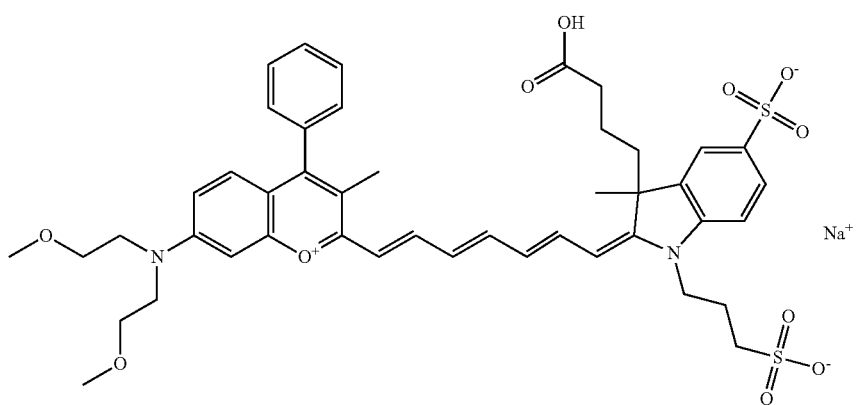

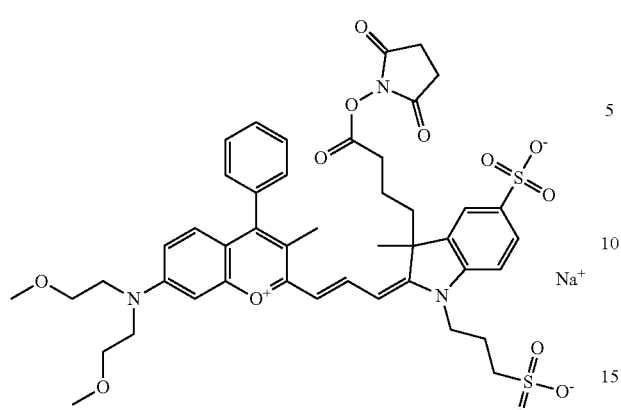

In one embodiment, the compound is 682 Compound 1, according to general formula I and shown below, which contains an ethylene glycol (PEG$_1$) on an aromatic ring position of the benzopyrylium, position R1, i.e., a methylated ethylene glycol, via a sulfonamide linker, and —COOH at R10:

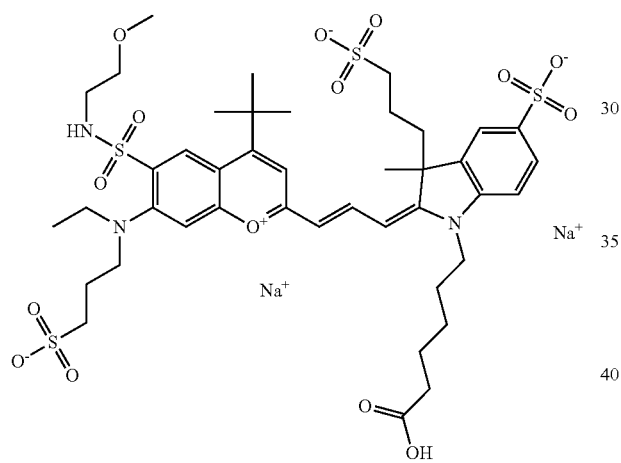

or according to general formula II shown below

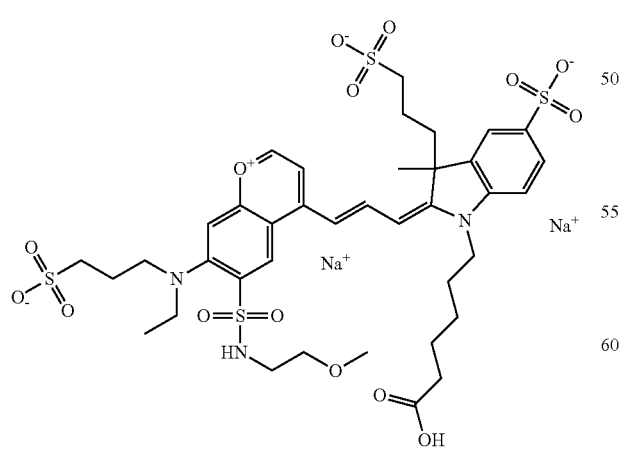

In one embodiment, the compound is 682 Compound 1, according to general formula I and shown below, which contains an ethylene glycol (PEG$_1$) on an aromatic ring position of the benzopyrylium, position R1, i.e., a methylated ethylene glycol, via a carboxamide linker, and —COOH at R10:

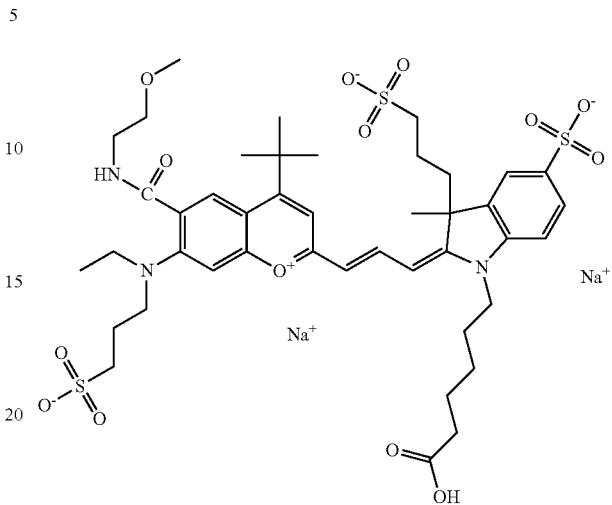

or according to general formula II shown below

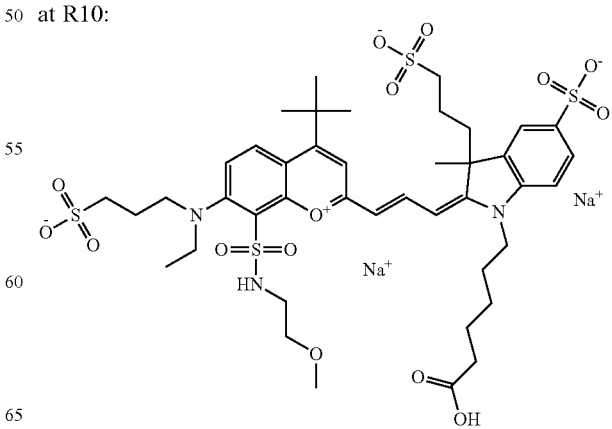

In one embodiment, the compound is 682 Compound 4, according to general formula I and shown below, which contains an ethylene glycol (PEG$_1$) on an aromatic ring position of the benzopyrylium, position R4, i.e., a methylated ethylene glycol, via a sulfonamide linker, and —COOH at R10:

or according to general formula II shown below

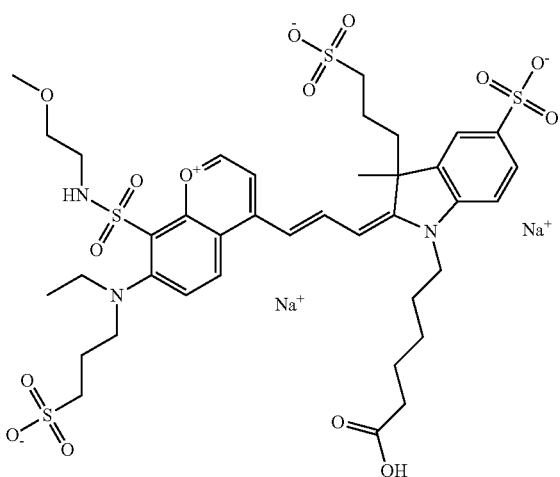

In one embodiment, the compound is 682 Compound 4, according to general formula I and shown below, which contains an ethylene glycol (PEG$_1$) on an aromatic ring position of the benzopyrylium, position R4, i.e., a methylated ethylene glycol, via a carboxamide linker, and —COOH at R10:

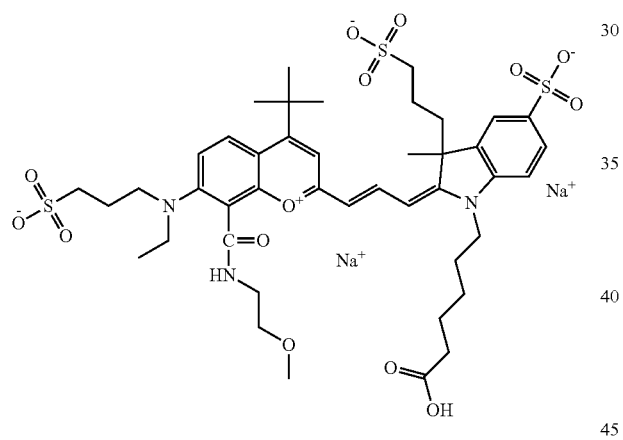

or according to general formula II shown below

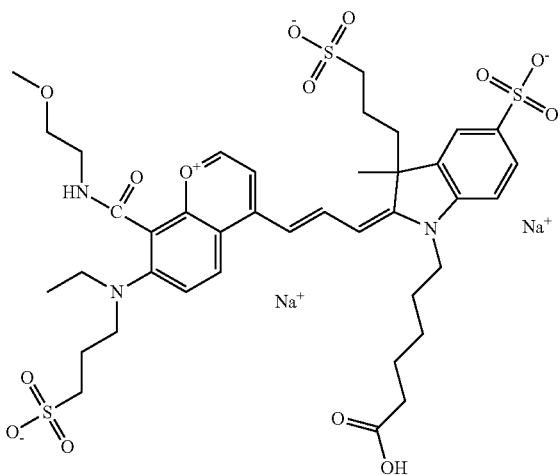

In one embodiment, the compound is 682 Compound 11, according to general formula I and shown below, which contains an ethylene glycol (PEG$_1$) on an aromatic ring position of the indole, position R11, i.e., a methylated ethylene glycol, by a sulfonamide linker, and —COOH at R10:

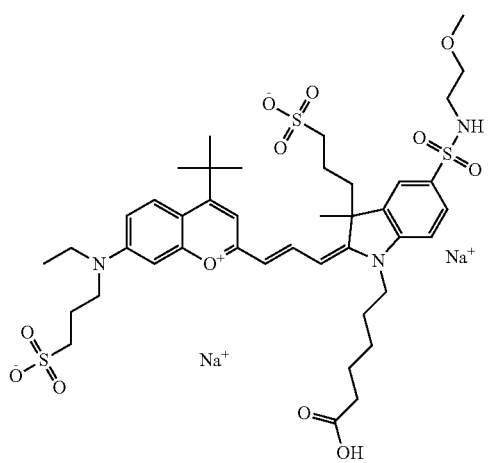

or according to general formula II shown below

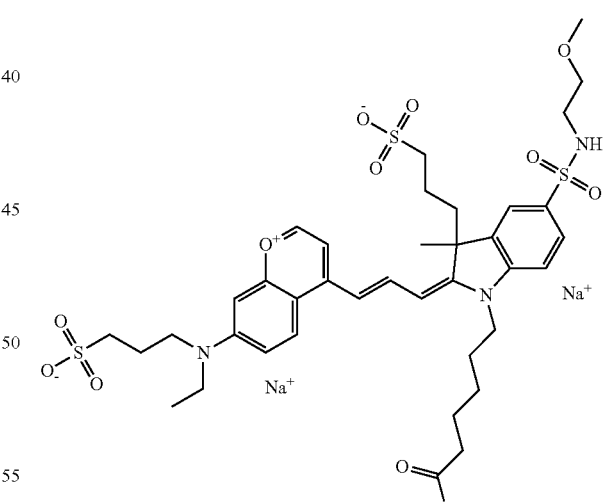

In one embodiment, the compound is 682 Compound 11, according to general formula I and shown below, which contains an ethylene glycol (PEG$_1$) on an aromatic ring position of the indole, position R11, i.e., a methylated ethylene glycol, by a carboxamide linker, and —COOH at R10:

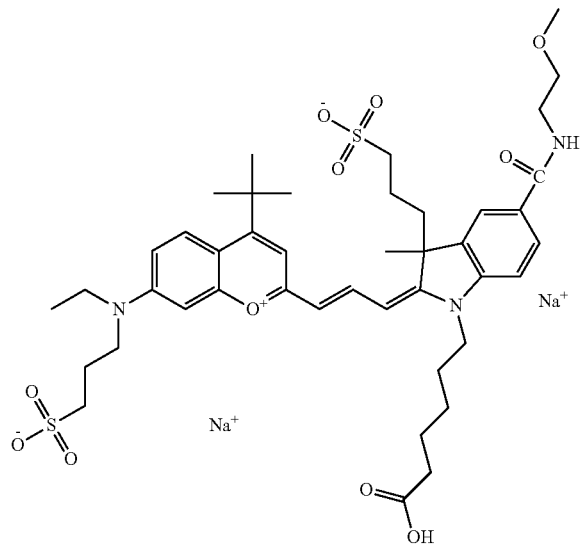

or according to general formula II shown below

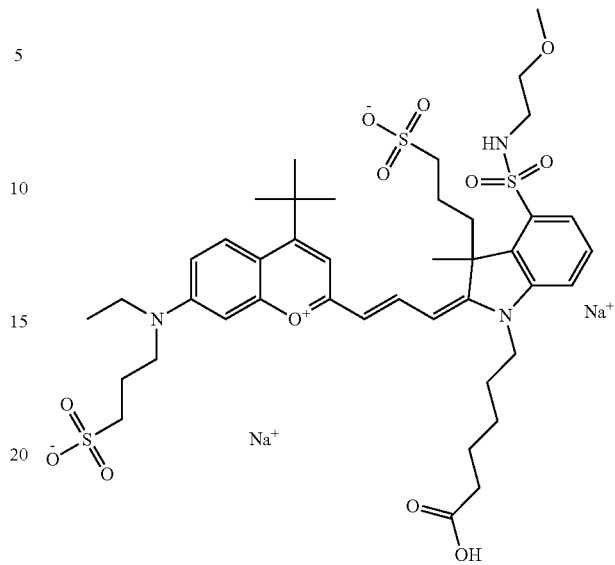

or according to general formula II shown below

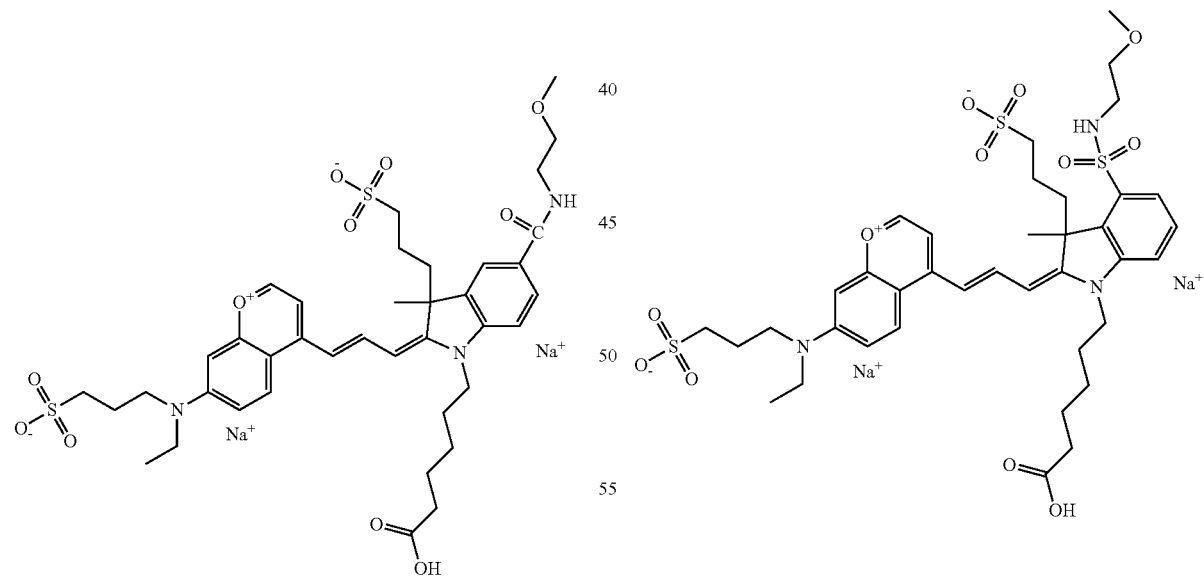

In one embodiment, the compound is 682 Compound 12, according to general formula I and shown below, which contains an ethylene glycol (PEG$_1$) on an aromatic ring position of the indole, position R12, i.e., a methylated ethylene glycol, by a sulfonamide linker, and —COOH at R10:

In one embodiment, the compound is 682 Compound 12, according to general formula I and shown below, which contains an ethylene glycol (PEG$_1$) on an aromatic ring position of the indole, position R12, i.e., a methylated ethylene glycol, via a carboxamide linker, and —COOH at R10:

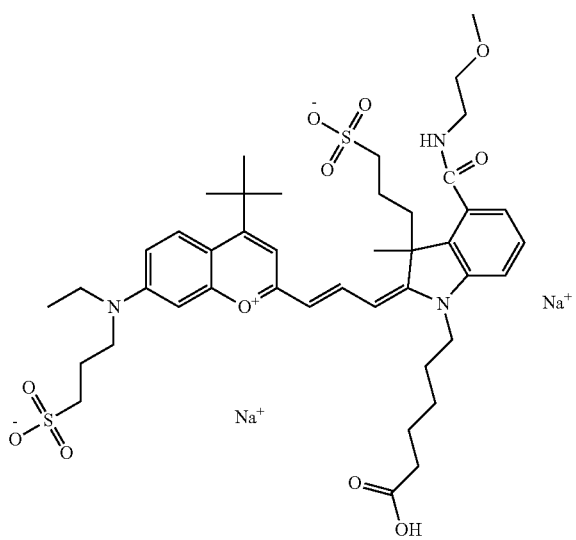

or according to general formula II shown below

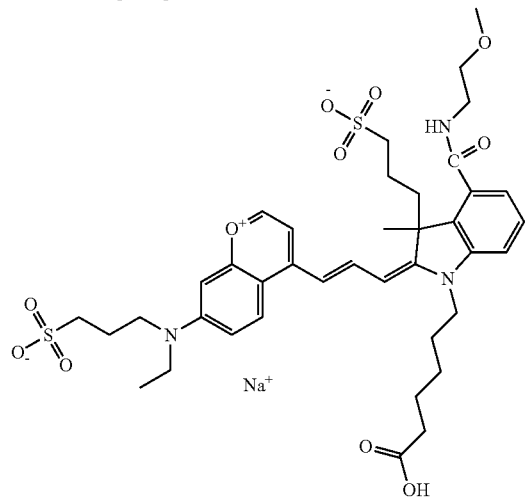

In one embodiment, the compound is 682 Compound 13, according to general formula I and shown below, which contains an ethylene glycol (PEG$_1$) on a ring position of the indole, position R13, i.e., a methylated ethylene glycol, and —COOH at R10:

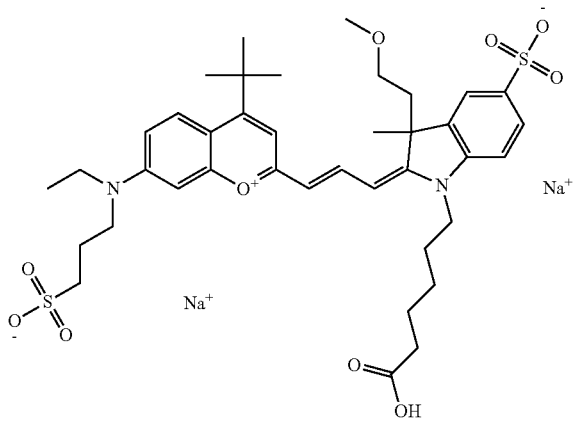

or according to general formula II shown below

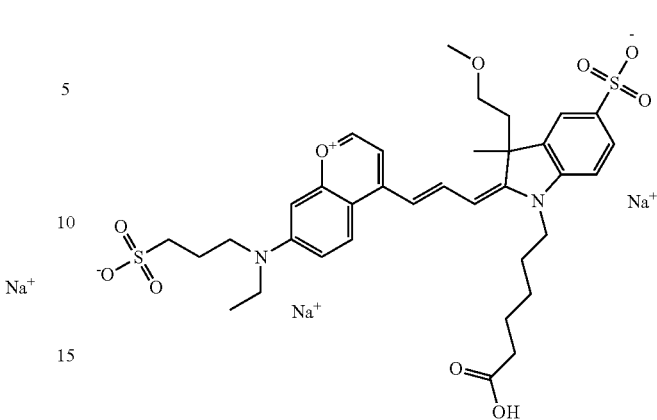

In one embodiment, the compound is 682 Compound 13, according to general formula I and shown below, which contains an diethylene glycol (PEG$_2$) on a ring position of the indole, position R13, i.e., a methylated diethylene glycol, and —COOH at R10:

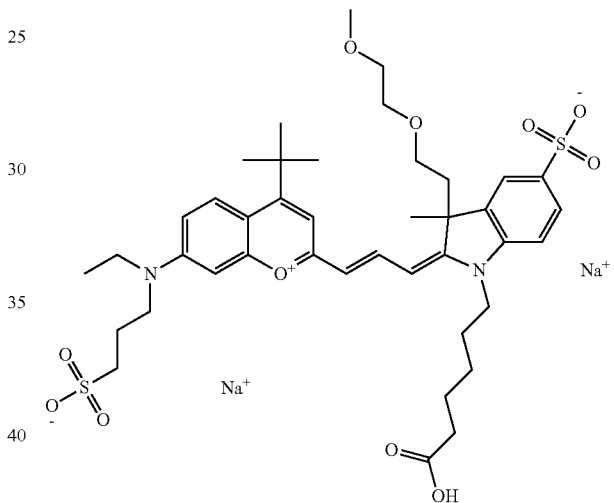

or according to general formula II shown below

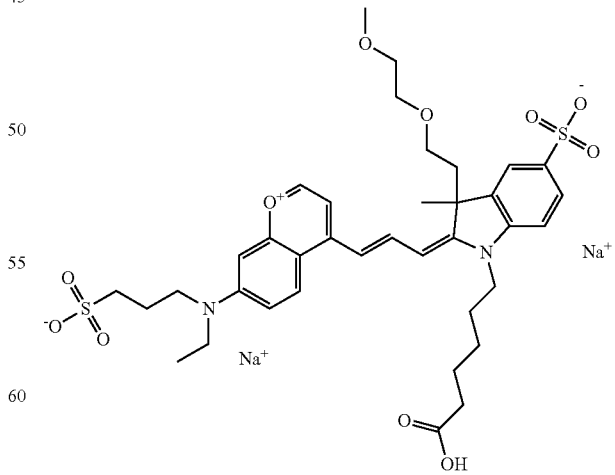

In one embodiment, the compound is 682 Compound 13, according to general formula I and shown below, which contains an polyethylene glycol (PEG$_3$) on a ring position of the indole, position R13, i.e., a methylated polyethylene glycol, and —COOH at R10:

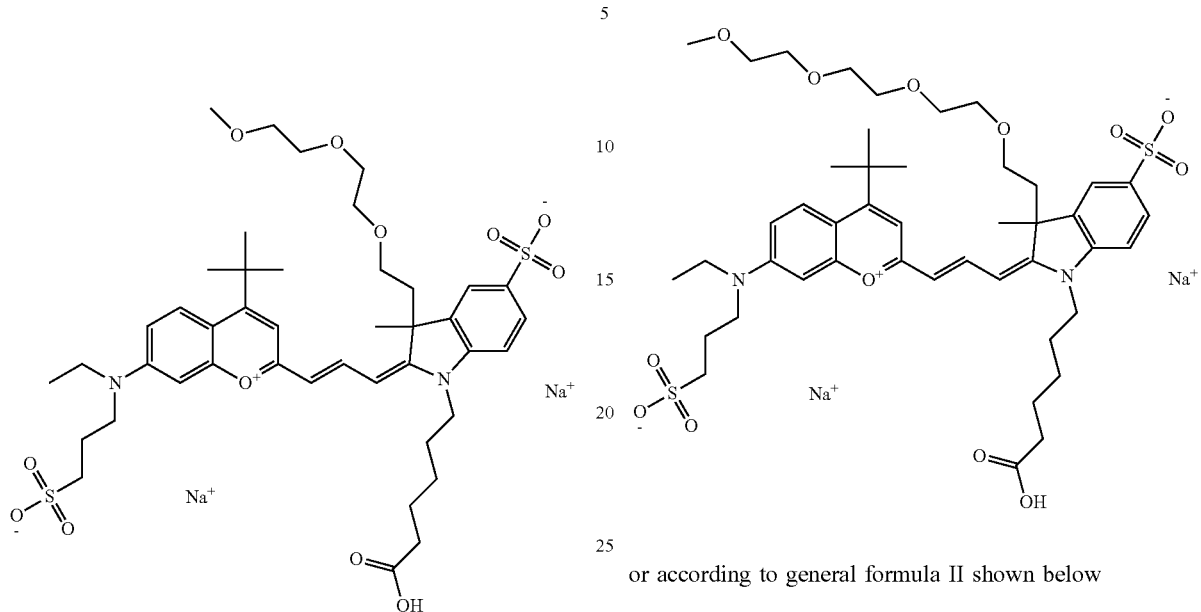

or according to general formula II shown below

In one embodiment, the compound is 682 Compound 13, according to general formula I and shown below, which contains an polyethylene glycol (PEG$_4$) on a ring position of the indole, position R13, i.e., a methylated polyethylene glycol, and —COOH at R10:

In one embodiment, the compound is 682 Compound 13, according to general formula I and shown below, which contains an polyethylene glycol (PEG$_5$) on a ring position of the indole, position R13, i.e., a methylated polyethylene glycol, and —COOH at R10:

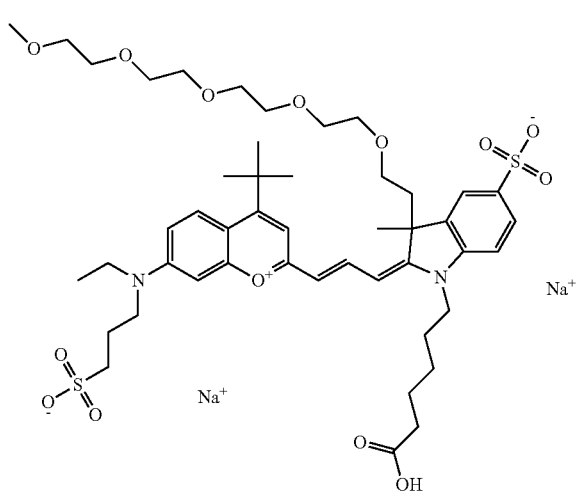
or according to general formula II shown below
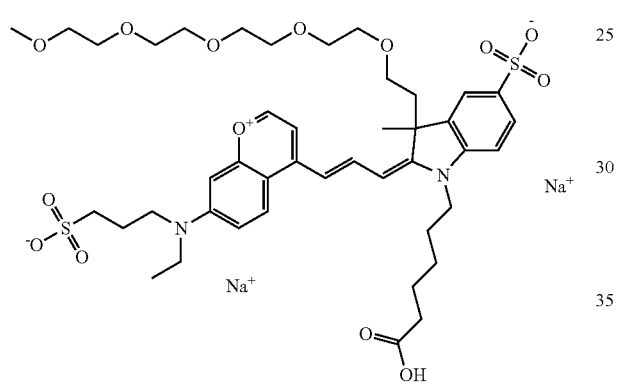
In one embodiment, the compound is 682 Compound 13, according to general formula I and shown below, which contains an polyethylene glycol (PEG$_6$) on a ring position of the indole, position R13, i.e., a methylated polyethylene glycol, and —COOH at R10:
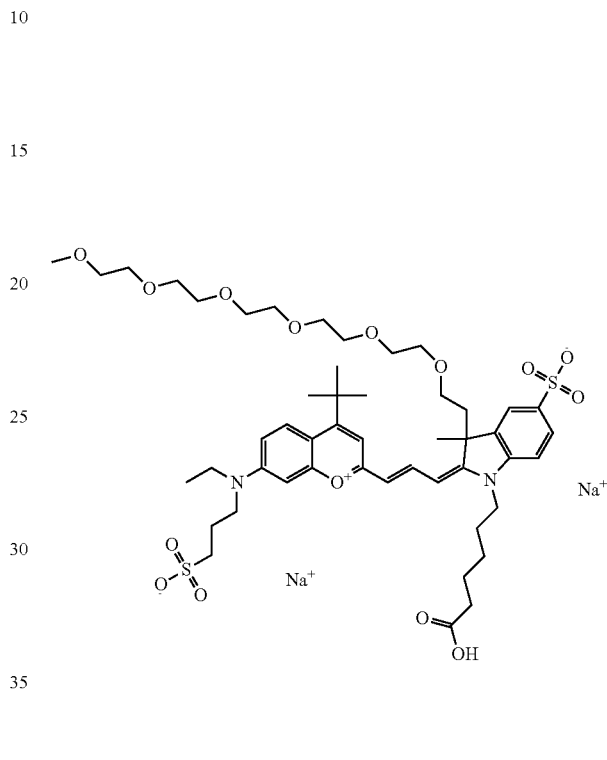
or according to general formula II shown below
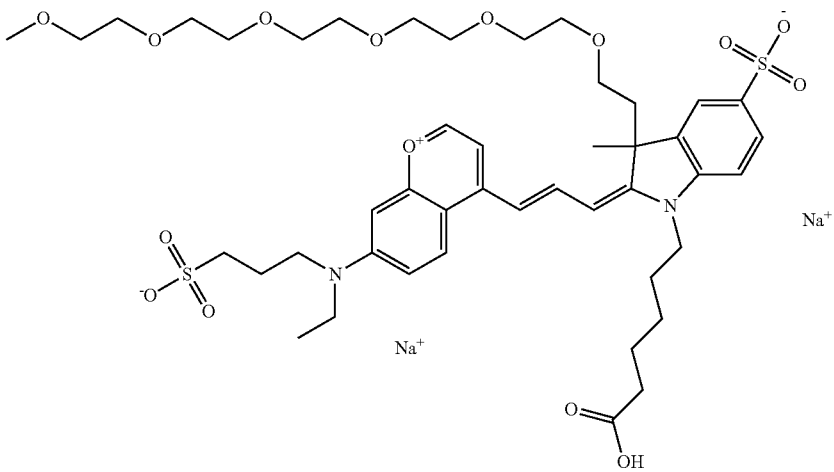

In one embodiment, the compound is 682 Compound 13, shown below, which contains an ethylene glycol (PEG$_1$) on a N-ring position of the indole, position R13, i.e., a methylated ethylene glycol, via a sulfonamide linker, and —COOH at R10.

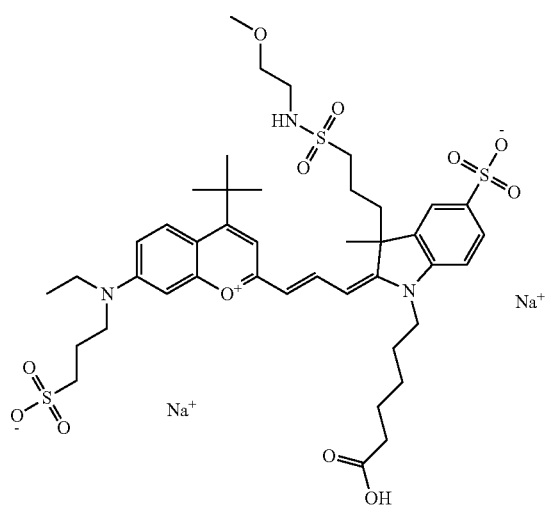 [SMILES: CCN(CCCS(=O)(=O)O)c1ccc2c(C(C)(C)C)cc(/C=C/C=C3/N(CCCCCC(=O)O)c4ccc(S(=O)(=O)O)cc4C3(C)CCCS(=O)(=O)NCCOC)[o+]c2c1 ; [Na+] ; [Na+]]

In one embodiment, the compound is 682 Compound 13, shown below, which contains an ethylene glycol (PEG$_1$) on a N-ring position of the indole, position R13, i.e., a methylated ethylene glycol, via a carboxamide linker, and —COOH at R10.

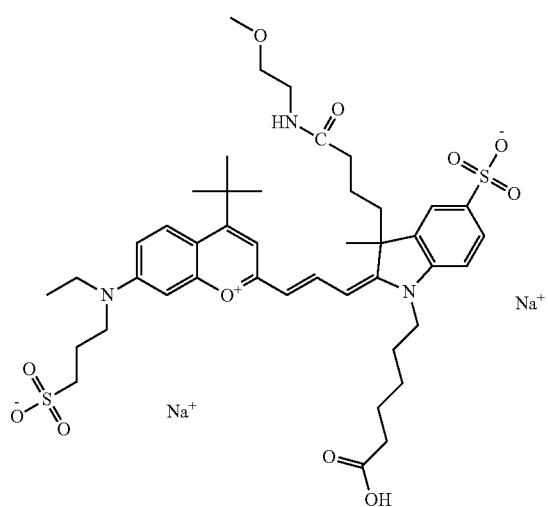 [SMILES: CCN(CCCS(=O)(=O)O)c1ccc2c(C(C)(C)C)cc(/C=C/C=C3/N(CCCCCC(=O)O)c4ccc(S(=O)(=O)O)cc4C3(C)CCCC(=O)NCCOC)[o+]c2c1 ; [Na+] ; [Na+]]

In one embodiment, the compound is 682 Compound 2/3/10, shown below, which contains two ethylene glycols (PEG$_1$) bound to the benzopyrylium by N, positions R2 and R3, i.e., a methylated ethylene glycol, and ethylene glycol at R10 that terminates in —COOH.

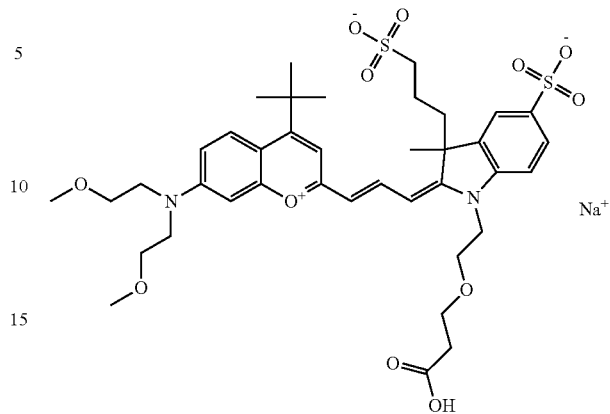

In one embodiment, the compound is 682 Compound 2/3/10/13, shown below, which contains two ethylene glycols (PEG$_1$) bound to the benzopyrylium by N, positions R2 and R3, i.e., a methylated ethylene glycol, ethylene glycol at R10 that terminates in —COOH, and ethylene glycol, i.e., a methylated ethylene glycol, at R13.

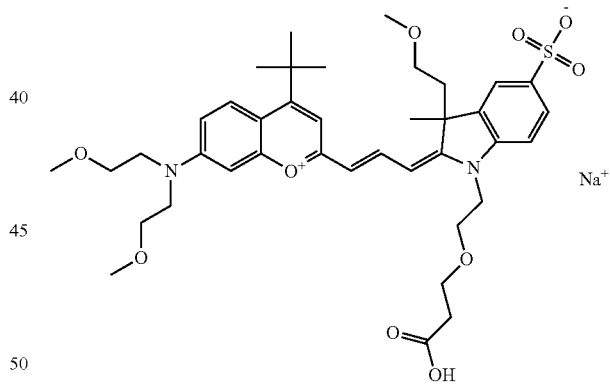

In one embodiment, the compound is 682 Compound 2 ((E)-2-((2E,4E,6E)-7-(7-(bis(2-methoxyethyl)amino)-3-methyl-4-phenylchromenylium-2-yl)hepta-2,4,6-trienylidene)-3-(3-carboxypropyl)-3-methyl-1-(3-sulfonatopropyl)indoline-5-sulfonate), according to general formula I and shown below, which contains a polyethylene glycol (PEG$_1$) bound to the benzopyrylium by N, at position R2, i.e., a methylated polyethylene glycol, sulfoalkyl at position R3, with a pentamethine linker connecting the benzopyrylium with the indole group, and —COOH at R13:

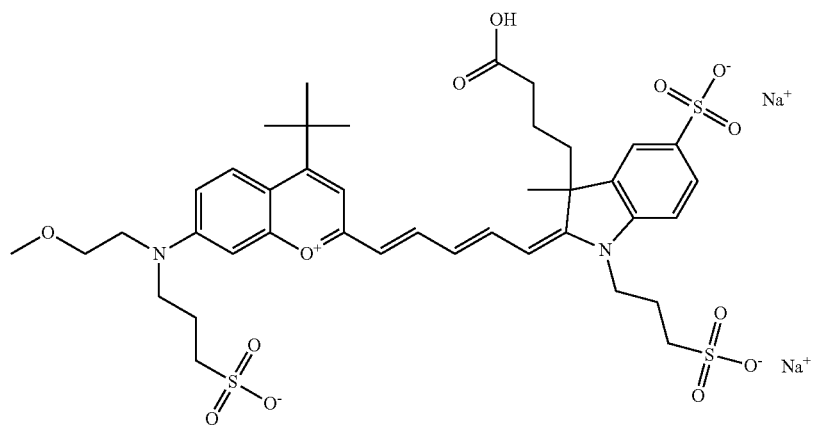

One non-limiting example of an activated compound according to general formula I is an NHS-ester of 682 Compound 2 (PEG$_1$), shown below:

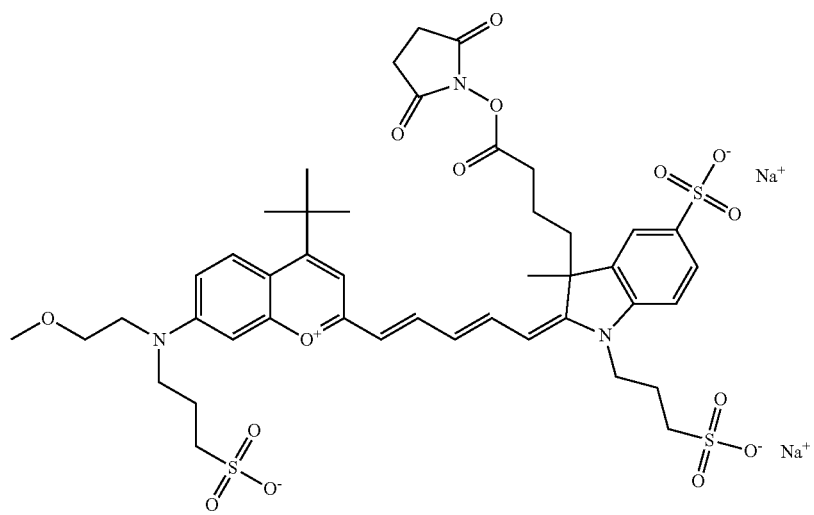

In one embodiment, the compound is 682 Compound 3 ((E)-2-((E)-3-(4-tert-butyl-7-(ethyl(2-methoxyethyl)amino) chromenylium-2-yl)allylidene)-1-(5-carboxypentyl)-3,3-dimethylindoline-5-sulfonate), according to general formula I and shown below, which contains a polyethylene glycol (PEG$_1$) bound to the benzopyrylium by N, at position R3, i.e., a methylated polyethylene glycol, with a trimethine linker connecting the benzopyrylium with the indole group, methyl at R13 and R14, t-butyl at R6, and —COOH at R10 (V08-17084):

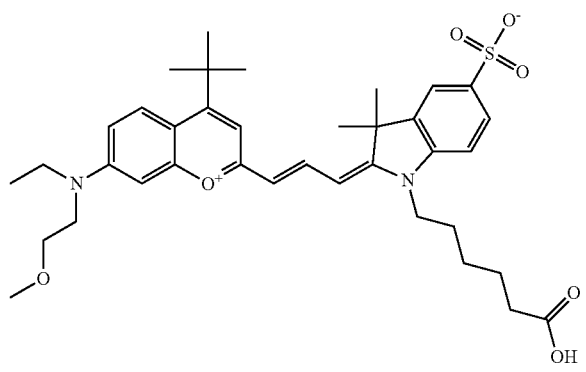 [SMILES: CCN(CCOC)c1ccc2c(C(C)(C)C)cc(/C=C/C=C3/N(CCCCCC(=O)O)c4ccc(S(=O)(=O)[O-])cc4C3(C)C)[o+]c2c1]

One non-limiting example of an activated compound according to general formula I is an NHS-ester of 682 Compound 3 (PEG$_1$), shown below:

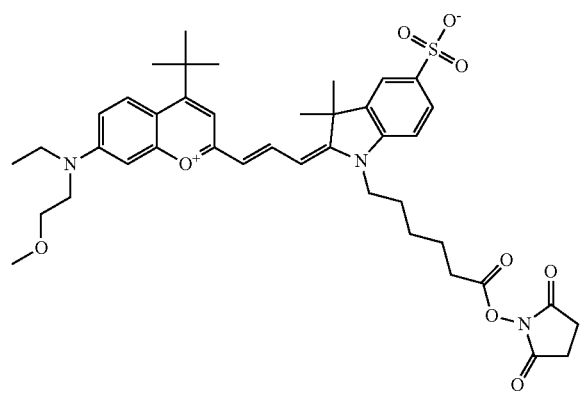

In one embodiment, the compound is 682 Compound 3 ((E)-2-((E)-3-(4-tert-butyl-7-(ethyl(2,5,8,11-tetraoxatridecan-13-yl)amino)chromenylium-2-yl)allylidene)-1-(5-carboxypentyl)-3,3-dimethylindoline-5-sulfonate), according to general formula I and shown below, which contains a polyethylene glycol (PEG$_4$) bound to the benzopyrylium by N, at position R3, i.e., a methylated polyethylene glycol, with a trimethine linker connecting the benzopyrylium with the indole group, methyl at R13 and R14, t-butyl at R6, and —COOH at R10:

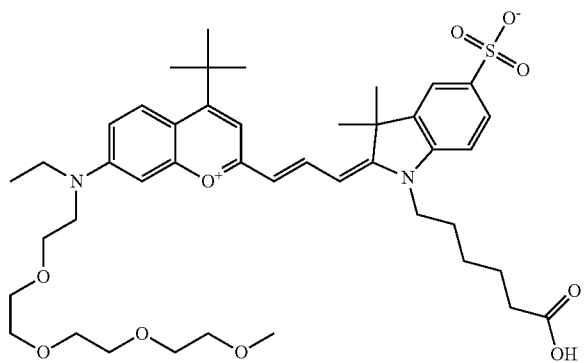

One non-limiting example of an activated compound according to general formula I is an NHS-ester of 682 Compound 3 (PEG$_4$), shown below:

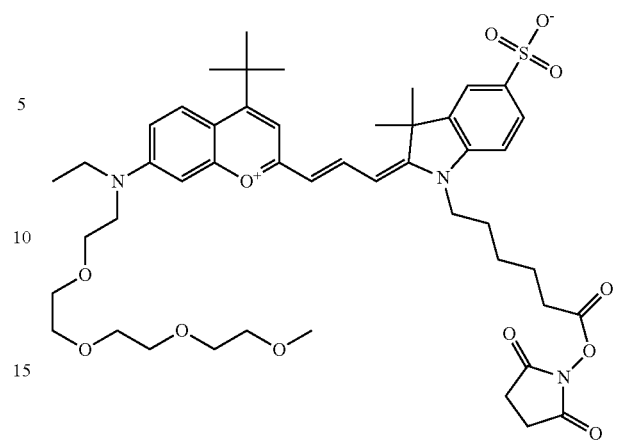

In one embodiment, the compound is 682 Compound 3 ((E)-2-((2E,4E)-5-(4-tert-butyl-7-(ethyl(2,5,8,11-tetraoxatridecan-13-yl)amino)chromenylium-2-yl)penta-2,4-dienylidene)-1-(5-carboxypentyl)-3,3-dimethylindoline-5-sulfonate), according to general formula I and shown below, which contains a polyethylene glycol (PEG$_4$) bound to the benzopyrylium by N, at position R3, i.e., a methylated polyethylene glycol, with a pentamethine linker connecting the benzopyrylium with the indole group, methyl at R13 and R14, t-butyl at R6, and —COOH at R10:

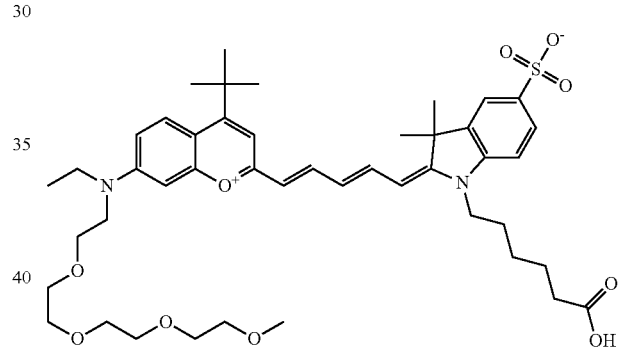

One non-limiting example of an activated compound according to general formula I is an NHS-ester of 682 Compound 3 (PEG$_4$), shown below:

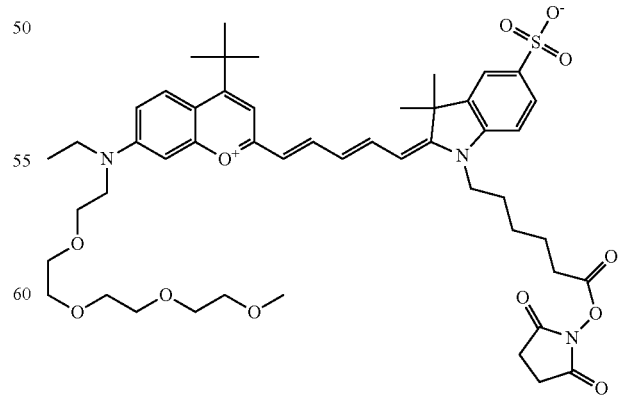

In one embodiment, the compound is 682 Compound 13 ((E)-2-((E)-3-(4-tert-butyl-7-(diethylamino)chromenylium- 2-yl)allylidene)-1-(5-carboxypentyl)-3-(2-methoxyethyl)-3-methylindoline-5-sulfonate), according to general formula I and shown below, which contains a polyethylene glycol (PEG$_1$) at position R13, i.e., a methylated polyethylene glycol, with a trimethine linker connecting the benzopyrylium with the indole group, methyl at R14, t-butyl at R6, and —COOH at R10:

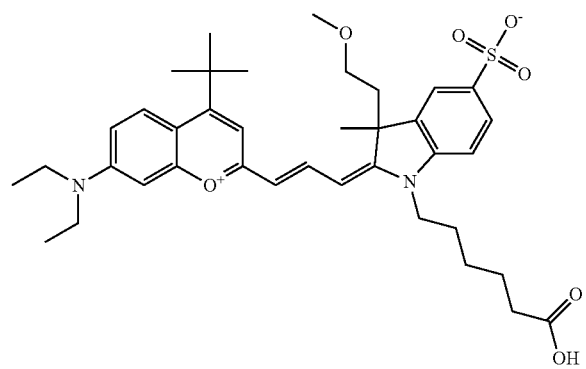

One non-limiting example of an activated compound according to general formula I is an NHS-ester of 682 Compound 13 (PEG$_1$), shown below:

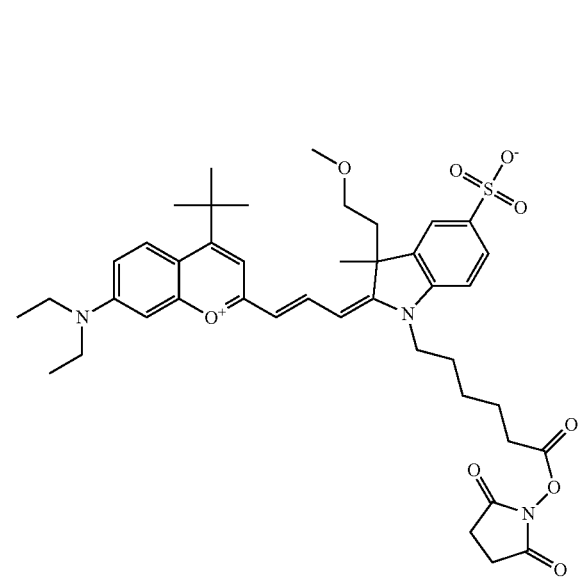

In one embodiment, the compound is 682 Compound 13 ((E)-2-((E)-3-(4-tert-butyl-7-(diethylamino)chromenylium-2-yl)allylidene)-1-(5-carboxypentyl)-3-methyl-3-(2,5,8,11-tetraoxatridecan-13-yl)indoline-5-sulfonate), according to general formula I and shown below, which contains a polyethylene glycol (PEG$_4$) at position R13, i.e., a methylated polyethylene glycol, with a trimethine linker connecting the benzopyrylium with the indole group, methyl at R14, t-butyl at R6, and —COOH at R10:

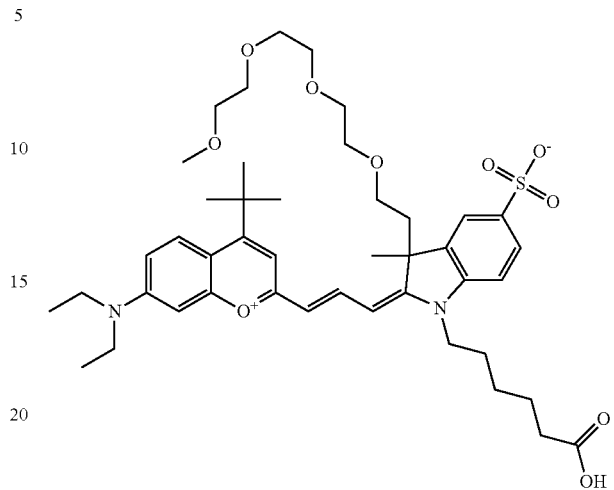

One non-limiting example of an activated compound according to general formula I is an NHS-ester of 682 Compound 13 (PEG$_4$), shown below:

In one embodiment, the compound is 682 Compound 13 ((E)-2-((2E,4E)-5-(4-tert-butyl-7-(diethylamino)chromenylium-2-yl)penta-2,4-dienylidene)-1-(5-carboxypentyl)-methyl-3-(2,5,8,11-tetraoxatridecan-13-yl)indoline-5-sulfonate), according to general formula I and shown below, which contains a polyethylene glycol (PEG$_4$) at position R13, i.e., a methylated polyethylene glycol, with a pentamethine linker connecting the benzopyrylium with the indole group, methyl at R14, t-butyl at R6, and —COOH at R10:

One non-limiting example of an activated compound according to general formula I is an NHS-ester of 682 Compound 13 (PEG₄), shown below:

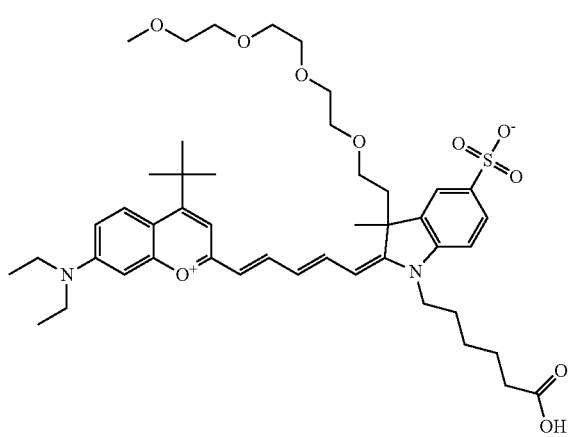

In one embodiment, the compound is 682 Compound 3 ((E)-3-(4-(2,5-dioxopyrrolidin-1-yloxy)-4-oxobutyl)-2-((9-(2-methoxyethyl)-6,8,8-trimethyl-2-phenyl-8,9-dihydropyrano[3,2-g]quinolin-1-ium-4-yl)methylene)-3-methyl-1-(3-sulfonatopropyl)indoline-5-sulfonate), according to general formula II and shown below, which contains a polyethylene glycol (PEG₁) bound to the benzopyrylium by N, at position R3, i.e., a methylated polyethylene glycol, R1 and R2 form a substituted ring, with a monomethine linker connecting the benzopyrylium with the indole group, and an NHS-ester at R13:

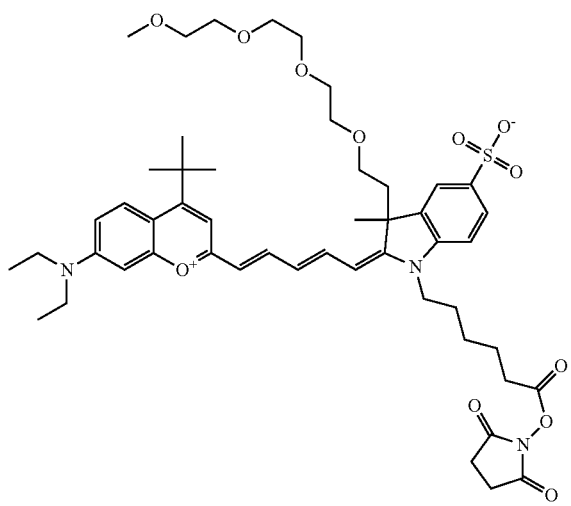 [SMILES: CCN(CC)c1ccc2c(C(C)(C)C)cc(/C=C/C=C/C=C3/N(CCCCCC(=O)ON4C(=O)CCC4=O)c4ccc(S(=O)(=O)[O-])cc4C3(C)CCOCCOCCOCCOC)[o+]c2c1]

In one embodiment, the compound is 682 Compound 3, according to general formula II and shown below, which contains a polyethylene glycol (PEG₂) bound to the benzopyrylium by N, at position R3, i.e., a methylated polyethylene glycol, R1 and R2 form a substituted ring, with a monomethine linker connecting the benzopyrylium with the indole group, and an NHS-ester at R13:

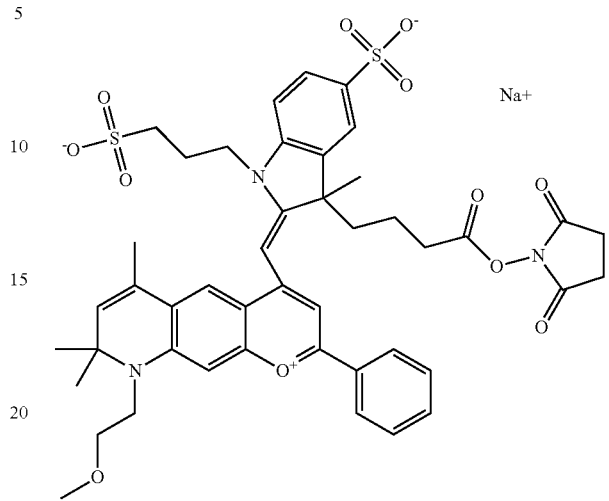

In one embodiment, the compound is 682 Compound 3, according to general formula II and shown below, which contains a polyethylene glycol (PEG₃) bound to the benzopyrylium by N, at position R3, i.e., a methylated polyethylene glycol, R1 and R2 form a substituted ring, with a monomethine linker connecting the benzopyrylium with the indole group, and an NHS-ester at R13:

161

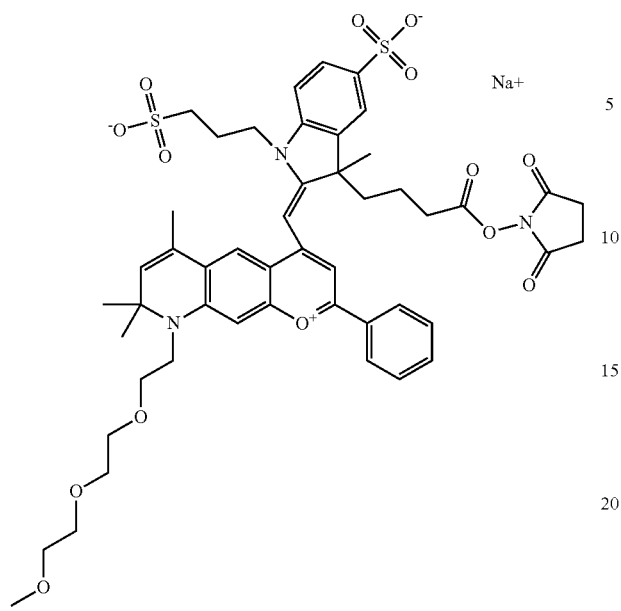

In one embodiment, the compound is 682 Compound 3, according to general formula II and shown below, which contains a polyethylene glycol (PEG₄) bound to the benzopyrylium by N, at position R3, i.e., a methylated polyethylene glycol, R1 and R2 form a substituted ring, with a monomethine linker connecting the benzopyrylium with the indole group, and NHS-ester at R13:

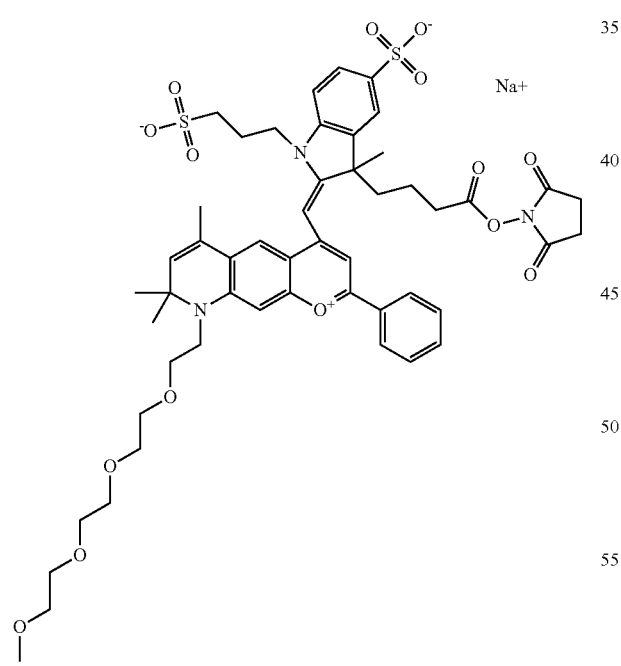

In one embodiment, the compound is 682 Compound 3, according to general formula II and shown below, which contains a polyethylene glycol (PEG₅) bound to the benzopyrylium by N, at position R3, i.e., a methylated polyethylene glycol, R1 and R2 form a substituted ring, with a monomethine linker connecting the benzopyrylium with the indole group, and NHS-ester at R13:

162

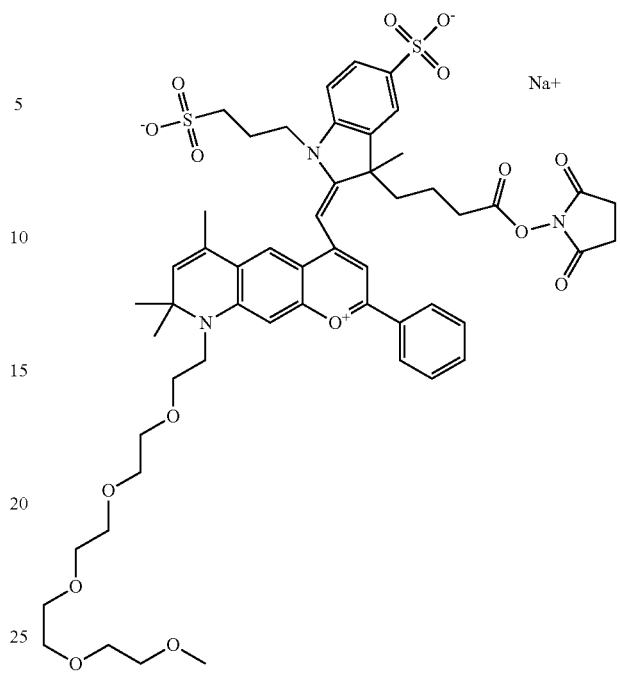

In one embodiment, the compound is 682 Compound 3, according to general formula II and shown below, which contains a polyethylene glycol (PEG₆) bound to the benzopyrylium by N, at position R3, i.e., a methylated polyethylene glycol, R1 and R2 form a substituted ring, with a monomethine linker connecting the benzopyrylium with the indole group, and NHS-ester at R13:

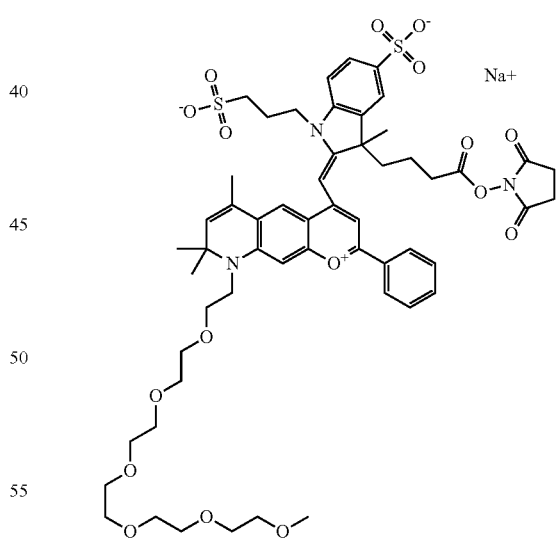

In one embodiment, the compound is 682 Compound 3 ((E)-3-(4-(2,5-dioxopyrrolidin-1-yloxy)-4-oxobutyl)-2-((E)-3-(9-(2-methoxyethyl)-6,8,8-trimethyl-2-phenyl-8,9-dihydropyrano[3,2-g]quinolin-1-ium-4-yl)allylidene)-3-methyl-1-(3-sulfonatopropyl)indoline-5-sulfonate), according to general formula II and shown below, which contains a polyethylene glycol (PEG₁) bound to the benzopyrylium by N, at position R3, i.e., a methylated polyethylene glycol, R1 and R2 form a substituted ring, with a trimethine linker connecting the benzopyrylium with the indole group, and NHS-ester at R13:

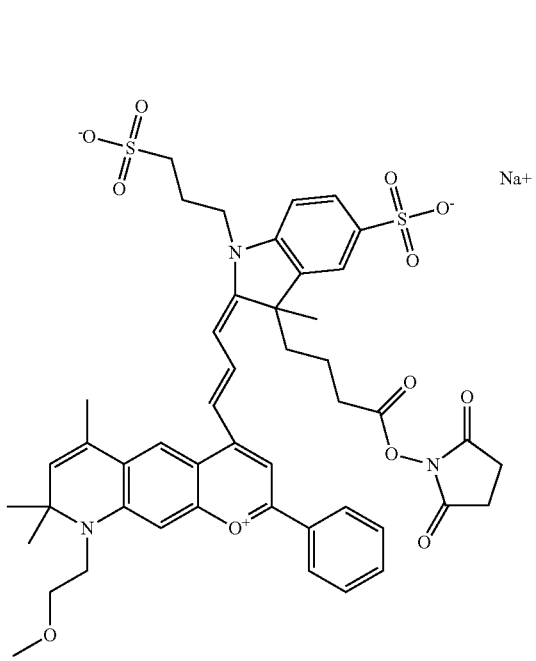

In one embodiment, the compound is 682 Compound 3, according to general formula II and shown below, which contains a polyethylene glycol (PEG$_2$) bound to the benzopyrylium by N, at position R3, i.e., a methylated polyethylene glycol, R1 and R2 form a substituted ring, with a trimethine linker connecting the benzopyrylium with the indole group, and NHS-ester at R13:

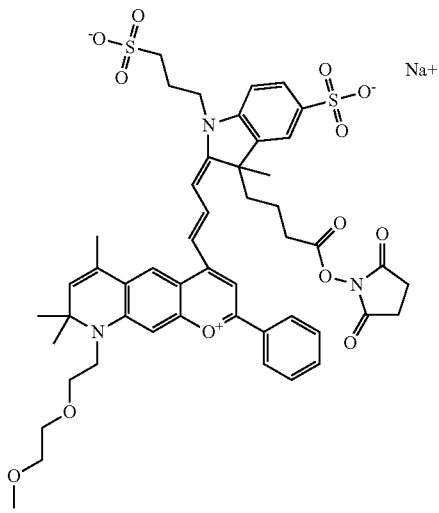

In one embodiment, the compound is 682 Compound 3, according to general formula II and shown below, which contains a polyethylene glycol (PEG$_3$) bound to the benzopyrylium by N, at position R3, i.e., a methylated polyethylene glycol, R1 and R2 form a substituted ring, with a trimethine linker connecting the benzopyrylium with the indole group, and NHS-ester at R13:

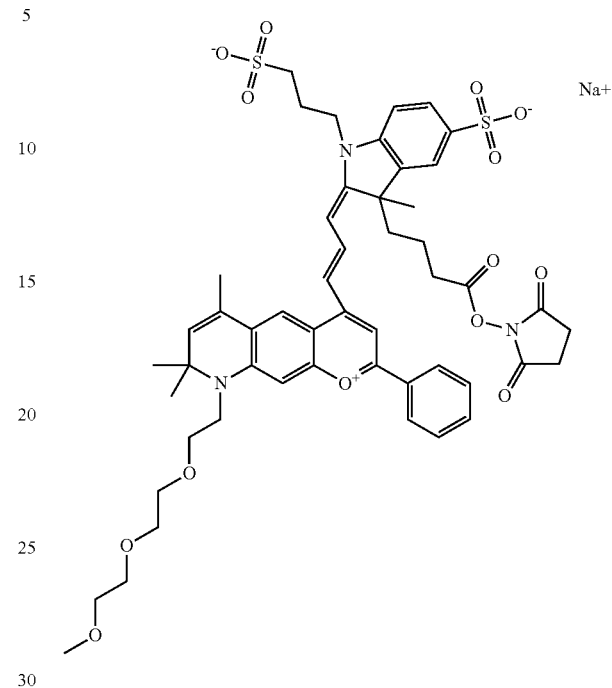

In one embodiment, the compound is 682 Compound 3, according to general formula II and shown below, which contains a polyethylene glycol (PEG$_4$) bound to the benzopyrylium by N, at position R3, i.e., a methylated polyethylene glycol, R1 and R2 form a substituted ring, with a trimethine linker connecting the benzopyrylium with the indole group, and NHS-ester at R13:

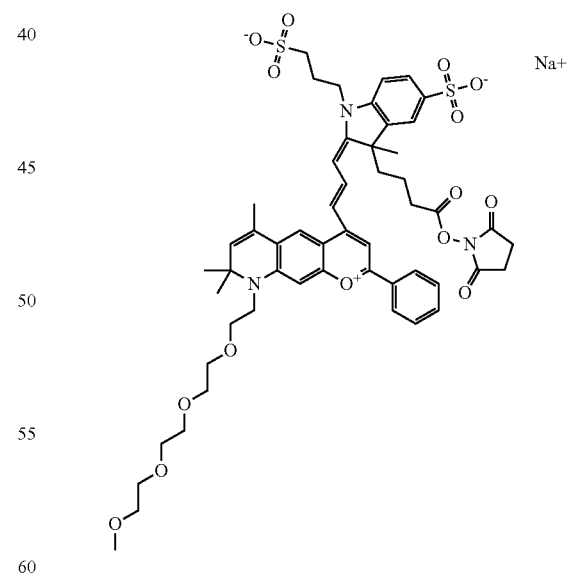

In one embodiment, the compound is 682 Compound 3, according to general formula II and shown below, which contains a polyethylene glycol (PEG$_5$) bound to the benzopyrylium by N, at position R3, i.e., a methylated polyethylene glycol, R1 and R2 form a substituted ring, with a trimethine linker connecting the benzopyrylium with the indole group, and NHS-ester at R13:

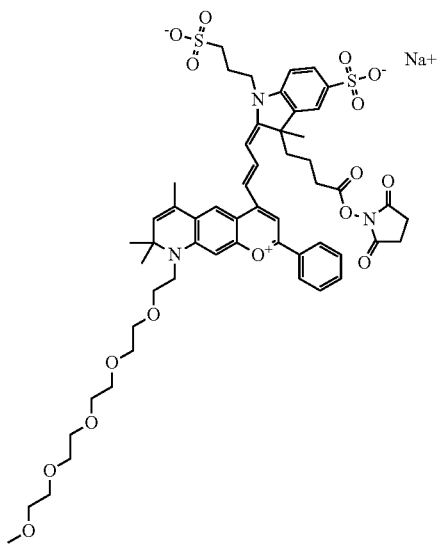

In one embodiment, the compound is 682 Compound 3, according to general formula II and shown below, which contains a polyethylene glycol (PEG$_6$) bound to the benzopyrylium by N, at position R3, i.e., a methylated polyethylene glycol, R1 and R2 form a substituted ring, with a trimethine linker connecting the benzopyrylium with the indole group, and NHS-ester at R13:

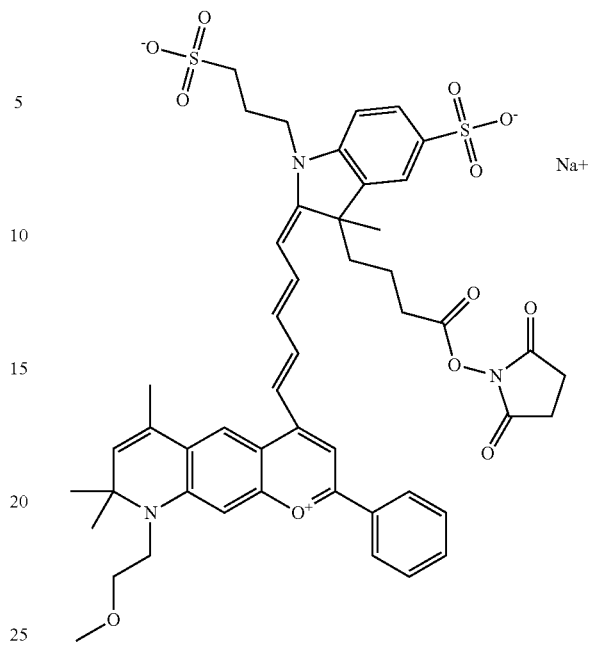

In embodiments, with an example below, substituents shown in non-limiting examples may be replaced with other disclosed substituents, such as 682 Compound 3, according to general formula II and shown below, which contains a —C(CH$_3$)$_3$ (t-butyl) group in place of the above shown phenyl group:

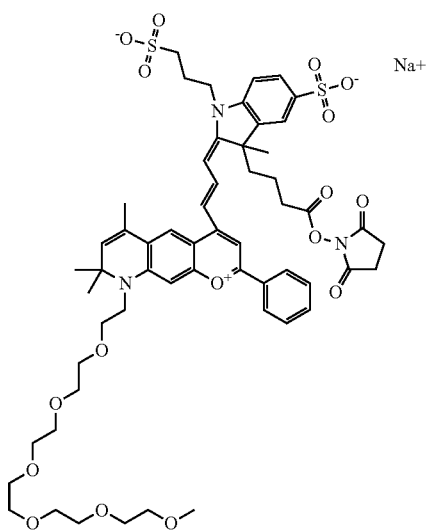

In one embodiment, the compound is 682 Compound 3 ((E)-3-(4-(2,5-dioxopyrrolidin-1-yloxy)-4-oxobutyl)-2-((2E,4E)-5-(9-(2-methoxyethyl)-6,8,8-trimethyl-2-phenyl-8,9-dihydropyrano[3,2-g]quinolin-1-ium-4-yl)penta-2,4-dienylidene)-3-methyl-1-(3-sulfonatopropyl)indoline-5-sulfonate), according to general formula II and shown below, which contains a polyethylene glycol (PEG$_1$) bound to the benzopyrylium by N, at position R3, i.e., a methylated polyethylene glycol, R1 and R2 form a substituted ring, with a pentamethine linker connecting the benzopyrylium with the indole group, and NHS-ester at R13:

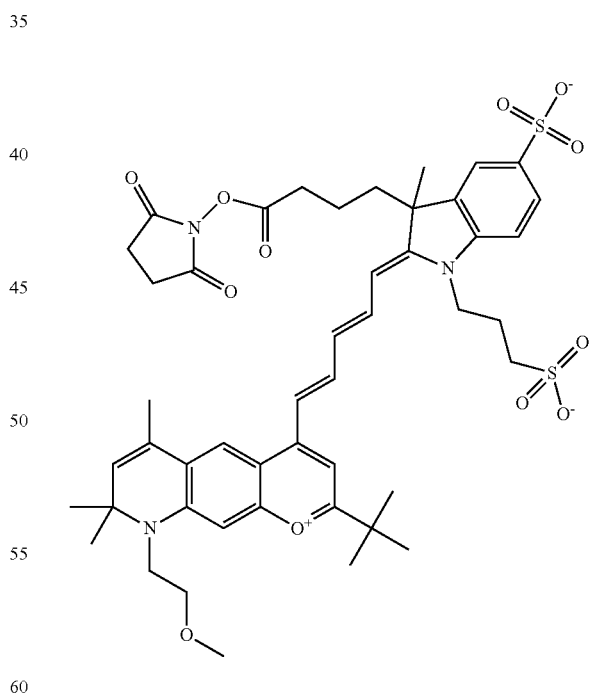

In one embodiment, the compound is 682 Compound 3, according to general formula II and shown below, which contains a polyethylene glycol (PEG$_2$) bound to the benzopyrylium by N, at position R3, i.e., a methylated polyethylene glycol, R1 and R2 form a substituted ring, with a pentamethine linker connecting the benzopyrylium with the indole group, and NHS-ester at R13:

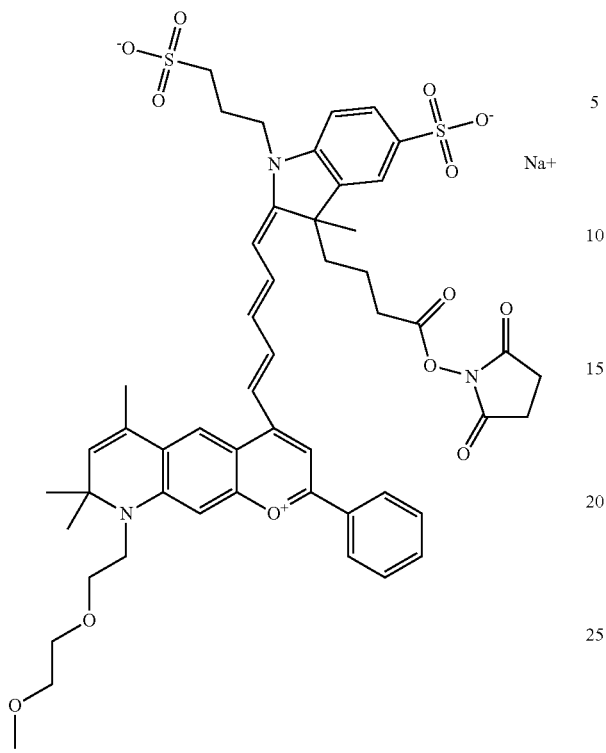

In one embodiment, the compound is 682 Compound 3, according to general formula II and shown below, which contains a polyethylene glycol (PEG$_3$) bound to the benzopyrylium by N, at position R3, i.e., a methylated polyethylene glycol, R1 and R2 form a substituted ring, with a pentamethine linker connecting the benzopyrylium with the indole group, and NHS-ester at R13:

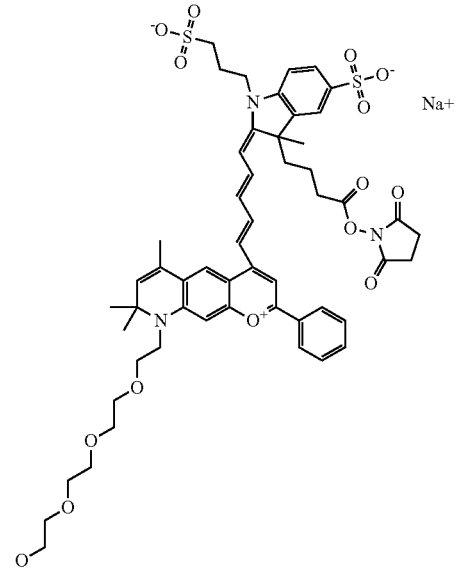

In one embodiment, the compound is 682 Compound 3, according to general formula II and shown below, which contains a polyethylene glycol (PEG$_5$) bound to the benzopyrylium by N, at position R3, i.e., a methylated polyethylene glycol, R1 and R2 form a substituted ring, with a pentamethine linker connecting the benzopyrylium with the indole group, and NHS-ester at R13:

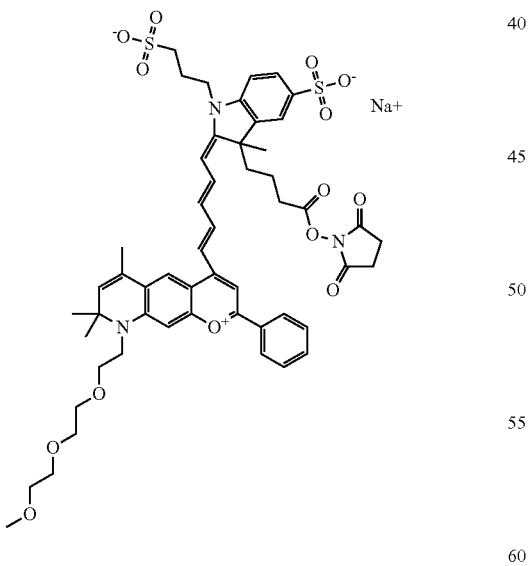

In one embodiment, the compound is 682 Compound 3, according to general formula II and shown below, which contains a polyethylene glycol (PEG$_4$) bound to the benzopyrylium by N, at position R3, i.e., a methylated polyethylene glycol, R1 and R2 form a substituted ring, with a pentamethine linker connecting the benzopyrylium with the indole group, and NHS-ester at R13:

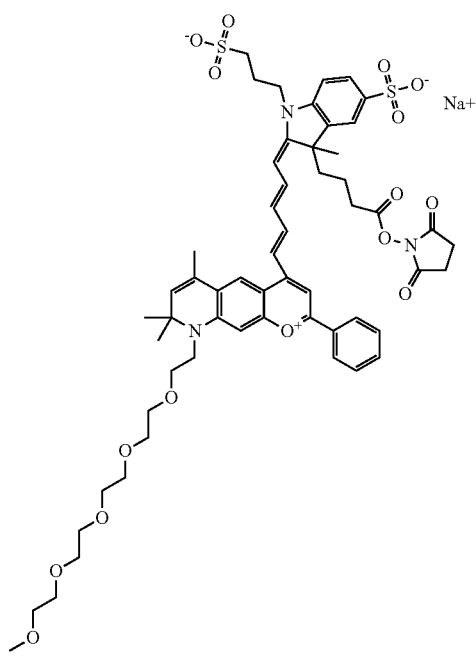

In one embodiment, the compound is 682 Compound 3, according to general formula II and shown below, which contains a polyethylene glycol (PEG$_6$) bound to the benzopyrylium by N, at position R3, i.e., a methylated polyethylene glycol, R1 and R2 form a substituted ring, with a pentamethine linker connecting the benzopyrylium with the indole group, and NHS-ester at R13:

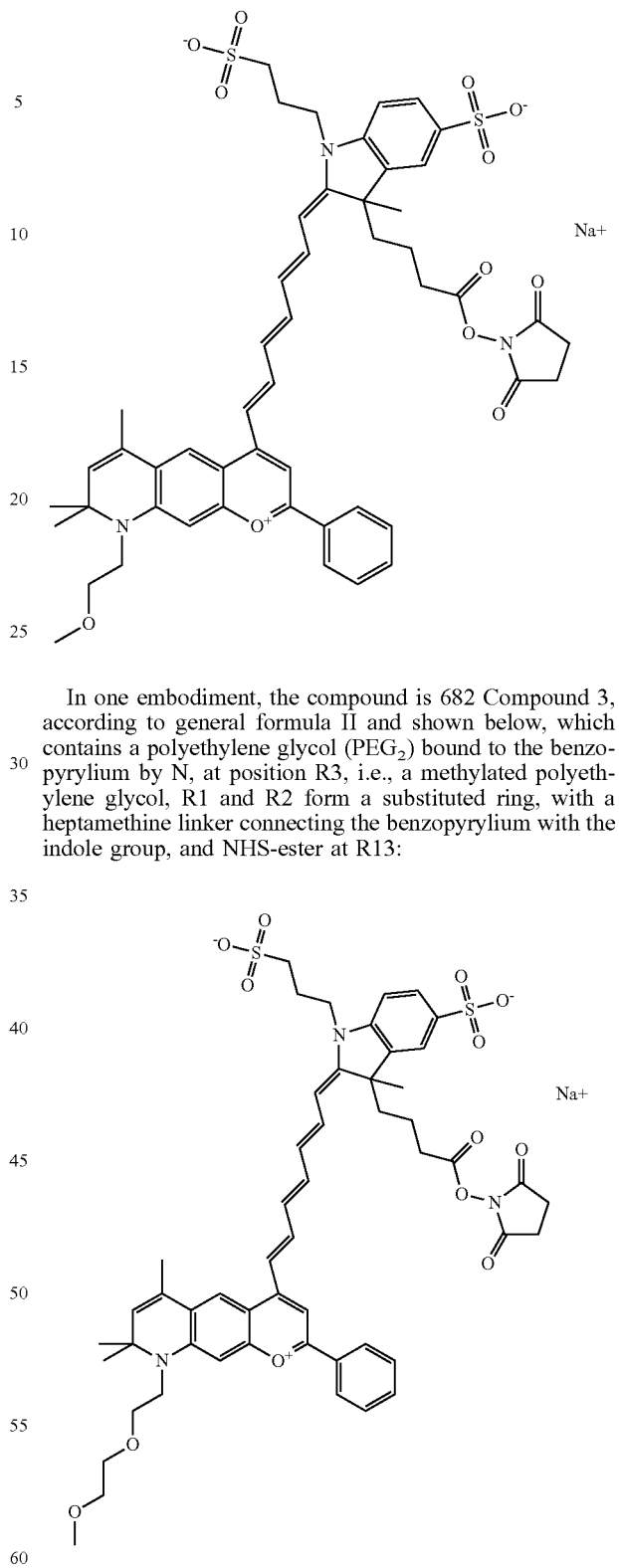

In one embodiment, the compound is 682 Compound 3, according to general formula II and shown below, which contains a polyethylene glycol (PEG$_2$) bound to the benzopyrylium by N, at position R3, i.e., a methylated polyethylene glycol, R1 and R2 form a substituted ring, with a heptamethine linker connecting the benzopyrylium with the indole group, and NHS-ester at R13:

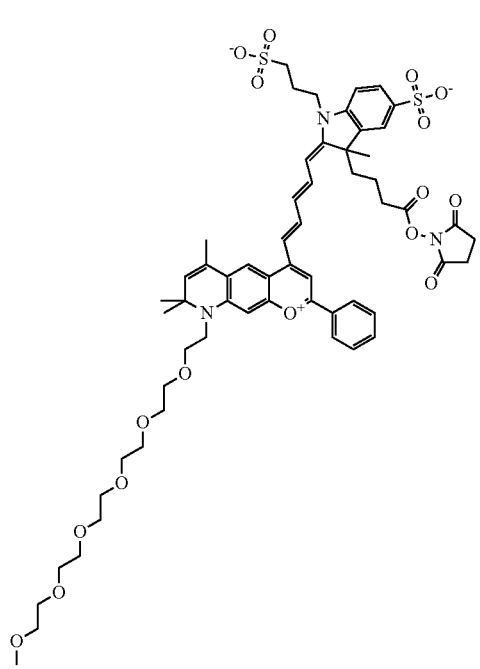

In one embodiment, the compound is 682 Compound 3 ((E)-3-(4-(2,5-dioxopyrrolidin-1-yloxy)-4-oxobutyl)-2-((2E,4E,6E)-7-(9-(2-methoxyethyl)-6,8,8-trimethyl-2-phenyl-8,9-dihydropyrano[3,2-g]quinolin-1-ium-4-yl)hepta-2,4,6-trienylidene)-3-methyl-1-(3-sulfonatopropyl)indoline-5-sulfonate), according to general formula II and shown below, which contains a polyethylene glycol (PEG$_1$) bound to the benzopyrylium by N, at position R3, i.e., a methylated polyethylene glycol, R1 and R2 form a substituted ring, with a heptamethine linker connecting the benzopyrylium with the indole group, and NHS-ester at R13:

In one embodiment, the compound is 682 Compound 3, according to general formula II and shown below, which contains a polyethylene glycol (PEG$_3$) bound to the benzopyrylium by N, at position R3, i.e., a methylated polyethylene glycol, R1 and R2 form a substituted ring, with a heptamethine linker connecting the benzopyrylium with the indole group, and NHS-ester at R13:

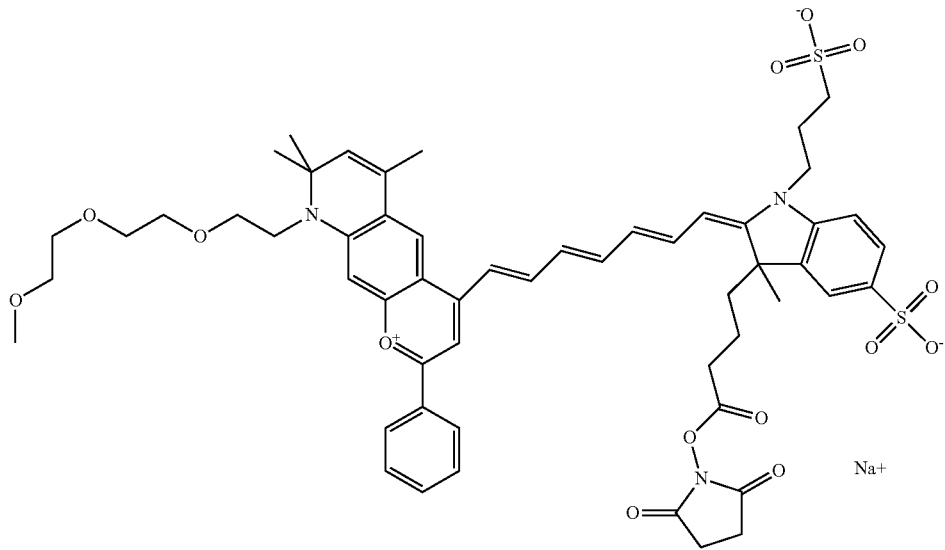

In one embodiment, the compound is 682 Compound 3, according to general formula II and shown below, which contains a polyethylene glycol (PEG₄) bound to the benzopyrylium by N, at position R3, i.e., a methylated polyethylene glycol, R1 and R2 form a substituted ring, with a heptamethine linker connecting the benzopyrylium with the indole group, and NHS-ester at R13:

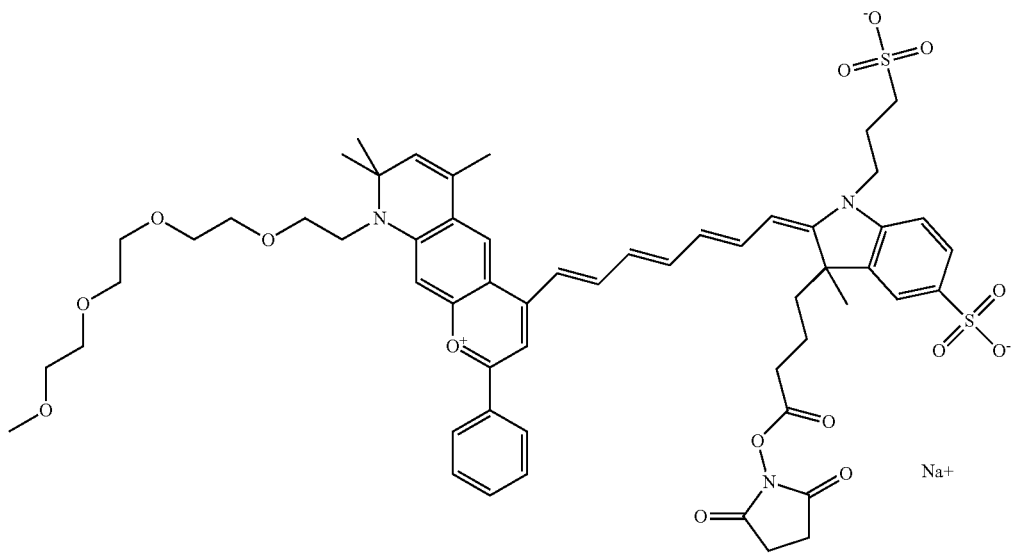

In one embodiment, the compound is 682 Compound 3, according to general formula II and shown below, which contains a polyethylene glycol (PEG₅) bound to the benzopyrylium by N, at position R3, i.e., a methylated polyethylene glycol, R1 and R2 form a substituted ring, with a heptamethine linker connecting the benzopyrylium with the indole group, and NHS-ester at R13:

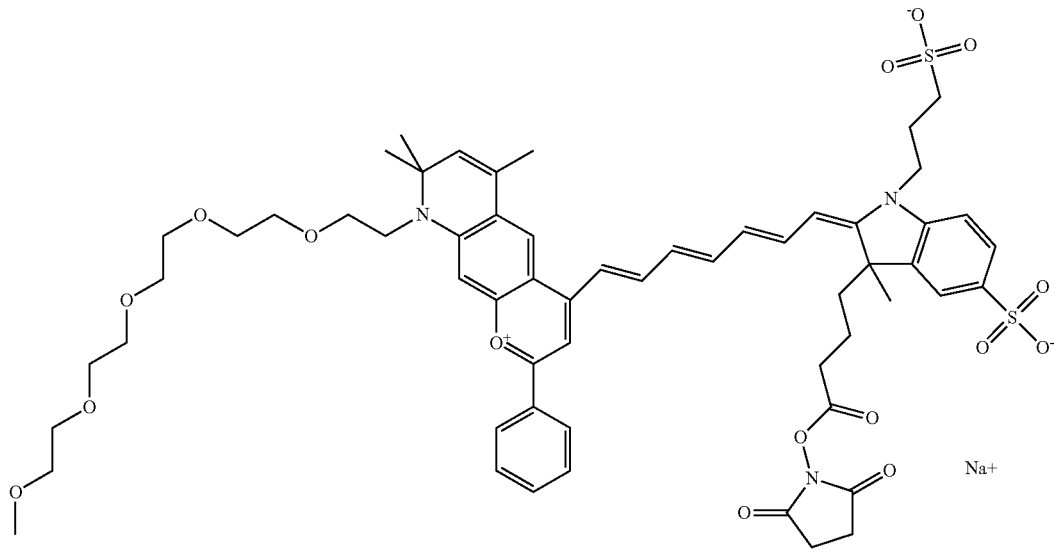

In one embodiment, the compound is 682 Compound 3, according to general formula II and shown below, which contains a polyethylene glycol (PEG$_6$) bound to the benzopyrylium by N, at position R3, i.e., a methylated polyethylene glycol, R1 and R2 form a substituted ring, with a heptamethine linker connecting the benzopyrylium with the indole group, and NHS-ester at R13:

In one embodiment, the compound is 682 Compound 3 ((Z)-1-(6-(2,5-dioxopyrrolidin-1-yloxy)-6-oxohexyl)-2-((9-(2-methoxyethyl)-6,8,8-trimethyl-2-phenyl-8,9-dihydropyrano[3,2-g]quinolin-1-ium-4-yl)methylene)-3,3-dimethylindoline-5-sulfonate), according to general formula II and shown below, which contains a polyethylene glycol (PEG$_1$) bound to the benzopyrylium by N, at position R3, i.e., a methylated polyethylene glycol, R1 and R2 form a substituted ring, with a monomethine linker connecting the benzopyrylium with the indole group, and NHS-ester at R10:

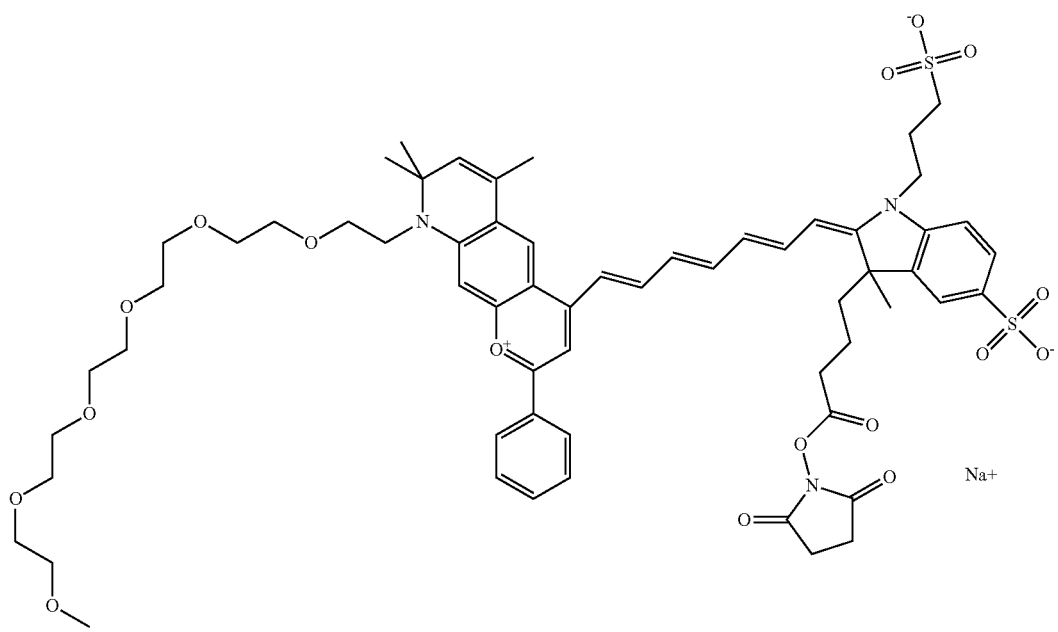

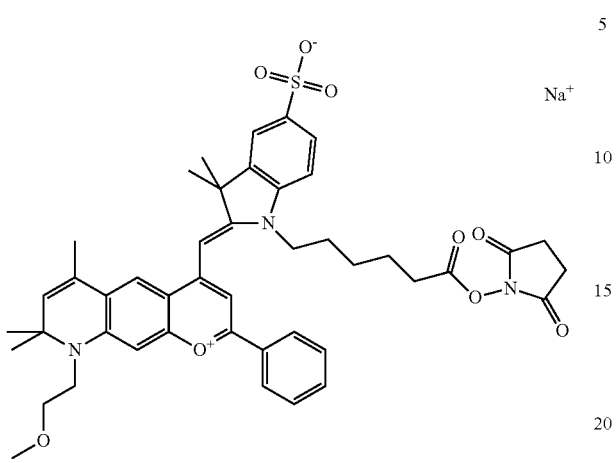

In one embodiment, the compound is 682 Compound 3, according to general formula II and shown below, which contains a polyethylene glycol (PEG$_2$) bound to the benzopyrylium by N, at position R3, i.e., a methylated polyethylene glycol, R1 and R2 form a substituted ring, with a monomethine linker connecting the benzopyrylium with the indole group, and NHS-ester at R10:

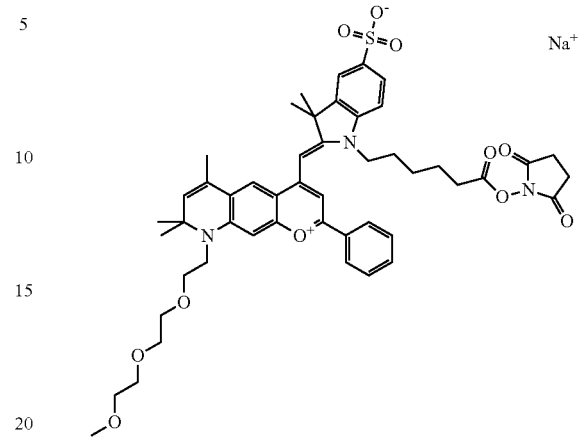

In one embodiment, the compound is 682 Compound 3, according to general formula II and shown below, which contains a polyethylene glycol (PEG$_4$) bound to the benzopyrylium by N, at position R3, i.e., a methylated polyethylene glycol, R1 and R2 form a substituted ring, with a monomethine linker connecting the benzopyrylium with the indole group, and NHS-ester at R10:

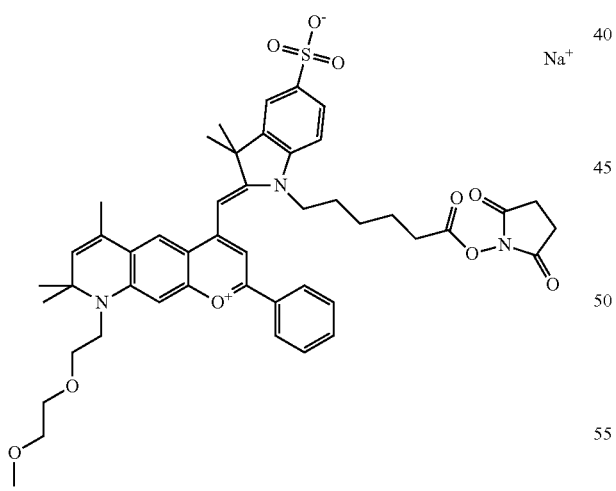

In one embodiment, the compound is 682 Compound 3, according to general formula II and shown below, which contains a polyethylene glycol (PEG$_3$) bound to the benzopyrylium by N, at position R3, i.e., a methylated polyethylene glycol, R1 and R2 form a substituted ring, with a monomethine linker connecting the benzopyrylium with the indole group, and NHS-ester at R10:

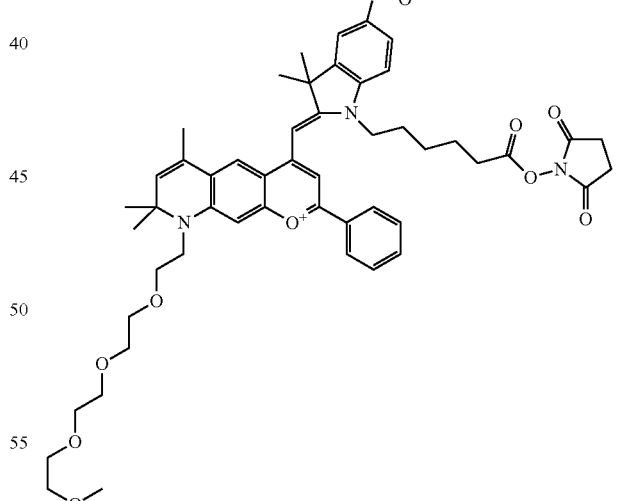

In one embodiment, the compound is 682 Compound 3, according to general formula II and shown below, which contains a polyethylene glycol (PEG$_5$) bound to the benzopyrylium by N, at position R3, i.e., a methylated polyethylene glycol, R1 and R2 form a substituted ring, with a monomethine linker connecting the benzopyrylium with the indole group, and NHS-ester at R10:

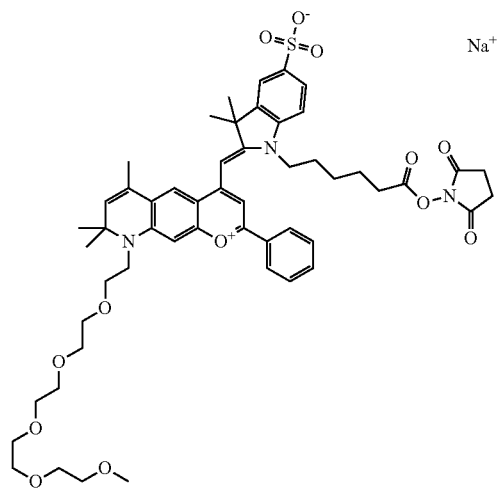 [SMILES: COCCOCCOCCOCCOCCN1c2cc3[o+]c(-c4ccccc4)cc(/C=C4\N(CCCCCC(=O)ON5C(=O)CCC5=O)c5ccc(S(=O)(=O)[O-])cc5C4(C)C)c3cc2C(C)=CC1(C)C ; [Na+]]

In one embodiment, the compound is 682 Compound 3, according to general formula II and shown below, which contains a polyethylene glycol (PEG$_6$) bound to the benzopyrylium by N, at position R3, i.e., a methylated polyethylene glycol, R1 and R2 form a substituted ring, with a monomethine linker connecting the benzopyrylium with the indole group, and NHS-ester at R10:

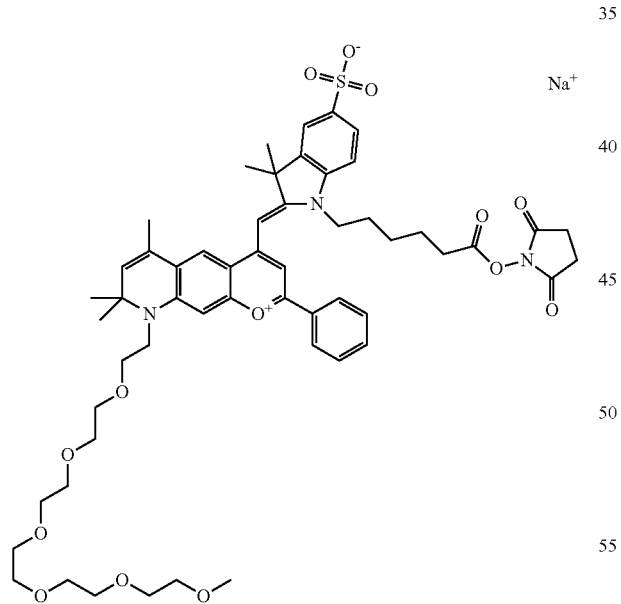

In one embodiment, the compound is 682 Compound 3 ((Z)-1-(6-(2,5-dioxopyrrolidin-1-yloxy)-6-oxohexyl)-2-((E)-3-(9-(2-methoxyethyl)-6,8,8-trimethyl-2-phenyl-8,9-dihydropyrano[3,2-g]quinolin-1-ium-4-yl)allylidene)-3,3-dimethylindoline-5-sulfonate), according to general formula II and shown below, which contains a polyethylene glycol (PEG$_1$) bound to the benzopyrylium by N, at position R3, i.e., a methylated polyethylene glycol, R1 and R2 form a substituted ring, with a trimethine linker connecting the benzopyrylium with the indole group, and NHS-ester at R10:

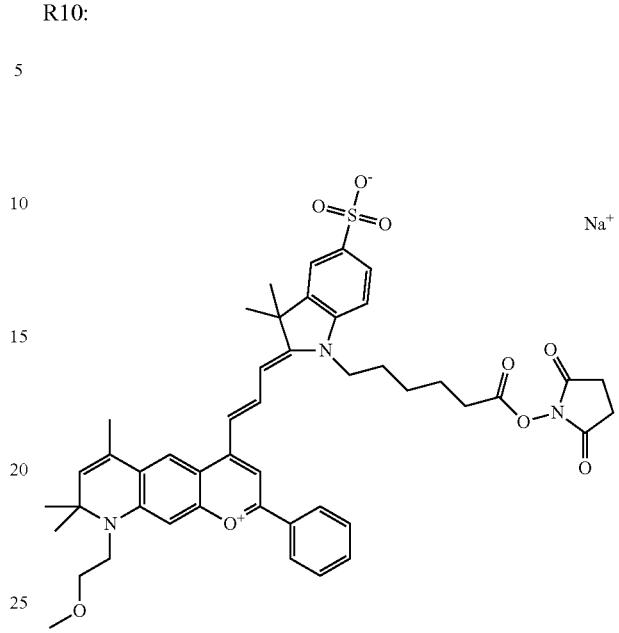

In one embodiment, the compound is 682 Compound 3, according to general formula II and shown below, which contains a polyethylene glycol (PEG$_2$) bound to the benzopyrylium by N, at position R3, i.e., a methylated polyethylene glycol, R1 and R2 form a substituted ring, with a trimethine linker connecting the benzopyrylium with the indole group, and NHS-ester at R10:

In one embodiment, the compound is 682 Compound 3, according to general formula II and shown below, which contains a polyethylene glycol (PEG$_3$) bound to the benzopyrylium by N, at position R3, i.e., a methylated polyethylene glycol, R1 and R2 form a substituted ring, with a trimethine linker connecting the benzopyrylium with the indole group, and NHS-ester at R10:

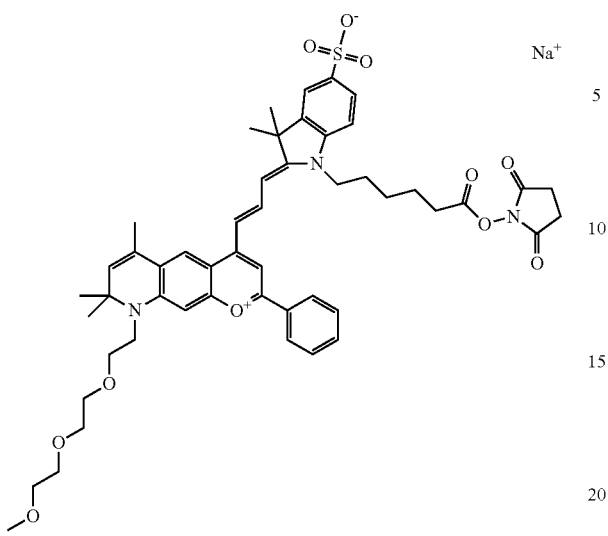

In one embodiment, the compound is 682 Compound 3, according to general formula II and shown below, which contains a polyethylene glycol (PEG$_4$) bound to the benzopyrylium by N, at position R3, i.e., a methylated polyethylene glycol, R1 and R2 form a substituted ring, with a trimethine linker connecting the benzopyrylium with the indole group, and NHS-ester at R10:

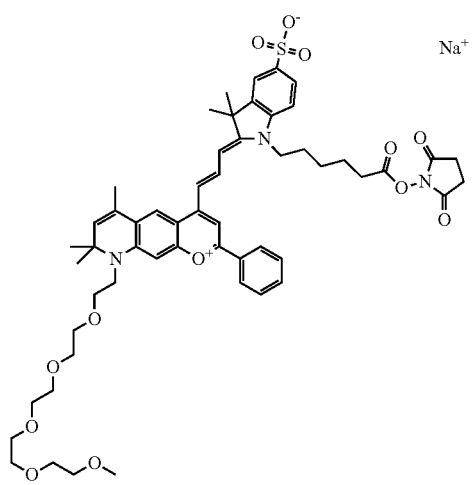 [SMILES: COCCOCCOCCOCCOCCN1c2cc3[o+]c(-c4ccccc4)cc(/C=C/C=C4\N(CCCCCC(=O)ON5C(=O)CCC5=O)c5ccc(S(=O)(=O)[O-])cc5C4(C)C)c3cc2C(C)=CC1(C)C ; [Na+]]

In one embodiment, the compound is 682 Compound 3, according to general formula II and shown below, which contains a polyethylene glycol (PEG$_6$) bound to the benzopyrylium by N, at position R3, i.e., a methylated polyethylene glycol, R1 and R2 form a substituted ring, with a trimethine linker connecting the benzopyrylium with the indole group, and NHS-ester at R10:

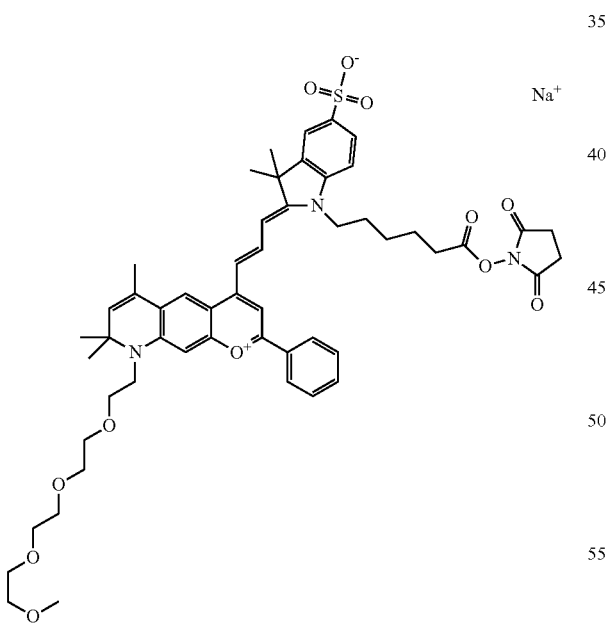

In one embodiment, the compound is 682 Compound 3, according to general formula II and shown below, which contains a polyethylene glycol (PEG$_5$) bound to the benzopyrylium by N, at position R3, i.e., a methylated polyethylene glycol, R1 and R2 form a substituted ring, with a trimethine linker connecting the benzopyrylium with the indole group, and NHS-ester at R10:

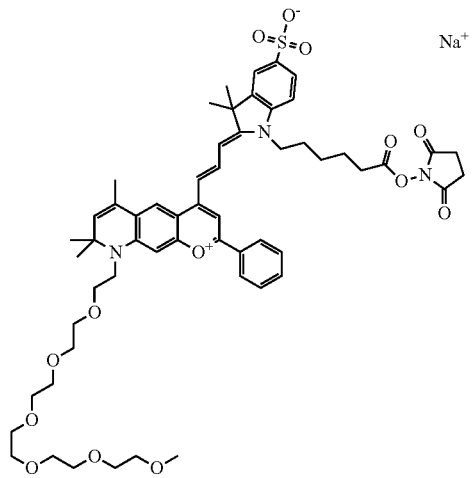 [SMILES: COCCOCCOCCOCCOCCOCCN1c2cc3[o+]c(-c4ccccc4)cc(/C=C/C=C4\N(CCCCCC(=O)ON5C(=O)CCC5=O)c5ccc(S(=O)(=O)[O-])cc5C4(C)C)c3cc2C(C)=CC1(C)C ; [Na+]]

In one embodiment, the compound is 682 Compound 3 ((Z)-1-(6-(2,5-dioxopyrrolidin-1-yloxy)-6-oxohexyl)-2-((2E,4E)-5-(9-(2-methoxyethyl)-6,8,8-trimethyl-2-phenyl-8,9-dihydropyrano[3,2-g]quinolin-1-ium-4-yl)penta-2,4-dienylidene)-3,3-dimethylindoline-5-sulfonate), according to general formula II and shown below, which contains a polyethylene glycol (PEG$_1$) bound to the benzopyrylium by N, at position R3, i.e., a methylated polyethylene glycol, R1 and R2 form a substituted ring, with a pentamethine linker connecting the benzopyrylium with the indole group, and NHS-ester at R10:

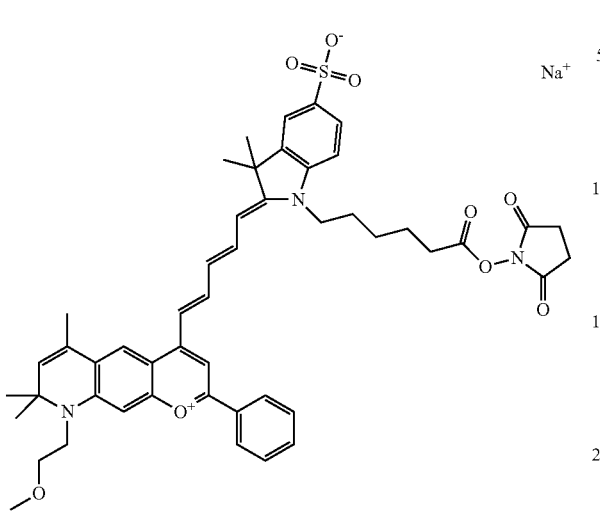

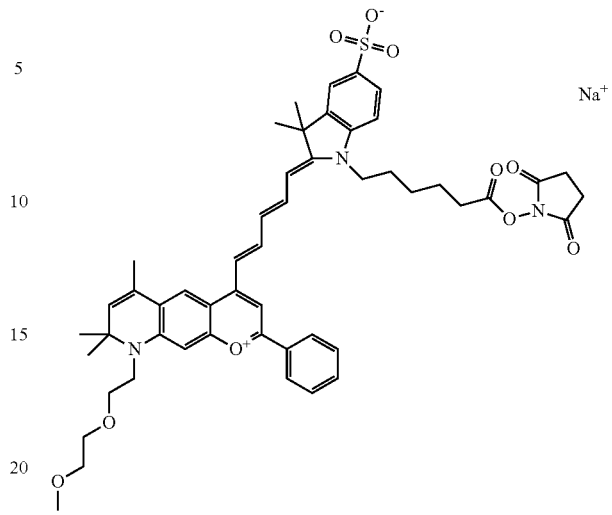

In various embodiments, and as but one example below, various substituents which have been shown in non-limiting examples may be replaced with other described substituents, such as 682 Compound 3, according to general formula II and shown below, which contains a —C(CH$_3$)$_3$ (t-butyl) group in place of the above shown phenyl group:

In one embodiment, the compound is 682 Compound 3, according to general formula II and shown below, which contains a polyethylene glycol (PEG$_3$) bound to the benzopyrylium by N, at position R3, i.e., a methylated polyethylene glycol, R1 and R2 form a substituted ring, with a pentamethine linker connecting the benzopyrylium with the indole group, and NHS-ester at R10:

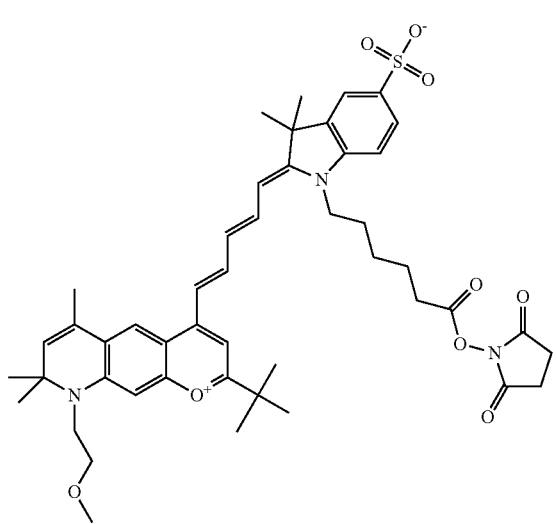 [SMILES: COCCN1c2cc3[o+]c(C(C)(C)C)cc(/C=C/C=C/C=C4\N(CCCCCC(=O)ON5C(=O)CCC5=O)c5ccc(S(=O)(=O)[O-])cc5C4(C)C)c3cc2C(C)=CC1(C)C]

In one embodiment, the compound is 682 Compound 3, according to general formula II and shown below, which contains a polyethylene glycol (PEG$_2$) bound to the benzopyrylium by N, at position R3, i.e., a methylated polyethylene glycol, R1 and R2 form a substituted ring, with a pentamethine linker connecting the benzopyrylium with the indole group, and NHS-ester at R10:

In one embodiment, the compound is 682 Compound 3, according to general formula II and shown below, which contains a polyethylene glycol (PEG$_4$) bound to the benzopyrylium by N, at position R3, i.e., a methylated polyethylene glycol, R1 and R2 form a substituted ring, with a pentamethine linker connecting the benzopyrylium with the indole group, and NHS-ester at R10:

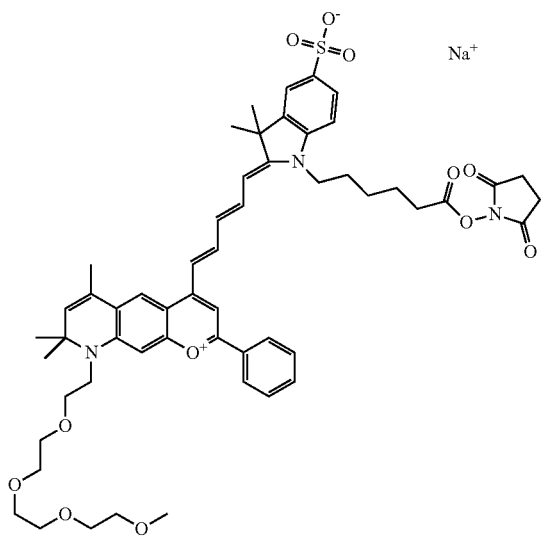 [SMILES: COCCOCCOCCOCCN1c2cc3[o+]c(-c4ccccc4)cc(/C=C/C=C/C=C4\N(CCCCCC(=O)ON5C(=O)CCC5=O)c5ccc(S(=O)(=O)[O-])cc5C4(C)C)c3cc2C(C)=CC1(C)C ; [Na+]]

In one embodiment, the compound is 682 Compound 3, according to general formula II and shown below, which contains a polyethylene glycol (PEG$_5$) bound to the benzopyrylium by N, at position R3, i.e., a methylated polyethylene glycol, R1 and R2 form a substituted ring, with a pentamethine linker connecting the benzopyrylium with the indole group, and NHS-ester at R10:

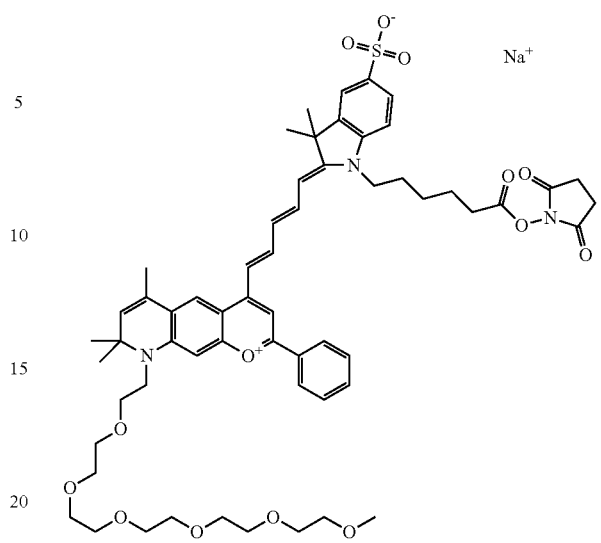

In one embodiment, the compound is 682 Compound 3 ((Z)-1-(6-(2,5-dioxopyrrolidin-1-yloxy)-6-oxohexyl)-2-((2E,4E,6E)-7-(9-(2-methoxyethyl)-6,8,8-trimethyl-2-phenyl-8,9-dihydropyrano[3,2-g]quinolin-1-ium-4-yl)hepta-2,4,6-trienylidene)-3,3-dimethylindoline-5-sulfonate), according to general formula II and shown below, which contains a polyethylene glycol (PEG$_1$) bound to the benzopyrylium by N, at position R3, i.e., a methylated polyethylene glycol, R1 and R2 form a substituted ring, with a heptamethine linker connecting the benzopyrylium with the indole group, and NHS-ester at R10:

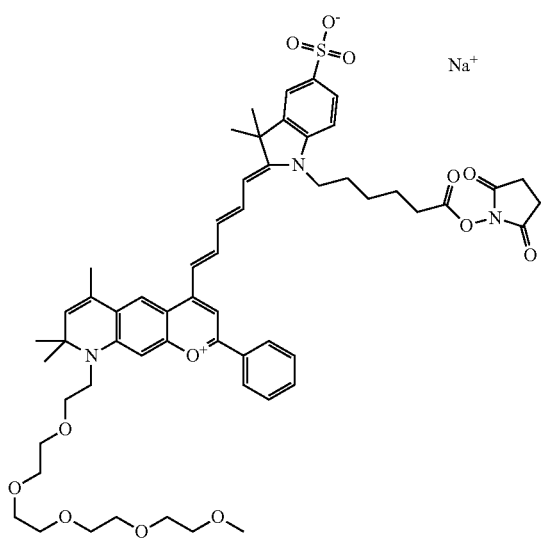 [SMILES: COCCOCCOCCOCCOCCN1c2cc3[o+]c(-c4ccccc4)cc(/C=C/C=C/C=C4\N(CCCCCC(=O)ON5C(=O)CCC5=O)c5ccc(S(=O)(=O)[O-])cc5C4(C)C)c3cc2C(C)=CC1(C)C ; [Na+]]

In one embodiment, the compound is 682 Compound 3, according to general formula II and shown below, which contains a polyethylene glycol (PEG$_6$) bound to the benzopyrylium by N, at position R3, i.e., a methylated polyethylene glycol, R1 and R2 form a substituted ring, with a pentamethine linker connecting the benzopyrylium with the indole group, and NHS-ester at R10:

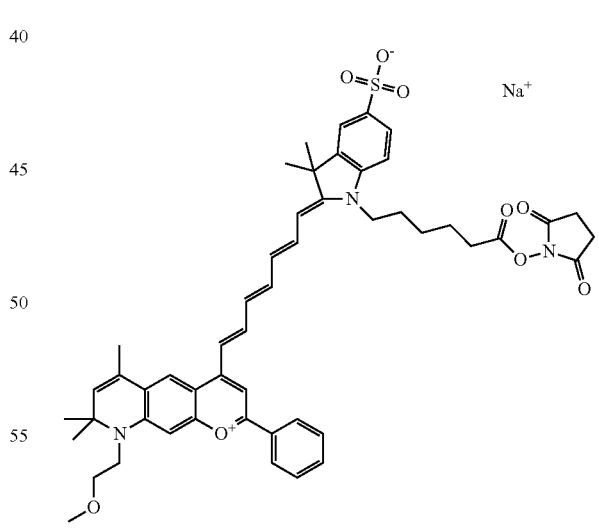

In one embodiment, the compound is 682 Compound 3, according to general formula II and shown below, which contains a polyethylene glycol (PEG$_2$) bound to the benzopyrylium by N, at position R3, i.e., a methylated polyethylene glycol, R1 and R2 form a substituted ring, with a heptamethine linker connecting the benzopyrylium with the indole group, and NHS-ester at R10:

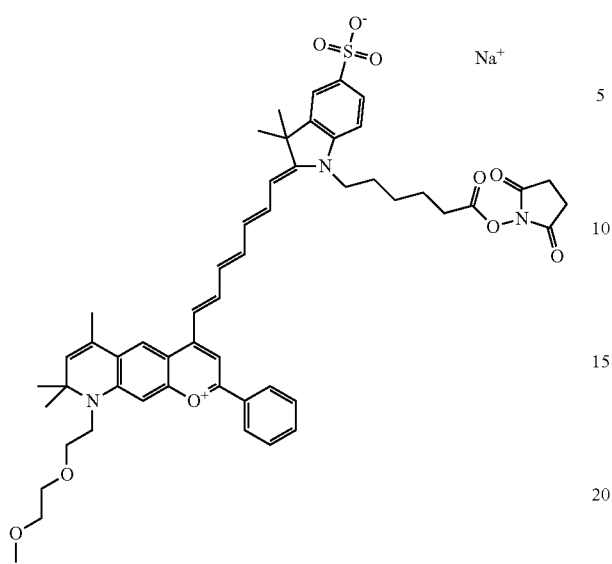

In one embodiment, the compound is 682 Compound 3, according to general formula II and shown below, which contains a polyethylene glycol (PEG₃) bound to the benzopyrylium by N, at position R3, i.e., a methylated polyethylene glycol, R1 and R2 form a substituted ring, with a heptamethine linker connecting the benzopyrylium with the indole group, and NHS-ester at R10:

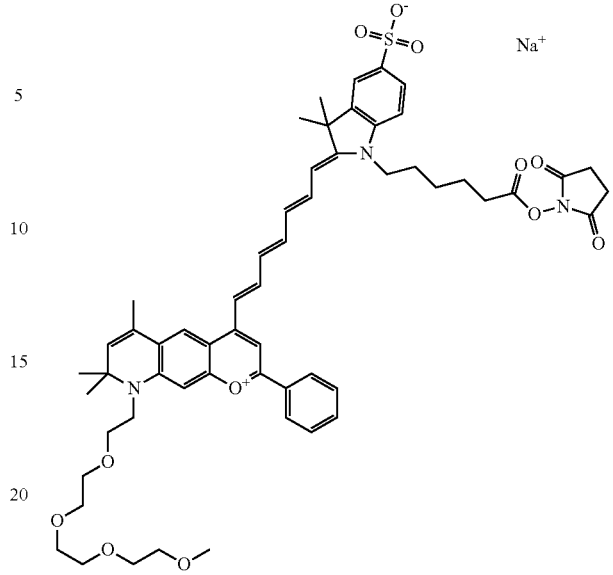

In one embodiment, the compound is 682 Compound 3, according to general formula II and shown below, which contains a polyethylene glycol (PEG₅) bound to the benzopyrylium by N, at position R3, i.e., a methylated polyethylene glycol, R1 and R2 form a substituted ring, with a heptamethine linker connecting the benzopyrylium with the indole group, and NHS-ester at R10:

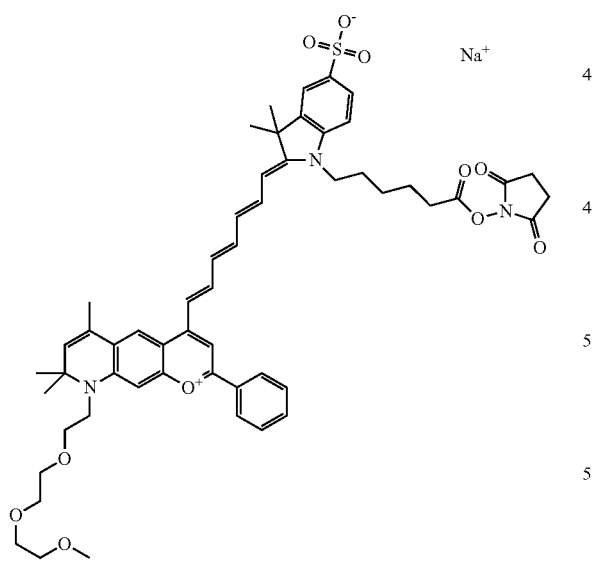

In one embodiment, the compound is 682 Compound 3, according to general formula II and shown below, which contains a polyethylene glycol (PEG₄) bound to the benzopyrylium by N, at position R3, i.e., a methylated polyethylene glycol, R1 and R2 form a substituted ring, with a heptamethine linker connecting the benzopyrylium with the indole group, and NHS-ester at R10:

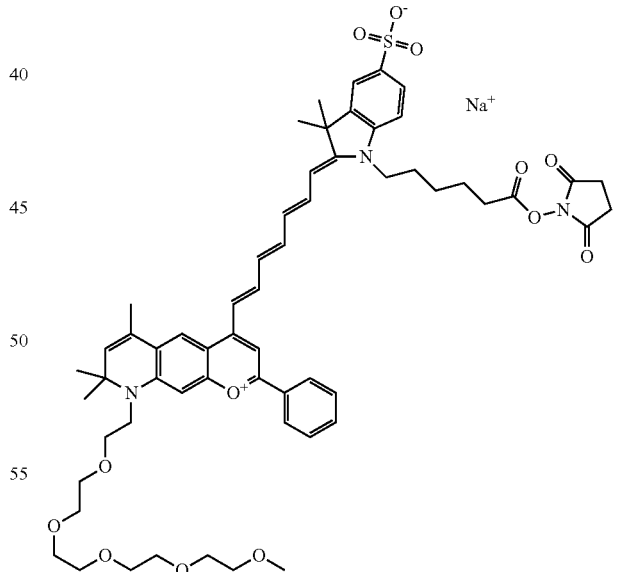

In one embodiment, the compound is 682 Compound 3, according to general formula II and shown below, which contains a polyethylene glycol (PEG₆) bound to the benzopyrylium by N, at position R3, i.e., a methylated polyethylene glycol, R1 and R2 form a substituted ring, with a heptamethine linker connecting the benzopyrylium with the indole group, and NHS-ester at R10:

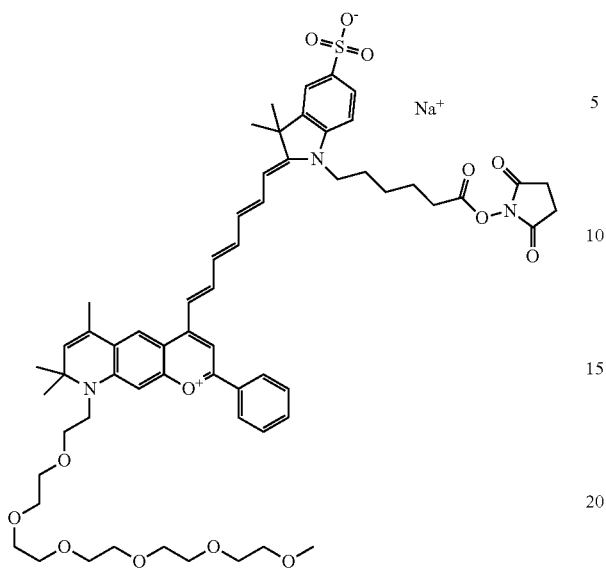

In one embodiment, the compound is 682 Compound 13 ((Z)-2-((2E,4E)-5-(2-tert-butyl-9-ethyl-6,8,8-trimethyl-8,9-dihydropyrano[3,2-g]quinolin-1-ium-4-yl)penta-2,4-dienylidene)-1-(5-carboxypentyl)-3-(2-methoxyethyl)-3-methylindoline-5-sulfonate), according to general formula II and shown below, which contains a polyethylene glycol ($PEG_1$) at position R13, i.e., a methylated polyethylene glycol, R1 and R2 form a substituted ring, with a pentamethine linker connecting the benzopyrylium with the indole group, and —COOH at R10:

In one embodiment, the compound is 682 Compound 13 ((Z)-2-((2E,4E)-5-(2-tert-butyl-9-ethyl-6,8,8-trimethyl-8,9-dihydropyrano[3,2-g]quinolin-1-ium-4-yl)penta-2,4-dienylidene)-1-(5-carboxypentyl)-3-methyl-3-(2,5,8,11-tetraoxatridecan-13-yl)indoline-5-sulfonate), according to general formula II and shown below, which contains a polyethylene glycol ($PEG_4$) at position R13, i.e., a methylated polyethylene glycol, R1 and R2 form a substituted ring, with a pentamethine linker connecting the benzopyrylium with the indole group, and COOH at R10:

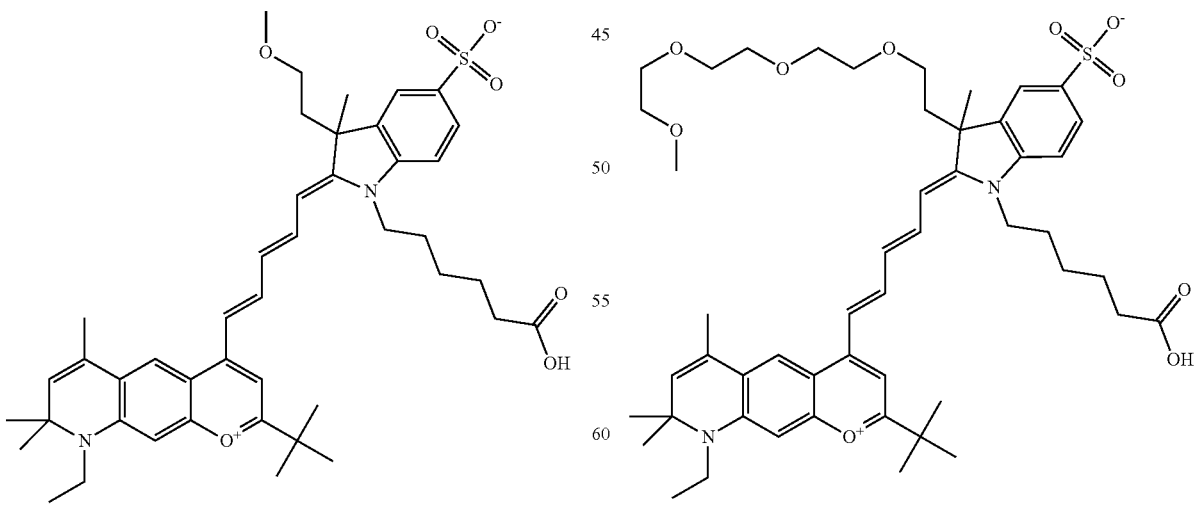

One non-limiting example of an activated compound according to general formula I is an NHS-ester of 682 Compound 13 ($PEG_1$), shown below:

One non-limiting example of an activated compound according to general formula I is an NHS-ester of 682 Compound 13 ($PEG_4$), shown below:

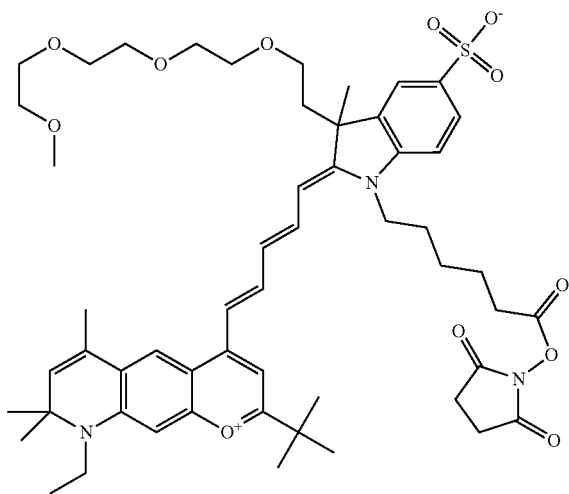

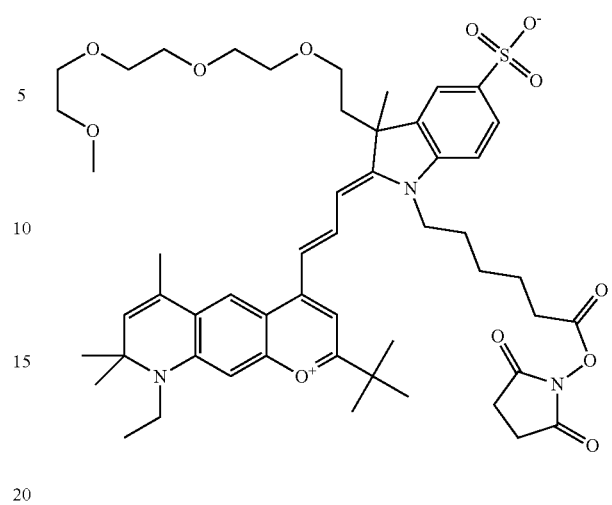

In one embodiment, the compound is 682 Compound 13 ((Z)-2-((E)-3-(2-tert-butyl-9-ethyl-6,8,8-trimethyl-8,9-dihydropyrano[3,2-g]quinolin-1-ium-4-yl)allylidene)-1-(5-carboxypentyl)-3-methyl-3-(2,5,8,11-tetraoxatridecan-13-yl)indoline-5-sulfonate), according to general formula II and shown below, which contains a polyethylene glycol (PEG$_4$) at position R13, i.e., a methylated polyethylene glycol, R1 and R2 form a substituted ring, with a trimethine linker connecting the benzopyrylium with the indole group, and —COOH at R10:

In one embodiment, the compound is 682 Compound 1, shown below, which contains one ethylene glycol (PEG$_1$), i.e., a methylated ethylene glycol, bound to the substituted ring formed by R1 and R2, sulfoalkyl at R3 and R10, and NHS-ester at R13:

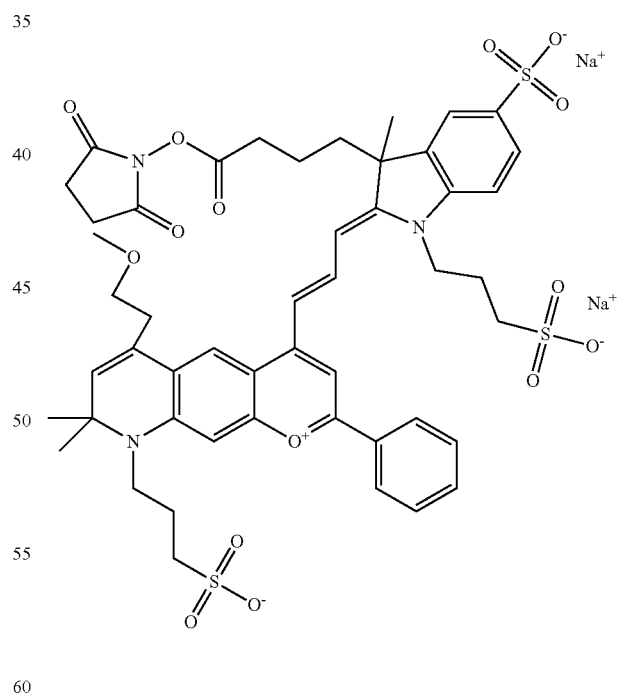

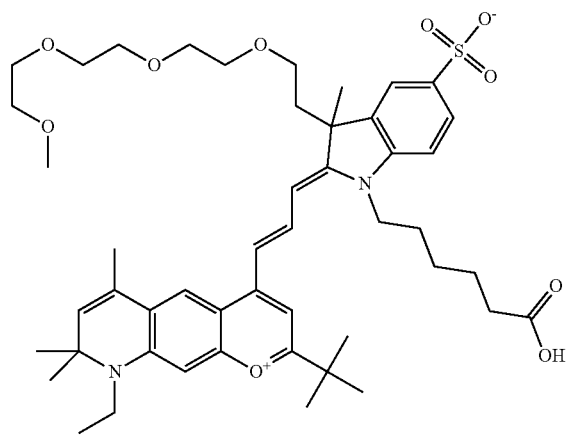 [SMILES: CCN1c2cc3[o+]c(C(C)(C)C)cc(/C=C/C=C4\N(CCCCCC(=O)O)c5ccc(S(=O)(=O)[O-])cc5C4(C)CCOCCOCCOCCOC)c3cc2C(C)=CC1(C)C]

One non-limiting example of an activated compound according to general formula I is an NHS-ester of 682 Compound 13 (PEG$_4$), shown below:

In one embodiment, the compound is 682 Compound 1, shown below, which contains one ethylene glycol (PEG$_2$), i.e., a methylated ethylene glycol, bound to the substituted ring formed by R1 and R2, sulfoalkyl at R3 and R10, and NHS-ester at R13:

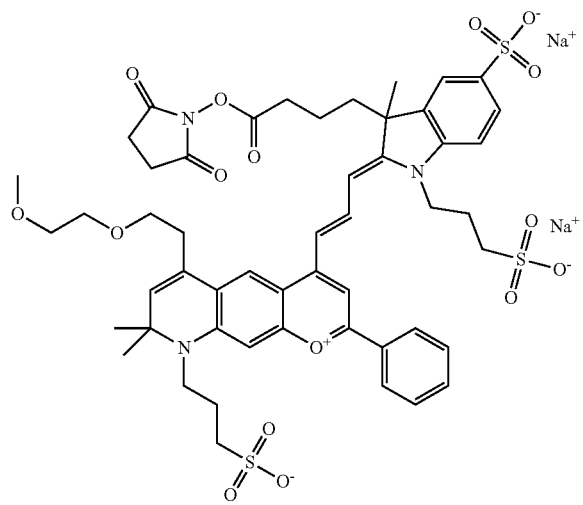 [SMILES: COCCOCCC1=CC(C)(C)N(CCCS(=O)(=O)[O-])c2cc3[o+]c(-c4ccccc4)cc(/C=C/C=C4\N(CCCS(=O)(=O)[O-])c5ccc(S(=O)(=O)[O-])cc5C4(C)CCCC(=O)ON4C(=O)CCC4=O)c3cc21 ; [Na+] ; [Na+]]

In one embodiment, the compound is 682 Compound 1, shown below, which contains one ethylene glycol (PEG$_3$), i.e., a methylated ethylene glycol, bound to the substituted ring formed by R1 and R2, sulfoalkyl at R3 and R10, and NHS-ester at R13:

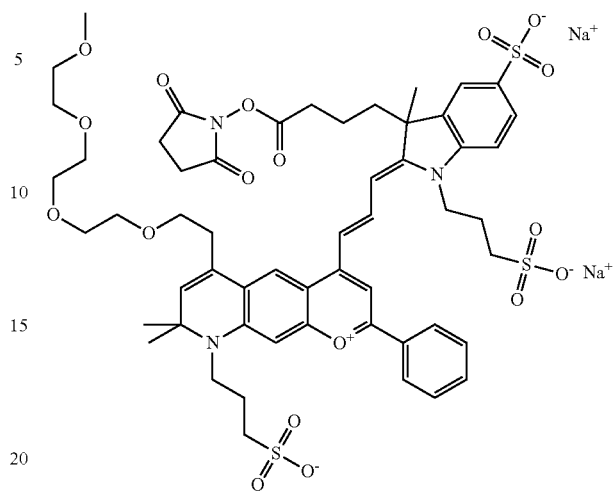

In one embodiment, the compound is 682 Compound 1, shown below, which contains one ethylene glycol (PEG$_5$), i.e., a methylated ethylene glycol, bound to the substituted ring formed by R1 and R2, sulfoalkyl at R3 and R10, and NHS-ester at R13:

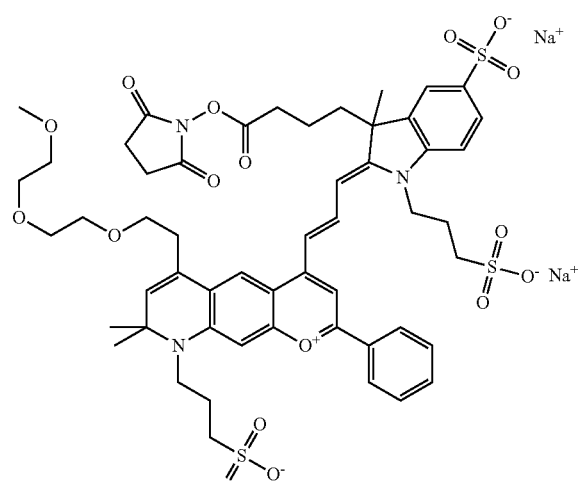

In one embodiment, the compound is 682 Compound 1, shown below, which contains one ethylene glycol (PEG$_4$), i.e., a methylated ethylene glycol, bound to the substituted ring formed by R1 and R2, sulfoalkyl at R3 and R10, and NHS-ester at R13:

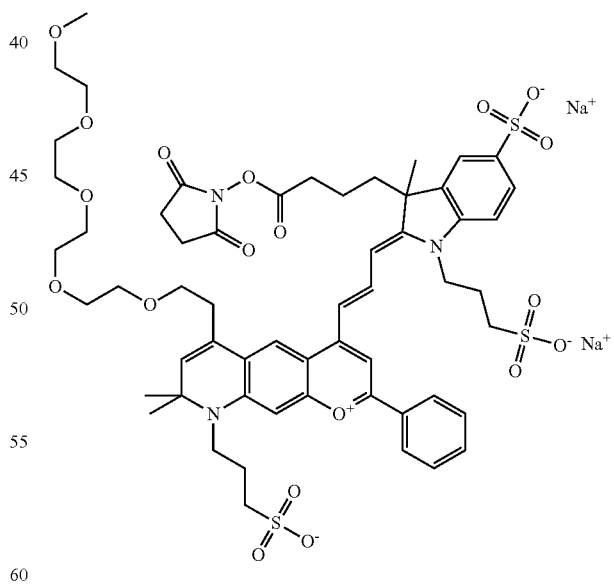

In one embodiment, the compound is 682 Compound 1, shown below, which contains one ethylene glycol (PEG$_6$), i.e., a methylated ethylene glycol, bound to the substituted ring formed by R1 and R2, sulfoalkyl at R3 and R10, and NHS-ester at R13:

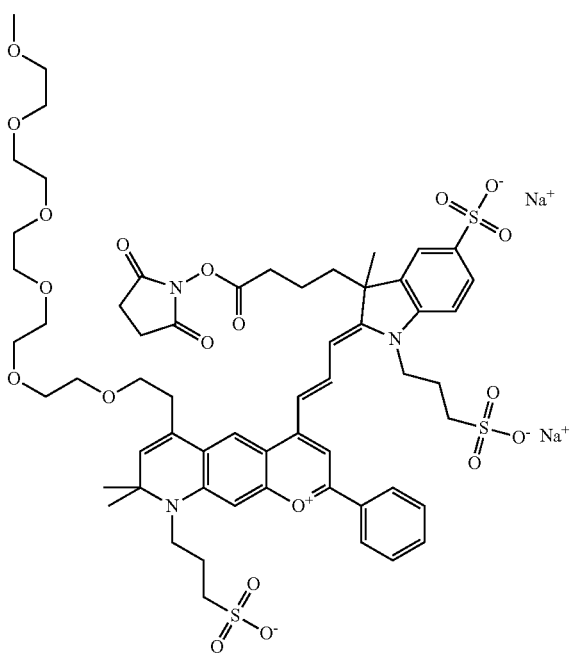 [SMILES: COCCOCCOCCOCCOCCOCCC1=CC(C)(C)N(CCCS(=O)(=O)[O-])c2cc3[o+]c(-c4ccccc4)cc(/C=C/C=C4\N(CCCS(=O)(=O)[O-])c5ccc(S(=O)(=O)[O-])cc5C4(C)CCCC(=O)ON4C(=O)CCC4=O)c3cc21 ; [Na+] ; [Na+]]

In one embodiment, the compound is 682 Compound 2, shown below, which contains two ethylene glycols (PEG$_1$), i.e., a methylated ethylene glycol, bound to the substituted ring formed by R1 and R2, sulfoalkyl at R3 and R10, and NHS-ester at R13:

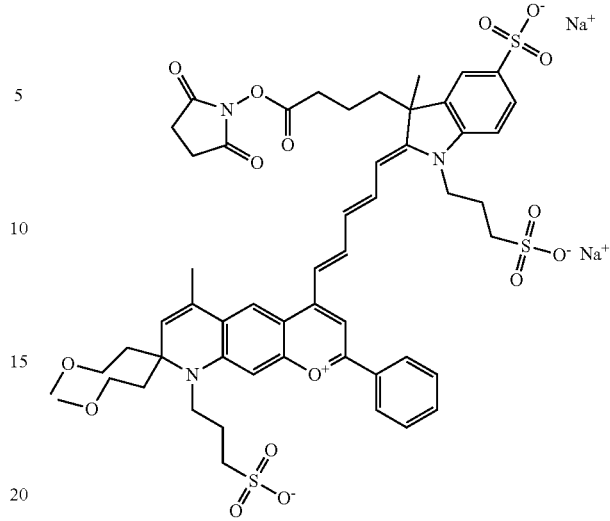

In one embodiment, the compound is 682 Compound 2, shown below, which contains two ethylene glycols (PEG$_2$), i.e., a methylated ethylene glycol, bound to the substituted ring formed by R1 and R2, sulfoalkyl at R3 and R10, and NHS-ester at R13:

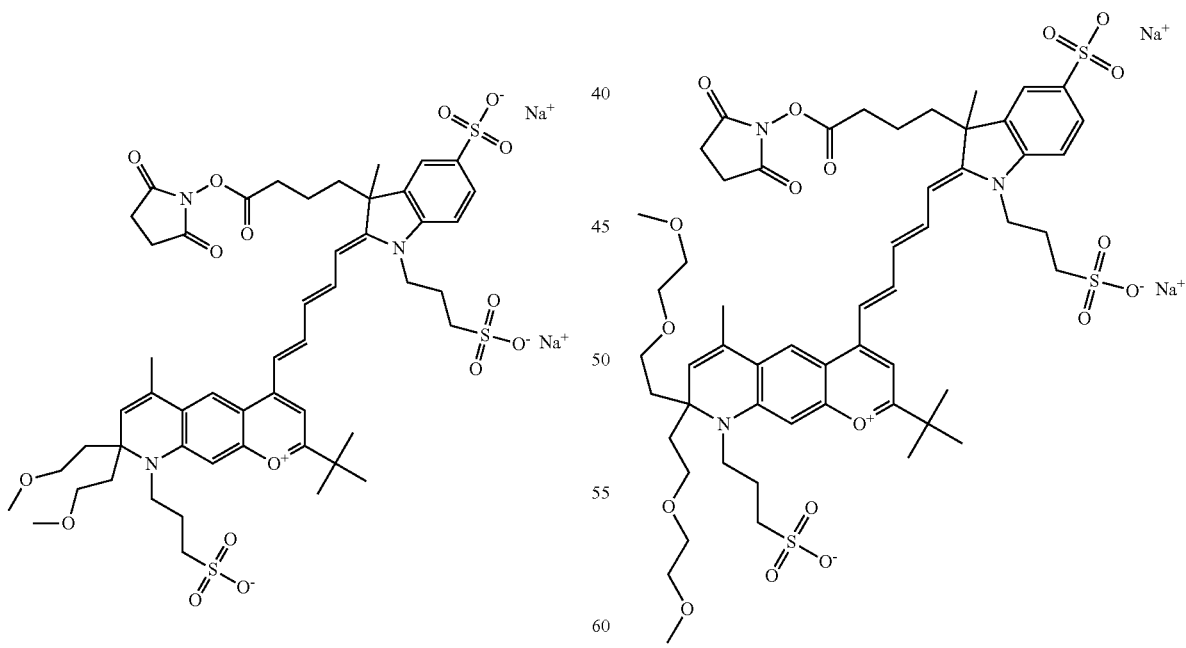

In embodiments, with one example below, substituents shown in non-limiting examples may be replaced with other disclosed substituents, such as 682 Compound 2, according to general formula II and shown below, which contains phenyl in place of the above shown —C(CH$_3$)$_3$ (t-butyl) group:

In one embodiment, the compound is 682 Compound 2, shown below, which contains two ethylene glycols (PEG$_3$), i.e., a methylated ethylene glycol, bound to the substituted ring formed by R1 and R2, sulfoalkyl at R3 and R10, and NHS-ester at R13:

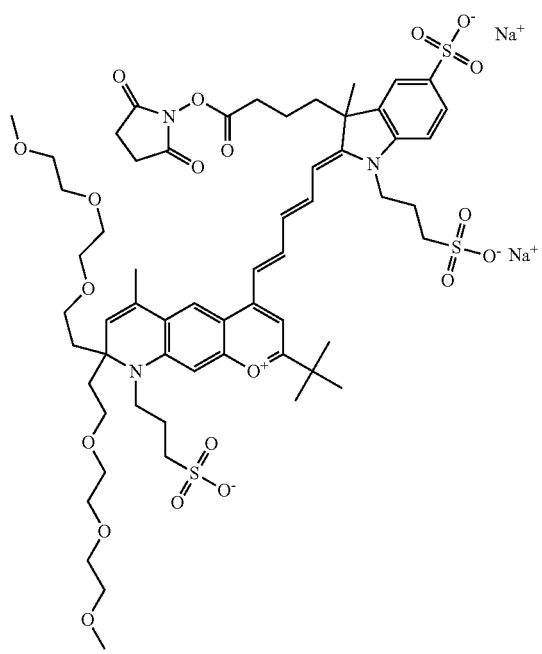 [SMILES: COCCOCCOCCC1(CCOCCOCCOC)C=C(C)c2cc3c(/C=C/C=C/C=C4\N(CCCS(=O)(=O)[O-])c5ccc(S(=O)(=O)[O-])cc5C4(C)CCCC(=O)ON4C(=O)CCC4=O)cc(C(C)(C)C)[o+]c3cc2N1CCCS(=O)(=O)[O-] ; [Na+] ; [Na+]]

In one embodiment, the compound is 682 Compound 2, shown below, which contains two ethylene glycols (PEG$_4$), i.e., a methylated ethylene glycol, bound to the substituted ring formed by R1 and R2, sulfoalkyl at R3 and R10, and NHS-ester at R13:

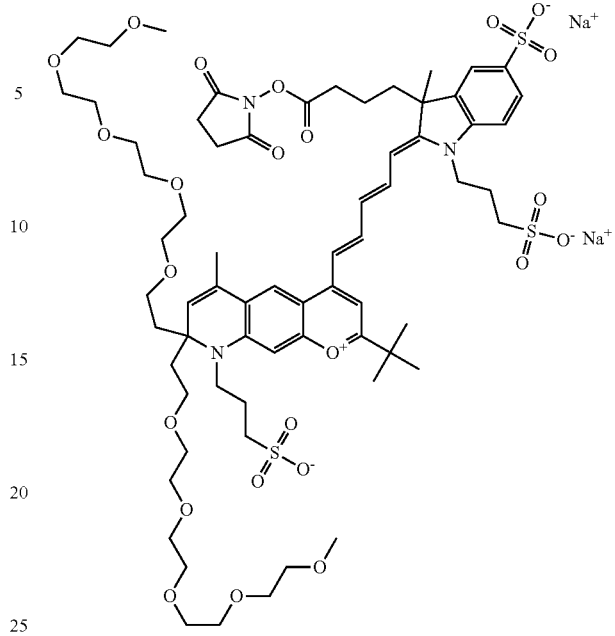

In one embodiment, the compound is 682 Compound 2, shown below, which contains two ethylene glycols (PEG$_6$), i.e., a methylated ethylene glycol, bound to the substituted ring formed by R1 and R2, sulfoalkyl at R3 and R10, and NHS-ester at R13:

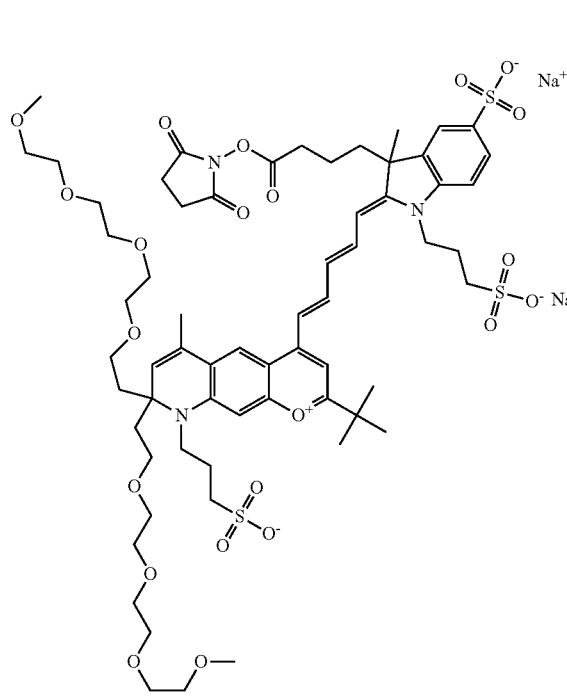

In one embodiment, the compound is 682 Compound 2, shown below, which contains two ethylene glycols (PEG$_5$), i.e., a methylated ethylene glycol, bound to the substituted ring formed by R1 and R2, sulfoalkyl at R3 and R10, and NHS-ester at R13:

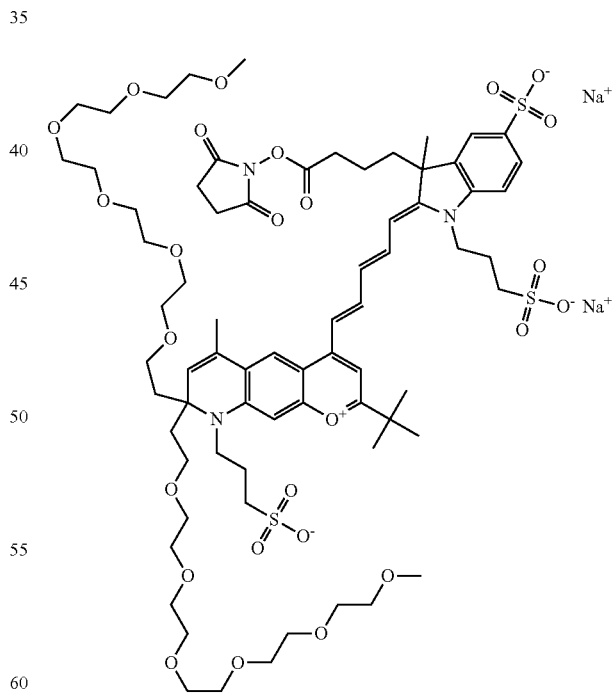

In embodiments, with one example below, substituents shown in non-limiting examples may be replaced with other disclosed substituents, such as 682 Compound 2, according to general formula II and shown below, which contains sulfoalkyl in place of the above shown alkyl group:

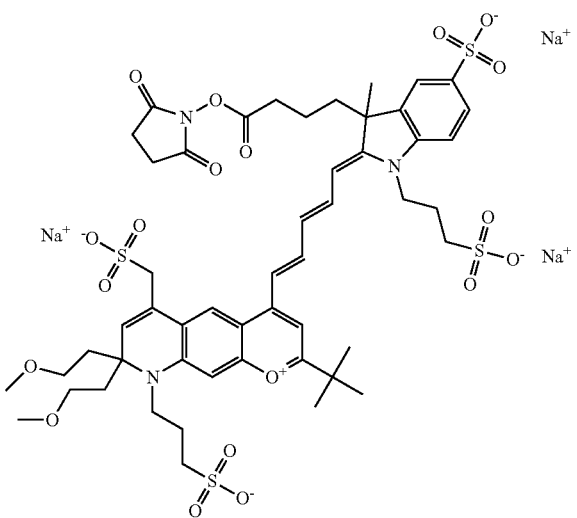

In embodiments, with one example below, substituents shown in non-limiting examples may be replaced with other disclosed substituents, such as 682 Compound 2, according to general formula II and shown below, which contains a phenyl group in place of the above shown —$C(CH_3)_3$ (t-butyl) group:

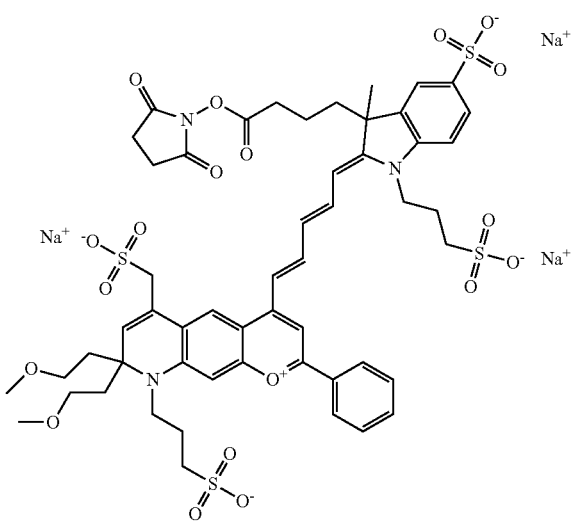

In embodiments, the degree and/or location of sulfonation is varied to, e.g., vary the compound's degree of hydrophilicity or hydrophobicity. A sulfo group may be added at any site, known to one skilled in the art. Thus, there is no maximum or minimum number of sulfo groups added.

In addition to their ability for direct detection, many fluorescent labels have the ability to also quench fluorescence of an adjacent, second, fluorescent label, particularly if the second label is held in proximity to the first label by being covalently bound to the same molecule, such as a protein. In such cases, fluorescence resonance energy transfer (FRET) may occur preferential to emission, thus inhibiting fluorescence. Other nonfluorescent analogs of fluorescent molecules can be designed solely for the purpose of accepting the energy transferred from a neighboring fluorescent label, and such dye analogs are termed quenchers. Quenchers provide a sensitive probe of molecular conformation, binding, and other interactions due to their dependence on the distance and magnitude of the interaction between the quencher and fluorophore. Quenchers may be used in a variety of assays, described in Hermanson (2013) Bioconjugate Techniques, Third Edition, Chapter 1, Section 3.1, Elsevier, 225 Wyman Street, Waltham Mass. In embodiments, quenchers are used in assays labeling a biomolecule, with a fluorophore and a quencher on opposite ends of the biomolecule. In one embodiment the biomolecule is a peptide or a protein and the assay measures protease activity. In one embodiment fluorescent reporter quencher pairs are used in nucleic acid detection and analysis.

Fluorescent nucleic acid probes are important tools for genetic analysis in both genomic research and development and in clinical medicine. One class of fluorescent probes includes self-quenching probes, also known as fluorescence energy transfer (FET) probes. The detailed design of different FET probes may vary, e.g., in one embodiment both a fluorophore and a quencher are tethered to nucleic acid with the probe configured such that the fluorophore is proximate to the quencher and the probe produces a signal only as a result of its hybridization to an intended target. One application for probes including a reporter-quencher molecule pair is use in nucleic acid amplification reactions such as polymerase chain reactions (PCR) to detect the presence and amplification of a target nucleic acid sequence.

The 5'-nuclease PCR assay, also referred to as TaqMan™ assay (Holland et al., Proc. Natl. Acad. Sci. USA 88 (1991) 7276; Lee et al., Nucleic Acids Res. 21 (1993) 3761), detects an amplification product without prior separation of primer and product. This assay detects accumulation of a specific PCR product by hybridization and cleavage of a doubly labeled fluorogenic "TaqMan" probe during the amplification reaction. The fluorogenic probe is a nucleic acid labeled with both a fluorescent reporter dye and a quencher dye. During PCR, this probe is cleaved by the 5'-exonuclease activity of DNA polymerase only if it hybridizes to the segment being amplified. Cleavage of the probe generates an increase in the fluorescence intensity of the reporter dye.

The "beacon probe" method (Tyagi et al. Nature Biotech. 14 (1996) 303; U.S. Pat. No. 5,312,728) is another method to detect amplification products using energy transfer. This method uses nucleic acid hybridization probes that can form hairpin structures. On one end of the hybridization probe, either the 5'- or the 3'-end, is a donor fluorophore. On the other end of the hybridization probe is an acceptor moiety. In this method the acceptor moiety is a quencher, absorbing energy from the donor. Thus, when the beacon is in the open conformation, the fluorescence of the donor fluorophore is detectable. When the beacon is in the closed hairpin conformation, the fluorescence of the donor fluorophore is quenched. When used in PCR, the molecular beacon probe, which hybridizes to one of the strands of the PCR product, is in open conformation and fluorescence is detected, while unhybridized probe does not fluoresce. As a result, the amount of fluorescence will increase as the amount of PCR product increases, and thus is used as a measure of PCR progress.

Certain limitations impede the application and use of FET probes, or result in assays that are less sensitive than they could be. One limitation is the presence of background fluorescence attributable to the emission of the quencher, giving the probe a higher than desirable fluorescent noise background. Using a quencher that is not a fluorophore, such as derivatives of 4-(dimethylamino)azobenzene (DABCYL) can ameliorate this problem. DABCYL is useful as a quenching agent for a limited group of fluorophores with emission characteristics that overlap the absorption characteristics of DABCYL. The limited absorption range of DABCYL restricts its utility by allowing only a limited number of fluorophores in conjunction with DABCYL. Because relatively few fluorophores can be used with DABCYL in FET pairs, multiplex applications, where use of two or more fluorophores with clearly resolved fluorescence emission spectra are desired, are difficult to design using this quencher.

In view of the limitations of available quenchers and probes, such as FET probes constructed with these quenchers, improved quenchers that can be incorporated into probes for detecting analytes rapidly, sensitively, reliably, and quantitatively are desired. Ideal quenchers have little to no fluorescent quenching signal. A series of quenchers with similar physical properties, but distinct spectral properties, would be useful.

In one embodiment, quenchers of excited state energy that are substantially non-fluorescent are provided. The inventive compounds provide a class of quenchers that are functionalized to allow their rapid attachment to probe components using techniques known in the art or modifications of such techniques without undue experimentation.

The inventive compounds provide a class of quenchers that can be engineered or tuned to have a desired light absorption profile. By varying the number and identity of the substituents of the inventive compounds, the spectral properties, e.g., absorbance, of a compound can be "tuned" to match the spectral characteristics, e.g., emission, of one or more fluorophores.

As used herein, energy transfer refers to the process by which the excited state energy of an excited group, such as an otherwise fluorescent molecule, is altered by a modifying group, such as to produce a quenching of the fluorescence. In this manner, if the excited state energy-modifying group is a quenching group, the fluorescence emission from the fluorescent group is attenuated, i.e., quenched. Energy transfer can occur through fluorescence resonance energy transfer (FRET), or through direct energy transfer (FET). The exact energy transfer mechanisms in these two cases are different. Any reference to energy transfer herein encompasses all of these mechanistically-distinct phenomena.

As used herein, energy transfer pair refers to any two molecules that participate in energy transfer. Typically, one of the molecules acts as a fluorescent group, and the other acts as a fluorescence-modifying group. In one embodiment, the energy transfer pair comprises a fluorescent group and a quenching group as described. There is no limitation on the identity of the individual members of the energy transfer pair; all that is required is that the spectroscopic properties of the energy transfer pair as a whole change in some measurable way if the distance between the individual members is altered by some critical amount. Energy transfer pair is used to refer to a group of molecules that form a complex within which energy transfer occurs. Such complexes may include, e.g., two fluorescent groups that may be different from one another and one quenching group, two quenching groups and one fluorescent group, or multiple fluorescent groups and multiple quenching groups. Where there are multiple fluorescent groups and/or multiple quenching groups, the individual groups may be different from one another.

As used herein, fluorescence-modifying group refers to a molecule that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including but not limited to attenuation, complete quenching, enhancement, a shift in wavelength, a shift in polarity, and a change in fluorescence lifetime. One example of a fluorescence-modifying group is a quenching group which, as used herein, refers to any fluorescence-modifying group that can attenuate at least partly the light emitted by a fluorescent group. This attenuation is referred to as quenching. Hence, illumination of the fluorescent group in the presence of the quenching group leads to an emission signal that is less intense than expected, or even is completely absent. Quenching typically occurs through energy transfer between the fluorescent group and the quenching group.

In one embodiment, a class of fluorescence modifiers, e.g., quenchers, of excited state energy is provided. These compounds absorb excited state energy from a reporter fluorophore, but are themselves substantially non-fluorescent. In embodiments, the fluorophore transferring the excited state energy to the quencher will be a label that is attached to an analyte, or a species that interacts with and allows detection and/or quantification of the analyte.

In one embodiment, the quencher contains a benzopyrylium group with an interrupted aromatic system that uses either a dihydro derivative or an azo bond to prevent fluorescence. In one embodiment, the quencher further contains a reactive functional group providing a locus for conjugation of the quencher to a carrier molecule. Although quenchers can be used in their free unbound form, they may be tethered to another species. Thus, in embodiments, quenchers further comprise a reactive functional group that provides a locus for conjugation of the quencher to a carrier molecule.

In embodiments, the disclosed quenchers have substantially no native fluorescence, particularly near their absorbance maxima or near the absorbance maxima of fluorophores used in conjunction with the quenchers. In one embodiment, quenchers have an absorbance maximum of from about 400 nm to about 760 nm. In one embodiment, quenchers have an absorbance maximum in the ultraviolet (UV) spectral range. In one embodiment, quenchers have an absorbance maximum in the near infrared (NIR) spectral range.

Selection of appropriate donor-acceptor pairs for particular probes is disclosed in, e.g., Pesce et al., Eds., Fluorescence Spectroscopy (Marcel Dekker, New York 1971); White et al., Fluorescence Analysis: A Practical Approach (Marcel Dekker, New York 1970); etc. Lists of fluorescent and chromogenic molecules and their relevant optical properties for choosing reporter-quencher pairs are available, e.g., Berlman, Handbook of Fluorescence Spectra of Aromatic Molecules, 2nd Edition (Academic Press, New York 1971); Griffiths, Colour and Constitution of Organic Molecules (Academic Press, New York 1976); Bishop, Ed., Indicators (Pergamon Press, Oxford 1972); Haugland, Handbook of Fluorescent Probes and Research Chemicals (Molecular Probes, Eugene Oreg. 1992); Pringsheim, Fluorescence and Phosphorescence (Interscience Publishers, New York 1949); etc. Methods for derivatizing reporter and quencher molecules for covalent attachment by common reactive groups that can be added to a nucleic acid are known, e.g., Haugland (supra); U.S. Pat. Nos. 3,996,345 and 4,351,760. Thus, one skilled in the art can select an energy exchange pair for a particular application, and can conjugate members of this pair to a probe molecule, e.g., a nucleic acid, peptide, or other polymer, without undue experimentation.

In one embodiment an absorbance band of the quencher substantially overlaps the fluorescence emission band of the donor. When the donor fluorophore is a component of a probe that uses donor-acceptor energy transfer, the donor fluorescent moiety and the quencher acceptor may be selected so that the donor and acceptor moieties exhibit donor-acceptor energy transfer when the donor moiety is excited. One factor in choosing the fluorophore-quencher pair is the efficiency of donor-acceptor energy transfer between them. In one embodiment, the efficiency of FRET between the donor and acceptor moieties is at least 10%, at least 50%, or at least 80%. The efficiency of FRET can be empirically tested using methods known in the art.

The efficiency of energy transfer between the donor-acceptor pair can be adjusted by changing the ability of the donor and acceptor groups to dimerize or closely associate. If the donor and acceptor moieties are known or determined to closely associate, an increase or decrease in association can be promoted by adjusting the length of a linker moiety or of the probe itself between the donor and acceptor. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, the association between the donor-acceptor pair can be increased by, e.g., using a donor bearing an overall negative charge and an acceptor with an overall positive charge.

In one embodiment quenchers contain a benzopyrylium group and have an interrupted aromatic system. Examples of modifications that disrupt the aromatic system of the compound include dihydro derivatives, an azo bond (R—N=N—R'), and addition of one or more phenyl groups at strategic locations.

In embodiments, as exemplified below, the described compounds can be modified to disrupt the aromatic system to result in a quencher.

In one embodiment, a pegylated benzopyrylium quencher compound is shown below, where R1 is methoxy or a PEG group as described above, R2 is sulfoalkyl or a PEG group as described above, and R3 is —OH or —NH—R, where R is a PEG group as described above, where the phenyl and methoxyl groups on the benzopyrylium moiety disrupt the aromatic system.

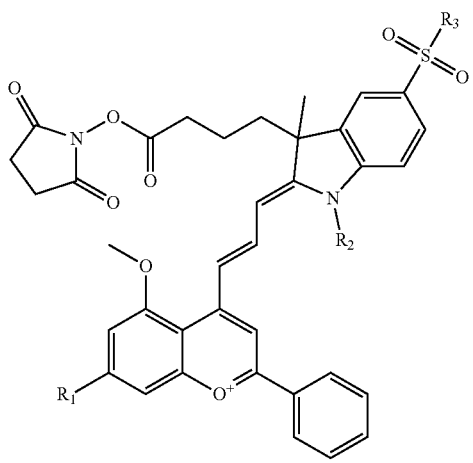

In one embodiment, a pegylated benzopyrylium quencher compound is shown below, where each of R1 and R2 is independently alkyl or a PEG group as described above, R3 is sulfoalkyl or a PEG group as described above, and R4 is —OH or —NH—R, where R is a PEG group as described above, where the phenyl and methyl groups on the benzopyrylium moiety disrupt the aromatic system.

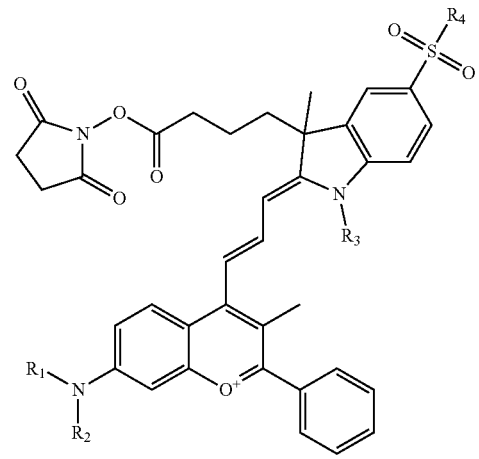

In one embodiment, a pegylated benzopyrylium quencher compound is shown below, where each of R1 and R2 is independently alkyl or a PEG group as described above, R3 is sulfoalkyl or a PEG group as described above, and R4 is —OH or —NH—R, where R is a PEG group as described above, where the phenyl and methyl groups on the benzopyrylium moiety disrupt the aromatic system.

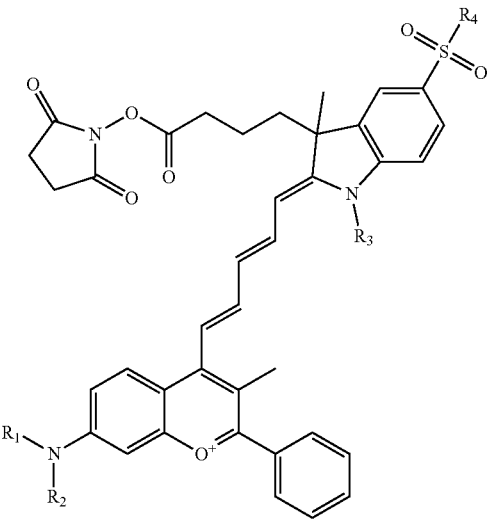

The disclosed compounds may be used as dyes for optical labeling, which may also be termed marking, of proteins, nucleic acids, oligomers, DNA, RNA, biological cells, lipids, mono-, oligo- and polysaccharides, ligands, receptors, polymers, pharmaceutical or polymer particles and coupled via functional groups to, for example, HO—, $H_2N$—, HS—, or $HO_2C$— function of the substances to be determined, as dyes used in systems determining the quality or quantity of proteins, nucleic acids, oligomers, DNA, RNA, biological cells, lipids, polymers, pharmaceutical or polymer particles.

This coupling reaction may be in organic or aqueous solutions.

The conjugates from the described compounds and biomolecules display fluorescing characteristics or deactivate the activated state without emitting light (quencher).

The described compounds have use in qualitative and quantitative optical and in particular optical fluorescent, determinations including immune tests, hybridization procedures, chromatographic or electrophoretic procedures, FRET systems and high-throughput screening, or for analysis of receptor-ligand change effects on a microarray. General formulas I and/or II polymethines may be used as dyes for optical marking of organic or inorganic identification units, e.g., amino acids, peptides, proteins, antigens, haptens, enzyme substrates, enzyme co-factors, biotins, carotinoids, hormones, neurohormones, neuro-transmitters, growth factors, lympholocines, lectins, toxins, carbohydrates, oligosaccharides, polysaccharides, dextrans, nucleic acids, oligonucleotides, DNA, RNA, biological cells, lipids, receptor-linking pharmaceutical or organic or inorganic polymer carriers.

In one embodiment, labeling of probes, also termed identification units, is achieved by forming ionic interactions between general formula I and/or II complexes and the materials to be labeled.

In one embodiment, the probe or identification unit is linked covalently with the described fluorophore. This coupling reaction can be achieved in an aqueous or mainly aqueous solution, preferably at room temperature. The resulting probe or conjugate determines the quality or quantity of different biomaterials or other organic and inorganic materials through the use of optical procedures.

Both general formula I and/or II complexes and derived systems can be used in qualitative and quantitative optical, and in particular optical fluorescent, determination procedures for diagnosing cell characteristics, e.g., molecular imaging, biosensors, e.g., point of care measurements, genome research, and miniaturization technologies. Applications occur in, e.g., cytometry and cell sorting, fluorescence correlation spectroscopy (FCS), ultra-high-throughput-screening (UHTS), multicolor fluorescence in situ hybridization (FISH), FRET systems, and microarrays e.g., DNA- and protein chips.

A microarray is a grid arrangement of molecules immobilized on at least one surface used, e.g., to study receptor-ligand change effects. A grid arrangement is more than two different surface molecules immobilized in known positions in varying pre-defined regions of the surface.

A receptor is a molecule with affinity to a given ligand. Receptors can be naturally occurring or synthetically produced molecules. They can be used in pure form or in association with another species. They can be linked covalently or non-covalently to a linkage partner either directly or using certain coupling mediators. Examples of receptors detectable using the inventive compounds and methods include, but are not limited to, agonists and antagonists for cell membrane receptors, toxins and other poisonous substances, viral epitopes, hormones such as steroids, hormone receptors, peptides, enzymes, enzyme substrates, active substances acting as co-factors, lectins, sugars, oligonucleotides, nucleic acids, oligosaccharides, cells, cell fragments, tissue fragments, proteins and antibodies.

A ligand is a molecule that is recognized by a certain receptor. Examples of ligands that are detectable using the inventive compounds and methods include, but are not limited to, agonists and antagonists for cell membrane receptors, toxins and other poisonous substances, viral epitopes, hormones such as steroids, hormone receptors, peptides, enzymes, enzyme substrates, active substances acting as co-factors, lectins, sugars, oligonucleotides, nucleic acids, oligosaccharides, proteins and antibodies.

The disclosed asymmetrical polymethines possess an easily derivatizable heterocycle and a 6 ring heterocycle, i.e., a novel substitution.

Relatively small molecules absorb in the spectral range>550 nm and display fundamentally improved photochemical and thermal stability, compared with previously known polymethines with maximum absorption maxima>650 nm (penta- and heptamethines).

It is possible, through molecular engineering, to control the position and intensity of absorption and emission maxima at will and to adjust them in line with emission wavelengths of different activating lasers, in particular diode lasers.

The inventive compounds were synthesized by condensing the two different heterocycles and a C-1, C-3, or C-5 component ("mulligan procedure"). Further manufacturing procedures involve condensation of one of the CH acid heterocycles with the C-1, C-3, or C-5 component at an initial reaction stage and, following isolation of the 1:1 condensation product, conversion to a polymethine with the second CH-acid heterocycle in a subsequent condensation process. The sequence of heterocycle applications involved is considerable. On this basis, many hydrophilic, variously functionalized dyes differing in total charge and the specificity/reactivity of the activated groups used for immobilization can be easily manufactured in few reaction steps.

Conjugates of the compounds were prepared by covalently coupling the compounds to a biomolecule using the functional substituent on the N-position of the indole ring. This functional substituent was activated by routine protein chemistry reaction methods known to one skilled in the art. The activated compound may be converted to, e.g., and without limitation, N-hydroxysuccinimide (NHS)-ester, acid fluoride, tetrafluorophenyl (TFP)- or sulfotetrafluorophenyl (STP)-ester, iodoacetyl group, maleimide, hydrazide, sulfonyl chloride, or phenylazide. Methods for preparing such compounds are known to one skilled in the art. In one embodiment, the activated substituent was then reacted with an amino group on the biomolecule under conditions to conjugate the desired biomolecule.

In one embodiment, a non-activated carboxyl group on the N-position of the indole in the compound was coupled to an amine using a carbodimide.

In one embodiment, a N-hydroxysuccinimidyl ester (X=—NHS) of a compound was formed as follows: 20 μmol dye with X=OH (carboxyalkyl group), 8 mg (40 μmol) dicyclohexylcarbodiimide, and 5 mg (40 μmol) N-hydroxysuccinimide were dissolved in 2 ml DMF and 100 μl water. Six μl (40 μmol) triethylamine was added. The reaction mixture was stirred at room temperature (about 19° C. to about 22° C.) for 24 hours and then filtered. The solvent was removed and the residue was washed with diethylether. The reaction proceeded quantitatively.

In one embodiment, a maleimide (X=—NH—CH$_2$CH$_2$-maleimide) of a compound is formed as follows: 20 μmol dye with X=—NHS (N-hydroxysuccinimid-ester) was dissolved in 2 ml DMF and 100 μl water and mixed with 7.6 mg (30 μmol) 2-maleimidoethylamine-trifluoracetate and 5 μl (30 μmol) N-ethyldiisopropyl-amine. The reaction mixture is stirred for three hours at room temperature. The solvent was evaporated under reduced pressure. The residue is washed with diethylether and acetone and dried in vacuum. The reaction proceeds quantitatively.

In one embodiment, a iodoacetamide (X=—NH—CH$_2$CH$_2$—NH—CO—CH$_2$—I) of a compound is formed as follows: 20 µmol dye with X=—NHS (N-hydroxysuccinimid-ester) was dissolved in 2 ml DMF and 100 µl water, followed by addition of 40 mg (300 µmol) ethylendiamindihydrochloride and 26 µl (150 µmol) N-ethyldiisopropylamine. The reaction mixture is stirred for three hours at room temperature. The solvent is then evaporated under reduced pressure, the residue was dissolved in methanol, and the ethylendiamindihydrochlorid was removed by filtration. Methanol is evaporated under reduced pressure. The residue is dissolved in 2 ml dry DMF, followed by addition of 7 mg (25 µmol) N-succinimidyl iodoacetate and 4 µl (25 µmol) N-ethyldiisopropylamine. The reaction mixture is stirred for three hours at room temperature. The solvent is evaporated under reduced pressure and the residue purified by reverse phase HPLC.

In one embodiment, a hydroxyl group, such as a terminal hydroxyl group, can be subsequently activated to a reactive derivative able to link with, e.g., proteins and other molecules. Examples of activating groups include tosyl chloride (TsCl), tresyl chloride (TrCl), disuccinimidyl carbonate (DSC), divinyl sulfone, bis-epoxy compounds, carbonyl diimidazole (CDI), 2-fluoro-1-methylpyridinium (FMP), and trichloro-s-triazine (TsT). In one embodiment, the hydroxyl group is activated to a succinimidyl carbonate, which is reactive with amines.

Coupling between the compound and the biomolecule may be performed as follows. The compound was reacted with the biomolecule in an organic or aqueous solution at pH between pH 5-12 inclusive. The compound need not be dissolved in an organic solvent, such as dimethyl formamide (DMF) or dimethyl sulfoxide (DMSO), prior to adding the biomolecule. In one embodiment, coupling may be performed in a 100% aqueous solution. In one embodiment, the coupling reaction occurs at room temperature (about 19° C. to about 22° C.).

To form a composition or dye, at least one biocompatible excipient was added to the compound(s), as known to one of ordinary skill in the art. Excipients include, but are not limited to, buffers, solubility enhancing agents, stabilizing agents, etc.

In one embodiment, a kit for performing an assay method contains at least one inventive compound, and instructions for performing the method using the compound.

The disclosed activated compounds, i.e., the compound modified with a reactive group, are useful to label macromolecules, e.g., antibodies, streptavidin, etc., using methods known to one skilled in the art, e.g., Hermanson, Bioconjugate Techniques, 2nd Ed., London, Elsevier Inc. 2008. The reaction was carried out for one to two hours at room temperature, and then desalted by dialyzing against several changes of phosphate buffered saline (pH 7.2) or purified by gel filtration to remove the unreacted fluorescent dye. The resulting compound-biomolecule conjugate was used to detect, e.g., specific proteins in immunoassays, sugars in glycoproteins with lectins, protein-protein interactions, oligonucleotides in nucleic acid, hybridization, and in electrophoretic mobility shift assays (EMSA).

The resulting compound-biomolecule conjugates exhibited fluorescent properties and could be used in optical methods including fluorescence optical qualitative and quantitative determination methods such as microscopy, immunoassays, hybridization methods, chromatographic and electrophoretic methods, fluorescence resonance energy transfer (FRET) systems, high throughput screenings, analysis of receptor-ligand interactions on a microarray, etc.

Compounds in any embodiment were used as dyes for optical labelling or marking of organic or inorganic biomolecules, referred to as recognition units. Recognition units are molecules having specificity and/or affinity for a specific group of molecules. Examples include, but are not limited to, antibodies that have affinity for antigens, enzymes that bind and/or react with a specific bond or bonds within a sequence of amino acids in a peptide or react with a substrate, cofactors such as metals that enhance or inhibit specific interactions, lectins that bind specific sugars or sugar sequences (e.g., oligosaccharides, polysaccharides, dextrans, etc.), biotin binding proteins such as avidin and streptavidin that bind biotin and biotinylated molecules, antibody binding proteins such as Protein A, Protein G, Protein A/G and Protein L, sequences of amino acids or metals that have affinity for each other (e.g., histidine sequences that bind nickel or copper, phosphate containing proteins that bind gallium, aluminium, etc.), specific sequences of nucleic acids such as DNA and/or RNA oligonucleotides that have affinity for proteins, specific sequences of amino acids that have affinity for DNA and/or RNA, haptens, carotenoids, hormones (e.g., neurohormones), neurotransmitters, growth factors, toxins, biological cells, lipids, receptor binding drugs or organic or inorganic polymeric carrier materials, fluorescent proteins such as phycobilliproteins (e.g., phycoethrin, allophycocyanin), etc. Ionic interactions between recognition units and the disclosed compounds results in labeling of the recognition units. The recognition unit and compound can be covalently bound. The result is a conjugate for qualitative or quantitative determination of various biomaterials or other organic or inorganic materials using optical methods.

The inventive compounds and/or conjugates are used in optical, including fluorescence optical, qualitative and/or quantitative determination methods to diagnose properties of cells, e.g. molecular imaging, in biosensors, e.g., point of care measurements, for investigation of the genome, and in miniaturizing technologies. Microscopy, cytometry, cell sorting, fluorescence correlation spectroscopy (FCS), ultra high throughput screening (UHTS), multicolor fluorescence in situ hybridisation (mc-FISH), FRET-systems and microarrays (DNA- and protein-chips) are exemplary application fields. The inventive compounds have utility in, e.g., in vivo imaging, ex vivo imaging, multispectral optoacoustic tomography (MSOT) imaging, photoacoustic imaging and imaging systems, tumor imaging with labeled peptides, NIR fluorescence (NIRF) imaging of labeled silica nanoparticles, NIR in vitro imaging and characterization, thermal stability determination, cytotoxicity assays, molecular imaging, UV-VIS-NIR spectroscopy, fluorescence correlation spectroscopy, magnetic resonance imaging (MRI) and applications, DNA sequencing, primer labeling for PCR, two-dimensional (2-D) gel electrophoresis, flow cytometry/fluorescence-activated cell sorting (FACS), laser scanning confocal microscopy, spectral fluorescence imaging, fluorescent Western blotting, protein arrays and microarrays, antibody labeling, peptide labeling, single molecule detection, nanoparticle conjugation, and biotin/streptavidin conjugation.

Adding PEG 1-6 at appropriate sites to strategically surround the core dye beneficially affected dye hydrophilicity and performance in biological applications. Previous attempts to render dyes more hydrophilic and less "sticky" toward biomolecules included the addition of multiple sulfonates and/or relatively longer PEG chains to some locations on dye molecules. However, the addition of too many sulfonates, while having the effect of increasing the relative water solubility of dyes, can create undesirable nonspecific binding character due to negative charge interactions with positively charged biomolecules, particularly proteins. Previous attempts to render dyes more water soluble by adding longer PEG chains to one or two sites on a dye had the detrimental effect of dramatically increasing the molecular weight of the dye, possibly preventing efficient access of dye-labeled antibodies and other dye-labeled targeting molecules to bind with inner cellular targets, while also not fully surrounding and masking the hydrophobic dye core structure.

In contrast, the use of such relatively short PEG chain modifications at critical sites on a dye molecule, limiting the total molecular size of labeled molecules, resulted in dramatically reduced nonspecificity by masking the hydrophobic dye core.

General Synthesis of General Formula I, Activated Forms, and Specific Exemplary Compounds The general procedure for synthesis of compounds according to general formula I was as follows:

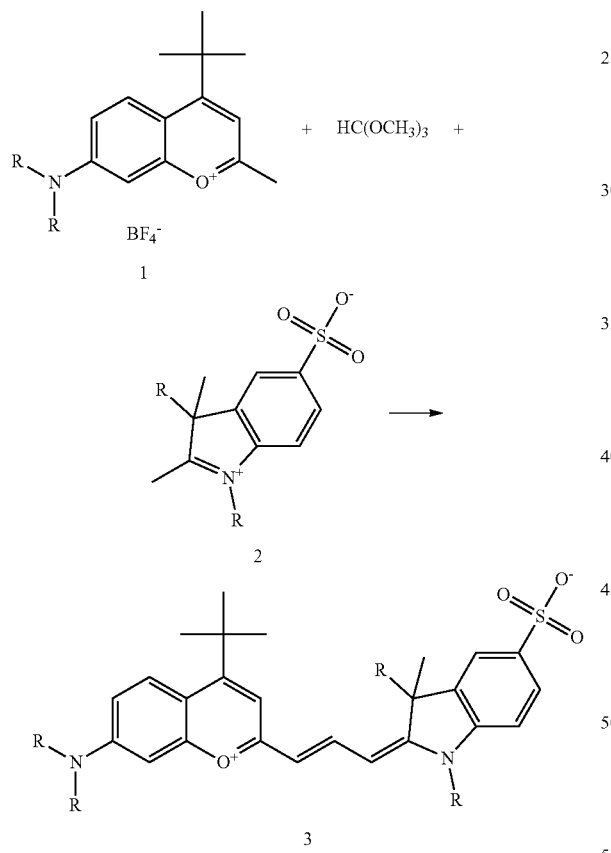

One mmol benzopyrylium salt 1 and 1 mmol indolium compound 2 were dissolved in a mixture of 25 ml acetic acid anhydride and 25 ml acetic acid, then 1 mmol trimethylorthoformate and 1 ml pyridine were added. The solution was stirred for about 30 minutes at about 140° C. After cooling to room temperature, the solvent was removed in vacuum.

The residue was heated to reflux for two hours in a mixture of 10 ml acetone and 10 ml 2 M hydrochloric acid, the reaction solution was neutralized with NaHCO$_3$ and the solvent was distilled off in vacuum. The residue was purified by column chromatography (reversed phase silica gel RP-18, eluent methanol/water). HPLC chromatography was the final purification step.

The general procedure for synthesis of dye-NHS esters was as follows:

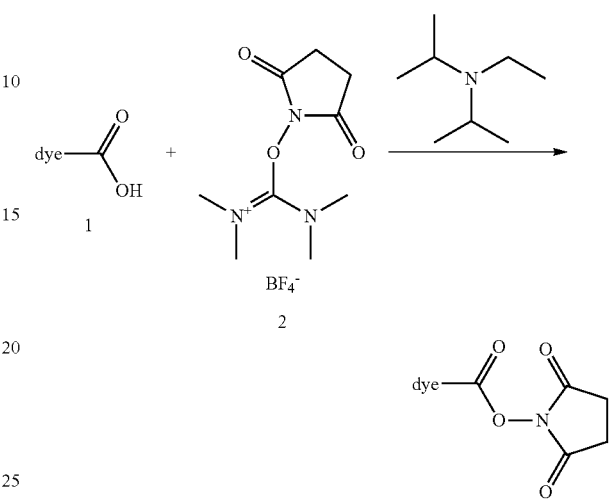

Fifty μmol dye, free acid 1 was dissolved in 4 ml of DMF and cooled to 0° C. To this solution 60 μmol O-succinimidyl-N,N,N',N'-tetramethyluronium tetrafluoroborate 2 and 60 μmol diisopropylethylamin were added. After 20 minutes at 0° C., the solvents were distilled off in high vacuum. The residue was purified by column chromatography (RP-18 silica gel; acetonitrile/water).

The general procedure for synthesis of dye-TFP ester was as follows:

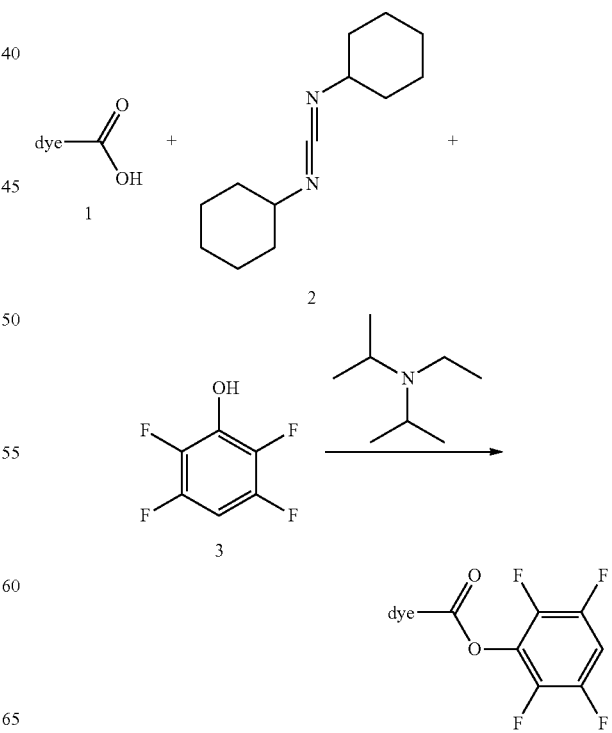

Fifty μmol dye, free acid 1 was dissolved in 4 ml DMF and cooled to 0° C. To this solution 0.3 mmol dicyclohexylcarbodiimide 2, 60 μmol 2,3,5,6-tetrafluoro-4-hydroxybenzene 3 and then 60 μmol diisopropylethylamin were added. After ten minutes at 0° C. the reaction mixture was warmed to room temperature and stirred for two hours. The solvents were distilled off in high vacuum. The residue was purified by column chromatography (RP-18 silica gel; acetonitrile/water).

The general procedure for synthesis of dye-STP ester was as follows:

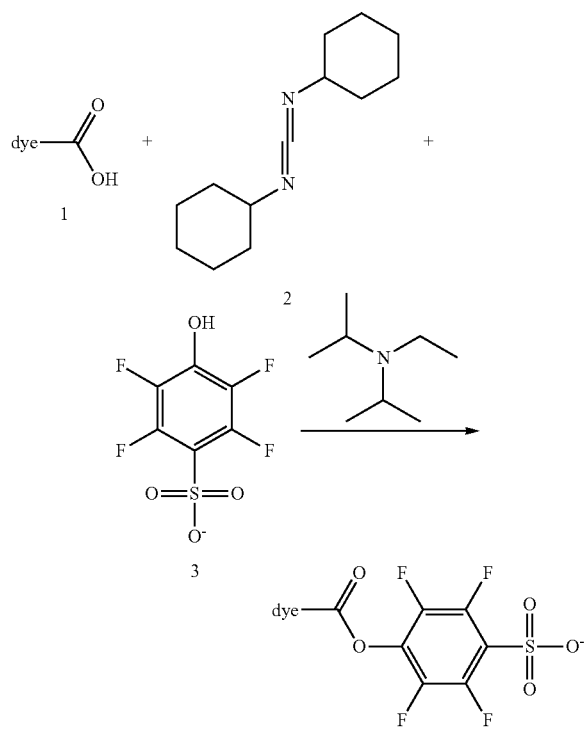

Fifty μmol dye, free acid 1 was dissolved in 4 ml DMF and cooled to 0° C. To this solution 60 μmol dicyclohexylcarbodiimide 2, 60 μmol 2,3,5,6-tetrafluoro-4-hydroxybenzene sulfonic acid sodium salt 3 and then 60 μmol diisopropylethylamin were added. After ten minutes at 0° C., the reaction mixture was warmed to room temperature and stirred for two hours. The solvents were distilled off in high vacuum. The residue was purified by column chromatography (RP-18 silica gel; acetonitrile/water).

The general procedure for synthesis of dye-maleimide was as follows:

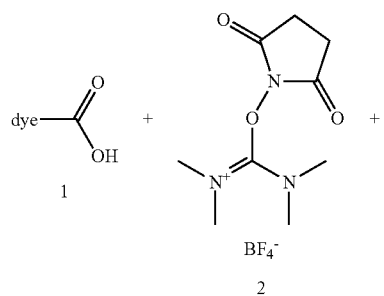

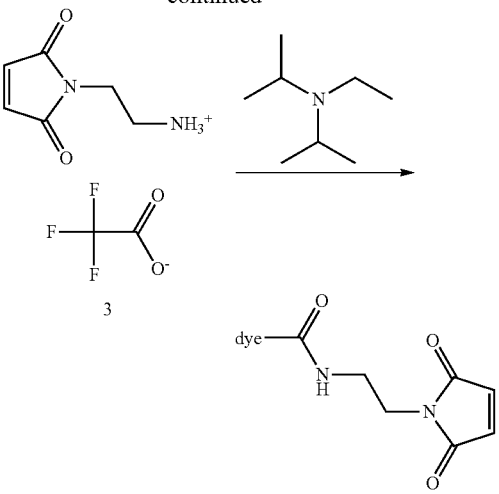

Fifty μmol dye, free acid 1 was dissolved in 4 ml DMF and cooled to 0° C. To this solution 60 μmol O-succinimidyl-N,N,N',N'-tetramethyluronium tetrafluoroborate 2 and 60 μmol diisopropylethylamine were added. After 20 minutes at 0° C., 60 μmol N-(2-aminoethyl)-maleimide trifluoroacetate salt and 60 μmol diisopropylethylamin were added. The reaction mixture was warmed to room temperature and stirred for two hours. The solvents were distilled off in high vacuum. The residue was purified by column chromatography (RP-18 silica gel; acetonitrile/water).

The general procedure for synthesis of dye-hydrazide was as follows:

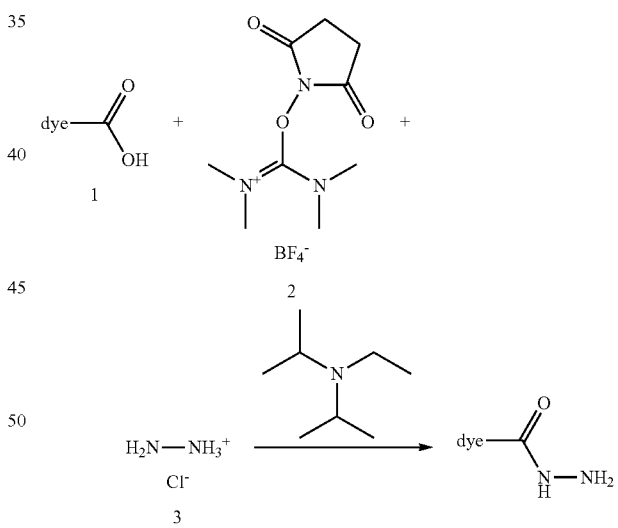

Fifty μmol dye, free acid 1 was dissolved in 4 ml DMF and cooled to 0° C. To this solution 60 μmol O-succinimidyl-N,N,N',N'-tetramethyluronium tetrafluoroborate 2 and 60 μmol diisopropylethylamin were added. After 20 minutes at 0° C., 50 μmol hydrazine monohydrochloride and 60 μmol diisopropylethylamin were added. The reaction mixture was warmed to room temperature and stirred for one hour. The solvents were distilled off in high vacuum. The residue was purified by column chromatography (RP-18 silica gel; acetonitrile/water).

The following compound (PEG4-682; V08-16072) according to general formula Ia, was synthesized according to the general procedure for general formula I, PEG4-682:

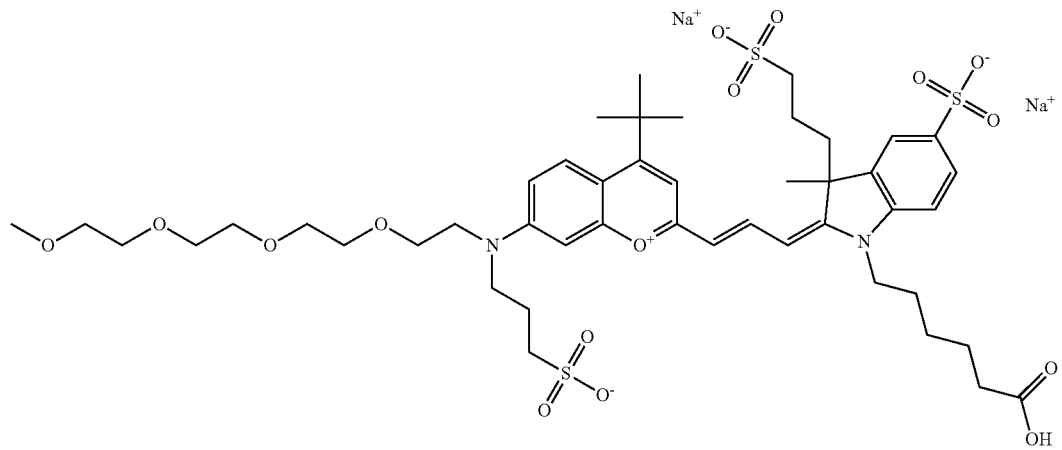
yield: 350 mg (35%)
UV-vis (ethanol): $\lambda_{abs}$=690 nm
$\lambda_{em}$=708 nm
MS (ESI−) [M/z]: 498.4 $[M]^{2-}$
The following compound according to general formula Ia was synthesized according to general procedure for compound I and general procedure for dye-NHS ester, PEG4-682-NHS-ester:
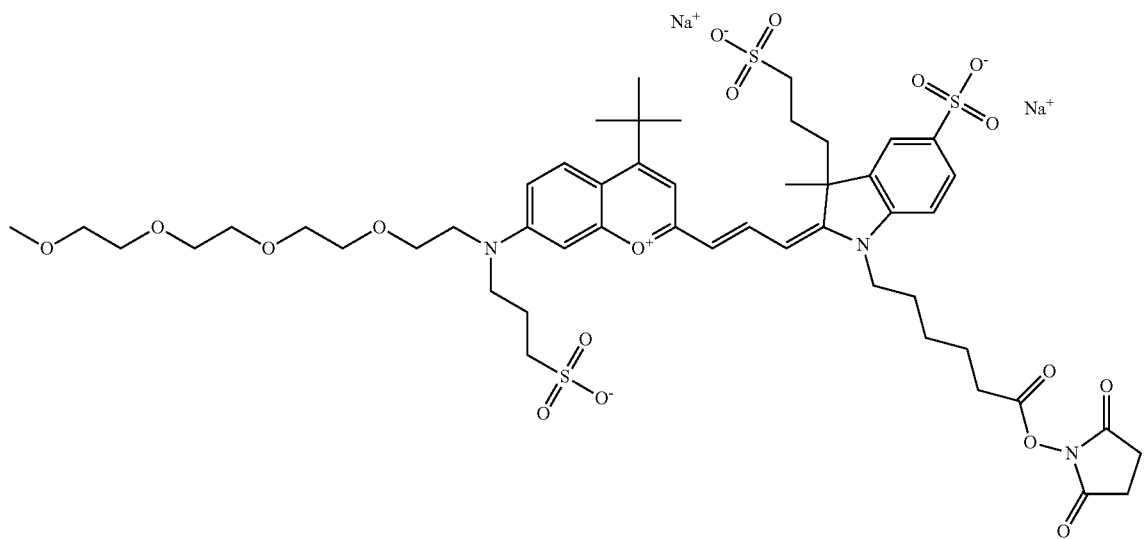

yield: 50 mg (88%)
UV-vis (ethanol): $\lambda_{abs}$=690 nm
$\lambda_{em}$=708 nm
MS (ESI−) [M/z]: 546.6 [M]$^{2-}$ The following compound according to general formula Ia is synthesized according to general procedure for compound I and general procedure for dye-TFP ester, PEG4-682-TFP-ester:

yield: 33 mg (50%)
UV-vis (ethanol): $\lambda_{abs}$=690 nm
$\lambda_{em}$=708 nm
MS (ESI−) [M/z]: 407.7 [M]$^{3-}$ The following compound according to general formula Ia is synthesized according to general procedure for compound I and general procedure for dye-maleimide. (PEG4-682-maleimide)

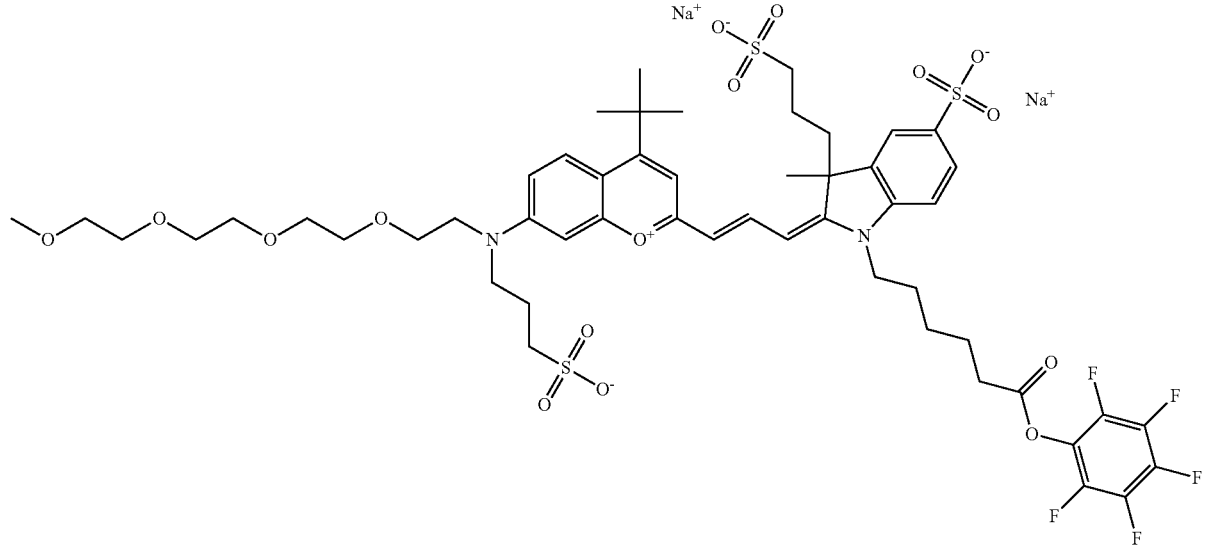

yield: 30 mg (50%)
UV-vis (ethanol): $\lambda_{abs}$=690 nm
$\lambda_{em}$=708 nm
MS (ESI−) [M/z]: 572.2 [M]$^{2-}$ The following compound according to general formula Ia is synthesized according to general procedure for compound I and general procedure for dye-STP ester, PEG4-682-STP-ester:

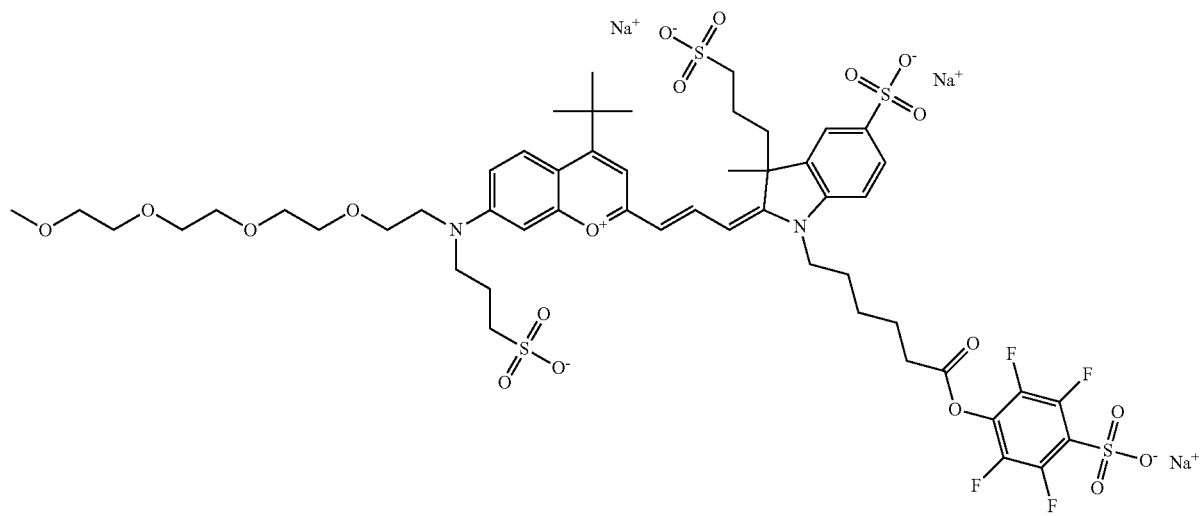

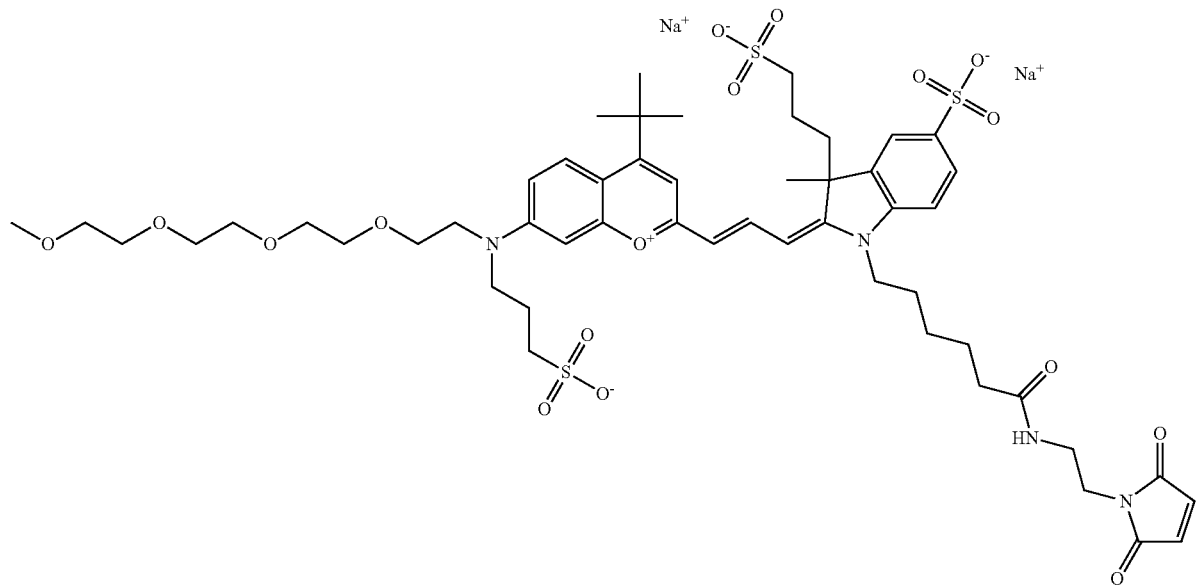

yield: 46 mg (79%)
UV-vis (ethanol): λ$_{abs}$=690 nm
λ$_{em}$=708 nm
MS (ESI−) [M/z]: 559.2 [M]$^{2-}$ The following compound according to general formula Ia is synthesized according to general procedure for compound I and general procedure for dye-hydrazide, PEG4-682-hydrazide:

yield: 30 mg (58%)
UV-vis (ethanol): λ$_{abs}$=690 nm
λ$_{em}$=708 nm
MS (ESI−) [M/z]: 1011.3 [M]$^{-}$ The following compound according to general formula Ib is synthesized according to general procedure for compound I, PEG4-682:

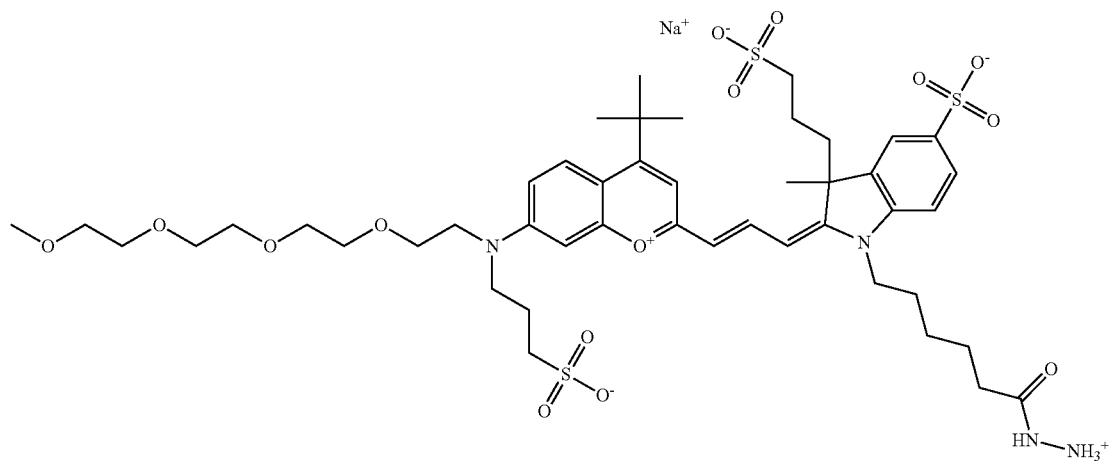

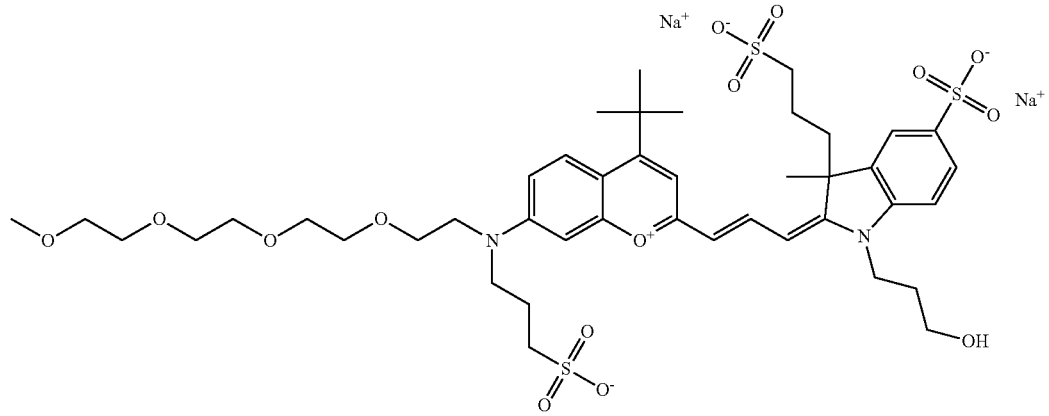

yield: 320 mg (32%)
UV-vis (ethanol): $\lambda_{abs}$=691 nm
$\lambda_{em}$=708 nm
MS (ESI−) [M/z]: 470.2 [M]$^{2-}$ The following compound according to general formula Ic was synthesized according to general procedure for compound I, PEG4-682 (V13-06190):

yield: 290 mg (25%)
UV-vis (ethanol): $\lambda_{abs}$=690 nm
$\lambda_{em}$=708 nm
MS (ESI−) [M/z]: 565.2 [M]$^{2-}$ The following compound according to general formula Id is synthesized according to general procedure for compound I, PEG4-682:

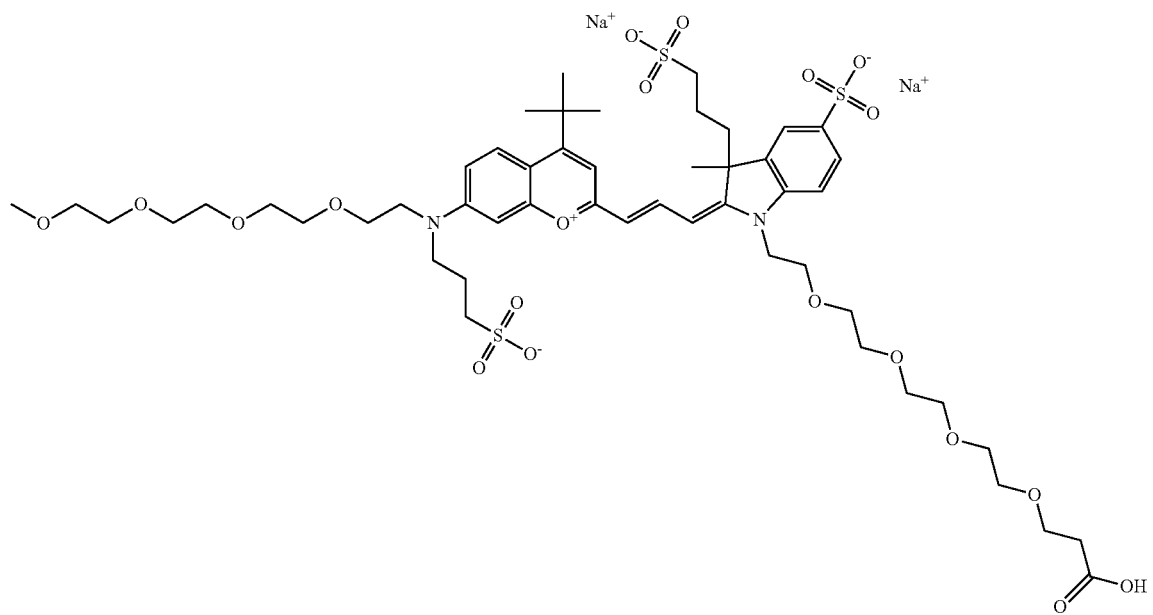

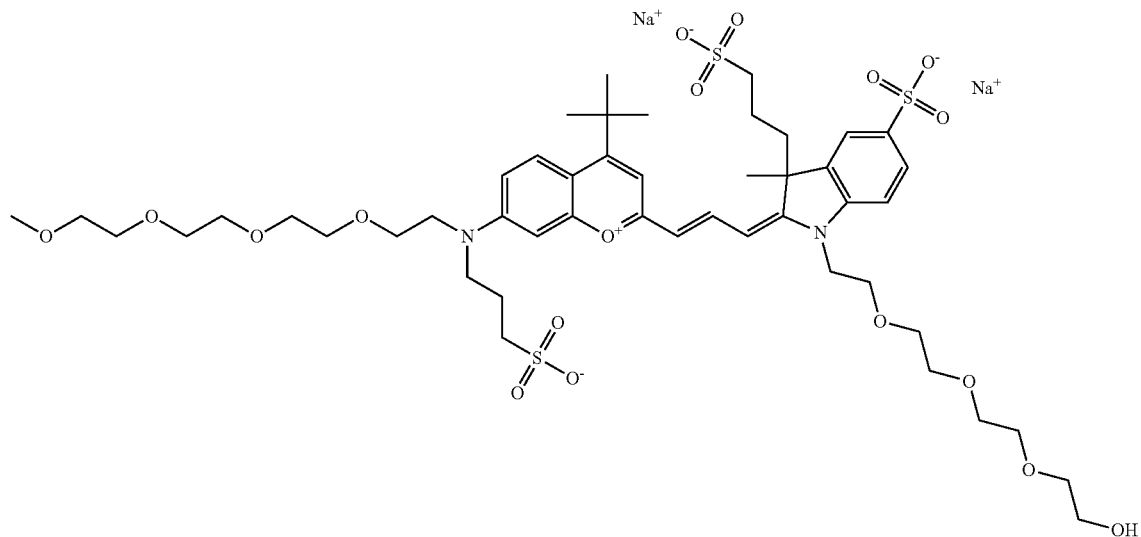

yield: 300 mg (27%)
UV-vis (ethanol): $\lambda_{abs}$=691 nm
$\lambda_{em}$=709 nm
MS (ESI−) [M/z]: 529.3 [M]$^{2-}$ The following compound according to general formula Ie is synthesized according to general procedure for compound I, PEG4-682:

yield: 300 mg (26%)
UV-vis (ethanol): $\lambda_{abs}$=690 nm
$\lambda_{em}$=709 nm
MS (ESI−) [M/z]: 565.1 [M]$^{2-}$ The following compound according to general formula If is synthesized according to general procedure for compound I, PEG4-682:

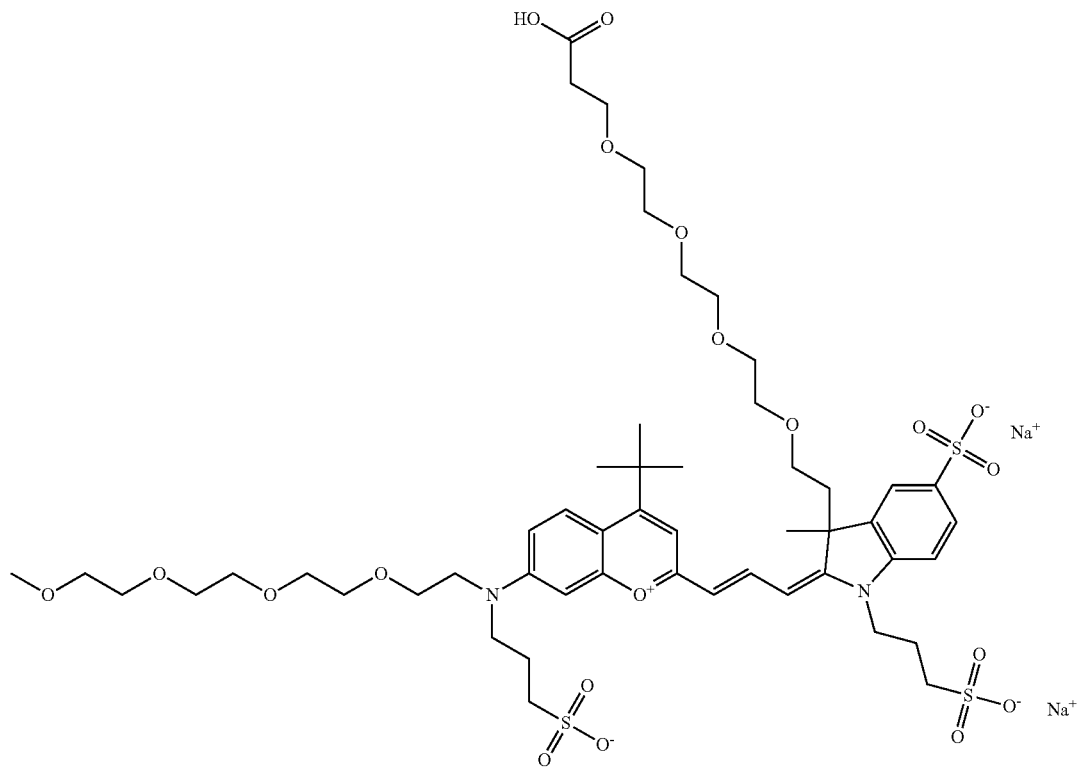

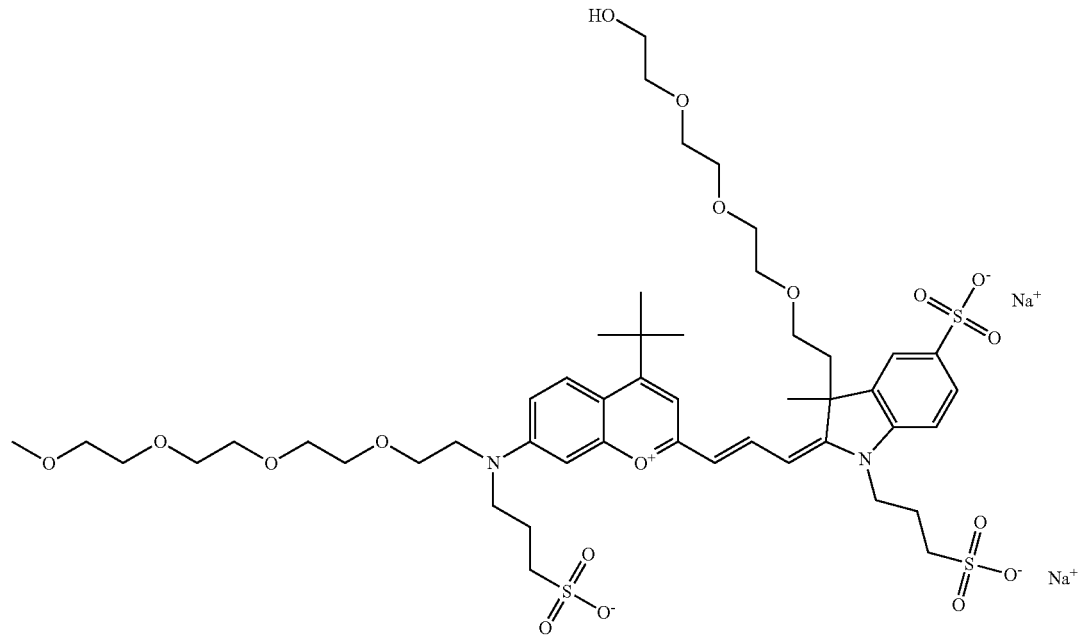

yield: 295 mg (27%)
UV-vis (ethanol): $\lambda_{abs}$=691 nm
$\lambda_{em}$=709 nm
MS (ESI−) [M/z]: 529.4 [M]$^{2-}$ The following compound according to general formula Ig was synthesized according to general procedure for compound I, PEG4-682 (V17-03019):

yield: 360 mg (36%)
UV-vis (ethanol): $\lambda_{abs}$=691 nm
$\lambda_{em}$=709 nm
MS (ESI−) [M/z]: 484.4 [M]$^{2-}$ The following compound according to general formula Ig was synthesized according to general procedure for compound I, (PEG4)$_2$-681 (V03-07005):

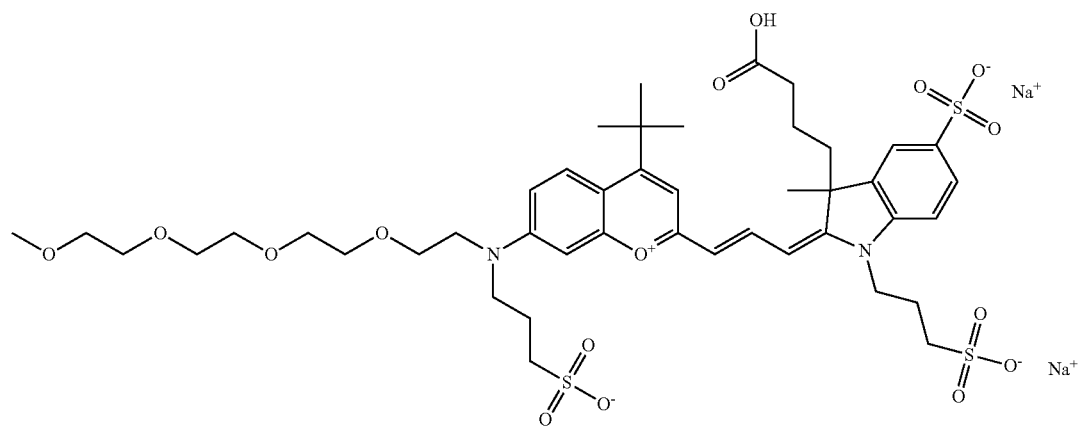

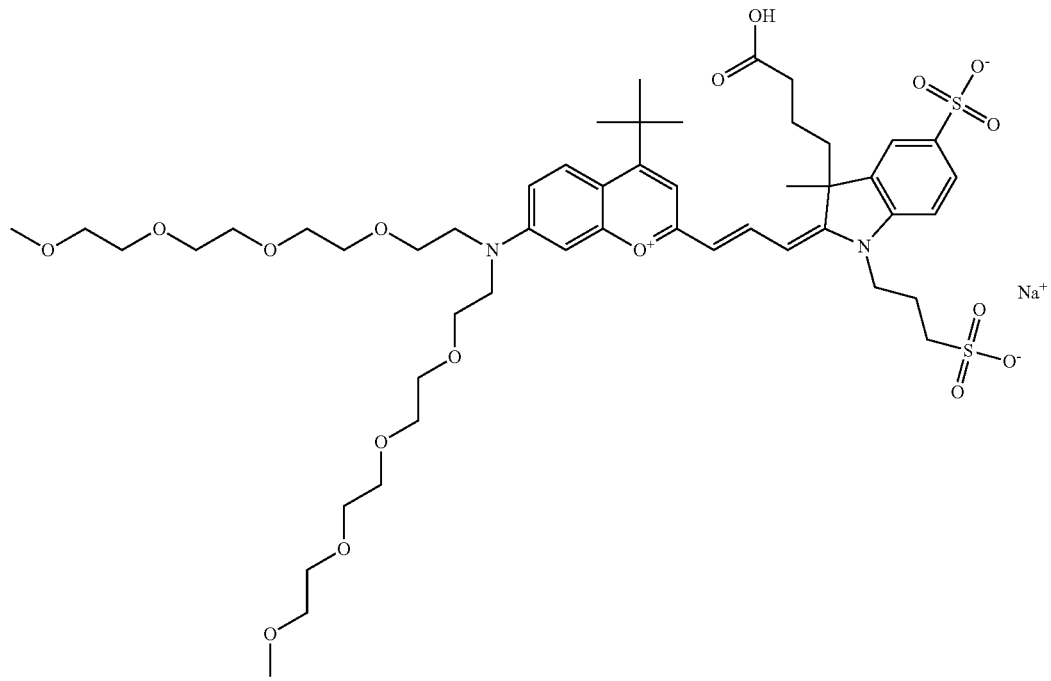

yield: 325 mg (31%)
UV-vis (ethanol): $\lambda_{abs}$=689 nm
$\lambda_{em}$=708 nm
MS (ESI−) [M/z]: 1037.2 [M]−

The following compound according to general formula Ih is synthesized according to general procedure for compound I, PEG4-682:

yield: 280 mg (28%)
UV-vis (ethanol): $\lambda_{abs}$=690 nm
$\lambda_{em}$=708 nm
MS (ESI−) [M/z]: 470.2 [M]$^{2-}$ The following compound according to general formula Ig is synthesized according to general procedure for compound I, (PEG4)$_2$-703:

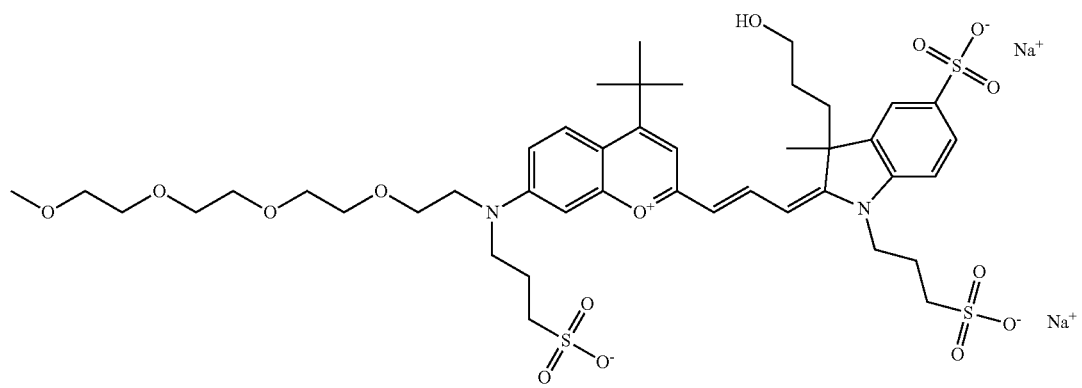

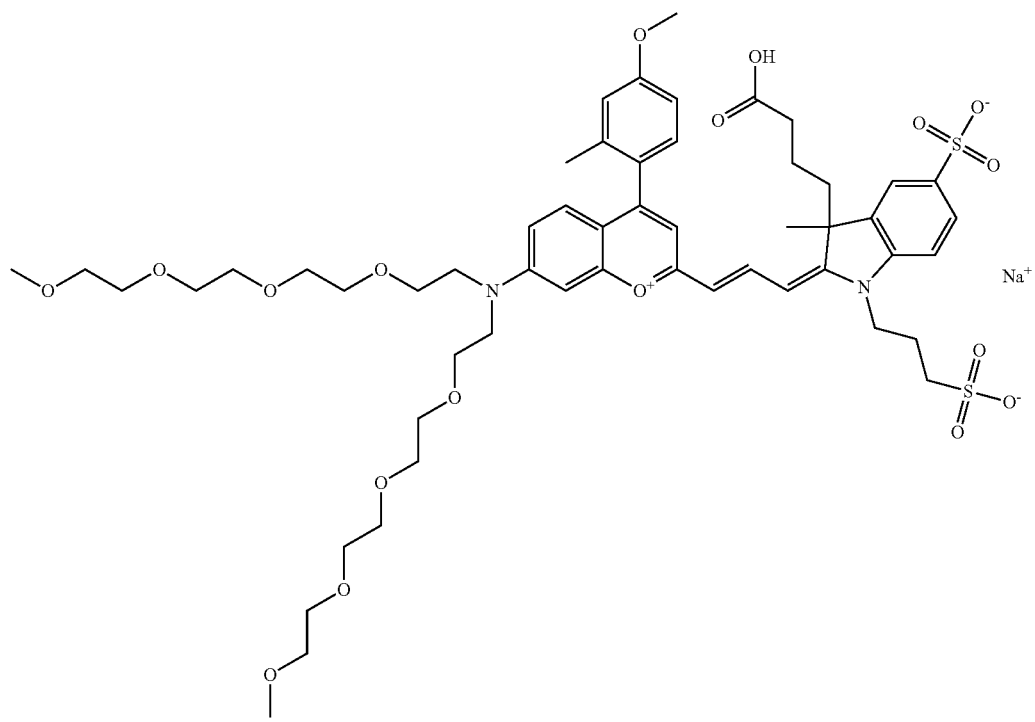

yield: 330 mg (30%)

UV-vis (ethanol): $\lambda_{abs}$=705 nm $\lambda_{em}$=721 nm

MS (ESI−) [M/z]: 1101.1 [M]⁻

General Synthesis of General Formula II, Activated Forms, and Specific Exemplary Compounds The general procedure for synthesis of dyes according general formula II was as follows:

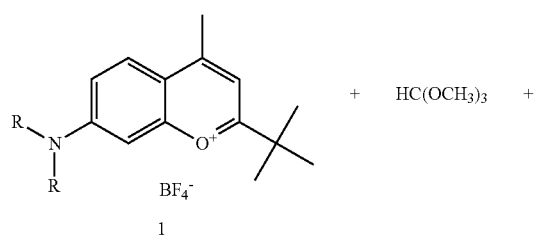

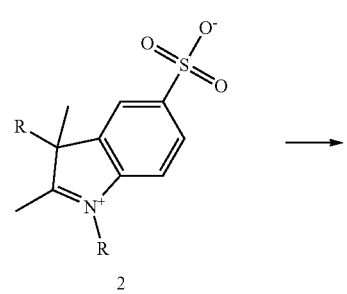

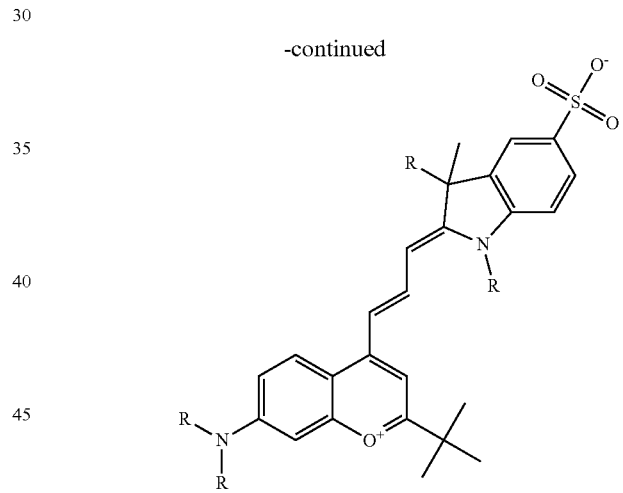

One mmol benzopyrylium salt 1 and 1 mmol indolium compound 2 were dissolved in a mixture of 25 ml acetic acid anhydride and 25 ml acetic acid, then 1 mmol trimethylorthoformate and 1 ml pyridine were added. The solution was stirred for about 30 min at about 140° C. After cooling to room temperature, the solvent was removed in vacuum.

The residue was heated to reflux for two hours in a mixture of 10 ml acetone and 10 ml 2 M hydrochloric acid, the reaction solution was neutralized with NaHCO₃ and the solvent was distilled off in vacuum. The residue was purified by column chromatography (reversed phase silica gel RP-18, eluent methanol/water). HPLC chromatography was used as final purification step.

The following compound according to general formula IIa is synthesized according to general procedure for compound II, PEG4-632:

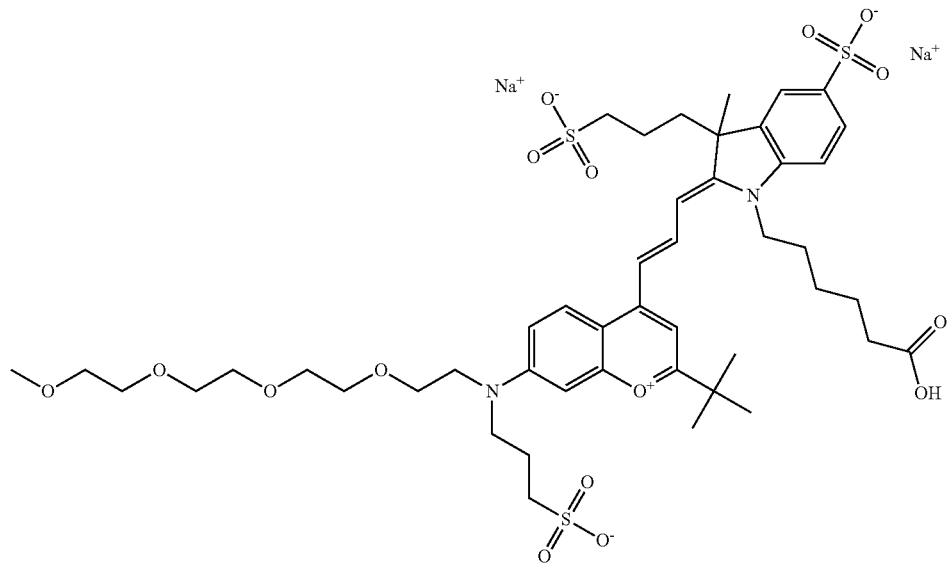

yield: 315 mg (30%)
UV-vis (ethanol): $\lambda_{abs}$=637 nm
$\lambda_{em}$=658 nm
MS (ESI−) [M/z]: 498.2 $[M]^{2-}$ The following compound according to general formula IIa is synthesized according to general procedure for compound II and general procedure for dye-NHS ester, PEG4-632-NHS ester:

yield: 51 mg (89%)
UV-vis (ethanol): $\lambda_{abs}$=637 nm
$\lambda_{em}$=658 nm
MS (ESI−) [M/z]: 546.7 $[M]^{2-}$ The following compound according to general formula IIa is synthesized according to general procedure for compound II and general procedure for dye-TFP ester, PEG4-632-TFP ester:

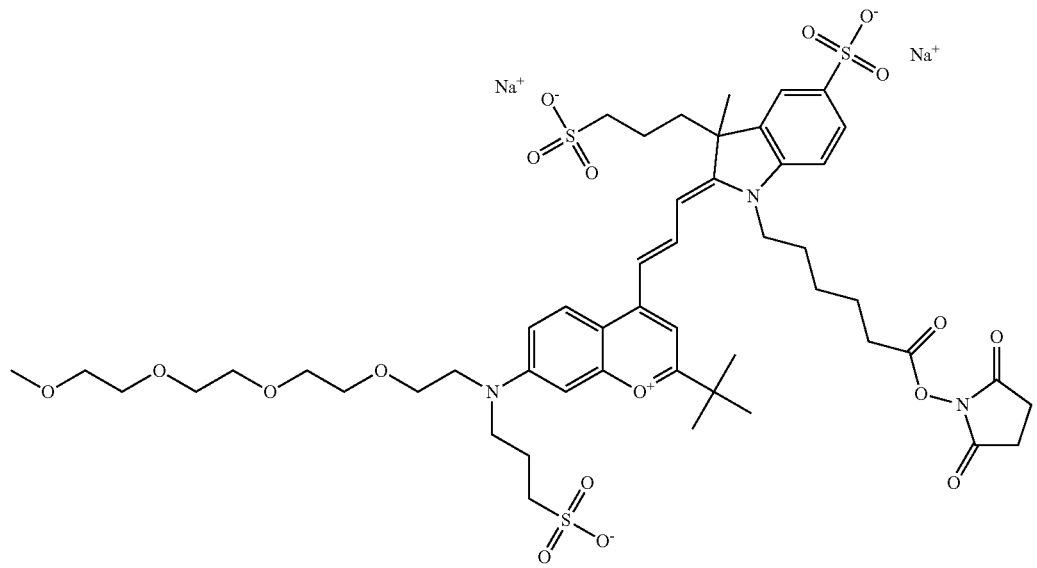

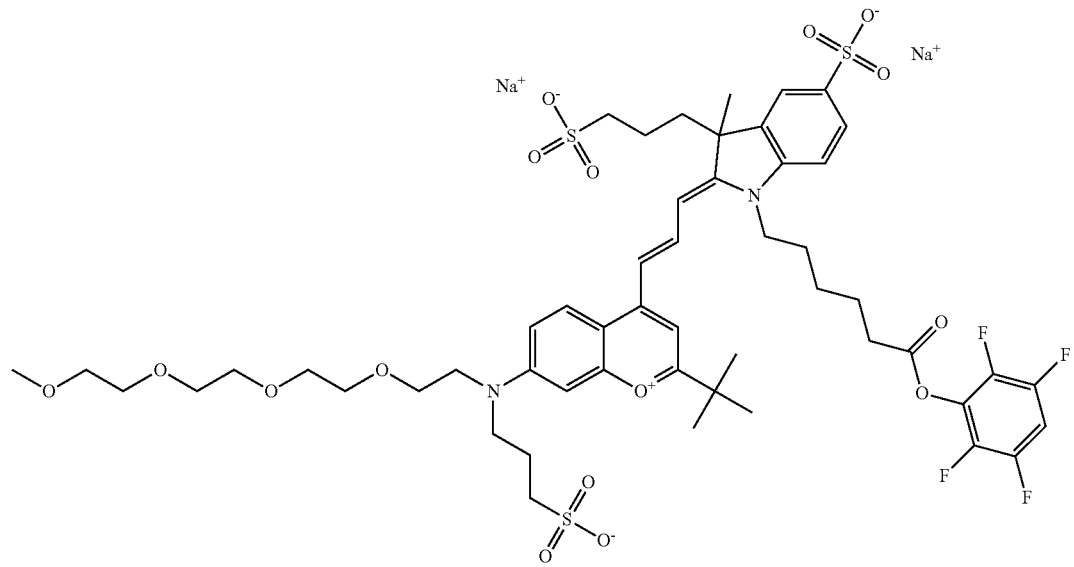

yield: 29 mg (48%)
UV-vis (ethanol): $\lambda_{abs}$=637 nm
$\lambda_{em}$=658 nm
MS (ESI−) [M/z]: 572.2 [M]−

The following compound according to general formula IIa is synthesized according to general procedure for compound II and general procedure for dye-STP ester, PEG4-632-STP ester:

yield: 30 mg (47%)
UV-vis (ethanol): $\lambda_{abs}$=637 nm
$\lambda_{em}$=658 nm
MS (ESI−) [M/z]: 383.7 [M]$^{3-}$ The following compound according to general formula IIa is synthesized according to general procedure for compound II and general procedure for dye-maleimide, PEG4-632-maleimide

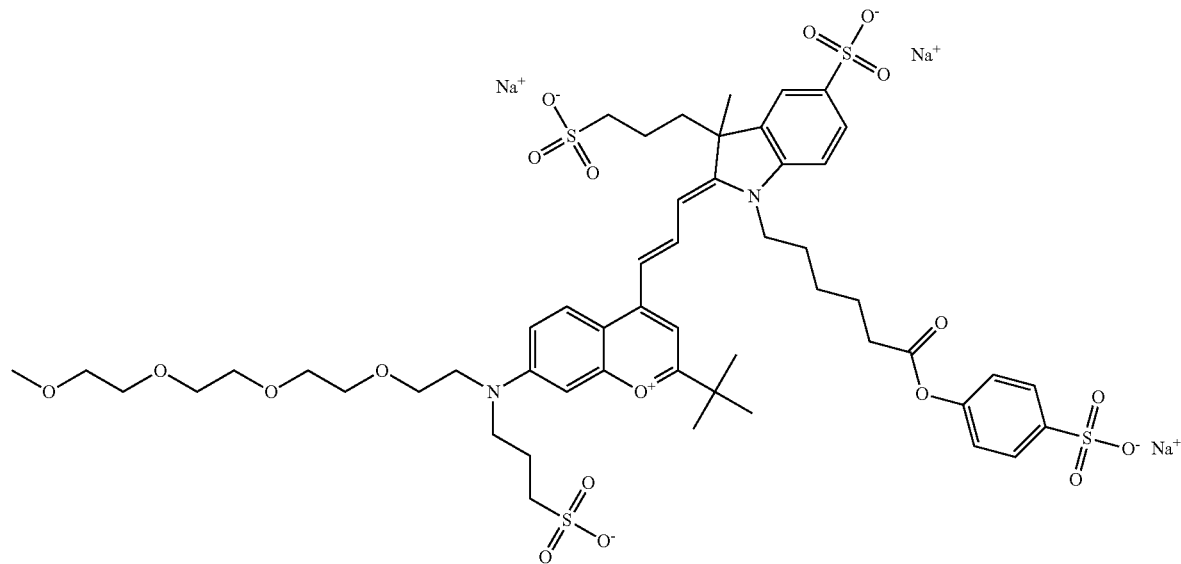

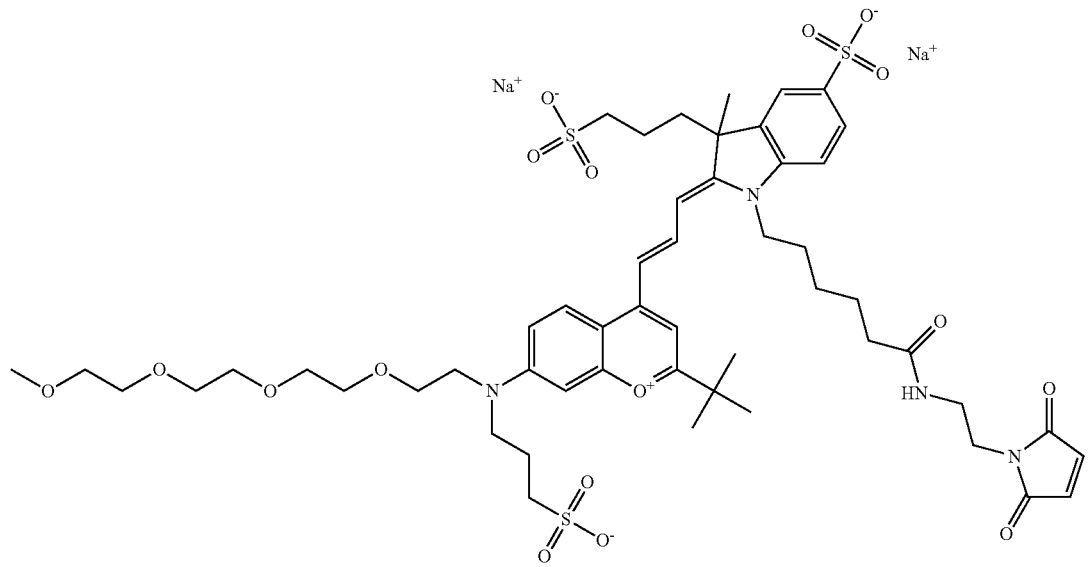

yield: 42 mg (72%)
UV-vis (ethanol): $\lambda_{abs}$=637 nm
$\lambda_{em}$=658 nm
MS (ESI−) [M/z]: 559.1 [M]$^{2-}$ The following compound according to general formula IIa is synthesized according to general procedure for compound II and general procedure for dye-hydrazide, PEG4-632-hydrazide:

yield: 34 mg (65%)
UV-vis (ethanol): $\lambda_{abs}$=637 nm
$\lambda_{em}$=658 nm
MS (ESI−) [M/z]: 1011.3 [M]$^{-}$ The following compound according to general formula IIb is synthesized according to general procedure for compound II, PEG4-632:

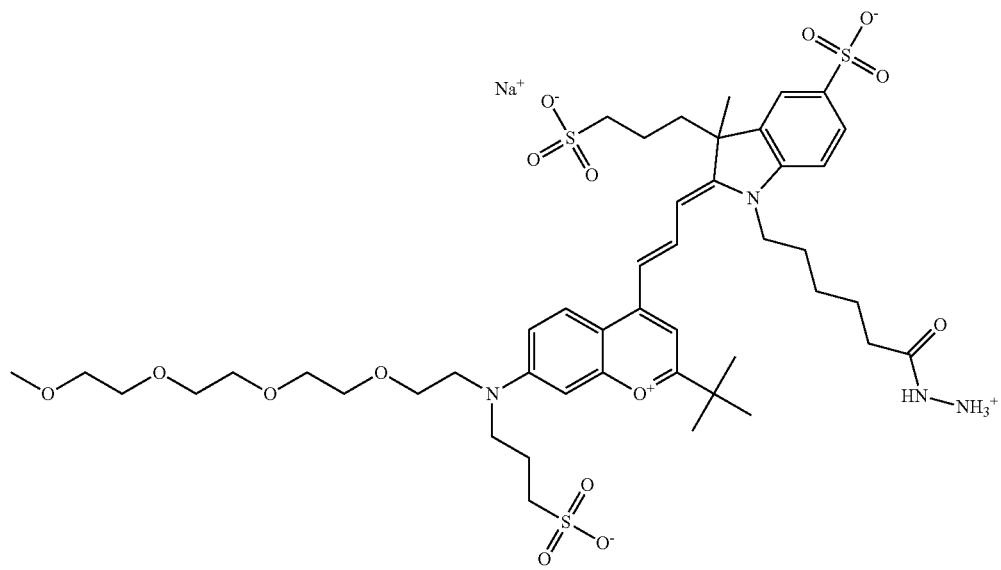

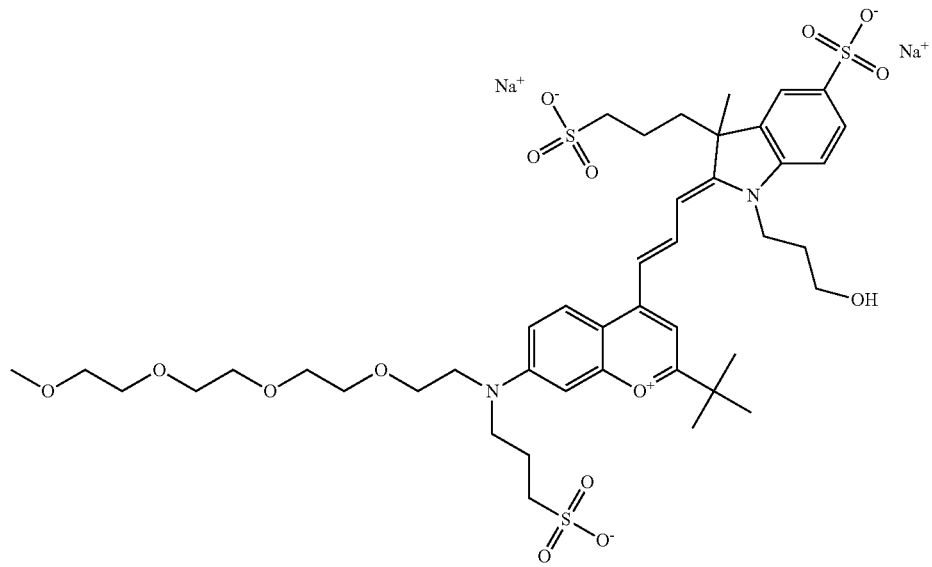

yield: 330 mg (33%)
UV-vis (ethanol): $\lambda_{abs}$=637 nm
$\lambda_{em}$=659 nm
MS (ESI-) [M/z]: 470.4 $[M]^{2-}$ The following compound according to general formula IIc is synthesized according to general procedure for compound II, PEG4-632:

yield: 375 mg (32%)
UV-vis (ethanol): $\lambda_{abs}$=638 nm
$\lambda_{em}$=659 nm
MS (ESI-) [M/z]: 565.3 $[M]^{2-}$ The following compound according to general formula IId is synthesized according to general procedure for compound II, PEG4-632:

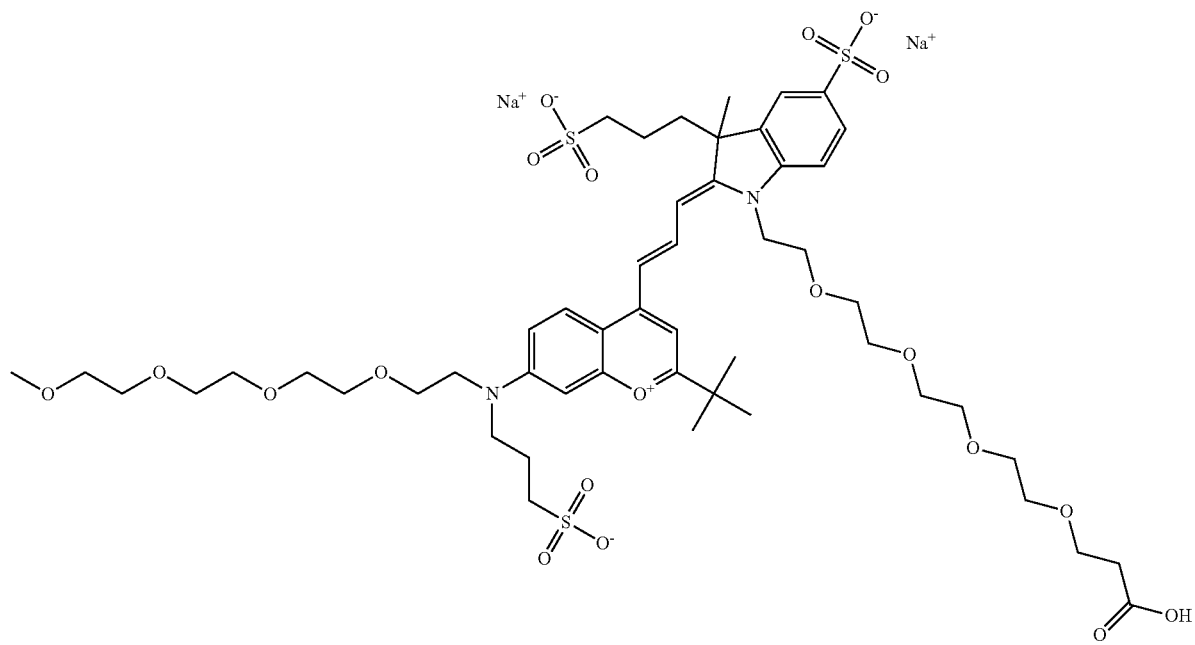

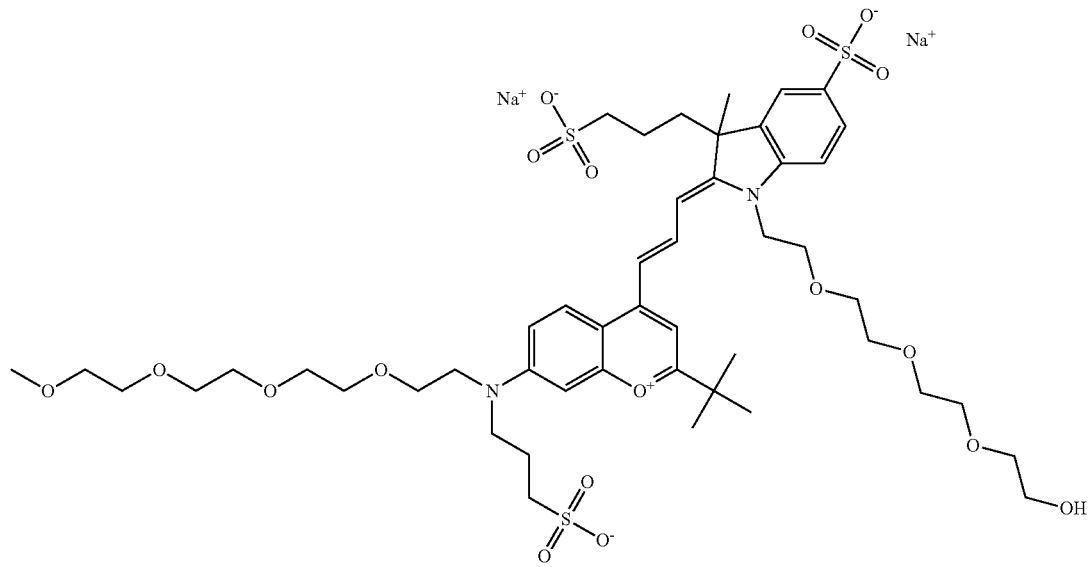

yield: 275 mg (25%)
UV-vis (ethanol): $\lambda_{abs}$=636 nm
$\lambda_{em}$=658 nm
MS (ESI−) [M/z]: 529.3 [M]$^{2-}$ The following compound according to general formula IIe is synthesized according to general procedure for compound II, PEG4-632:

yield: 280 mg (24%)
UV-vis (ethanol): $\lambda_{abs}$=638 nm
$\lambda_{em}$=659 nm
MS (ESI−) [M/z]: 565.2 [M]$^{2-}$ The following compound according to general formula IIf is synthesized according to general procedure for compound II, PEG4-632:

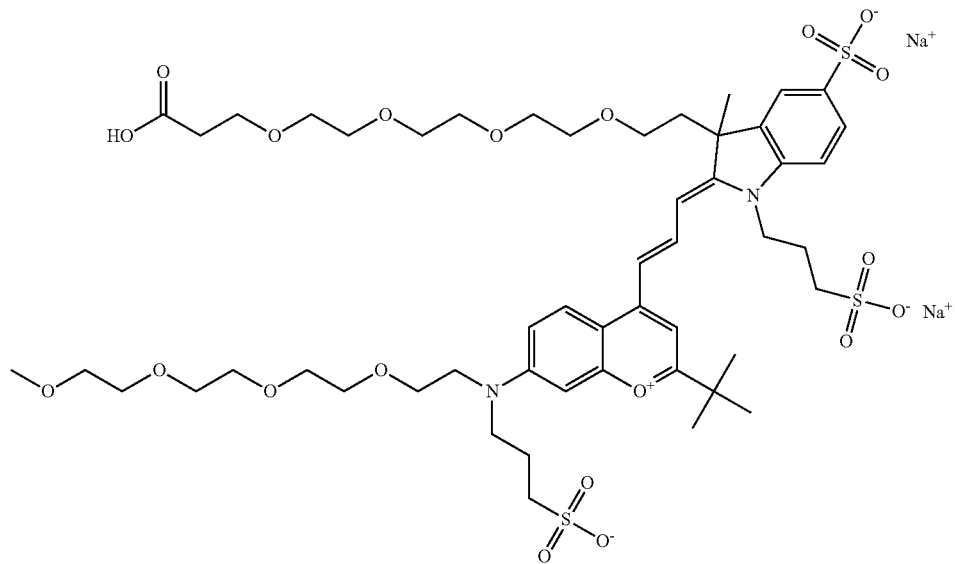

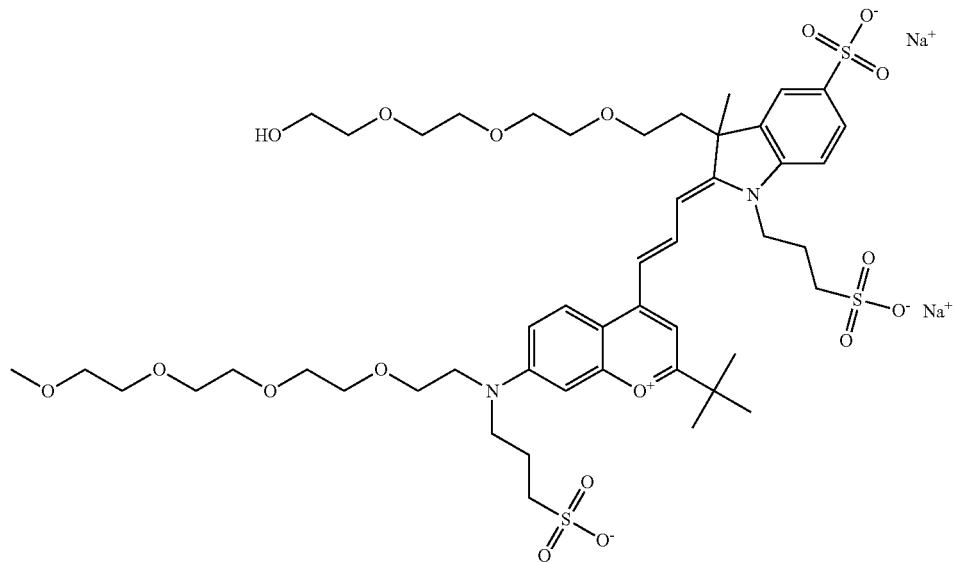
yield: 330 mg (30%)
UV-vis (ethanol): $\lambda_{abs}$=638 nm $\lambda_{em}$=659 nm
MS (ESI−) [M/z]: 529.2 [M]$^{2-}$
The following compound according to general formula IIg is synthesized according to general procedure for compound II, PEG4-632:
yield: 330 mg (30%)
UV-vis (ethanol): $\lambda_{abs}$=637 nm
$\lambda_{em}$=658 nm
MS (ESI−) [M/z]: 484.1 [M]$^{2-}$
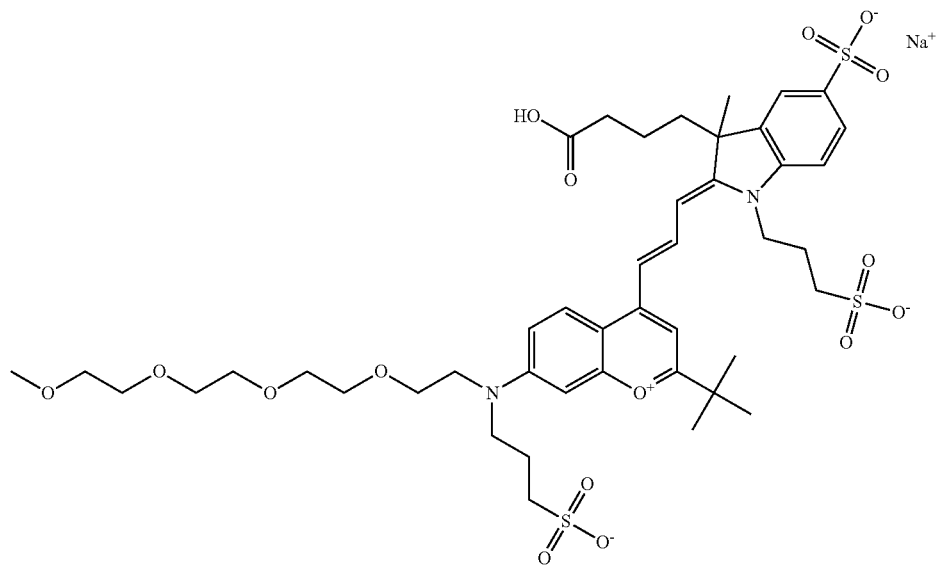 [SMILES: COCCOCCOCCOCCN(CCCS(=O)(=O)[O-])c1ccc2c(/C=C/C=C3\N(CCCS(=O)(=O)[O-])c4ccc(S(=O)(=O)[O-])cc4C3(C)CCCC(=O)O)cc(C(C)(C)C)[o+]c2c1 ; [Na+]]

The following compound according to general formula IIg is synthesized according to general procedure for compound II, (PEG4)$_2$-631:

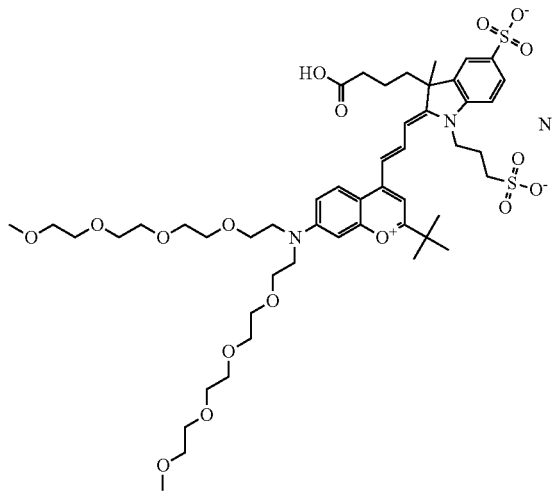

yield: 345 mg (32%)
UV-vis (ethanol): $\lambda_{abs}$=637 nm
$\lambda_{em}$=659 nm
MS (ESI−) [M/z]: 1037.4 [M]$^-$ The following compound according to general formula IIh is synthesized according to general procedure for compound II, PEG4-632:

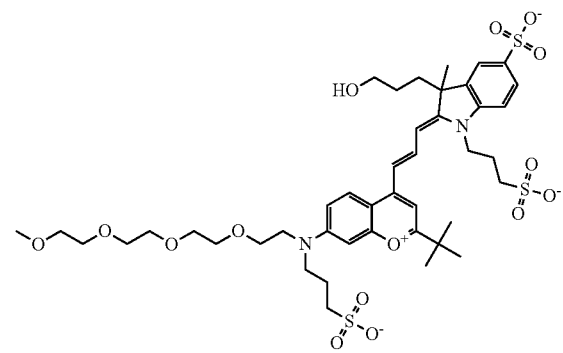

yield: 340 mg (34%)
UV-vis (ethanol): $\lambda_{abs}$=637 nm
$\lambda_{em}$=658 nm
MS (ESI−) [M/z]: 470.1 [M]$^{2-}$ The following compound according to general formula IIa is synthesized according to general procedure for compound II, PEG4-650:

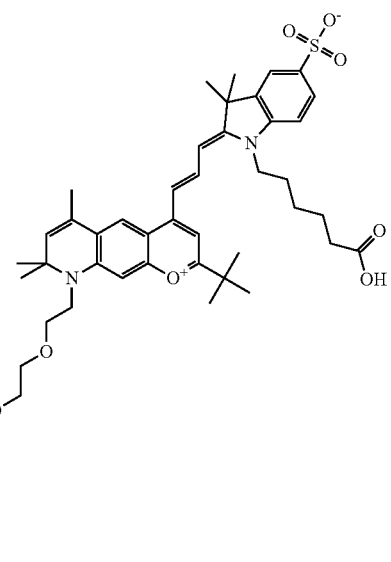

yield: 300 mg (35%)
UV-vis (ethanol): $\lambda_{abs}$=655 nm
$\lambda_{em}$=676 nm
MS (ESI+) [M/z]: 849.1 [M+H]$^+$ The following compound according to general formula IIa is synthesized according to general procedure for compound II, PEG4-675:

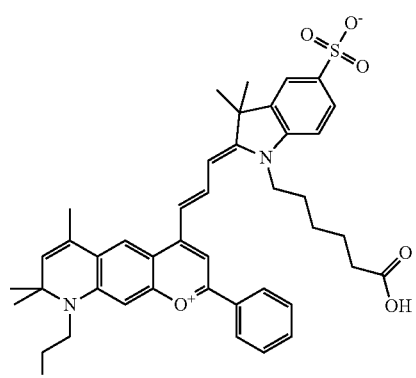

yield: 320 mg (37%)
UV-vis (ethanol): $\lambda_{abs}$=675 nm
$\lambda_{em}$=699 nm
MS (ESI+) [M/z]: 869.2 [M+H]$^+$ The following compound according to general formula IIc is synthesized according to general procedure for compound II, PEG4-635:

241

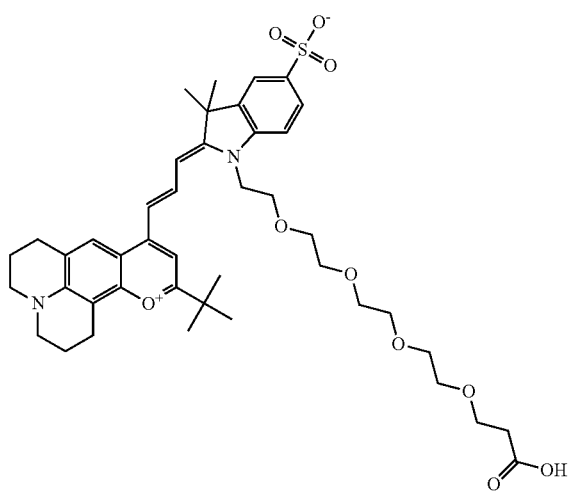 [SMILES: CC(C)(C)c1cc(/C=C/C=C2\N(CCOCCOCCOCCOCCC(=O)O)c3ccc(S(=O)(=O)[O-])cc3C2(C)C)c2cc3c4c(c2[o+]1)CCCN4CCC3]

yield: 300 mg (35%)
UV-vis (ethanol): $\lambda_{abs}$=648 nm
$\lambda_{em}$=670 nm
MS (ESI+) [M/z]: 793.2 [M+H]$^+$ The following non-limiting examples further describe the compounds, methods, compositions, uses, and embodiments. Vacuum is 30-150 mbar pressure range. Liquid mixing ratios are by volume. NHS is N-hydroxy-succinimide. DCC is dicyclohexylcarbodiimide. DMF is N,N-dimethylformamide.

SYNTHESIS EXAMPLE 1. SYNTHESIS OF DY-631

242

180 mg (0.5 mmol) 2-tert-butyl-7-diethylamino-4-methyl-chromenylium-tetrafluoro-borate and 242 mg (0.5 mmol) 3-(3-ethoxycarbonylpropyl)-2,3-dimethyl-5-sulfonato-1-(3-sulfonatopropyl)-3H-indolium sodium salt were dissolved in 50 ml acetanhydride, with 75 µl (0.6 mmol) trimethylorthoformate and 1 ml pyridine. The solution was stirred for about 30 min at about 140° C. After cooling to room temperature, the solvent was removed in the vacuum.

The residue was heated to reflux for two hours in a mixture of 10 ml acetone and 10 ml of 2 M hydrochloric acid, the reaction solution neutralized with NaHCO$_3$ and the solvent distilled in the vacuum. The residue was chromatographed (SiO$_2$ RP-18, eluent methanol/water 6:4).

145 mg (39%) yield —UV/Vis (ethanol) $\lambda_{max}$ ($\varepsilon$)=637 nm (185.000 l·mol$^{-1}$·cm$^{-1}$). —fluorescence $\lambda_{em}$=658 nm. —MS (ESI$^-$): 713.2 [M]$^-$; 356.4 [M–H]$^{2-}$. —C$_{36}$H$_{45}$N$_2$O$_9$S$_2$Na (736.88).

SYNTHESIS EXAMPLE 2. SYNTHESIS OF DY-631 N-HYDROXYSUCCINIMIDYL ESTER

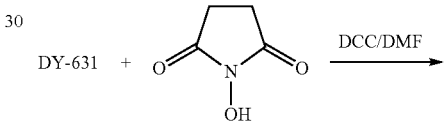

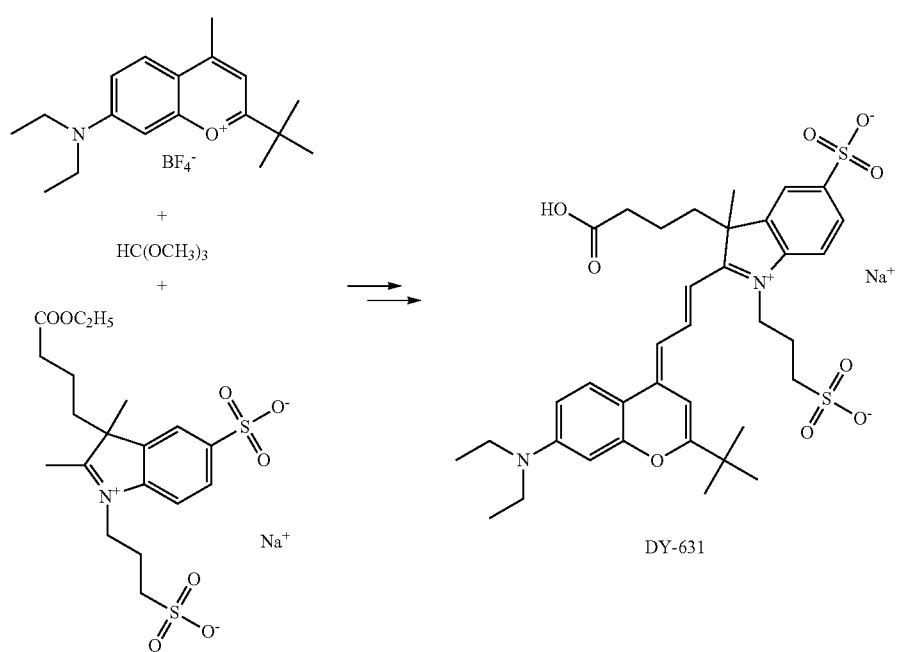

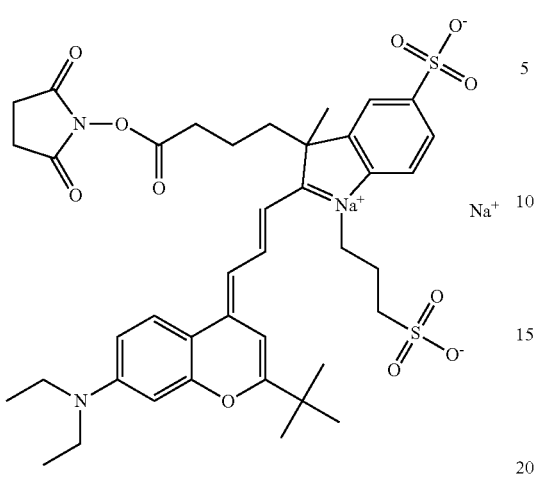

15 mg DY-631, 14 mg DCC, 4 mg NHS and 10 µl pyridine were dissolved in 2 ml DMF and stirred at room temperature for 24 h. The solvent was removed in vacuum. The residue was washed with diethylether and dried in vacuum. The reaction was quantitative.

SYNTHESIS EXAMPLE 3. SYNTHESIS OF DY-636

206 mg (0.5 mmol) 10-tert-butyl-8-methyl-2,3,5,6-tetrahydro-1H,4H-11-oxonia-3a-aza-benzo[de] anthracene-tetrafluoroborate and 242 mg (0.5 mmol) 3-(3-ethoxy-carbonyl-propyl)-2,3-dimethyl-5-sulfonato-1-(3-sulfonatopropyl)-3H-indolium sodium salt were reacted and processed in accord with example 1.

135 mg (36%) yield —UV/Vis (ethanol) $\lambda_{max}$ ($\epsilon$)=645 nm (155.000 l·mol$^{-1}$·cm$^{-1}$). —fluorescence $\lambda_{em}$=670 nm. —MS (ESI$^-$): 737.1 [M]$^-$; 368.4 [M–H]$^{2-}$. —C$_{38}$H$_{45}$N$_2$O$_9$S$_2$Na (760.91).

EXAMPLE 4. SYNTHESIS OF DY-636 N-HYDROXYSUCCINIMIDYL ESTER

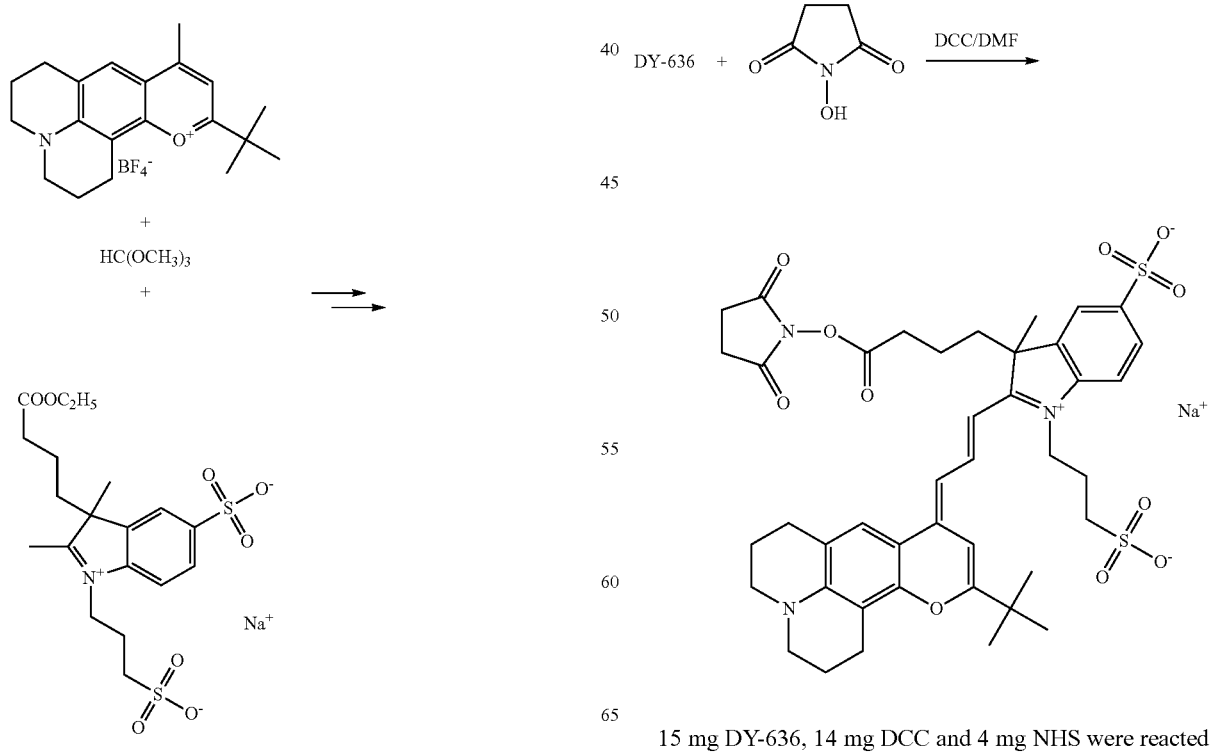

15 mg DY-636, 14 mg DCC and 4 mg NHS were reacted and processed in accord with example 2.

SYNTHESIS EXAMPLE 5. SYNTHESIS OF DY-651

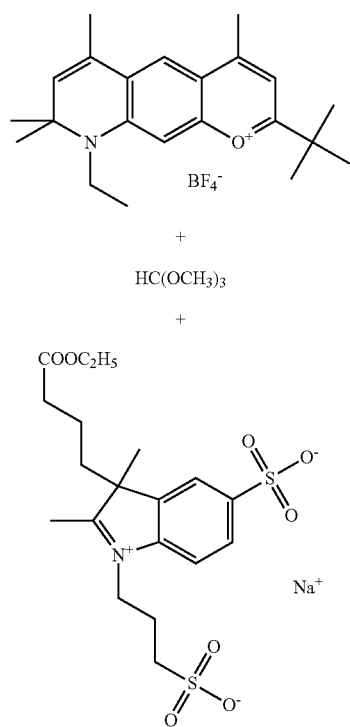

206 mg (0.5 mmol) 2-tert-butyl-8-ethyl-4,5,7,7-tetramethyl-7,8-dihydro-1-oxonia-8-aza-anthracene-tetrafluoroborate and 242 mg (0.5 mmol) 3-(3-ethoxycarbonylpropyl)-2,3-dimethyl-5-sulfonato-1-(3-sulfonatopropyl)-3H-indolium sodium salt were reacted and processed in accordance with example 1.

145 mg (38%) yield —UV/Vis (Ethanol) $\lambda_{max}$ ($\varepsilon$)=653 nm (160.000 l·mol$^{-1}$ cm$^{-1}$). —fluorescence $\lambda_{em}$=678 nm. —MS (ESI$^-$): 765.1 [M]$^-$; 382.4 [M–H]$^2$. —$C_{40}H_{49}N_2O_9S_{Na}$ (888.96).

SYNTHESIS EXAMPLE 6. SYNTHESIS OF DY-651 N-HYDROXYSUCCINIMIDYL ESTER

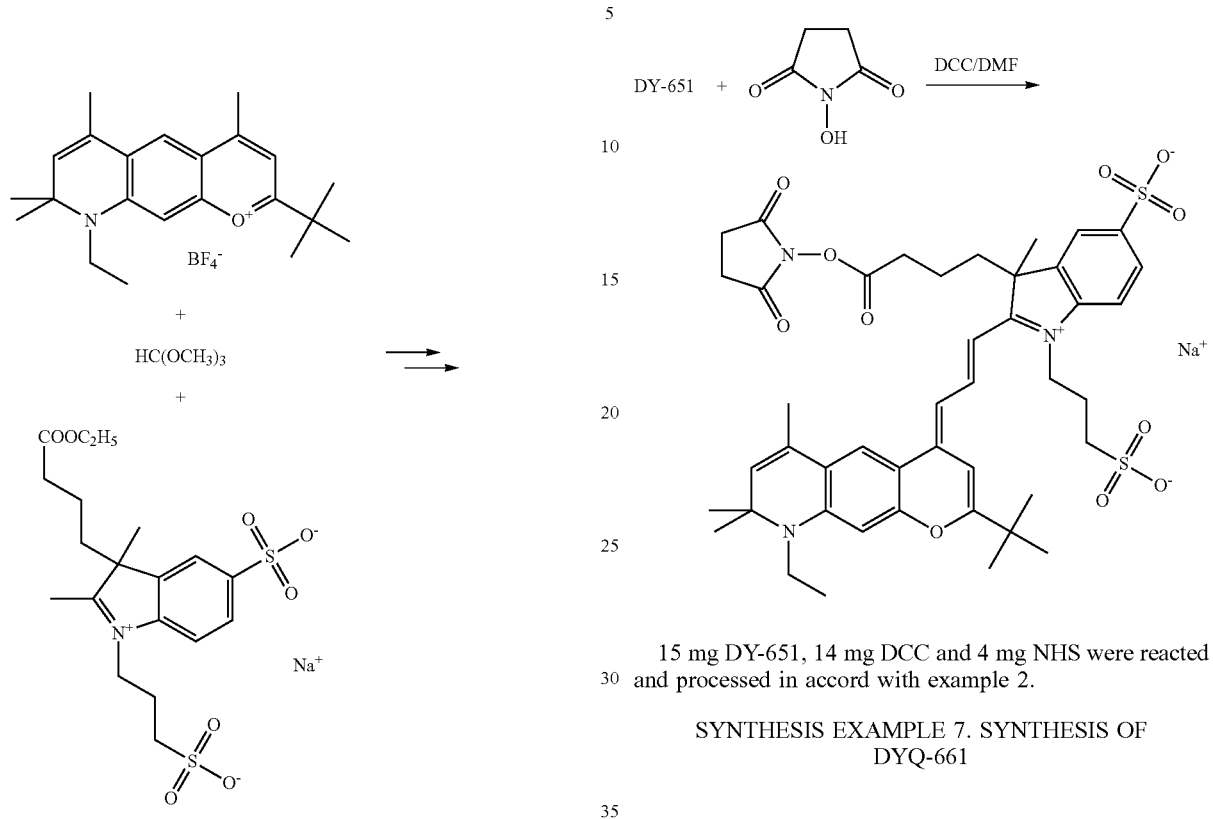

15 mg DY-651, 14 mg DCC and 4 mg NHS were reacted and processed in accord with example 2.

SYNTHESIS EXAMPLE 7. SYNTHESIS OF DYQ-661

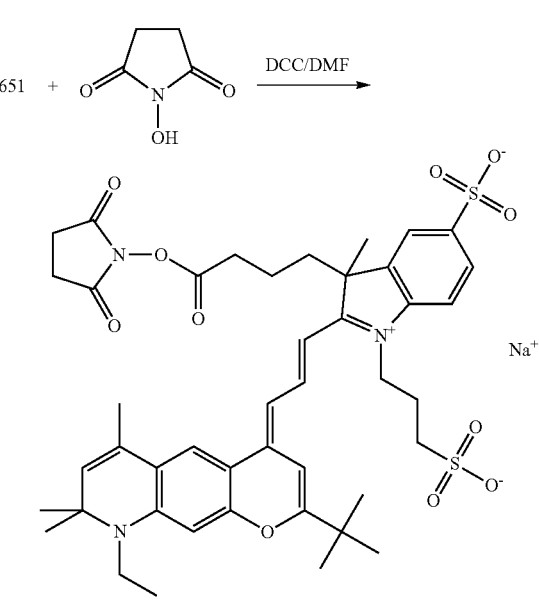

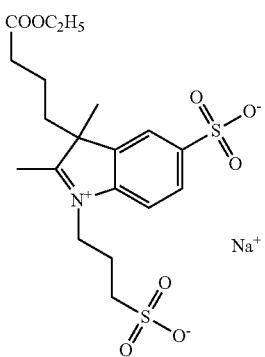

-continued

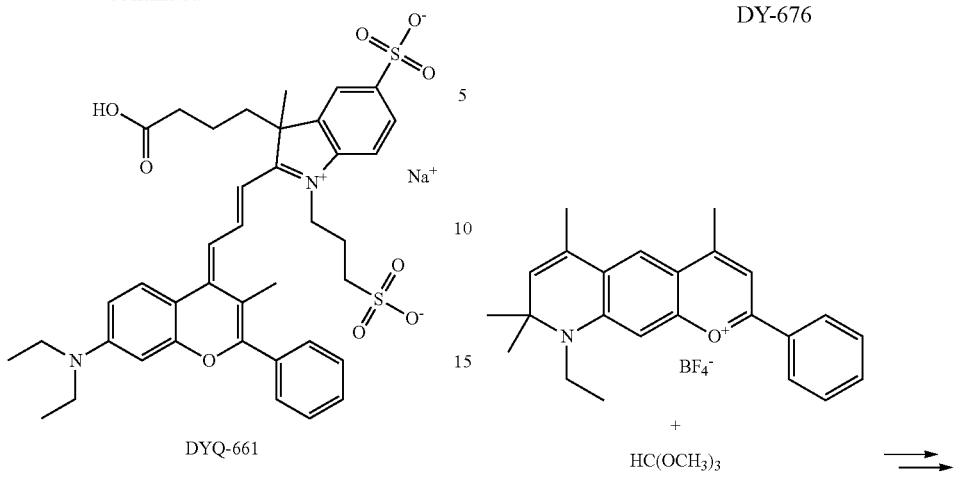

DYQ-661

196 mg (0.5 mmol) 7-diethylamino-3,4-dimethyl-2-phenyl-chromenylium-tetra-fluoroborate and 242 mg (0.5 mmol) 3-(3-ethoxycarbonylpropyl)-2,3-dimethyl-5-sulfonato-1-(3-sulfonatopropyl)-3H-indolium sodium salt were reacted and processed in accord with example 1.

145 mg (37%) yield —UV/Vis (Ethanol) $\lambda_{max}$ ($\varepsilon$)=661 nm (116.000 l·mol$^{-1}$ cm$^{-1}$). —MS (ESI): 747.1 [M]$^-$, 373.6 [M−H]$^{2-}$. —$C_{39}H_{43}N_2O_9S_2Na$ (770.90).

SYNTHESIS EXAMPLE 8. SYNTHESIS OF DYQ-661 N-HYDROXYSUCCINIMIDYL ESTER

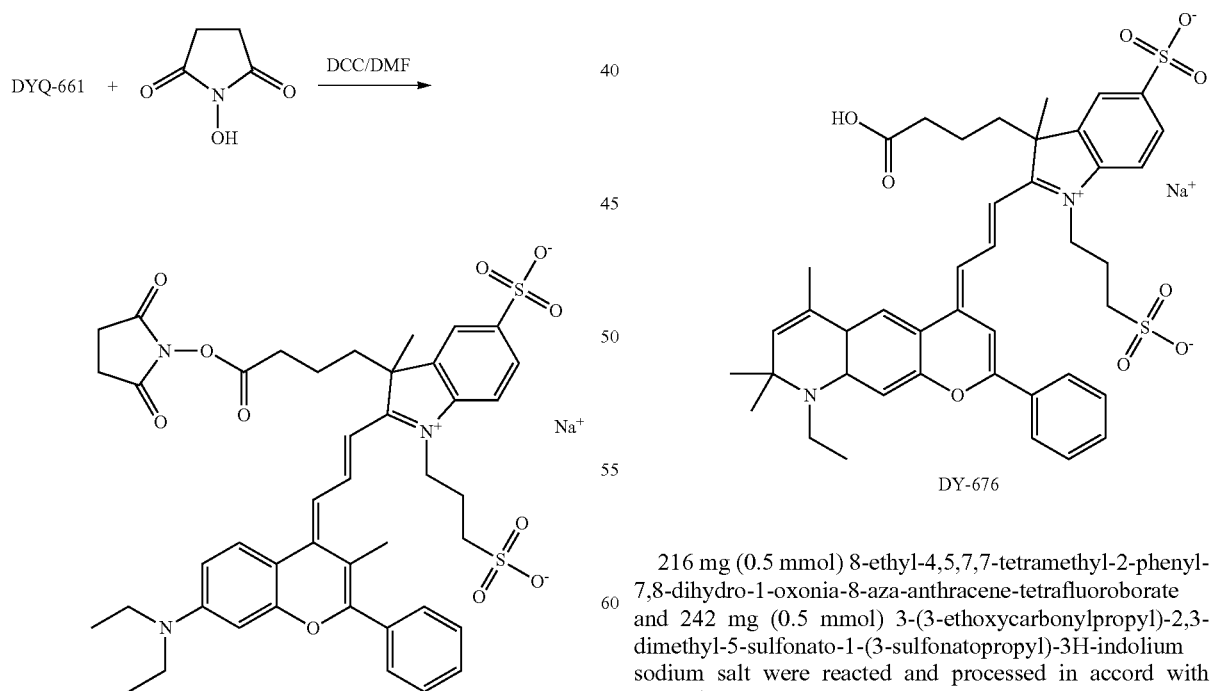

15 mg DYQ-661, 14 mg DCC and 4 mg NHS were reacted and processed in accord with example 2.

SYNTHESIS EXAMPLE 9. SYNTHESIS OF DY-676

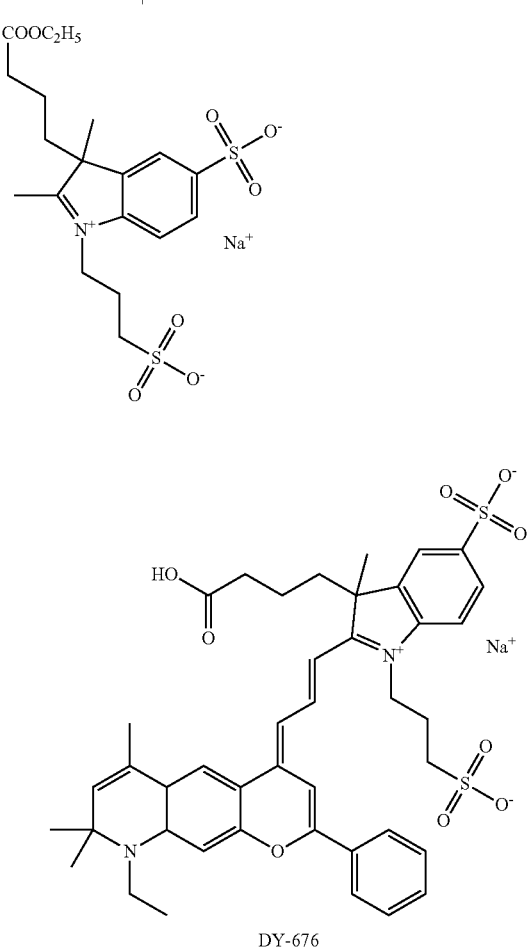

DY-676

216 mg (0.5 mmol) 8-ethyl-4,5,7,7-tetramethyl-2-phenyl-7,8-dihydro-1-oxonia-8-aza-anthracene-tetrafluoroborate and 242 mg (0.5 mmol) 3-(3-ethoxycarbonylpropyl)-2,3-dimethyl-5-sulfonato-1-(3-sulfonatopropyl)-3H-indolium sodium salt were reacted and processed in accord with example 1.

150 mg (37%) yield —UV/Vis (Ethanol) $\lambda_{max}$ ($\varepsilon$)=674 nm (84.000 l·mol$^{-1}$·cm$^{-1}$). —fluorescence $\lambda_{em}$=699 nm. —MS (ESI$^+$): 785.5 [M]$^+$. —$C_{42}H_{45}N_2O_9S_2Na$ (807.95).

SYNTHESIS EXAMPLE 10. SYNTHESIS OF DY-676 N-HYDROXYSUCCINIMIDYL ESTER

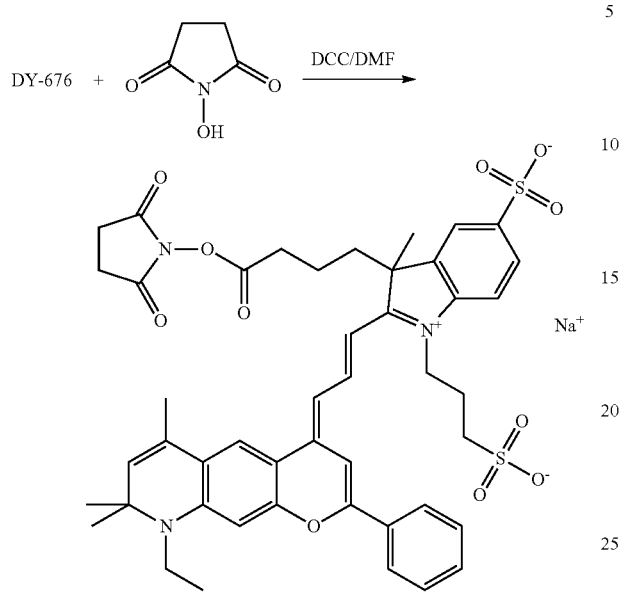

15 mg DY-676, 14 mg DCC and 4 mg NHS were reacted and processed in accord with example 2.

SYNTHESIS EXAMPLE 11. SYNTHESIS OF DY-731

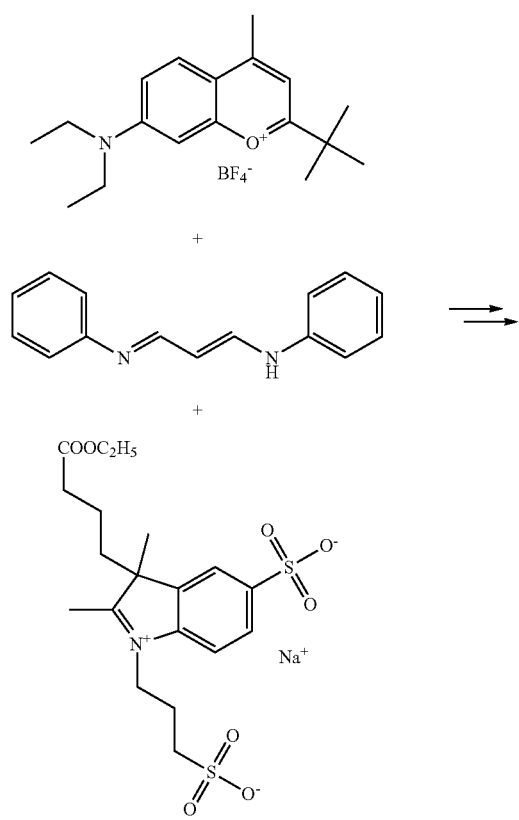

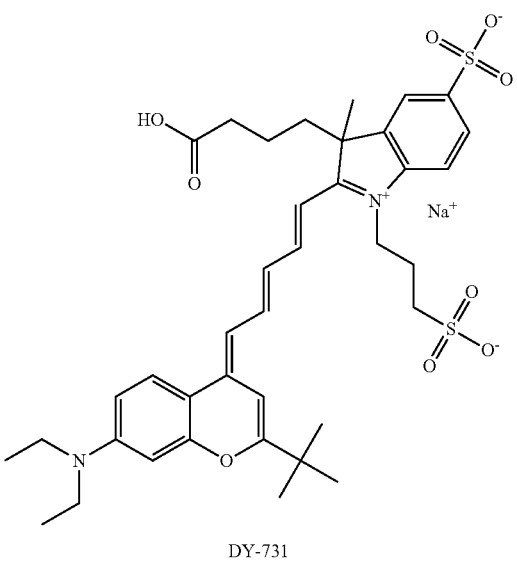

DY-731

180 mg (0.5 mmol) 2-tert butyl-7-diethylamino-4-methyl-chromenylium-tetrafluoro-borate and 307 mg (0.5 mmol) 3-(3-ethoxycarbonylpropyl)-3-methyl-2-(4-phenyl-amin-obuta-1,3-dienyl)-5-sulfonato-1-(3-sulfonatopropyl)-3H-indolium sodium salt were dissolved in 50 ml of acetanhydride with 1 ml of pyridine. The solution was stirred for approx. 30 min at approx. 140° C. After cooling to RT, the solvent was removed in the vacuum.

The residue was refluxed for 2 hours in a mixture of 10 ml acetone and 10 ml 2-M hydrochloric acid, the reaction solution neutralized with NaHCO$_3$ and the solvent distilled in the vacuum. The residue was chromatographed (SiO$_2$—RP-18, eluent methanol/water—6:4).

120 mg (31%) yield —UV/Vis (ethanol) $\lambda_{max}$ ($\varepsilon$)=736 nm (225.000 l·mol$^{-1}$·cm$^{-1}$). —fluorescence $\lambda_{em}$=759 nm. —MS (ESI): 739.2 [M]$^-$, 369.5 [M–H]$^{2-}$. —C$_{38}$H$_{47}$N$_2$O$_9$S$_2$Na (762.92).

SYNTHESIS EXAMPLE 12. SYNTHESIS OF DY-731 N-HYDROXYSUCCINIMIDYL ESTER

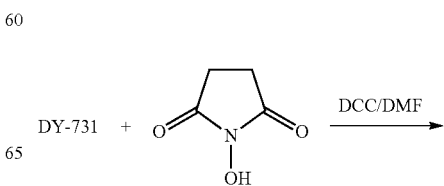

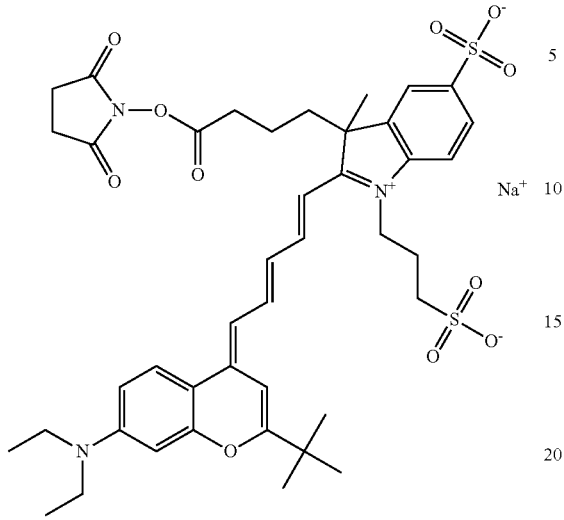

15 mg DY-731, 14 mg DCC and 4 mg NHS were reacted and processed in accordance with example 2.

SYNTHESIS EXAMPLE 13. SYNTHESIS OF DY-751

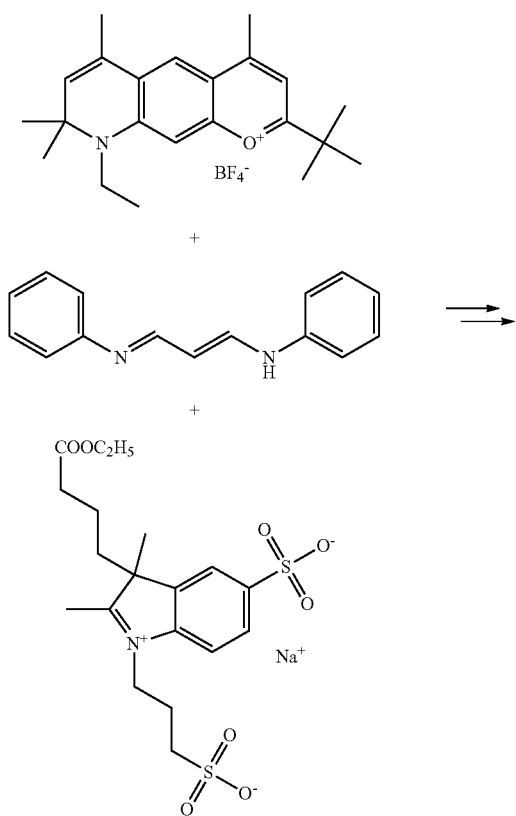

206 mg (0.5 mmol) 2-tert-butyl-8-ethyl-4,5,7,7-tetramethyl-7,8-dihydro-1-oxonia-8-aza-anthracene-tetrafluoroborate and 307 mg (0.5 mmol) 3-(3-ethoxycarbonylpropyl)-3-methyl-2-(4-phenyl-aminobuta-1,3-dienyl)-5-sulfonato-1-(3-sulfonatopropyl)-3H-indolium sodium salt were reacted and processed in accordance with example 11.

120 mg (29%) yield —UV/Vis (ethanol) $\lambda_{max}$ ($\epsilon$)=751 nm (220.000 l·mol$^{-1}$·cm$^{-1}$). —fluorescence $\lambda_{em}$=779 nm. —MS (ESI$^+$): 793.1 [M+H]$^+$, 419.4 [M+2 Na]$^{2+}$, 408.4 [M+H+Na]$^{2+}$, 397.4 [M+2H]$^{2+}$. —C$_{42}$H$_{51}$N$_2$O$_9$S$_2$Na (814.99).

SYNTHESIS EXAMPLE 14. SYNTHESIS OF DY-751 N-HYDROXYSUCCINIMIDYL ESTER

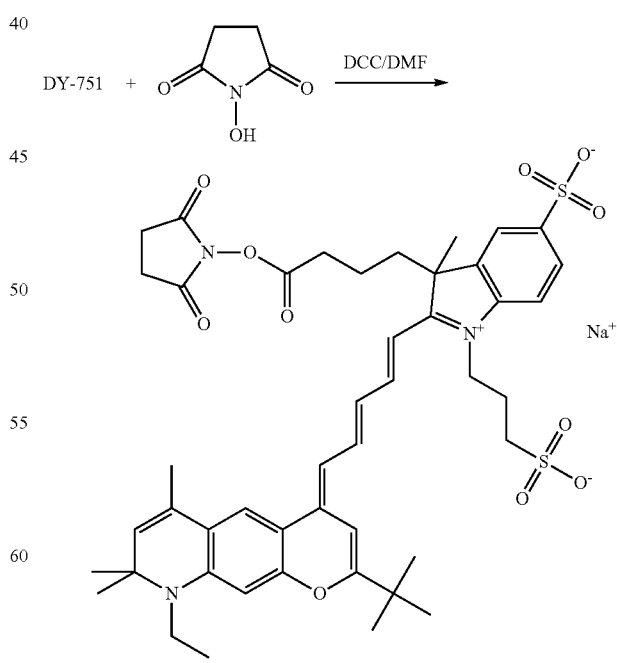

15 mg DY-751, 14 mg DCC and 4 mg NHS were reacted and processed in accord with example 2.

253
SYNTHESIS EXAMPLE 15. SYNTHESIS OF DY-776

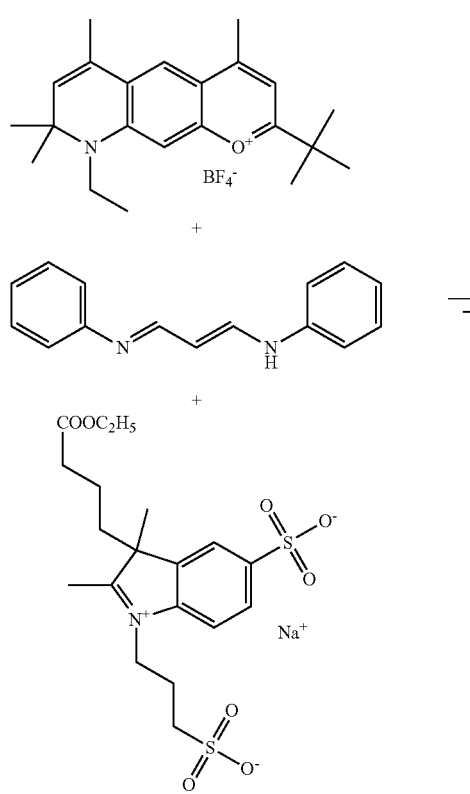

254
SYNTHESIS EXAMPLE 16. SYNTHESIS OF DY-776 N-HYDROXYSUCCINIMIDYL ESTER

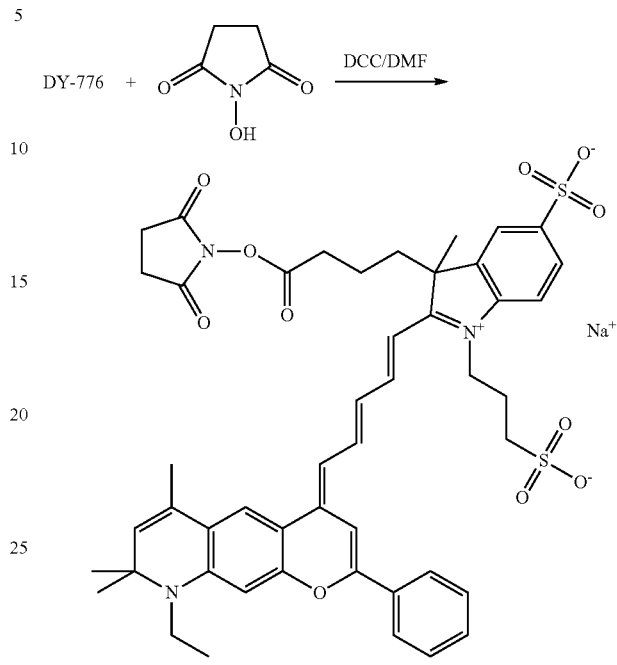

15 mg DY-776, 14 mg DCC and 4 mg NHS were reacted and processed in accord with example 2.

Examples 17-22 illustrate a general synthesis scheme for formula I compounds.

EXAMPLE 17. SYNTHESIS OF DY-681

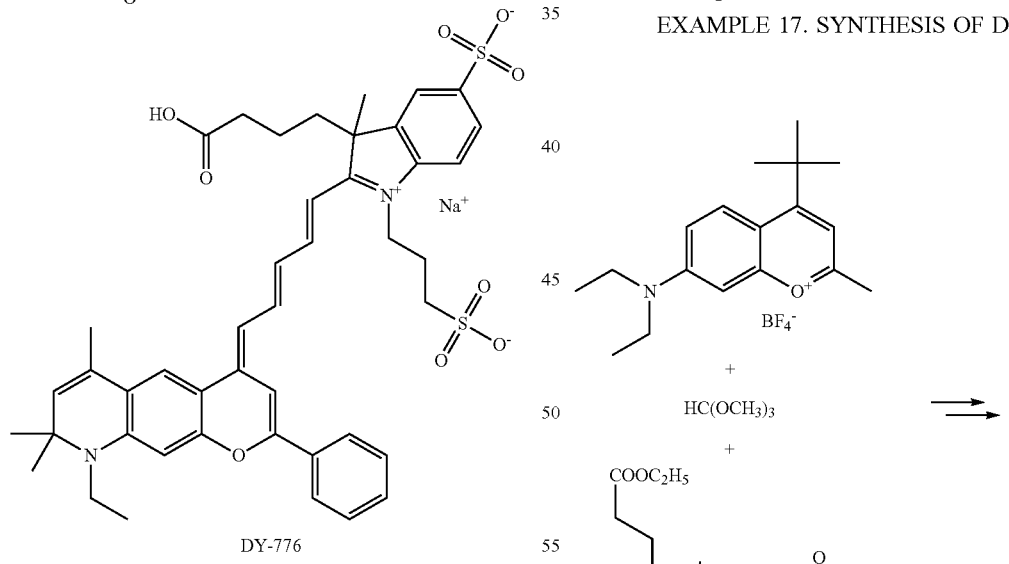

216 mg (0.5 mmol) 8-ethyl-4,5,7,7-tetramethyl-2-phenyl-7,8-dihydro-1-oxonia-8-aza-anthracene-tetrafluoroborate and 307 mg (0.5 mmol) 3-(3-ethoxycarbonylpropyl)-3-methyl-2-(4-phenylamino-buta-1,3-dienyl)-5-sulfonato-1-(3-sulfonatopropyl)-3H-indolium sodium salt were reacted and processed in accordance with example 11.

110 mg (26%) yield —UV/Vis (Ethanol) $\lambda_{max}$ ($\epsilon$)=771 nm (147.000 $l \cdot mol^{-1} \cdot cm^{-1}$). —fluorescence $\lambda_{em}$=801 nm. —MS (ESI$^+$): 813.1 [M+H]$^+$, 429.2 [M+2 Na]$^{2+}$, 418.3 [M+H+Na]$^{2+}$, 407.3 [M+2H]$^{2+}$. —$C_{44}H_{47}N_2O_9S_2Na$ (834.98).

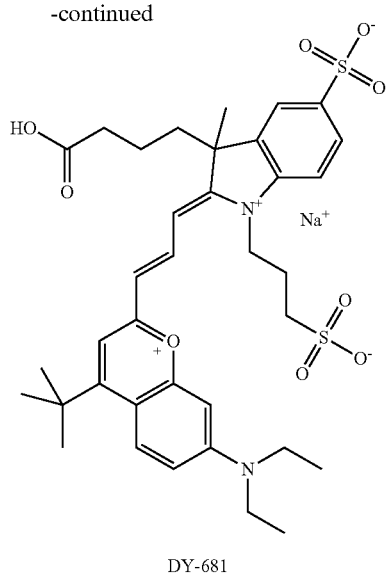

DY-681

180 mg (0.5 mmol) 4-tert-butyl-7-diethylamino-2-methyl-chromenylium-tetrafluoro-borate and 242 mg (0.5 mmol) 3-(3-ethoxycarbonylpropyl)-2,3-dimethyl-5-sulfonato-1-(3-sulfonatopropyl)-3H-indolium sodium salt were reacted and processed in accordance with example 1.

140 mg (39%) yield —UV/Vis (Ethanol) $\lambda_{max}$ ($\epsilon$)=691 nm (125.000 l·mol$^{-1}$·cm$^{-1}$). —fluorescence $\lambda_{em}$=708 nm. —MS (ESI$^-$): 713.2 [M]$^-$; 356.4 [M–H]$^{2-}$. —C$_{36}$H$_{45}$N$_2$O$_9$S$_2$Na (736.88).

SYNTHESIS EXAMPLE 18. SYNTHESIS OF DY-681 N-HYDROXYSUCCINIMIDYL ESTER

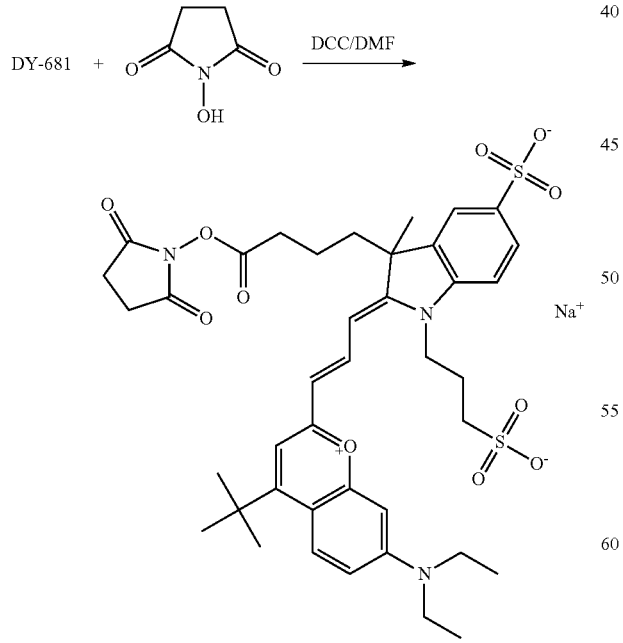

15 mg DY-681, 14 mg DCC and 4 mg NHS were reacted and processed in accordance with example 2.

SYNTHESIS EXAMPLE 19. SYNTHESIS OF DY-701

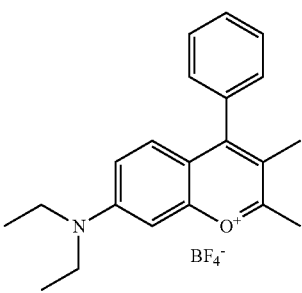

+ HC(OCH$_3$)$_3$ +

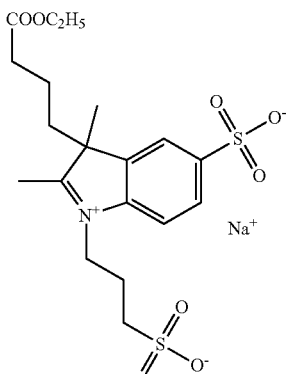

$\longrightarrow$

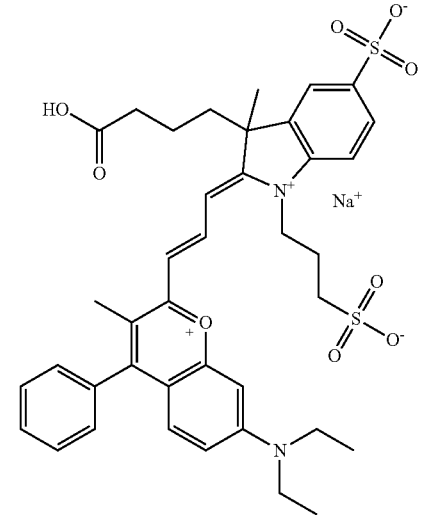

DY-701

196 mg (0.5 mmol) 7-diethylamino-2,3-dimethyl-4-phenyl-chromenylium-tetrafluoro-borate and 242 mg (0.5 mmol) 3-(3-ethoxycarbonylpropyl)-2,3-dimethyl-5-sulfonato-1-(3-sulfonatopropyl)-3H-indolium sodium salt were reacted and processed in accordance with example 1.

150 mg (39%) yield —UV/Vis (Ethanol) $\lambda_{max}$ ($\epsilon$)=706 nm (115.000 l·mol$^{-1}$·cm$^{-1}$). —fluorescence $\lambda_{em}$=731 nm. —MS (ESI$^-$): 747.2 [M]$^-$; 373.4 [M–H]$^{2-}$. —C$_{39}$H$_{43}$N$_2$O$_9$S$_2$Na (770.90).

SYNTHESIS EXAMPLE 20. SYNTHESIS OF DY-701 N-HYDROXYSUCCINIMIDYL ESTER

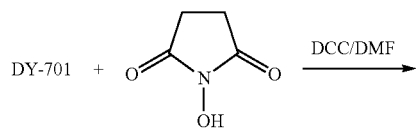

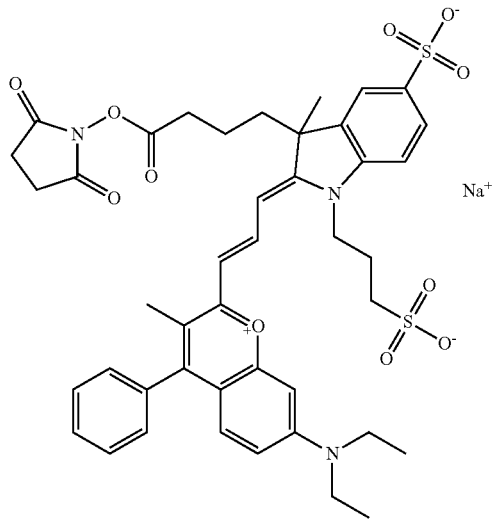

15 mg DY-701, 14 mg DCC and 4 mg NHS were reacted and processed in accord with example 2.

SYNTHESIS EXAMPLE 21. SYNTHESIS OF DY-781

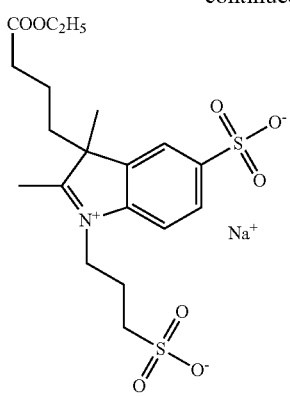

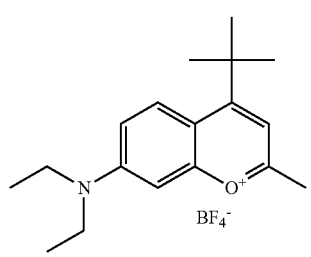

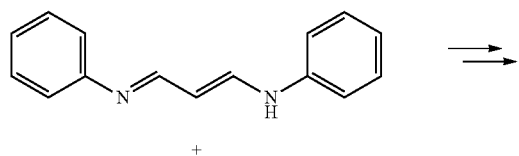

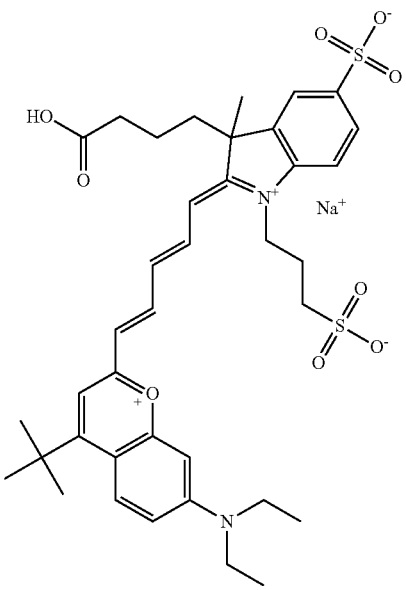

180 mg (0.5 mmol) 4-tert-butyl-7-diethylamino-2-methyl-chromenylium-tetrafluoro-borate and 307 mg (0.5 mmol) 3-(3-ethoxycarbonylpropyl)-3-methyl-2-(4-phenyl-aminobuta-1,3-dienyl)-5-sulfonato-1-(3-sulfonatopropyl)-3H-indolium sodium salt were made to react and processed in accordance with example 11.

125 mg (33%) yield —UV/Vis (Ethanol) $\lambda_{max}$ ($\varepsilon$)=783 nm (98.000 l·mol$^{-1}$·cm$^{-1}$). —fluorescence $\lambda_{em}$=800 nm. —MS (ESI$^+$): 785.3 [M+Na]$^+$; 763.3 [M+H]$^+$; 404.4 [M+2Na]$^{2+}$; 393.5 [M+H+Na]$^{2+}$. —$C_{38}H_{47}N_2O_9S_2Na$ (762.92).

SYNTHESIS EXAMPLE 22. SYNTHESIS OF DY-781 N-HYDROXYSUCCINIMIDYL ESTER

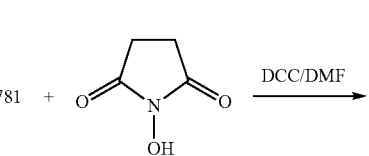

-continued

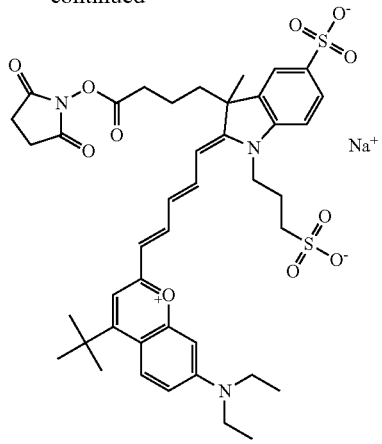

15 mg DY-781, 14 mg DCC and 4 mg NHS were reacted and processed in accord with example 2.

EXAMPLE 1

The following properties of V03-07005, V08-16072, V13-06190, and V17-03019 were compared with commercially available dyes. DyLight 680 NHS is a non-pegylated benzopyrylium dye and the 'V' dyes are pegylated dyes described above.

|  | DyLight 680-NHS | V03-07005-NHS | V08-16072-NHS | V13-06190-NHS | V17-03019-NHS | Alexa Fluor 680-NHS |
|---|---|---|---|---|---|---|
| MW (g/mol) | 950 | 1158.33 | 1140.25 | 1274.38 | 1112.22 | ~1150 |
| Ex (nm) | 682 | 690 (EtOH) 675 (PBS)* | 691 (EtOH) 679 (PBS)* | 691 (EtOH) 679 (PBS)* | 691 (EtOH) 675 (PBS)* | 679 |
| Em (nm) | 715 | 708 | 712 | 712 | 712 | 702 |
| ε ($M^{-1}cm^{-1}$) (theoretical) | 140,000 | 140,000 | 140,000 | 140,000 | 140,000 | 184,000 |
| PEG (length/# of chain) | 0 | 4/2 (on same N) | 4/1 | 4/2 (different N) | 4/1 | N/A |
| Sulfonate | 3 | 2 | 3 | 3 | 3 | 3 |

* Excitation of V03-07005, V08-16072, V13-06190, and V1703019 NHS was shifted from 690 nm in ethanol to about 675 nm in PBS.

EXAMPLE 2

Inventive and commercial compounds, each as the NHS ester, were conjugated to goat anti-mouse (GAM) and goat anti-rabbit (GAR) antibodies. GAM and GAR, at 10 mg/ml in phosphate buffered saline (PBS), were dialyzed against 50 mM borate buffer, pH 8.5. The compounds were reconstituted in dimethylformamide (DMF) at 10 mg/ml and combined at 2.5×, 5×, 7.5×, 10×, and 15× molar excess with GAM or GAR for 65 minutes at room temperature to label the antibodies.

The labeled compounds, also termed dyes or labels, were subjected to Pierce Dye Removal Resin (PDDR) to remove the unlabeled (free) compound; 100 μl of the packed resin was used per mg protein purified. The purified antibody-labeled dyes were then diluted by adding 150 μl PBS. All conjugates were diluted 1:20 and scanned for absorbance from 700 nm to 230 nm to determine the protein concentration, and to determine the mole dye to mole protein ratio on a UV Cary spectrophotometer. Labeling efficiency, indicated as dye to protein ratio (D/P), was compared, with results showing degree of labeling below.

|  | 2.5X | 5X | 10X | 15X |
|---|---|---|---|---|
| GAM-V03-07005 | 1.5 | 2.6 | 4.0 | 3.9 |
| GAR-V03-07005 | 1.3 | 2.5 | 4.2 | 3.7 |
| GAM-V08-16072 | 1.4 | 2.5 | 4.1 | 5.8 |
| GAR-V08-16072 | 1.6 | 2.5 | 3.9 | 4.8 |
| GAM-V13-06190 | 1.5 | 2.7 | 4.0 | 5.2 |
| GAR-V13-06190 | 1.2 | 2.5 | 4.1 | 5.1 |
| GAM-V17-03019 | 1.3 | 2.2 | 3.9 | 4.7 |
| GAR-V17-03019 | 1.1 | 2.2 | 3.1 | 3.2 |
| GAM-DyLight 680 | 1.3 | 2.5 | 2.7 | 2.1 |
| GAR-DyLight 680 | 1.2 | 2.0 | 2.6 | 2.1 |
| GAM-Alexa Fluor-680 | 1.6 | 2.2 | 4.4 | 7.0 |
| GAR-Alexa Fluor-680 | 1.7 | 2.9 | 4.7 | 4.8 |

|  | D/P |
|---|---|
| GAM-Alexa Fluor-680 | 5.0 |
| GAM-DyLight 680 | 3.1 |

Labeling efficiency of GAM and GAR was similar for all benzopyrylium dyes at low molar excesses.

EXAMPLE 3

Performance of dye-GAM and dye-GAR conjugates was evaluated in a functional assay. Wells of a 96-well black clear-bottom plate were coated with target protein mouse or rabbit IgG immunoglobulin. One hundred μl mouse or rabbit IgG, at 10 μg/ml, was applied to the corresponding wells in row 1. The target proteins were serially diluted 1:1 from the wells in rows 2 to 7 using 100 μl PBS. One hundred μl of samples from the wells in row 7 were discarded. One hundred μl PBS was added to the wells in row 8. Plates were incubated overnight at 4° C. and then blocked 2×200 μl with Thermo Scientific SuperBlock® Blocking Buffer. The coated plates were washed 2×200 μl with PBS-Tween and 1×200 μl with PBS. Based on the calculated concentrations, conjugates were diluted 1:250 (of 1 mg/ml) in PBS, added to the corresponding plates (100 μl/well) and then incubated for one hour in the dark. The plates were washed with 2×200 μl with PBS-Tween and 1×200 μl with PBS and filled with PBS buffer (100 μl/well) prior to scanning the black clear-bottom plates on LiCor Odyssey at 700 channel, to detect fluorescence intensity.

As shown in FIGS. 1-10, RFU and/or signal to background ratio (S/B) of the dyes conjugated to the indicated antibody were compared at various concentrations, using the indicated conjugation conditions.

Figure 2:
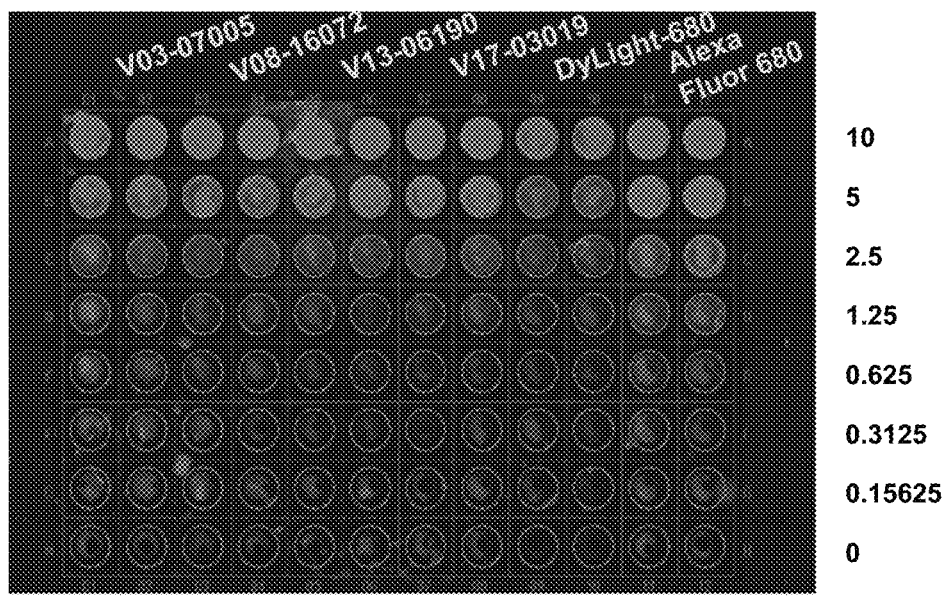
FIG. 2 shows functional assay results with commercial dyes and the inventive compounds in one embodiment.

FIG. 1 shows binding intensity results expressed as RFU of a functional assay using GAR conjugated with 5× molar excess of V03-07005 (green diamond; plate column 1 and 2), V08-16072 (blue triangle; plate column 3 and 4), V13-06190 (purple diamond; plate column 5 and 6), V17-03019 (orange circle; plate column 7 and 8), DyLight 680 (red square; plate column 9 and 10), and Alexa Fluor 680 (black square; plate column 11 and 12). FIG. 2 shows an image of the plate of FIG. 1. Based on the data, at 5× molar excess, Alexa Fluor 680-GAR showed the highest binding intensity. All pegylated benzopyrylium-GAR conjugates performed better than non-pegylated DyLight 680-GAR conjugates.

Figure 3:
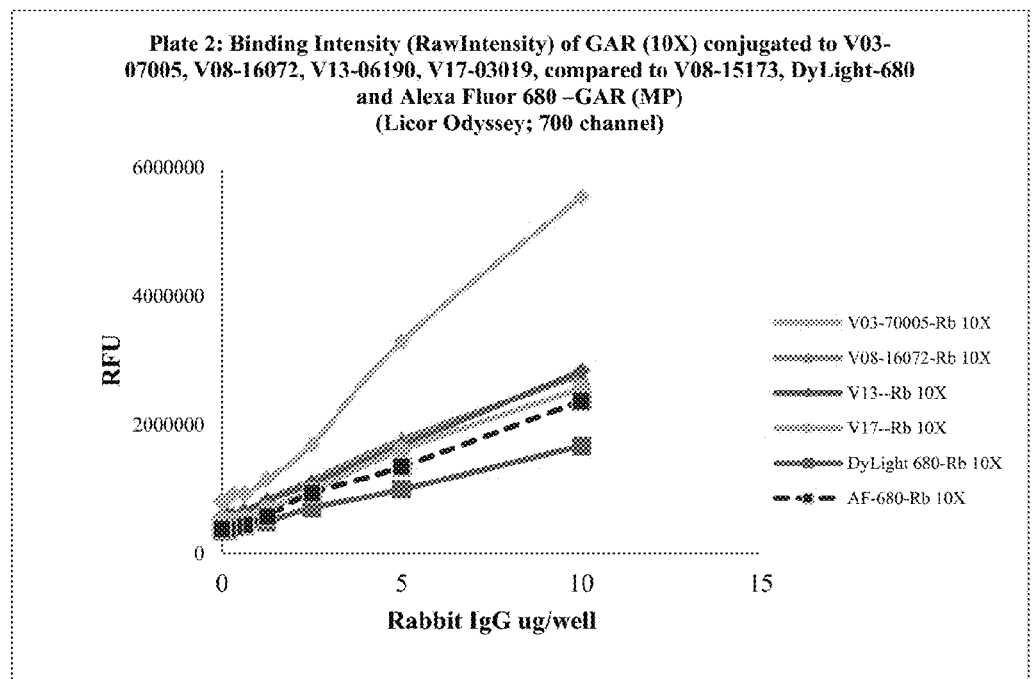
FIG. 3 shows functional assay results with commercial dyes and the inventive compounds in one embodiment.
Figure 4:
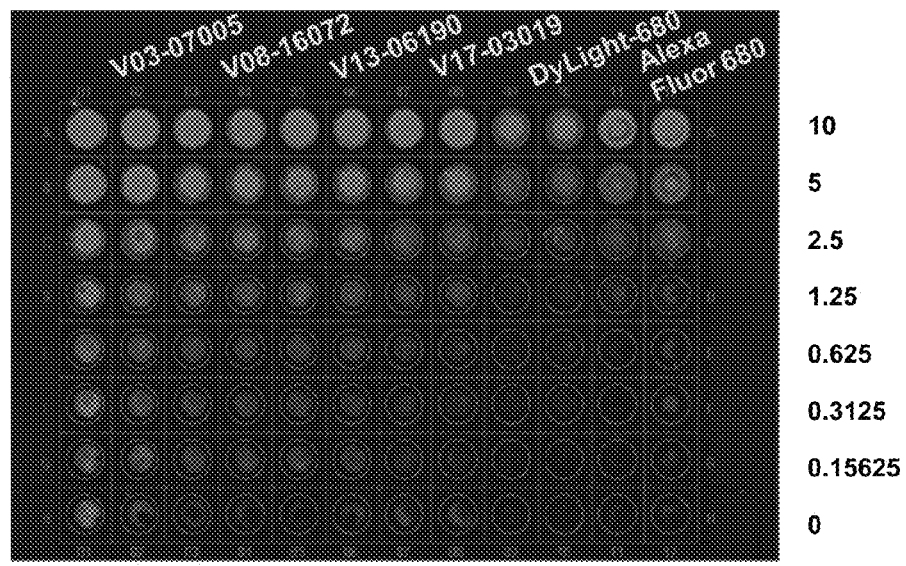
FIG. 4 shows functional assay results with commercial dyes and the inventive compounds in one embodiment.

FIG. 3 shows binding intensity results expressed as RFU of a functional assay using GAR conjugated with 10× molar excess of V03-07005 (green diamond; plate column 1 and 2), V08-16072 (blue triangle; plate column 3 and 4), V13-06190 (purple diamond; plate column 5 and 6), V17-03019 (orange circle; plate column 7 and 8), DyLight 680 (red square; plate column 9 and 10), and Alexa Fluor 680 (black square; plate column 11 and 12). FIG. 4 shows an image of the plate of FIG. 3. Based on the data, at 10× molar excess, V03-07005-GAR showed the highest binding intensity. Non-pegylated DyLight 680-GAM showed the lowest binding intensity.

Figure 5:
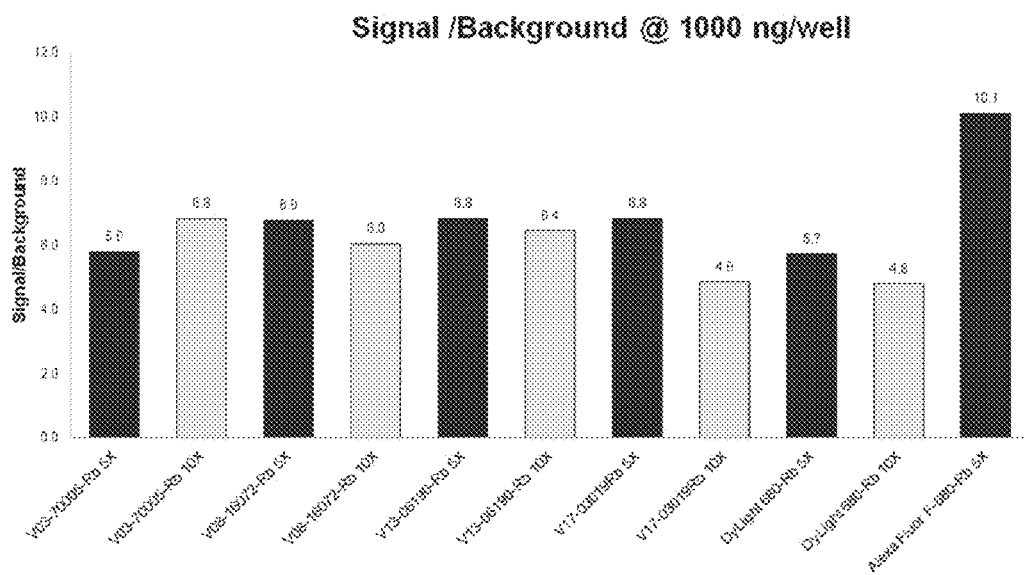
FIG. 5 shows functional assay results with commercial dyes and the inventive compounds in one embodiment.

FIG. 5 shows LiCOR Odyssey results expressed as S/B of a functional assay using GAR conjugated with 5× molar excess (blue bars) or 10× molar excess (yellow bars) of the indicated compound.

Figure 6:
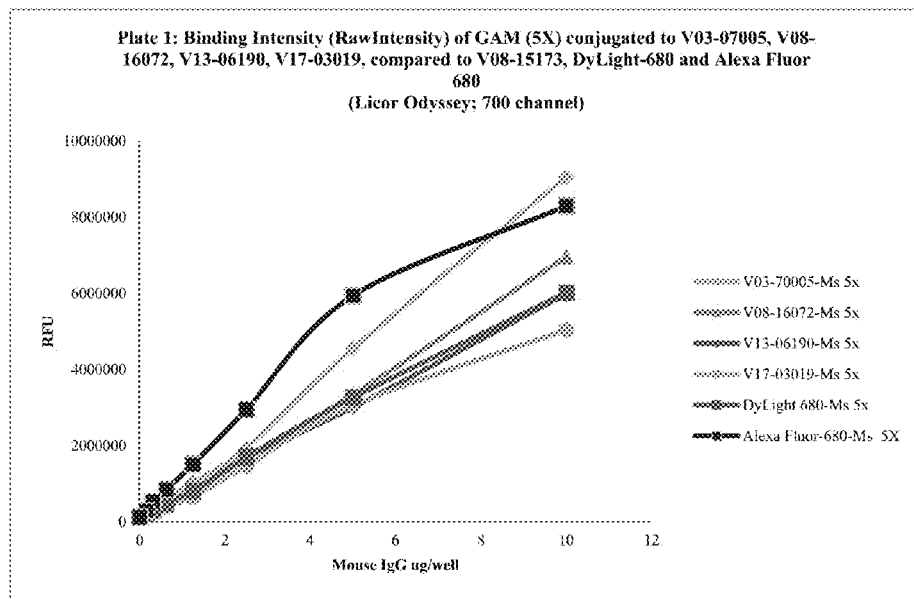
FIG. 6 shows functional assay results with commercial dyes and the inventive compounds in one embodiment.
Figure 7:
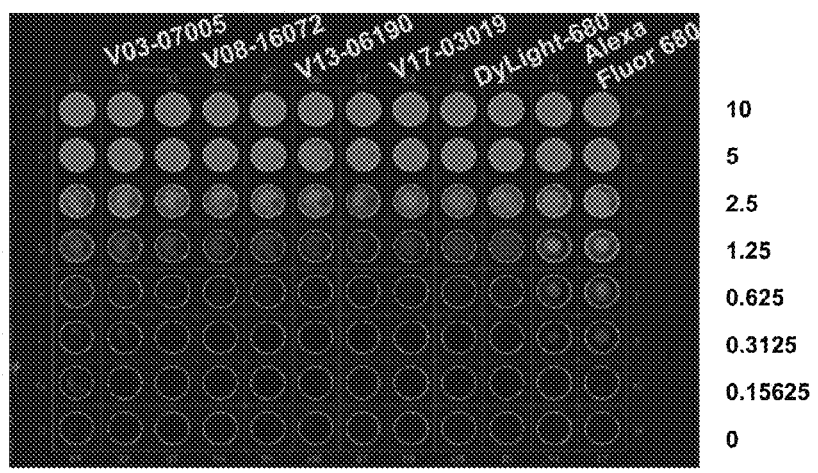
FIG. 7 shows functional assay results with commercial dyes and the inventive compounds in one embodiment.

FIG. 6 shows binding intensity results expressed as RFU of a functional assay using GAM conjugated with 5× molar excess of V03-07005 (green diamond; plate column 1 and 2), V08-16072 (blue triangle; plate column 3 and 4), V13-06190 (magenta diamond; plate column 5 and 6), V17-03019 (orange circle; plate column 7 and 8), DyLight 680 (red square; plate column 9 and 10), and Alexa Fluor 680 (black square; plate column 11 and 12). FIG. 7 shows an image of the plate of FIG. 6. Based on the data, at 5× molar excess, Alexa Fluor 680-GAM showed the highest binding intensity. V03-07005 performed best of the benzopyrylium dyes.

Figure 8:
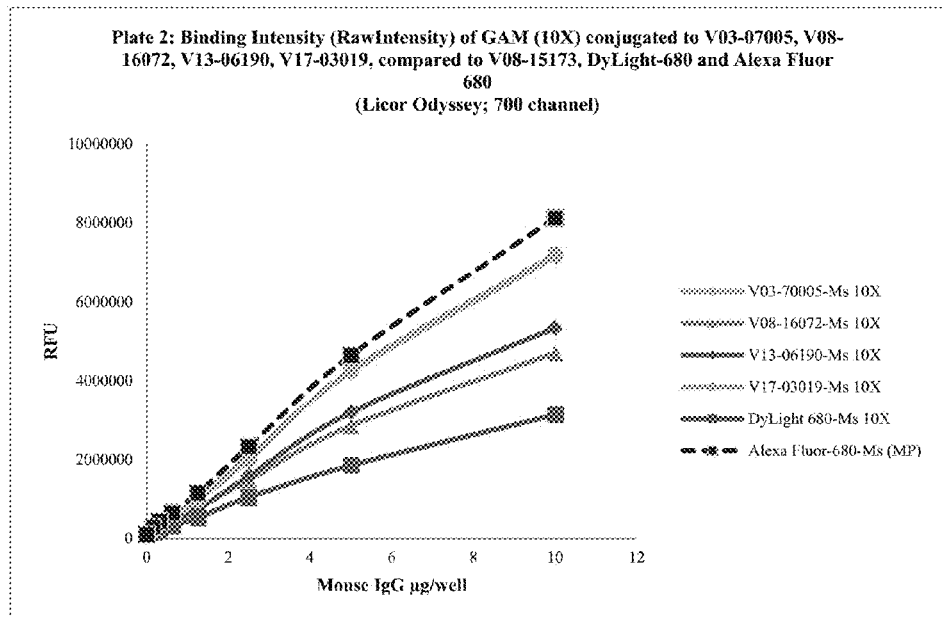
FIG. 8 shows functional assay results with commercial dyes and the inventive compounds in one embodiment.
Figure 9:
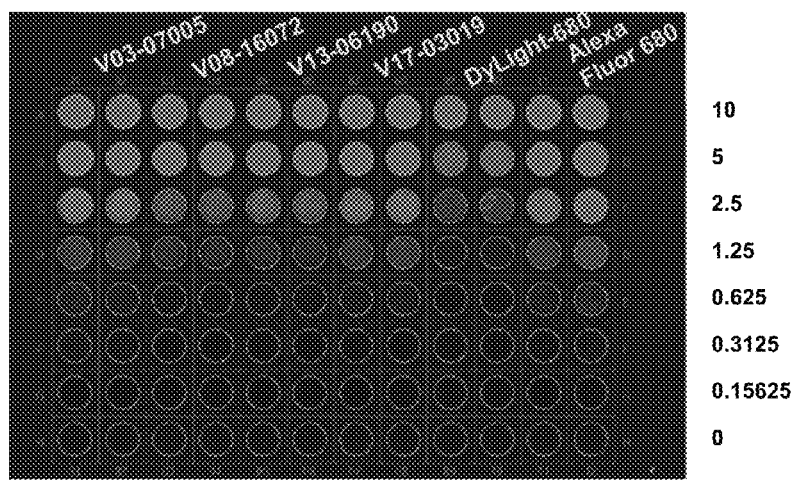
FIG. 9 shows functional assay results with commercial dyes and the inventive compounds in one embodiment.

FIG. 8 shows binding intensity results expressed as RFU of a functional assay using GAM conjugated with 10× molar excess of V03-07005 (green diamond; plate column 1 and 2), V08-16072 (blue triangle; plate column 3 and 4), V13-06190 (purple diamond; plate column 5 and 6), V17-03019 (orange circle; plate column 7 and 8), DyLight 680 (red square; plate column 9 and 10), and Alexa Fluor 680 (black square; plate column 11 and 12). FIG. 9 shows an image of the plate of FIG. 8. Based on the data, at 10× molar excess, GAM conjugated to V03-07005 and V17-03019 dyes showed similar binding intensity as Alexa Fluor 680-GAM. These dyes performed better than V08-16072 and V013-06190. Non-pegylated DyLight 680-GAM showed the lowest binding intensity.

Figure 10:
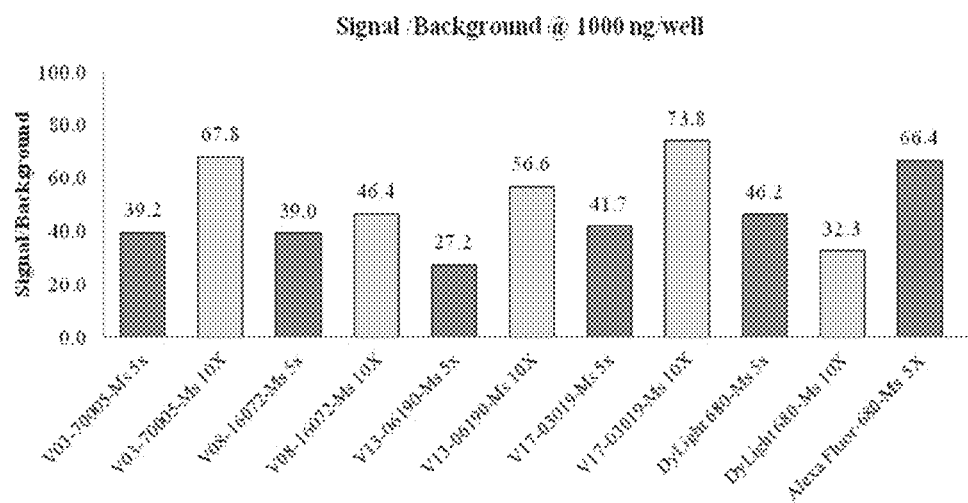
FIG. 10 shows functional assay results with commercial dyes and the inventive compounds in one embodiment.

FIG. 10 shows LiCOR Odyssey results expressed as S/B of a functional assay using GAM conjugated with 5× molar excess (blue bars) or 10× molar excess (beige bars) of the indicated compound.

EXAMPLE 4

In the indicated experiments, the inventive compounds and commercial dye were evaluated for immunofluorescence in a cell based assay using the following protocol. Frozen U2OS cell plates stored at −80° C. were thawed for 30 minutes at 50° C. Storage buffer (PBS) was removed and the cells were permeabilized for 15 minutes with 0.1% Triton-X100 in 1×PBS buffer (100 μl/well). The cell plate was blocked for 60 minutes in 2% BSA/PBS-0.1% Triton-X100. Primary antibody, either rabbit anti-lamin B1 or rabbit anti-HDAC2 (10 μg/ml), diluted in 2% BSA/PBS-0.1% Triton-X100 was added to the plate and incubated for one hour at room temperature. Control wells contained only 2% BSA/PBS-0.1% Triton-X100 blocker. After incubation, antibody solution was removed from the plate and the plate was washed three times with 100 μl/well PBS-0.5% Tween-20 and one time with 100 μl/well PBS. GAR secondary antibodies labeled with various molar excess of the inventive or commercial compound were diluted to 4 μg/ml in PBS and incubated for one hour at room temperature. Plates were washed three times with 100 μl/well PBST and once with 100 μl/well PBS, and Hoechst (diluted to 0.1 μg/ml in PBS) was added to each well (100 μl/well). The plates were scanned on ArrayScan Plate Reader.

Figure 11:
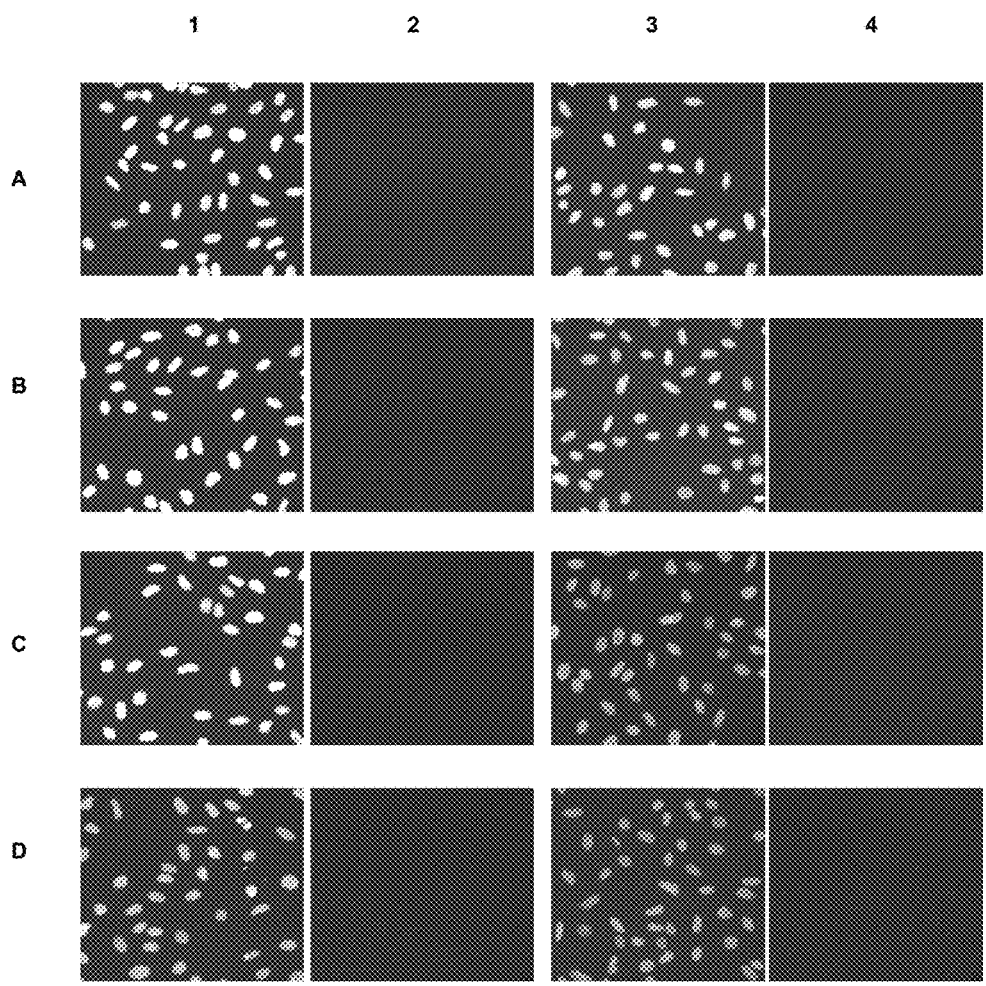
FIG. 11 shows immunofluorescence assay results with commercial dyes and the inventive compounds in one embodiment.
Figure 12:
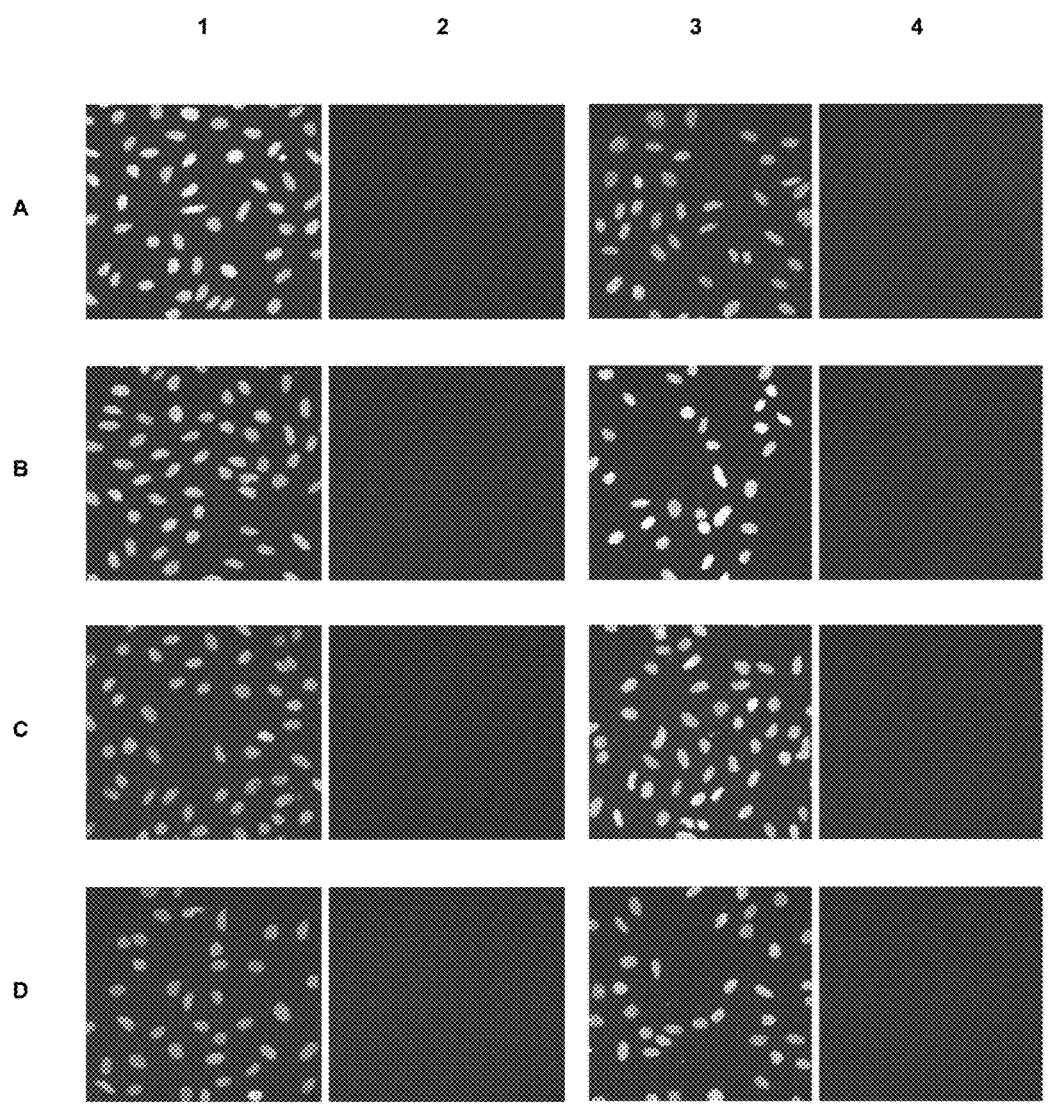
FIG. 12 shows immunofluorescence assay results with commercial dyes and the inventive compounds in one embodiment.
Figure 13:
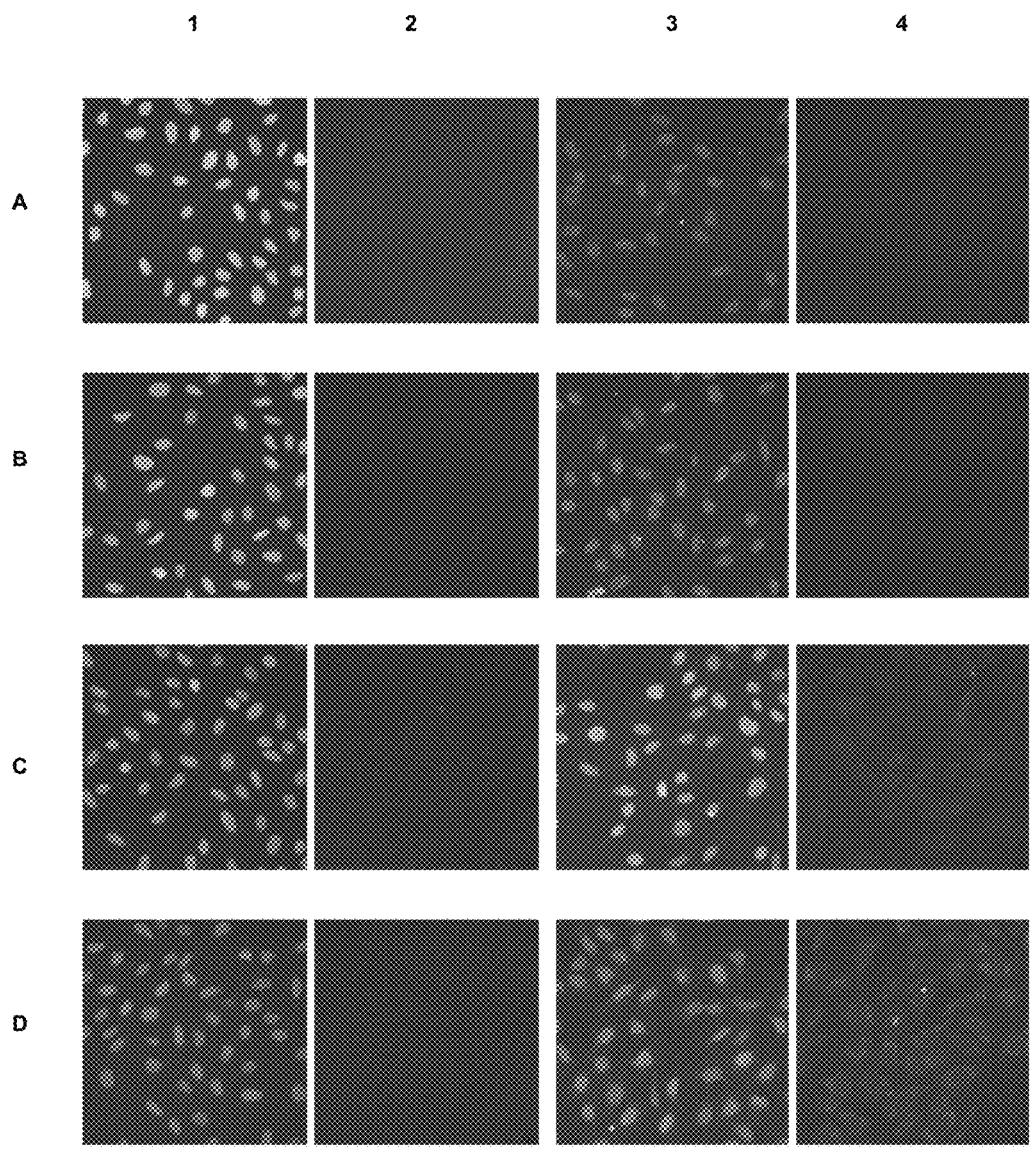
FIG. 13 shows immunofluorescence assay results with commercial dyes and the inventive compounds in one embodiment.

FIG. 11 shows detection of lamin B1 in U2OS cells with V03-07005-GAR (column 1) and V08-16072-GAR (column 3) at a 2.5× molar excess (row A), 5× molar excess (row B), 10× molar excess (row C), and 15× molar excess (row D); and associated controls (columns 2 and 4). FIG. 12 shows detection of lamin B1 in U2OS cells with V13-06190-GAR (column 1) and V17-03019-GAR (column 3) at a 2.5× molar excess (row A), 5× molar excess (row B), 10× molar excess (row C), and 15× molar excess (row D); and associated controls (columns 2 and 4). FIG. 13 shows detection of lamin B1 in U2OS cells with DyLight 680-GAR (column 1) and Alexa Fluor 680-GAR (column 3) at a 2.5× molar excess (row A), 5× molar excess (row B), 10× molar excess (row C), and 15× molar excess (row D); and associated controls (columns 2 and 4). Overall, benzopyrylium dye conjugates showed brighter staining than DyLight 680, and all conjugates performed better than Alexa-Fluor 680 conjugate at similar D/Ps. Benzopyrylium dyes performed best at low molar excesses (2.5-5×). The best performing benzopyrylium dye was V03-07005, which has two $PEG_4$ on the same nitrogen. Non-specific binding in the absence of primary antibody is observed only with Alexa Fluor 680, and is increased with the amount of dye used.

Quantitative analysis of the data of FIGS. 11-13, expressed as Mean Total Intensity, which is the average total intensity of all pixels within a defined area or defined primary object such as a nucleus, is shown below; "Neg" indicates negative control.

|  | V03-07005-GAR | | V08-16072-GAR | | V13-06190-GAR | | V17-03019-GAR | | DyLight 680-GAR | | Alexa Fluor-680-GAR | |
| --- | --- | --- | --- | --- | --- | --- | --- | --- | --- | --- | --- | --- |
|  | Lamin B1 | Neg | Lamin B1 | Neg | Lamin B1 | Neg | Lamin B1 | Neg | Lamin B1 | Neg | Lamin B1 | Neg |
| 2.5X | 236323 | 3186 | 209340 | 2933 | 145133 | 2993 | 143740 | 3177 | 131853 | 3256 | 27862 | 3004 |
| 5X | 271178 | 3093 | 158162 | 3146 | 153454 | 3041 | 184109 | 2809 | 112778 | 3331 | 37292 | 3135 |
| 10X | 235611 | 3211 | 120370 | 3075 | 103925 | 2926 | 152450 | 3649 | 66049 | 2797 | 64073 | 5907 |
| 15X | 154466 | 3217 | 106816 | 3275 | 98440 | 3217 | 103931 | 2412 | 73837 | 3752 | 66025 | 9958 |

Quantitative analysis of the data of FIGS. 11-13, expressed as S/B, is shown below.

| S/B | V03-07005-GAR | V08-16072-GAR | V13-06190-GAR | V17-03019-GAR | DyLight 680-GAR | Alexa Fluor-680-GAR |
|---|---|---|---|---|---|---|
| 2.5X | 74.2 | 71.4 | 48.5 | 45.2 | 40.5 | 9.3 |
| 5X | 87.7 | 50.3 | 50.5 | 65.5 | 33.9 | 11.9 |
| 10X | 73.4 | 39.1 | 35.5 | 41.8 | 23.6 | 10.8 |
| 15X | 48.0 | 32/6 | 30.6 | 43.1 | 19.7 | 6.6 |

Based on S/B data, the best performing benzopyrylium dye was V03-07005, with two PEG$_4$ and two sulfo groups, followed by V17-03019. All benzopyrylium dyes quenched at high molar excesses, with V08-16072 and V13-06190 gradually quenching from 2.5× molar excess condition. Alexa Fluor 680 began quenching at molar excesses greater than 10×. Due to strong non-specific binding at higher molar excesses, Alexa-680 showed decreasing signal to background.

Figure 14:
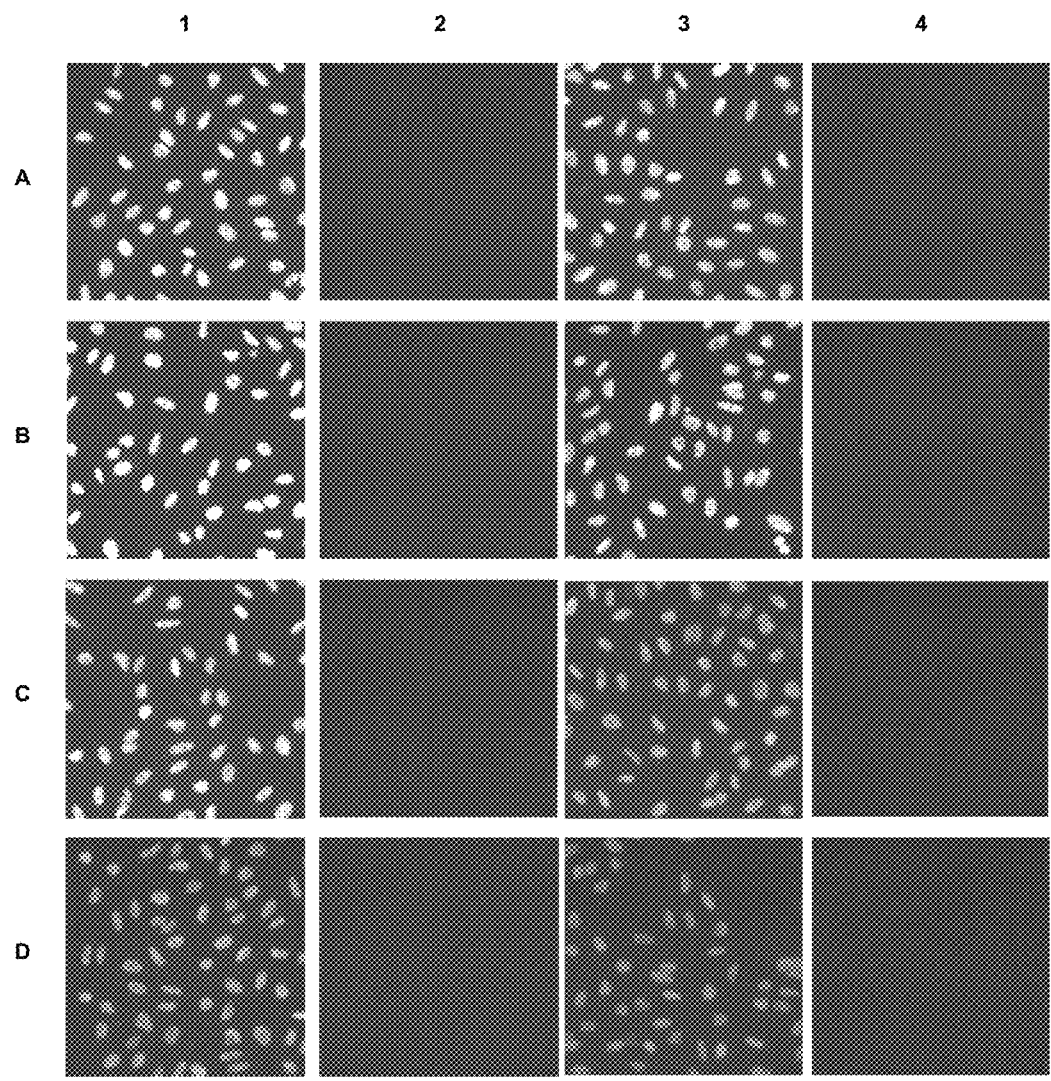
FIG. 14 shows immunofluorescence assay results with commercial dyes and the inventive compounds in one embodiment.
Figure 15:
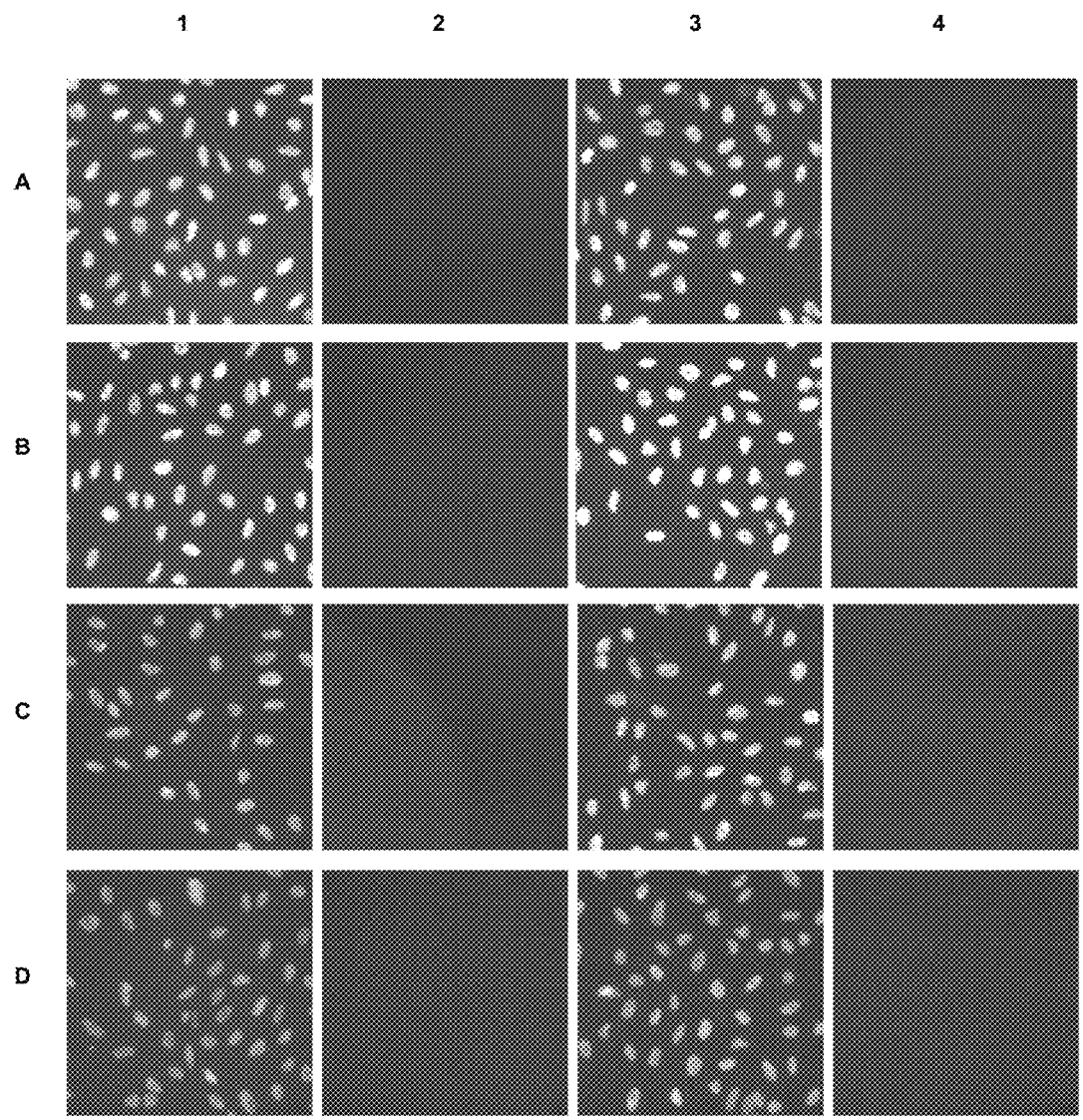
FIG. 15 shows immunofluorescence assay results with commercial dyes and the inventive compounds in one embodiment.
Figure 16:
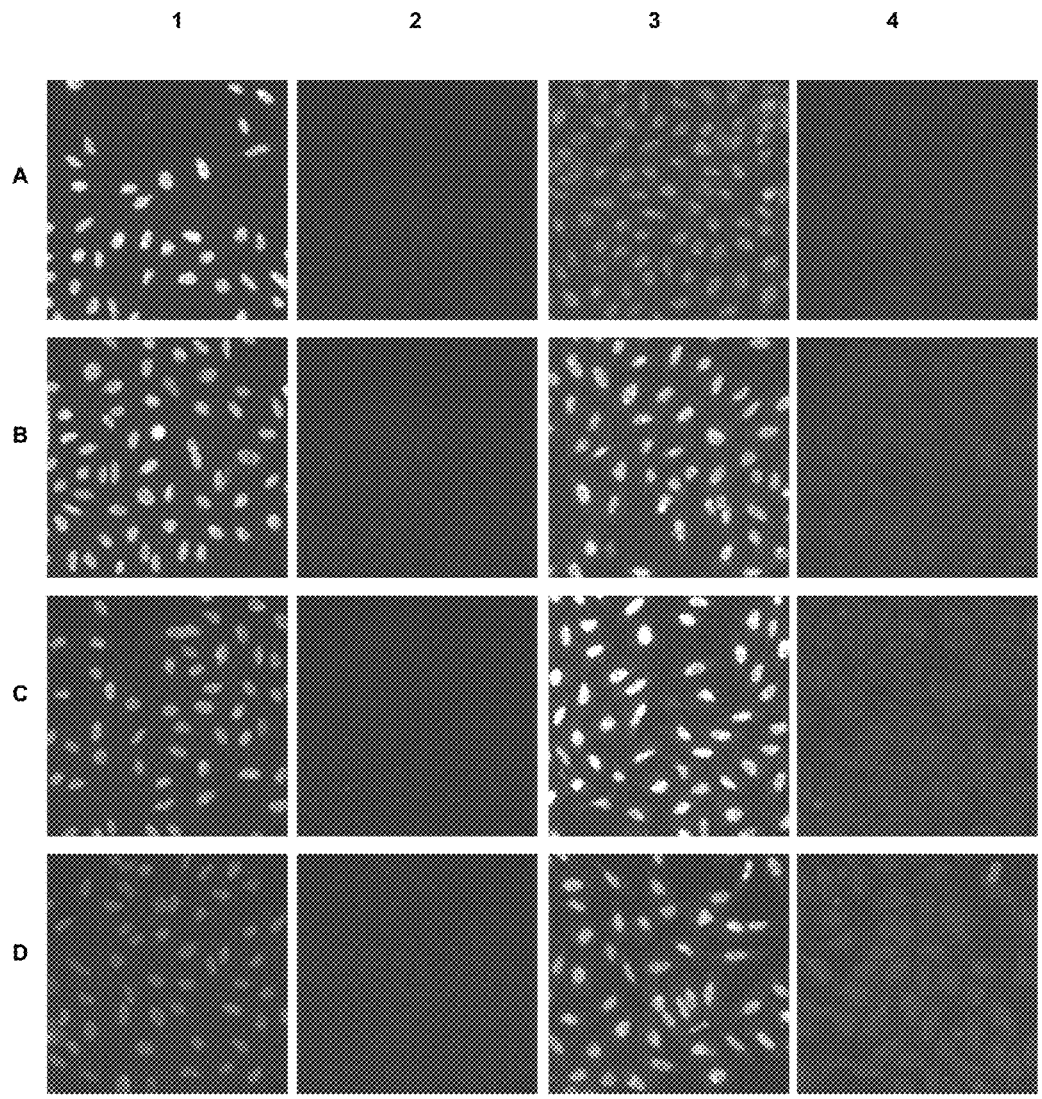
FIG. 16 shows immunofluorescence assay results with commercial dyes and the inventive compounds in one embodiment.

FIG. 14 shows nuclear detection of HDAC2 in U2OS cells with V03-07005-GAR (column 1) and V08-16072-GAR (column 3) at a 2.5× molar excess (row A), 5× molar excess (row B), 10× molar excess (row C), and 15× molar excess (row D); and associated controls (columns 2 and 4). FIG. 15 shows nuclear detection of HDAC2 in U2OS cells with V13-06190-GAR (column 1) and V17-03019-GAR (column 3) at a 2.5× molar excess (row A), 5× molar excess (row B), 10× molar excess (row C), and 15× molar excess (row D); and associated controls (columns 2 and 4). FIG. 16 shows nuclear detection of HDAC2 in U2OS cells with DyLight 680-GAR (column 1) and Alexa Fluor 680-GAR (column 3) at a 2.5× molar excess (row A), 5× molar excess (row B), 10× molar excess (row C), and 15× molar excess (row D); and associated controls (columns 2 and 4). Conjugates made with pegylated benzopyrylium dyes showed brighter staining than conjugates with DyLight 680, and all conjugates performed better than Alexa-Fluor 680 conjugate at similar D/Ps. Benzopyrylium dyes performed best at low molar excesses. The best performing benzopyrylium dye was V03-07005, with two PEG$_4$ on the same nitrogen. Non-specific binding in the absence of primary antibody is observed only with Alexa Fluor 680, where background increased with the amount of dye used.

Quantitative analysis of the data of FIGS. 14-16, expressed as Mean Total Intensity, which is the average total intensity of all pixels within a defined area or defined primary object such as a nucleus, is shown below; "Neg" indicates negative control.

| | V03-07005-GAR | | V08-16072-GAR | | V13-06190-GAR | | V17-03019-GAR | | DyLight 680-GAR | | Alexa Fluor-680-GAR | |
|---|---|---|---|---|---|---|---|---|---|---|---|---|
| | HDAC2 | Neg | HDAC2 | Neg | HDAC2 | Neg | HDAC2 | Neg | HDAC2 | Neg | HDAC2 | Neg |
| 2.5X | 80067 | 2158 | 86477 | 2150 | 79222 | 2142 | 83377 | 2043 | 64437 | 2116 | 22746 | 2167 |
| 5X | 104865 | 2127 | 72981 | 2136 | 73258 | 2192 | 101760 | 1978 | 54336 | 2194 | 43923 | 2512 |
| 10X | 88650 | 2488 | 44540 | 2111 | 43725 | 2337 | 68080 | 2303 | 31295 | 1817 | 65089 | 2839 |
| 15X | 47052 | 2213 | 28685 | 2327 | 36184 | 2344 | 38914 | 1749 | 20077 | 2466 | 44209 | 6320 |

Quantitative analysis of the data of FIGS. 14-16, expressed as S/B, is shown below.

| S/B | V03-07005-GAR | V08-16072-GAR | V13-06190-GAR | V17-03019-GAR | DyLight 680-GAR | Alexa Fluor-680-GAR |
|---|---|---|---|---|---|---|
| 2.5X | 37.1 | 40.2 | 37.0 | 40.8 | 30.4 | 10.5 |
| 5X | 49.3 | 34.2 | 33.4 | 51.5 | 24.8 | 17.5 |
| 10X | 35.6 | 21.1 | 18.7 | 29.6 | 17.2 | 22.9 |
| 15X | 21.3 | 12.3 | 15.4 | 22.3 | 8.1 | 7.0 |

The best performing benzopyrylium dye was V03-07005, with two PEG$_4$ and two sulfo groups, then, V17-03019. All benzopyrylium dyes quenched at high molar excesses, with V08-16072 and V13-06190 gradually quenching from 2.5× molar excess condition. Alexa Fluor 680 began quenching at molar excesses greater than 10×. Due to the strong non-specific binding at higher molar excesses, Alexa-680 showed decreasing signal to background.

In the indicated experiments, the inventive compounds and commercial dye were evaluated for immunofluorescence in a cell based assay using the following protocol. Frozen U2OS cell plates which were stored at −80° C. were thawed for 30 minutes at 50° C. Storage buffer (PBS) was removed and cells were permeabilized for 15 minutes with 0.1% Triton-X100 in 1×PBS buffer (100 µl/well). The cell plate was blocked for 60 minutes in 2% BSA/PBS-0.1% Triton-X100. Primary antibody, either mouse anti-ezrin (1.3 µg/ml) or mouse anti-NCoR2 (20 µg/ml), diluted in 2% BSA/PBS-0.1% Triton-X100 was added to the plate and incubated for one hour at room temperature. Control wells contained only 2% BSA/PBS-0.1% Triton-X100 blocker. After incubation, the antibody solution was removed from the plate and the plate was washed three times with 100 µl/well of PBS-0.5% Tween-20 and one time with 100 µl/well PBS. GAM secondary antibodies labeled with various molar excess of the inventive or commercial compound were diluted to 4 µg/ml in PBS and incubated for one hour at room temperature. The plates were washed three times with 100 µl/well of PBST and once with 100 µl/well PBS, and Hoechst (diluted to 0.1 µg/ml in PBS) was added to each well (100 µl/well). The plates were scanned on ArrayScan Plate Reader.

Figure 17:
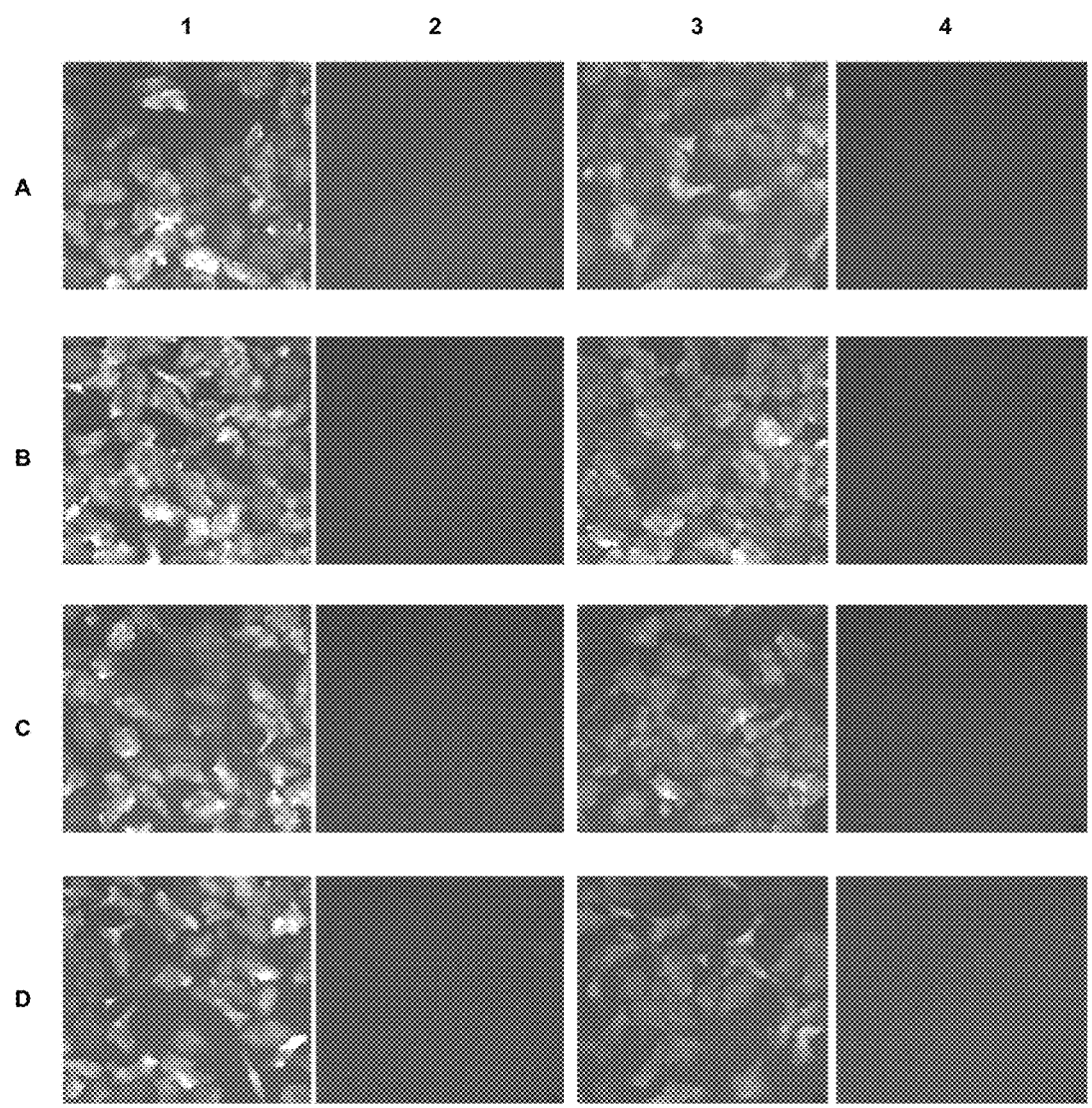
FIG. 17 shows immunofluorescence assay results with commercial dyes and the inventive compounds in one embodiment.
Figure 18:
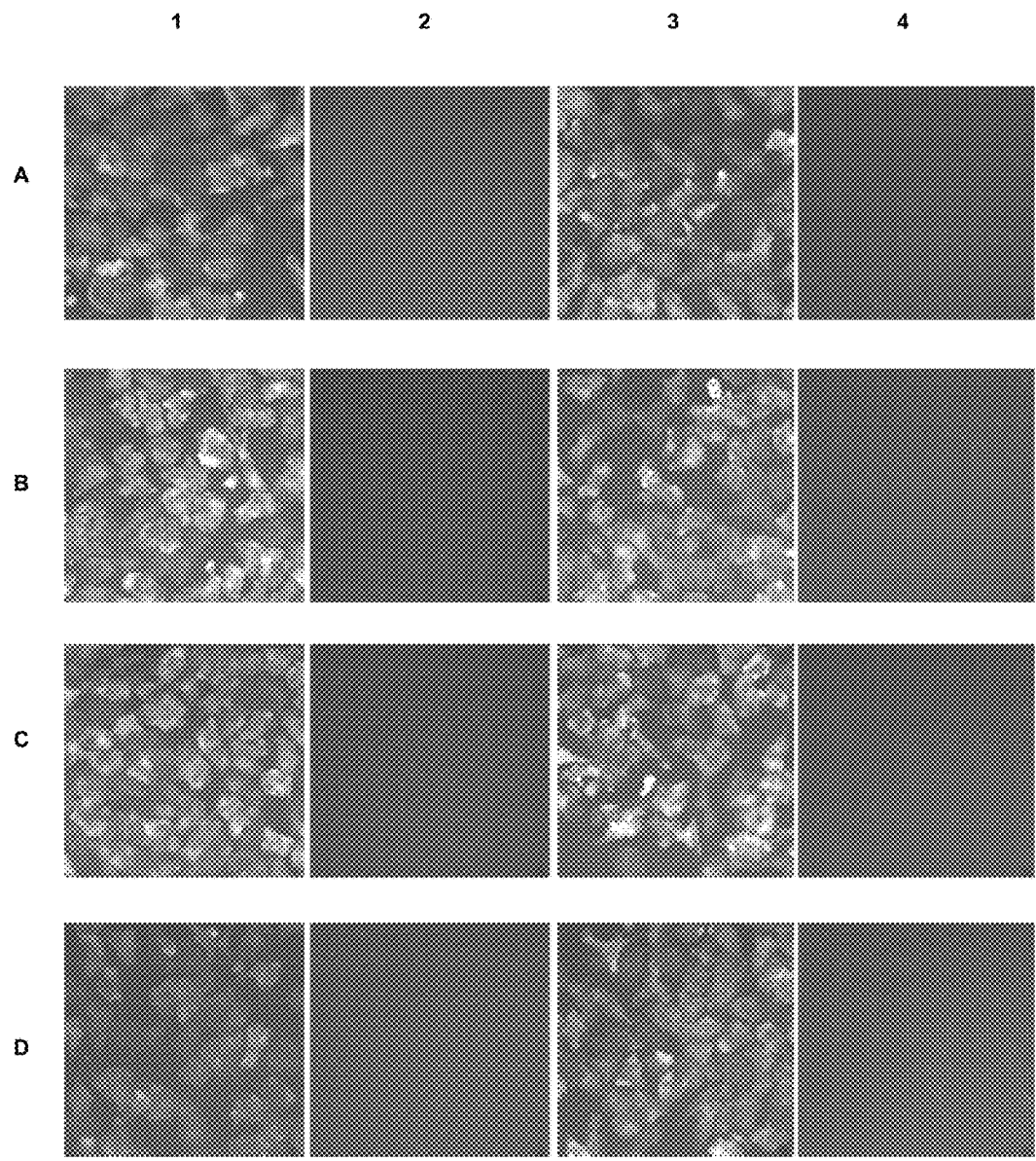
FIG. 18 shows immunofluorescence assay results with commercial dyes and the inventive compounds in one embodiment.
Figure 19:
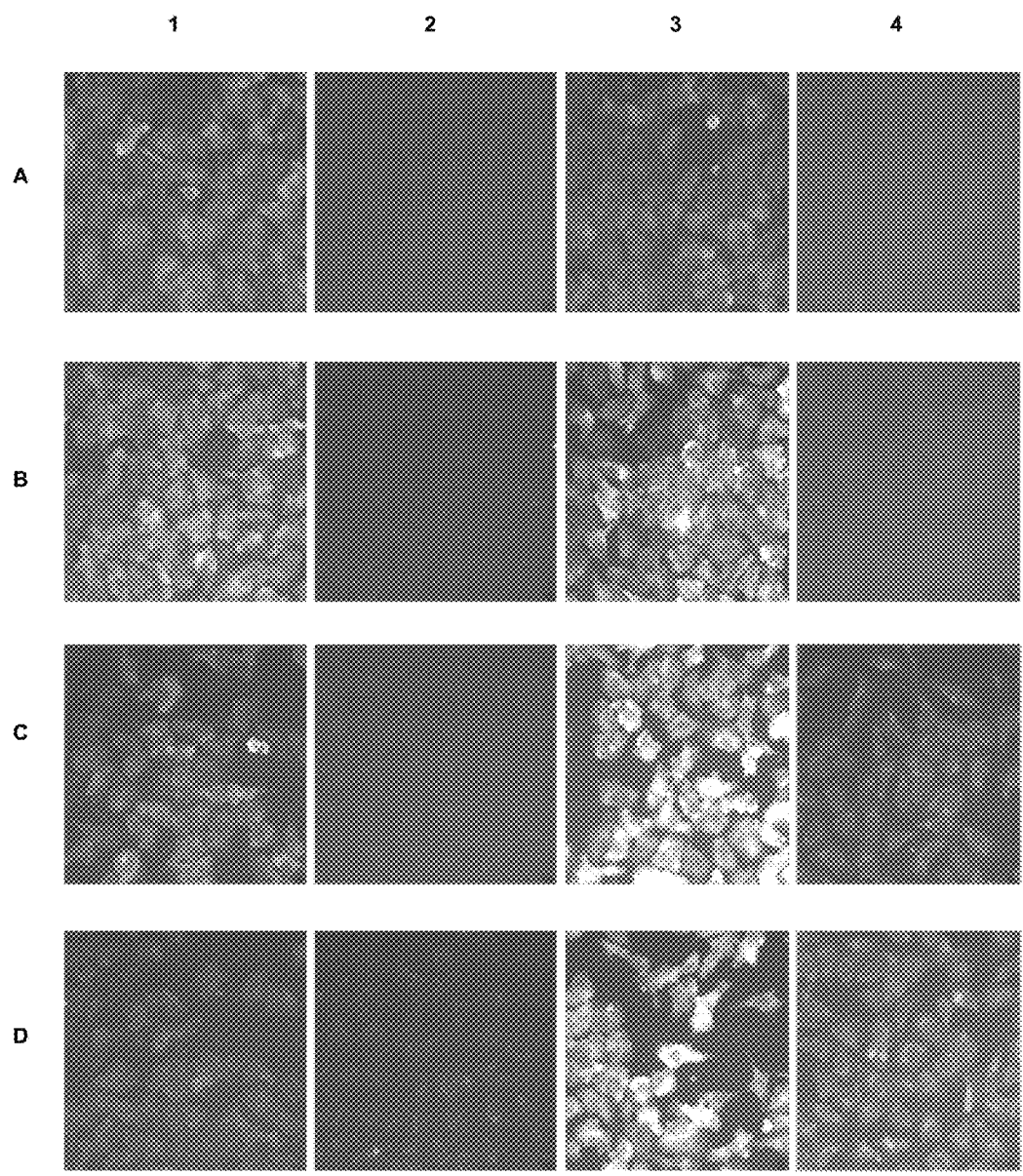
FIG. 19 shows immunofluorescence assay results with commercial dyes and the inventive compounds in one embodiment.

FIG. 17 shows detection of ezrin in U2OS cells with V03-07005-GAM (column 1) and V08-16072-GAM (column 3) at a 2.5× molar excess (row A), 5× molar excess (row B), 10× molar excess (row C), and 15× molar excess (row D); and associated controls (columns 2 and 4). FIG. 18 shows detection of ezrin in U2OS cells with V13-06190-GAM (column 1) and V17-03019-GAM (column 3) at a 2.5× molar excess (row A), 5× molar excess (row B), 10× molar excess (row C), and 15× molar excess (row D); and associated controls (columns 2 and 4). FIG. 19 shows detection of ezrin in U2OS cells with DyLight 680-GAM (column 1) and Alexa Fluor 680-GAM (column 3) at a 2.5× molar excess (row A), 5× molar excess (row B), 10× molar excess (row C), and 15× molar excess (row D); and associated controls (columns 2 and 4). The conjugates made with the benzopyrylium dyes showed brighter staining than DyLight 680, and all conjugates performed better than Alexa-Fluor 680 conjugate at similar D/Ps. The benzopyrylium dyes performed best at low molar excesses. The best performing benzopyrylium dye was V03-07005. Non-specific binding in the absence of primary antibody was observed only with Alexa Fluor 680, and increased with the amount of dye used.

Quantitative analysis of the data of FIGS. 17-19, expressed as Mean Total Intensity, which is the average total intensity of all pixels within a defined area or defined primary object such as a nucleus, is shown below; "Neg" indicates negative control.

|  | V03-07005-GAM | | V08-16072-GAM | | V13-06190-GAM | | V17-03019-GAM | | DyLight 680-GAM | | Alexa Fluor-680-GAM | |
| --- | --- | --- | --- | --- | --- | --- | --- | --- | --- | --- | --- | --- |
|  | Ezrin | Neg | Ezrin | Neg | Ezrin | Neg | Ezrin | Neg | Ezrin | Neg | Ezrin | Neg |
| 2.5X | 92921 | 18678 | 69367 | 16412 | 81937 | 16244 | 85736 | 18039 | 61819 | 16866 | 44076 | 20621 |
| 5X | 117420 | 17542 | 79695 | 16082 | 89901 | 15736 | 88404 | 16994 | 66550 | 19346 | 115695 | 21620 |
| 10X | 100740 | 16998 | 78398 | 16434 | 89417 | 17205 | 117698 | 17612 | 62670 | 18444 | 212611 | 42689 |
| 15X | 91676 | 16926 | 67010 | 17775 | 59436 | 22790 | 85383 | 18930 | 39345 | 24576 | 204288 | 74581 |

Quantitative analysis of the data of FIGS. 17-19, expressed as S/B, is shown below.

| S/B | V03-07005-GAR | V08-16072-GAR | V13-06190-GAR | V17-03019-GAR | DyLight 680-GAR | Alexa Fluor-680-GAR |
| --- | --- | --- | --- | --- | --- | --- |
| 2.5X | 5.0 | 4.2 | 5.0 | 4.8 | 3.7 | 2.1 |
| 5X | 6.7 | 5.0 | 5.7 | 5.2 | 3.4 | 5.4 |
| 10X | 5.9 | 4.8 | 5.2 | 6.7 | 3.4 | 5.0 |
| 15X | 5.4 | 3.8 | 2.6 | 4.5 | 1.6 | 2.7 |

The best performing benzopyrylium dye was V03-07005, with two PEG4 and two sulfo groups, then, V17-03019. All benzopyrylium dyes quenched at high molar excesses. Alexa Fluor 680 began quenching at molar excesses greater than 10×. Due to strong non-specific binding at higher molar excesses, Alexa-680-GAM showed decreased signal to background.

NCoR2 was detected in U2OS cells with V03-07005-GAM, V08-16072-GAM, V13-06190-GAM, V17-03019-GAM, DyLight 680-GAM, and Alexa Fluor 680-GAM at a 2.5×, 5×, 10×, and 15× molar excesses. Quantitative analysis of the data, expressed as Mean Total Intensity, which is the average total intensity of all pixels within a defined area or defined primary object such as a nucleus, is shown below, where "Neg" indicates the negative control condition.

|      | V03-07005-GAM | | V08-16072-GAM | | V13-06190-GAM | | V17-03019-GAM | | DyLight 680-GAM | | Alexa Fluor-680-GAM | |
|------|-------|-------|-------|-------|-------|-------|-------|-------|-------|-------|-------|-------|
|      | NCoR2 | Neg | NCoR2 | Neg | NCoR2 | Neg | NCoR2 | Neg | NCoR2 | Neg | NCoR2 | Neg |
| 2.5X | 89539 | 17648 | 76027 | 17163 | 87251 | 23790 | 82175 | 17104 | 76596 | 30478 | 81523 | 22614 |
| 5X   | 107778 | 17676 | 70711 | 18149 | 104629 | 18115 | 80594 | 17864 | 71774 | 17394 | 98164 | 23026 |
| 10X  | 77837 | 18395 | 59411 | 17553 | 66955 | 17479 | 87665 | 20020 | 45648 | 18873 | 174913 | 63422 |
| 15X  | 72466 | 18356 | 48666 | 18072 | 55363 | 16732 | 80476 | 17863 | 46945 | 24948 | 190341 | 85250 |

Quantitative analysis of the NCoR2 data, expressed as S/B, is shown below.

| S/B | V03-07005-GAR | V08-16072-GAR | V13-06190-GAR | V17-03019-GAR | DyLight 680-GAR | Alexa Fluor-680-GAR |
|-----|------|------|------|------|------|------|
| 2.5X | 5.1 | 4.4 | 3.7 | 4.8 | 2.5 | 3.6 |
| 5X   | 6.1 | 3.9 | 5.8 | 4.5 | 4.1 | 4.3 |
| 10X  | 4.2 | 3.4 | 3.8 | 4.4 | 2.4 | 2.8 |
| 15X  | 3.9 | 2.7 | 3.3 | 4.5 | 1.9 | 2.2 |

The best performing benzopyrylium dye was V03-07005, with two PEG$_4$ and two sulfo groups, then, V17-03019. All benzopyrylium dyes quenched at high molar excesses, V08-16072 and V13-06190 gradually quenched from the 2.5× molar excess condition. Alexa Fluor 680 began quenching at molar excesses greater than 10×. Due to the strong non-specific binding at higher molar excesses, Alexa-680 showed decreasing signal to background.

The excitation/emission spectra (Ex/Em spectra) were within +/−10 nm compared to DyLight 680 NHS ester. Excitation of V03-07005, V08-16072, V13-06190, and V1703019 NHS were shifted from 690 nm in ethanol to about 675 nm in PBS.

At low molar excesses, e.g., less than 10×, labeling efficiency of GAM and GAR was similar for all benzopyrylium dyes including non-pegylated DyLight 680.

Conjugates made with the pegylated benzopyrylium dyes showed brighter staining than the non-pegylated DyLight 680, and all stained with higher intensity than Alexa-Fluor 680 conjugates. The pegylated benzopyrylium dyes performed best at low molar excesses as opposed to the benzocyanine dye V08-15173, which showed increasing staining with higher amount of dye. The best performing benzopyrylium dye was V03-07005, with two PEG$_4$ groups on same nitrogen and two sulfo groups, followed by V17-03019, with one PEG$_4$ group and three sulfo groups. Absence or low non-specific binding was observed with all benzopyrylium dyes. Non-specific binding was observed with Alexa Fluor 680 at higher molar excess of 10× and 15×. All the benzopyrylium dye-conjugates quenched at high molar excesses, e.g., greater than 10×, V08-16072 and V13-06190 showed gradual quenching from 2.5× molar excess condition.

EXAMPLE 5

In vivo imaging of inventive and commercial compounds was performed, and biodistribution, clearance and cytotoxicity were assessed.

One hundred µL of 1 mg/mL hydrolyzed dye solution was intravenously (IV) injected in the retro orbital plexus. Animals were imaged on a Carestream MSFX using excitation of 690 nm and emission of 750 nm for 60 seconds with no binning at 140 mm FOV. Images were taken before injection, and at 0 hour, 3 hour, 6 hour, 12 hour, and 24 hour post injection. After the final time point, animals were sacrificed and tissues collected for ex vivo imaging. Heart, liver, spleen, lungs, and kidney were gathered from one mouse from each cohort, and fixed and stained using hemotaxylin and eosin (H&E). Colorimetric images were acquired at 20× on a Nikon 90i microscope (excluding DyLight 700B1).

Figure 20:
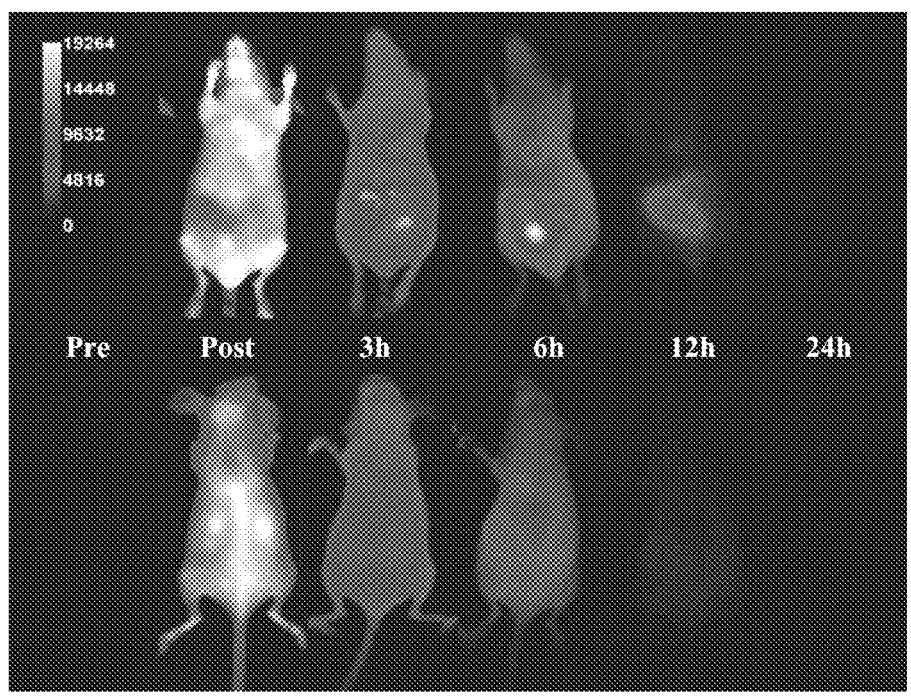
FIG. 20 shows in vivo imaging and biodistribution of one inventive compound 675-P (V03-07005).
Figure 21:
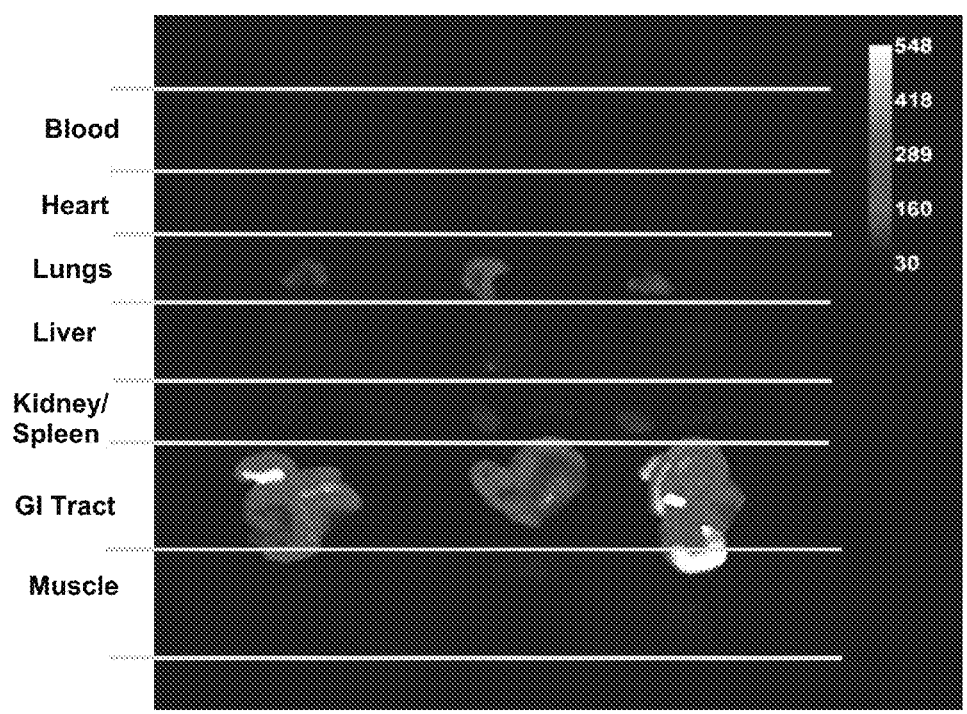
FIG. 21 shows ex vivo accumulation in an in vivo assay of one inventive compound 675-P (V03-07005).
Figure 22:
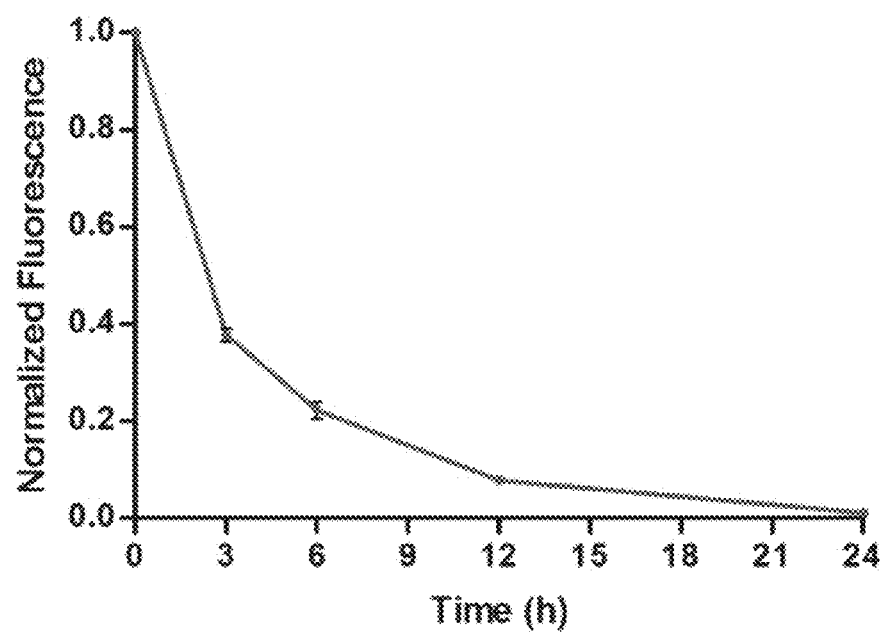
FIG. 22 shows in vivo clearance of one inventive compound 675-P (V03-07005).
Figure 23A:
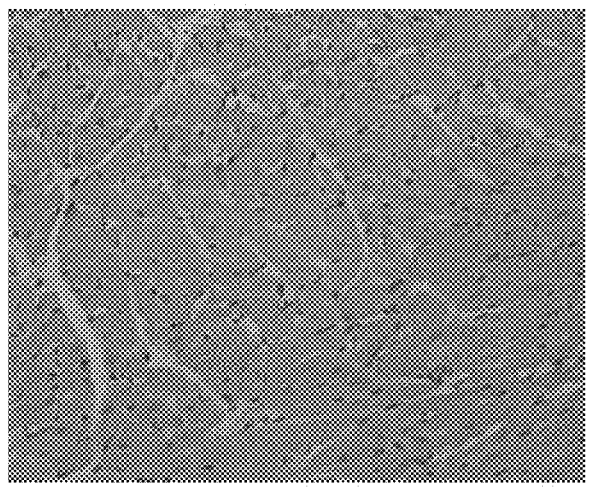
FIGS. 23A-E show histology of one inventive compound 675-P (V03-07005) in an in vivo assay.
Figure 23B:
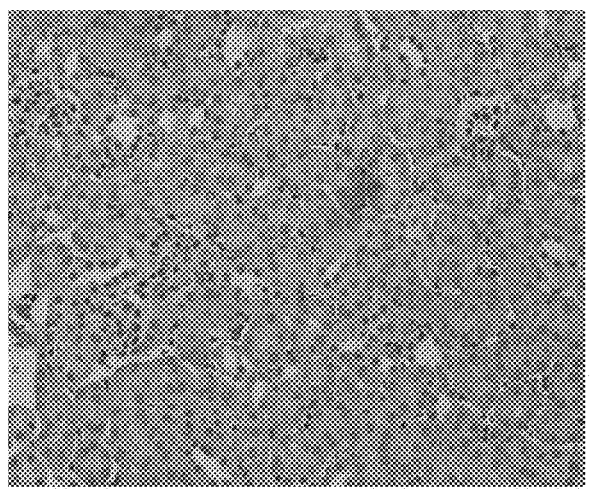
Figure 23C:
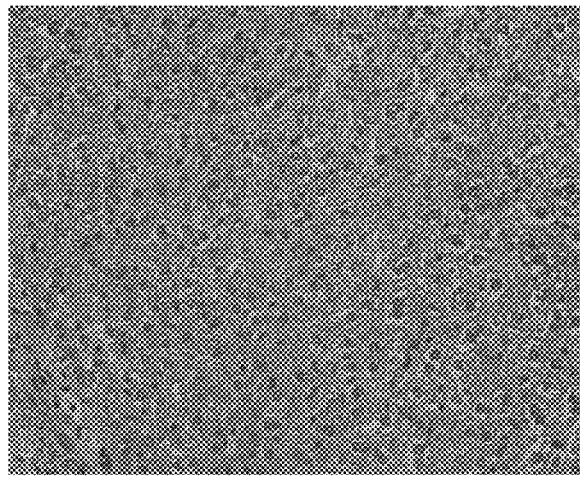
Figure 23D:
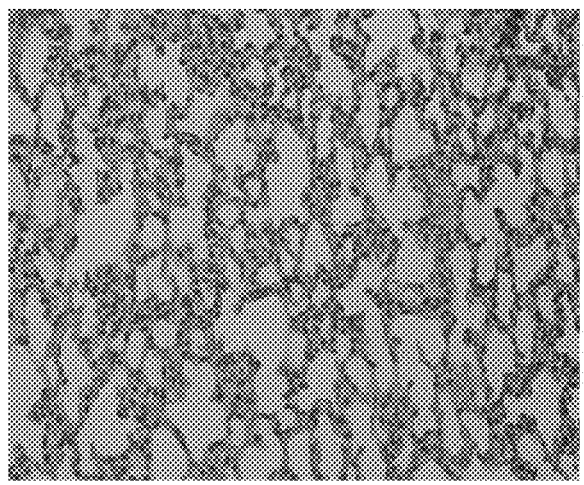
Figure 23E:
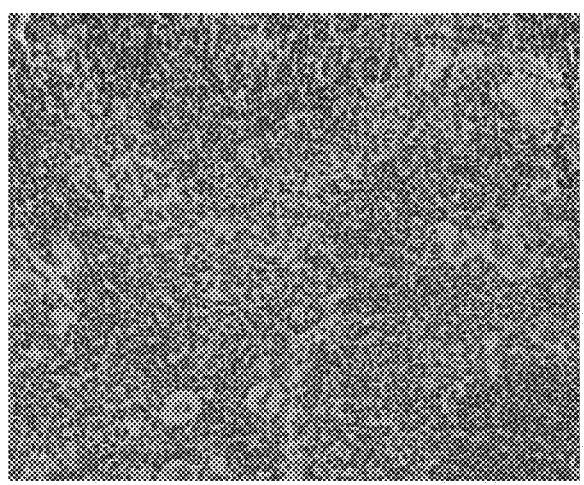

682 Compound 2/3 (V03-07005) was used in in vivo imaging as described above. Biodistribution is shown in FIG. 20 at the time points shown. Ex-vivo accumulation in various organs (blood, heart, lungs, liver, kidney, spleen, GI tract, and muscle) is shown in FIG. 21. Clearance is shown in FIG. 22. Tissue toxicity of 682 Compound 2/3 (V03-07005) was determined for heart (FIG. 23A), kidney (FIG. 23B), liver (FIG. 23C), lung (FIG. 23D), and spleen (FIG. 23E).

Figure 24:
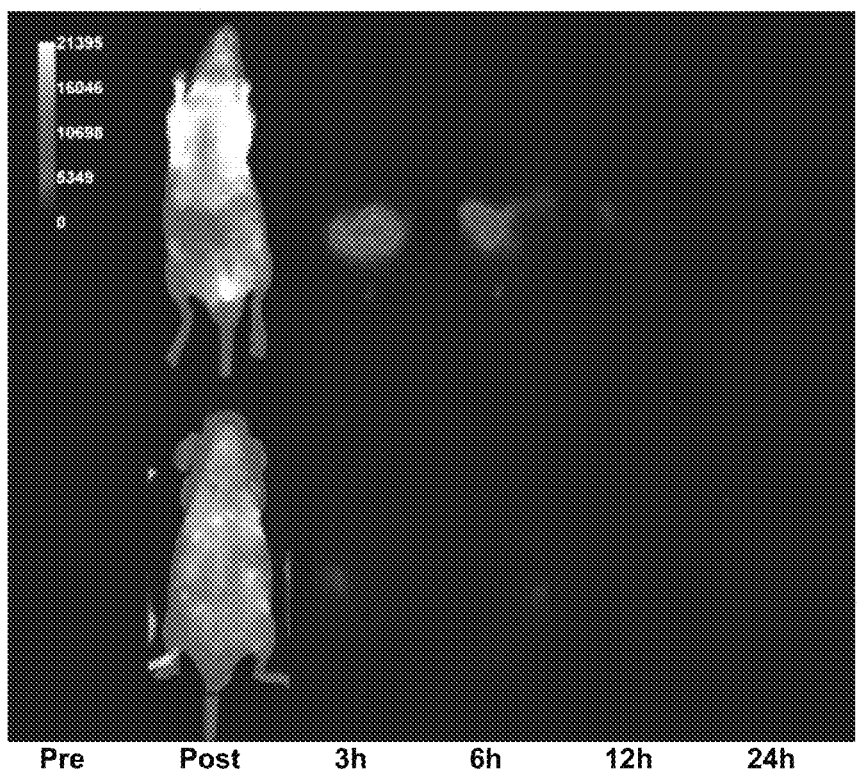
FIG. 24 shows in vivo imaging and biodistribution of a commercial compound (DyLight 680).
Figure 25:
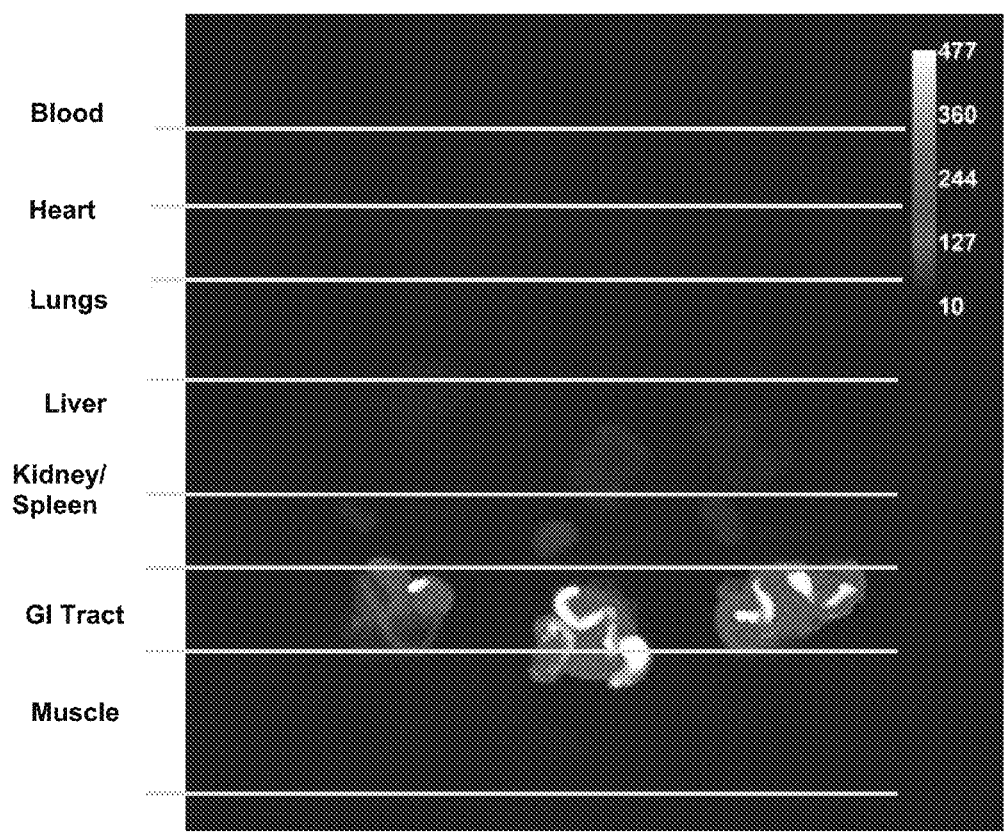
FIG. 25 shows ex vivo accumulation in an in vivo assay of a commercial compound (DyLight 680).
Figure 26:
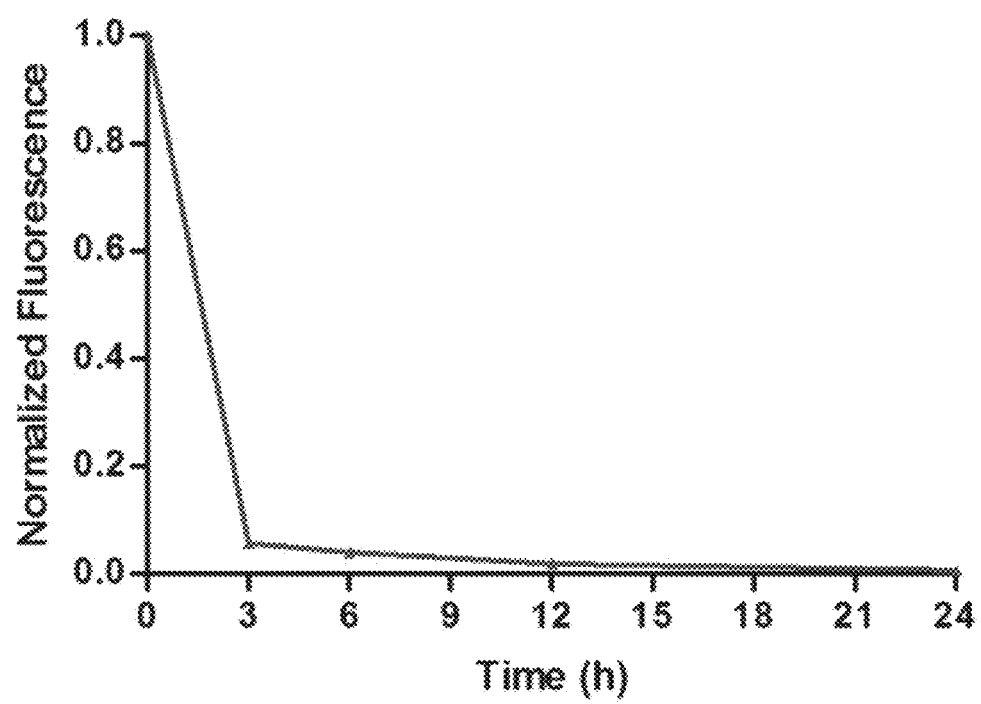
FIG. 26 shows in vivo clearance of a commercial compound (DyLight 680).
Figure 27A:
FIGS. 27A-E show histology in an in vivo assay of a commercial compound (DyLight 680).
Figure 27B:
Figure 27C:
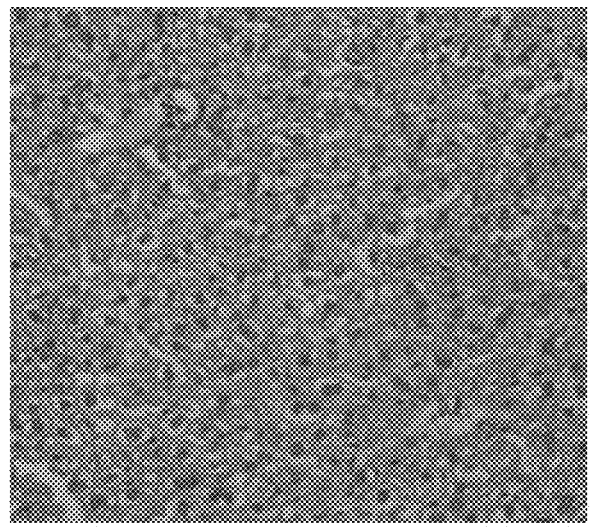
Figure 27D:
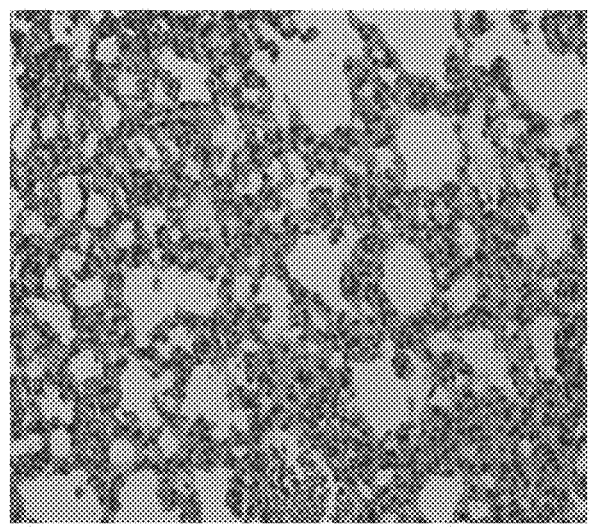
Figure 27E:
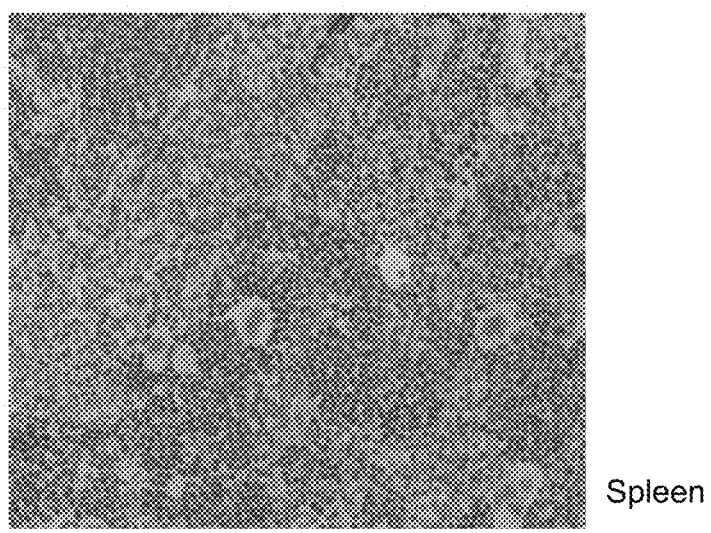

DyLight 680 was used in in vivo imaging as described above. Biodistribution is shown in FIG. FIG. 24 at the time points shown. Ex-vivo accumulation in various organs (blood, heart, lungs, liver, kidney/spleen, GI tract, and muscle) is shown in FIG. 25. Clearance is shown in FIG. 26. Tissue toxicity of DyLight 680 was determined for heart (FIG. 27A), kidney (FIG. 27B), liver (FIG. 27C), lung (FIG. 27D), and spleen (FIG. 27E).

DyLight 680 displayed fast optical clearance profile with no histologic observations of tissue damage. Clearance pathways (renal, hepatic-GI) were visualized from in vivo data and ex vivo images.

DyLight 700B1 showed rapid hepatic uptake, followed by GI clearance. In one embodiment, such an inventive compound is used similarly to Gastrosense (Perkin Elmer). In one embodiment, such an inventive compound is made multimodal by incorporating both fluorescent and X-ray opaque elements.

EXAMPLE 6

Near infra red (NIR) fluorophores are commonly used in cell-based assays or in vivo imaging applications. They can be useful in specific imaging or assay application based on the dye's characteristic excitation and emission spectra properties, or relative hydrophilicity/hydrophobicity attributes. In general, dyes that contain a greater number of negative charges display high water solubility and clearance, while more hydrophobic dyes often clear by a hepatic pathway. In one embodiment, the dye is conjugated to primary and secondary antibodies that are then used for fluorescence immunostaining in various cell types. In one embodiment, the dye is conjugated to a targeting moiety such as a protein or peptide, e.g., the integrin binding peptide RGD, or a carbohydrate, e.g., 2-deoxyglucose. In addition, the dye is tested in in vivo for optical biodistribution and clearance in nude mice. For in vivo studies, the mice receive an IV injection of dye by the retro orbital plexus, and are imaged on a Carestream MSFX imager (690 nm excitation/ 750 nm emission) before injection and at 0 h, 3 h, 6 h, 12 h, and 24 h post injection. After the final time point, animals are sacrificed and organs are collected for ex vivo imaging. Toxicity of the dye is evaluated by histological analysis of the dissected tissue section.

The data show that dye conjugated to an antibody at low molar excess has high labeling efficiency, resulting in high fluorescence intensity, good specificity, high signal-to-background ratio, and photostability in cellular imaging. Dye biodistribution and clearance shows rapid clearance through kidney and/or gastrointestinal tract. The NIR dye is an excellent tool for imaging through tissues to circumvent endogenous fluorescent biomolecule interference or quenching.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A compound according to any of general formula Ia

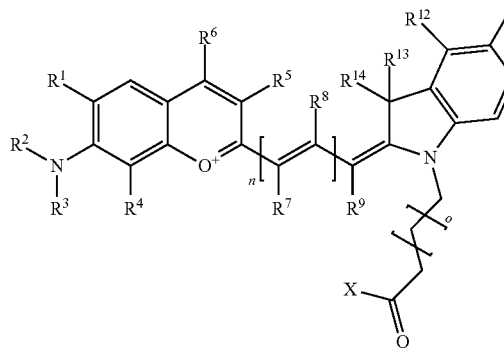

general formula Ib

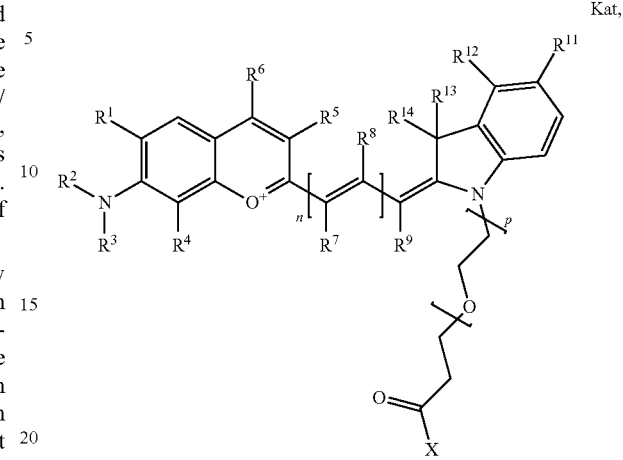

general formula Ic

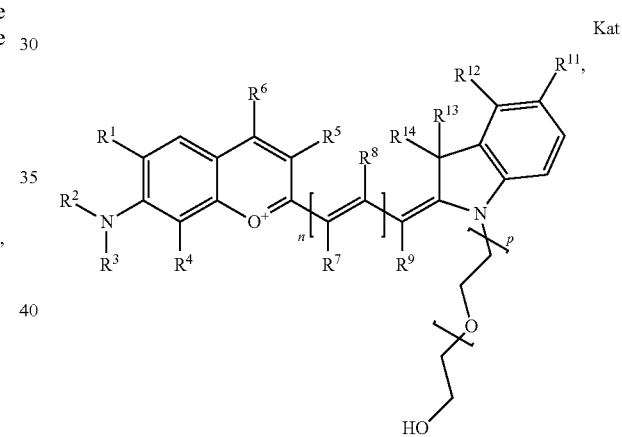

general formula Id

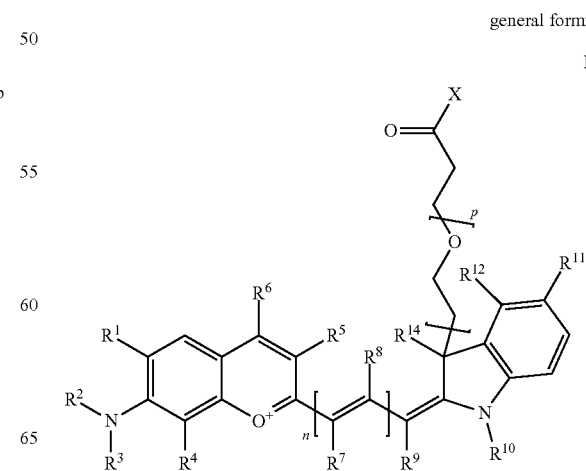

general formula Ie general formula If
Kat,
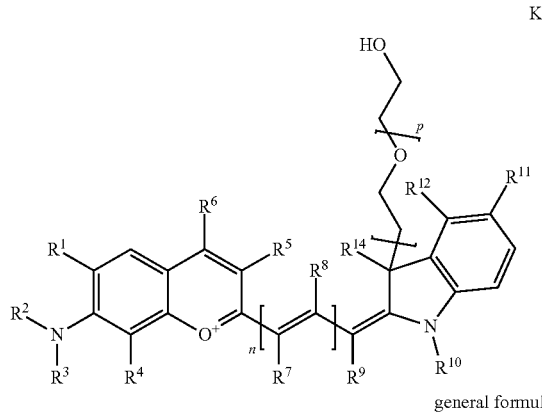
general formula Ig
Kat,
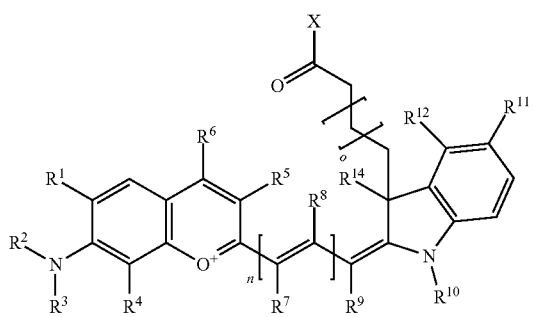
general formula Ih
Kat,
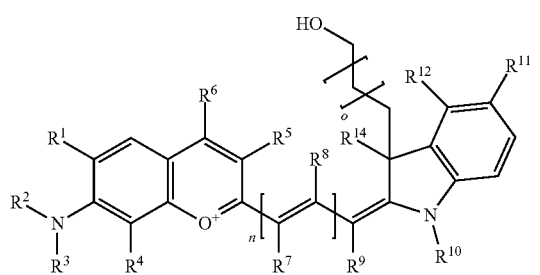
general formula IIa
Kat,
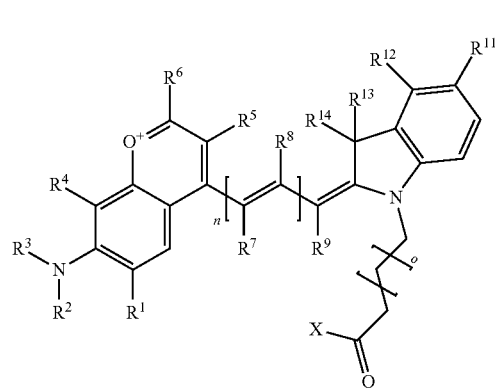
general formula IIb
Kat,
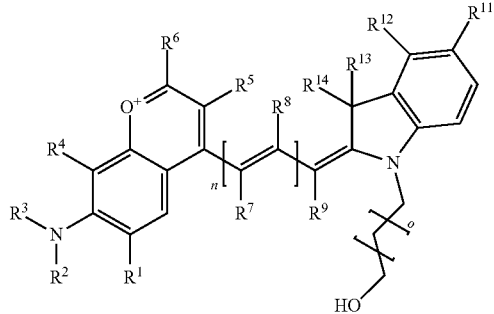
general formula IIc
Kat,
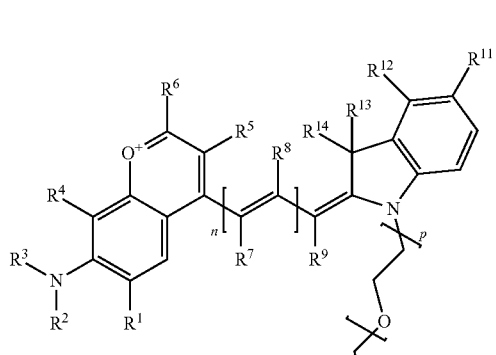
general formula IId
Kat,
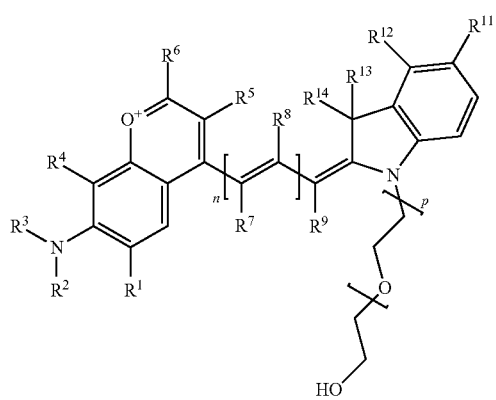

-continued general formula IIe

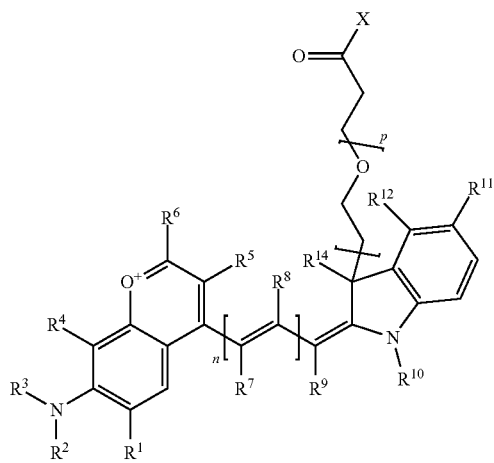

general formula IIf

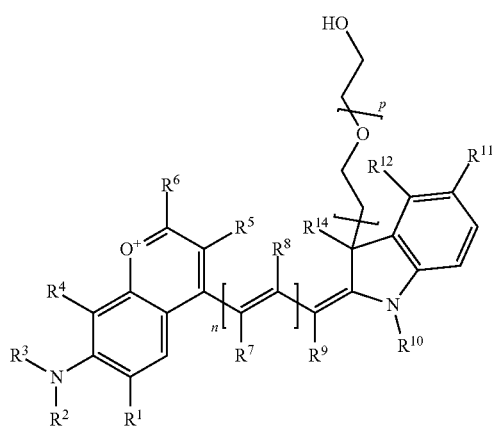

general formula IIg

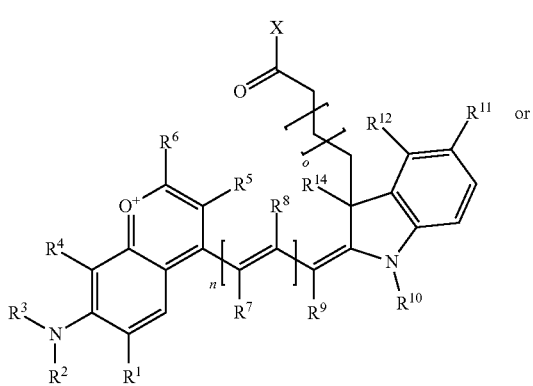

-continued general formula IIh

[structure image]

wherein
each of $R^1$, $R^2$, $R^3$, $R^4$, $R^5$, $R^6$, $R^{11}$, and $R^{12}$ is the same or different and is independently selected from H, $SO_3$, Z, L-Z, a PEG group P-L-Z where P is an ethylene glycol group, a diethylene glycol group, or a polyethylene glycol group, where the polyethylene glycol group is $(CH_2CH_2O)_s$, where s is an integer from 3-6 inclusive, a sulfonamide group -L-$SO_2$NH—P-L-Z, a caboxamide group -L-CONH—P-L-Z, hydrogen, alkyl-, tert-alkyl, aryl-, carboxyaryl-, dicarboxyaryl, heteroaryl-, cycloalkyl-, heterocycloalkyl-, alkyloxy-, alkylmercapto- with alkyl and cycloalkyl including olefin linkage residues, aryloxy-, arylmercapto-, heteroaryloxy-, heteroarylmercapto-, hydroxy-, nitro-, a carboxylic acid, an amino group, or cyano residues; where L is a divalent linear ($-(CH_2)_t-$, t=0 to 15), branched, or cyclic alkane group that is optionally substituted by at least one atom of oxygen, nitrogen, substituted nitrogen, and/or sulfur; where Z is H, $CH_3$, alkyl group, sulfoalkyl, heteroalkyl group, $NH_2$, —$COO^-$, —COON, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-L-$COO^-$, —CONR'-L-COOH, —CONR'-L-COO-Su, —CONR'-L-COO-STP, —CONR'-L-COO-TFP, —CONR'-L-CONR"$_2$, —CONR'-L-CO—NH—$NH_2$, —CONR'-L-OH, —CONR'-L-O-phosphoramidite, —CONR'-L-CHO, —CONR'-L-maleimide, or CONR'-L-NH—CO—$CH_2$—I; each of R' and R" is H, aliphatic group, or heteroaliphatic group;
X is selected from —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, or —NR-L-NH—CO—$CH_2$—I, where R is —H or an aliphatic or heteroaliphatic group;
each of $R^{10}$, $R^{13}$, and $R^{14}$ is the same or different and is independently selected from aliphatic, heteroaliphatic, sulfoalkyl group, carboxyalkyl group, heteroaliphatic with terminal $SO_3$, Z, L-Z, PEG group P-L-Z where P is an ethylene glycol group, a diethylene glycol group, or a polyethylene glycol group where the polyethylene glycol group is $(CH_2CH_2O)_s$, where s is an integer from 3-6 inclusive, a sulfonamide group -L-$SO_2$NH—P-L-Z, or a caboxamide group -L-CONH—P-L-Z;

each of $R^7$ and $R^9$ is the same or different and is independently hydrogen, aliphatic group, heteroaliphatic group, or PEG group P-L-Z where P is selected from an ethylene glycol group, a diethylene glycol group, or a polyethylene glycol group where the polyethylene glycol group is $(CH_2CH_2O)_s$, where s is an integer from 3-6 inclusive; or R7 and R9 together form a cyclic structure where R3 and R4 are joined using a divalent structural element selected from —$(CH_2)_q$—, —$(CH_2)_qO(CH_2)_{q'}$—, —$(CH_2)_qS(CH_2)_{q'}$—, —$(CH_2)_q$CH=CH—, —OCH=CH— where each of q and q' is the same or different and is a integer from 1 to 6 inclusive; and $R^8$ is selected from hydrogen, alkyl, sulfoalkyl, fluorine, chlorine, bromine, and PEG group P-L-Z where P is selected from an ethylene glycol group, a diethylene glycol group, or a polyethylene glycol group, where the polyethylene glycol group is $(CH_2CH_2O)_s$, where s is an integer from 3-6 inclusive;

each of $R^1$ and $R^2$, $R^2$ and $R^3$, $R^3$ and $R^4$, $R^5$ and $R^6$, $R^5$ and $R^8$, $R^9$ and $R^{10}$, $R^{11}$ and $R^{12}$, or $R^{12}$ and $R^{13}$ may form one or more aliphatic, heteroaliphatic or aromatic rings, and where the resultant ring(s) is optionally substituted by at least one alkyl-, sulfoalkyl, tert-alkyl, aryl-, carboxyaryl-, dicarboxyaryl, heteroaryl-, cycloalkyl-, heterocycloalkyl-, alkyloxy-, alkylmercapto- with alkyl and cycloalkyl including olefin linkage residues, aryloxy-, arylmercapto-, heteroaryloxy-, heteroarylmercapto-, hydroxy-, nitro-, sulfonic acid, a carboxylic acid, an amino group, or cyano residues;

at least one of $R^1$-$R^{14}$ contains at least one PEG and optionally an additional solubilizing, ionizing, or ionized substituent selected from $SO_3^-$, $PO_3^{2-}$, $CO_2H$, OH, $NR_3^+$, cyclodextrins or sugars providing hydrophilic characteristics; the substituents optionally linked to chromophore by an aliphatic or heteroaliphatic or cyclical spacer;

Kat is a number of $Na^+$, $K^+$, $Ca^{2+}$, ammonia, or other cation(s) needed to compensate the negative charge(s); n is 0, 1, 2, or 3; o is an integer from 0 to 12 inclusive; and p is an integer from 1 to 6 inclusive, wherein the compound is covalently coupled to a biomolecule via X in general formula Ia, Ic, Ie, Ig, IIa, IIc, IIe or IIg, or the terminal —OH group in general formula Ib, Id, If, Ih, IIb, IId, IIf or IIh.

2. The compound of claim 1 wherein
when the compound is according to general formula Ia or IIa each of $R^2$ and $R^3$ is independently selected from sulfoalkyl or a PEG group P-L-Z; $R^5$ is alkyl; $R^6$ is t-butyl or an unsubstituted or substituted phenyl; $R^{11}$ is sulfonic acid, carboxylic acid, or an amino group; each of $R^{13}$ and $R^{14}$ is independently selected from alkyl, sulfoalkyl, or a PEG group P-L-Z; and each of $R^1$, $R^4$, $R^7$, $R^8$, $R^9$, and $R^{12}$ is H;
when the compound is according to general formula Ib or IIb each of $R^2$ and $R^3$ is independently selected from sulfoalkyl or a PEG group P-L-Z; $R^5$ is alkyl; $R^6$ is t-butyl or an unsubstituted or substituted phenyl; $R^{11}$ is sulfonic acid, carboxylic acid, or an amino group; each of $R^{13}$ and $R^{14}$ is independently selected from alkyl, sulfoalkyl, or a PEG group P-L-Z; and each of $R^1$, $R^4$, $R^7$, $R^8$, $R^9$, and $R^{12}$ is H;
when the compound is according to general formula Ic or IIc each of $R^2$ and $R^3$ is independently selected from sulfoalkyl or a PEG group P-L-Z; $R^5$ is alkyl; $R^6$ is t-butyl or an unsubstituted or substituted phenyl; $R^{11}$ is sulfonic acid, carboxylic acid, or an amino group; each of $R^{13}$ and $R^{14}$ is independently selected from alkyl, sulfoalkyl, or a PEG group P-L-Z; and each of $R^1$, $R^4$, $R^7$, $R^8$, $R^9$, and $R^{12}$ is H; and
when the compound is according to general formula Id or IId each of $R^2$ and $R^3$ is independently selected from sulfoalkyl or a PEG group P-L-Z; $R^5$ is alkyl; $R^6$ is t-butyl or an unsubstituted or substituted phenyl; $R^{11}$ is sulfonic acid, carboxylic acid, or an amino group; each of $R^{13}$ and $R^{14}$ is independently selected from alkyl, sulfoalkyl, or a PEG group P-L-Z; and each of $R^1$, $R^4$, $R^7$, $R^8$, $R^9$, and $R^{12}$ is H.

3. The compound of claim 2 wherein at least one of $R^2$ or $R^3$ is sulfopropyl, $R^5$ is methyl, and at least one of $R^{13}$ or $R^{14}$ is sulfopropyl.

4. The compound of claim 1 wherein
when the compound is according to general formula Ie or IIe each of $R^2$ and $R^3$ is independently selected from sulfoalkyl or a PEG group P-L-Z; $R^5$ is alkyl; $R^6$ is t-butyl or an unsubstituted or substituted phenyl; $R^{11}$ is sulfonic acid, carboxylic acid, or an amino group; $R^{10}$ is alkyl, sulfoalkyl, or a PEG group P-L-Z; $R^{14}$ is alkyl; and each of $R^1$, $R^4$, $R^7$, $R^8$, $R^9$, and $R^{12}$ is H;
when the compound is according to general formula If or IIf each of $R^2$ and $R^3$ is independently selected from sulfoalkyl or a PEG group P-L-Z; $R^5$ is alkyl; $R^6$ is t-butyl or an unsubstituted or substituted phenyl; $R^{11}$ is sulfonic acid, carboxylic acid, or an amino group; $R^{10}$ is alkyl, sulfoalkyl, or a PEG group P-L-Z; $R^{14}$ is alkyl; and each of $R^1$, $R^4$, $R^7$, $R^8$, $R^9$, and $R^{12}$ is H;
when the compound is according to general formula Ig or IIg each of $R^2$ and R3 is independently selected from sulfoalkyl or a PEG group P-L-Z; $R^5$ is alkyl; $R^6$ is t-butyl or an unsubstituted or substituted phenyl; $R^{11}$ is sulfonic acid, carboxylic acid, or an amino group; $R^{10}$ is alkyl, sulfoalkyl, or a PEG group P-L-Z; $R^{14}$ is alkyl; and each of $R^1$, $R^4$, $R^7$, $R^8$, $R^9$, and $R^{12}$ is H; and
when the compound is according to general formula Ih or IIh each of $R^2$ and $R^3$ is independently selected from sulfoalkyl or a PEG group P-L-Z; $R^5$ is alkyl; $R^6$ is t-butyl or an unsubstituted or substituted phenyl; $R^{11}$ is sulfonic acid, carboxylic acid, or an amino group; $R^{10}$ is alkyl, sulfoalkyl, or a PEG group P-L-Z; $R^{14}$ is alkyl; and each of $R^1$, $R^4$, $R^7$, $R^8$, $R^9$, and $R^{12}$ is H.

5. The compound of claim 4 wherein at least one of $R^2$ or $R^3$ is sulfopropyl, $R^5$ is methyl, $R^{10}$ is sulfopropyl, and $R^{14}$ is methyl.

6. A method for in vivo imaging, the method comprising intravenously injecting a compound of claim 1 into a living animal, and obtaining at least one image of at least a portion of the animal using the compound.

7. The method of claim 6 further comprising obtaining the image during injection, after injection, or both during and after injection of the compound.

8. The method of claim 6 where the compound is injected into a circulatory system.

9. The method of claim 6 further comprising obtaining ex vivo images of at least a portion of the animal.

10. The compound of claim 1 wherein the biomolecule is a peptide, a protein, a nucleotide, an oligonucleotide, a nucleic acid, a sugar, an enzyme substrate, an enzyme antagonist, an enzyme inhibitor, or a receptor-binding compound.

11. A method of detecting the compound of claim 1, said method comprising providing a composition comprising at least one excipient and the compound of claim 1 in an effective concentration to label at least one biomolecule under conditions sufficient for labeling the biomolecule with the compound, and detecting the compound by at least one of fluorescence microscopy, flow cytometry, immunoassay, hybridization, chromatographic assay, electrophoretic assay, microwell plate based assay, fluorescence resonance energy transfer (FRET) system, high throughput screening, or microarray.

12. A method of labeling at least one biomolecule, the method comprising combining a composition comprising a compound according to any of general formula Ia

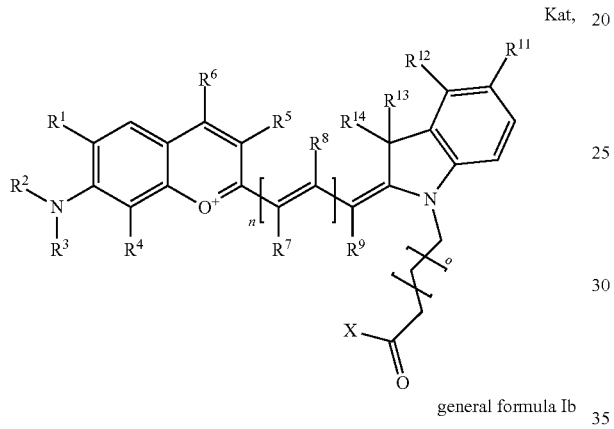

general formula Ib

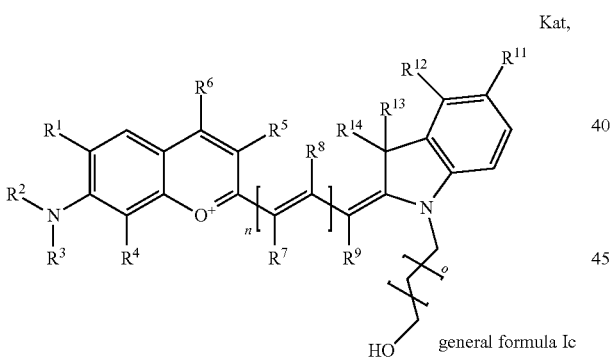

general formula Ic

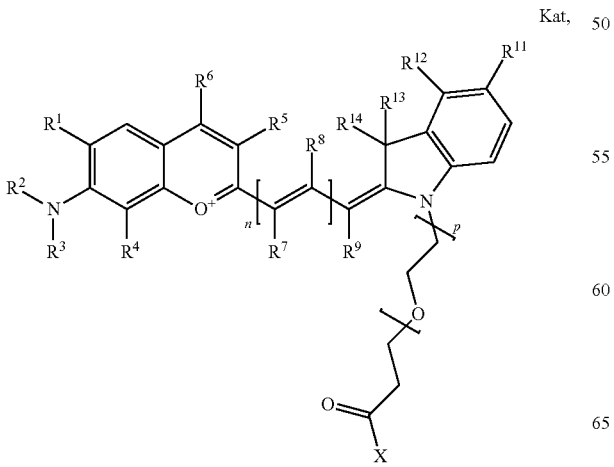

general formula Id

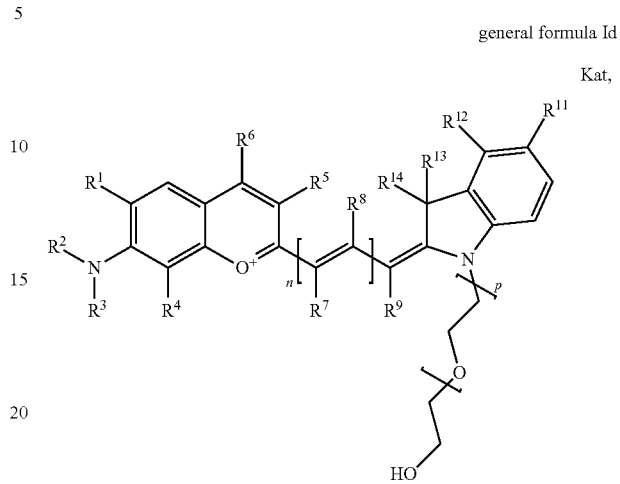

general formula Ie

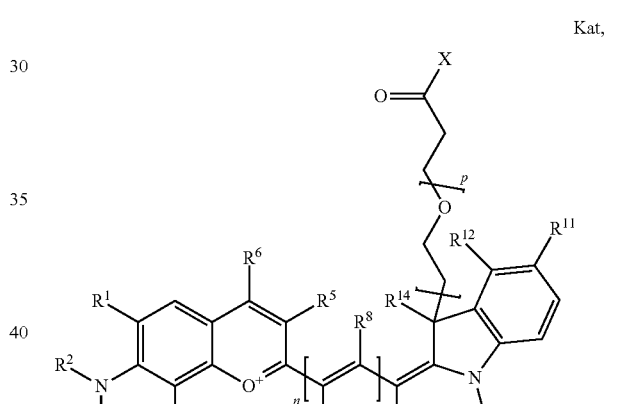

general formula If

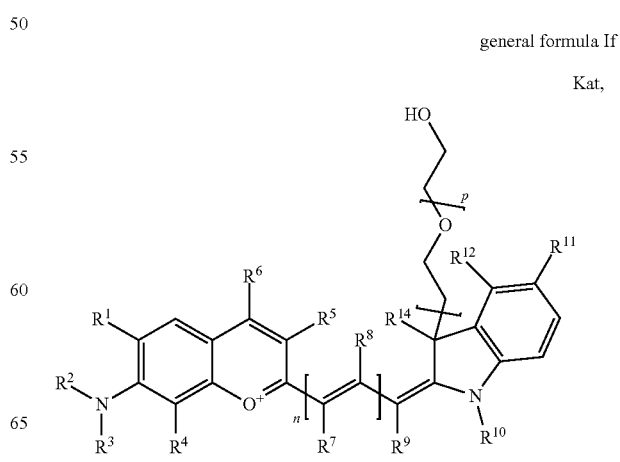

-continued
general formula Ig
Kat,
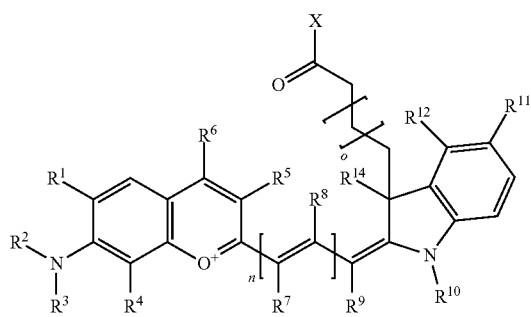
general formula Ih
Kat,
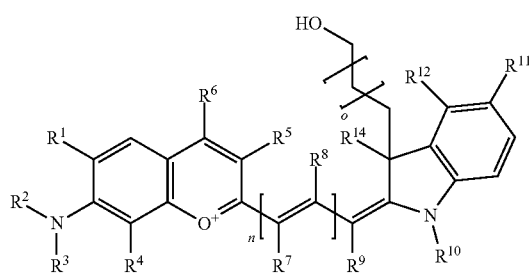
general formula IIa
Kat,
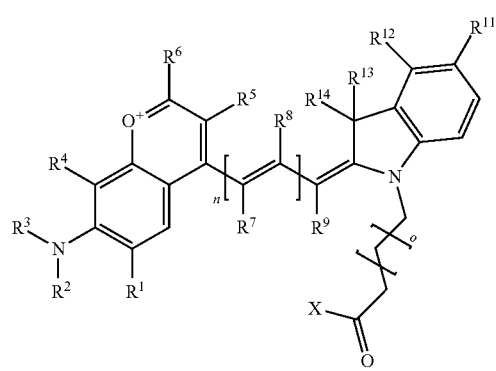
general formula IIb
Kat,
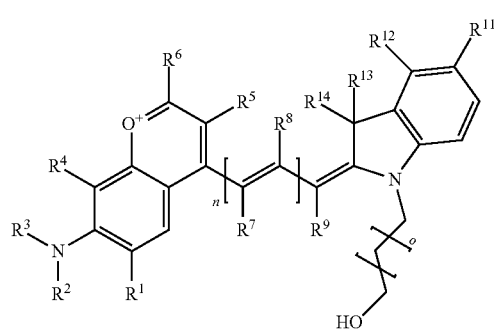
-continued
general formula IIc
Kat,
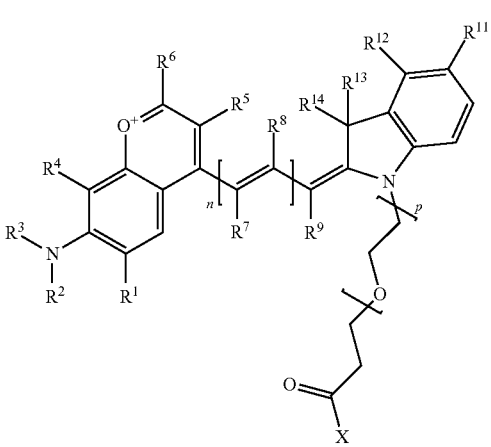
general formula IId
Kat,
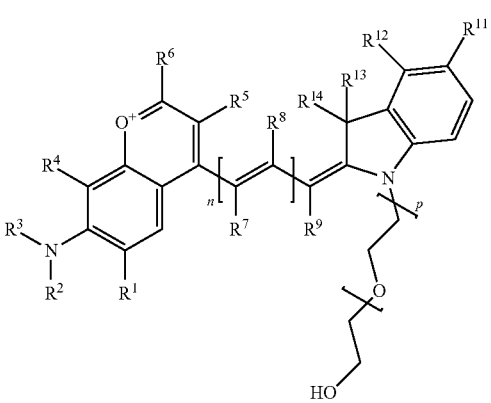
general formula IIe
Kat,
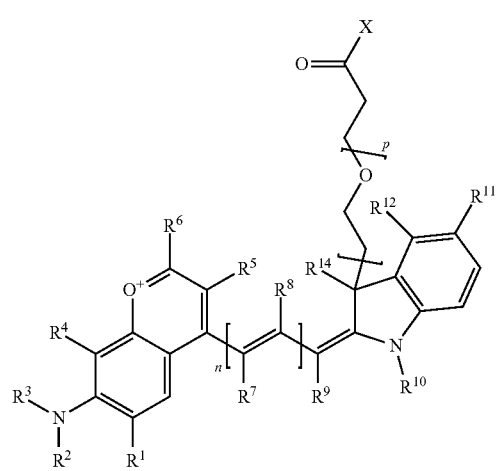

-continued general formula IIf

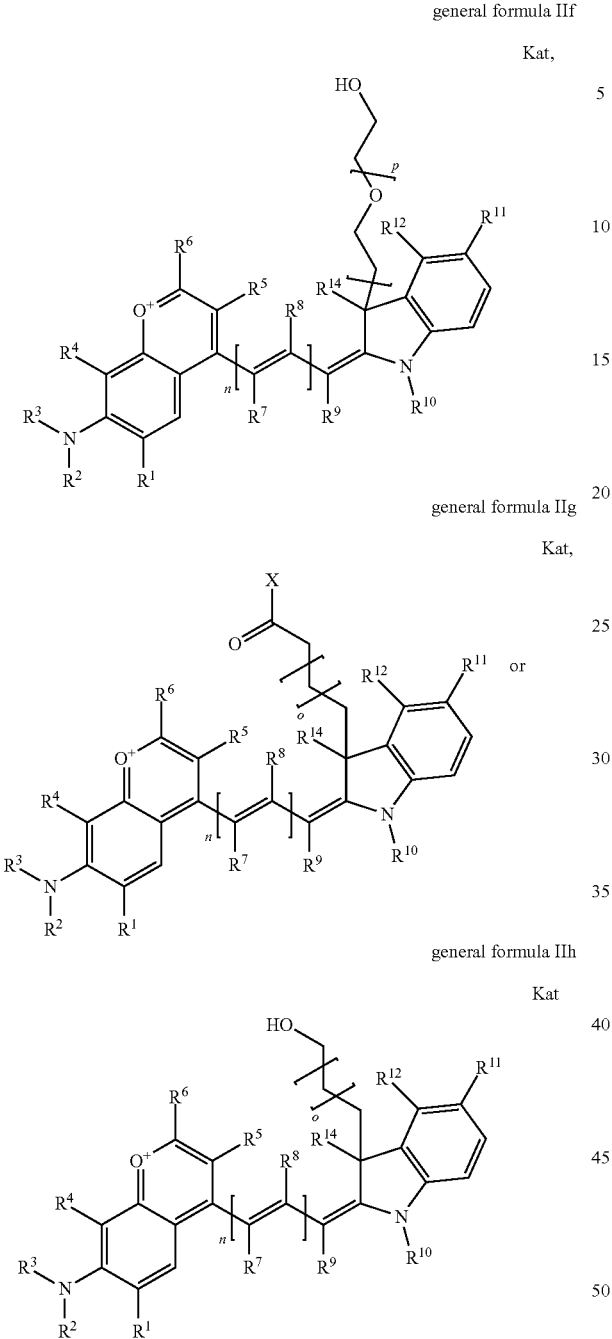

general formula IIg general formula IIh wherein
each of $R^1$, $R^2$, $R^3$, $R^4$, $R^5$, $R^6$, $R^{11}$, and $R^{12}$ is the same or different and is independently selected from H, $SO_3$, Z, L-Z, a PEG group P-L-Z where P is an ethylene glycol group, a diethylene glycol group, or a polyethylene glycol group, where the polyethylene glycol group is $(CH_2CH_2O)_s$, where s is an integer from 3-6 inclusive, a sulfonamide group -L-$SO_2$NH—P-L-Z, a caboxamide group -L-CONH—P-L-Z, hydrogen, alkyl-, tert-alkyl, aryl-, carboxyaryl-, dicarboxyaryl, heteroaryl-, cycloalkyl-, heterocycloalkyl-, alkyloxy-, alkylmercapto- with alkyl and cycloalkyl including olefin linkage residues, aryloxy-, arylmercapto-, heteroaryloxy-, heteroarylmercapto-, hydroxy-, nitro-, a carboxylic acid, an amino group, or cyano residues; where L is a divalent linear (—$(CH_2)_t$—, t=0 to 15), branched, or cyclic alkane group that can be substituted by at least one atom of oxygen, nitrogen, substituted nitrogen, and/or sulfur; where Z is H, $CH_3$, alkyl group, sulfoalkyl, heteroalkyl group, $NH_2$, —$COO^-$, —COOH, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-biomolecule, —CONR'-L-$COO^-$, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR-L-CO—NH—$NH_2$, —CONR'-L-OH, —CONR'-L-O-phosphoramidite, —CONR'-L-CHO, —CONR'-L-maleimide, or —CONR'-L-NH—CO—$CH_2$—I; each of R' and R" is selected from H, aliphatic group, or heteroaliphatic group;
X is selected from —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, or —NR-L-NH—CO—$CH_2$—I, where R is —H or an aliphatic or heteroaliphatic group;
each of $R^{10}$, $R^{13}$, and $R^{14}$ is the same or different and is independently selected from aliphatic, heteroaliphatic, sulfoalkyl group, carboxyalkyl group, heteroaliphatic with terminal $SO_3$, Z, L-Z, PEG group P-L-Z where P is an ethylene glycol group, a diethylene glycol group, or a polyethylene glycol group where the polyethylene glycol group is $(CH_2CH_2O)_s$, where s is an integer from 3-6 inclusive, a sulfonamide group -L-$SO_2$NH—P-L-Z, or a caboxamide group -L-CONH—P-L-Z;
each of $R^7$ and $R^9$ is the same or different and is independently hydrogen, aliphatic group, heteroaliphatic group, or PEG group P-L-Z where P is selected from an ethylene glycol group, a diethylene glycol group, or a polyethylene glycol group where the polyethylene glycol group is $(CH_2CH_2O)_s$, where s is an integer from 3-6 inclusive; or R7 and R9 together form a cyclic structure where R3 and R4 are joined using a divalent structural element selected from —$(CH_2)_q$—, —$(CH_2)_qO(CH_2)_{q'}$—, —$(CH_2)_qS(CH_2)_{q'}$—, —$(CH_2)_q$CH=CH—, —OCH=CH— where each of q and q' is the same or different and is a integer from 1 to 6 inclusive; and
$R^8$ is selected from hydrogen, alkyl, sulfoalkyl, fluorine, chlorine, bromine, and PEG group P-L-Z where P is selected from an ethylene glycol group, a diethylene glycol group, or a polyethylene glycol group, where the polyethylene glycol group is $(CH_2CH_2O)_s$, where s is an integer from 3-6 inclusive;
each of $R^1$ and $R^2$, $R^2$ and $R^3$, $R^3$ and $R^4$, $R^5$ and $R^6$, $R^8$, $R^9$ and $R^{10}$, $R^{11}$ and $R^{12}$, or $R^{12}$ and $R^{13}$ may form one or more aliphatic, heteroaliphatic or aromatic rings, and where the resultant ring(s) is optionally substituted by at least one alkyl-, sulfoalkyl, tert-alkyl, aryl-, carboxyaryl-, dicarboxyaryl, heteroaryl-, cycloalkyl-, heterocycloalkyl-, alkyloxy-, alkylmercapto- with alkyl and cycloalkyl including olefin linkage residues, aryloxy-, arylmercapto-, heteroaryloxy-, heteroarylmercapto-, hydroxy-, nitro-, sulfonic acid, a carboxylic acid, an amino group, or cyano residues;

at least one of $R^1$-$R^{14}$ contains at least one PEG and optionally an additional solubilizing, ionizing, or ionized substituent selected from $SO_3^-$, $PO_3^{2-}$, $CO_2H$, $OH$, $NR_3^+$, cyclodextrins or sugars providing hydrophilic characteristics; the substituents optionally linked to chromophore by an aliphatic or heteroaliphatic or cyclical spacer;

Kat is a number of $Na^+$, $K^+$, $Ca^{2+}$, ammonia, or other cation(s) needed to compensate the negative charge(s); n is 0, 1, 2, or 3; o is an integer from 0 to 12 inclusive; and p is an integer from 1 to 6 inclusive, in an effective concentration to the at least one biomolecule under conditions sufficient for labeling the biomolecule with the compound.

13. The method of claim 12 further comprising detecting the labeled biomolecule by at least one of fluorescence microscopy, flow cytometry, immunoassay, hybridization, chromatographic assay, electrophoretic assay, microwell plate based assay, fluorescence resonance energy transfer (FRET) system, high throughput screening, or microarray.

14. The method of claim 12 where the biomolecule is selected from a protein, antibody, enzyme, nucleoside triphosphate, oligonucleotide, biotin, hapten, cofactor, lectin, antibody binding protein, carotenoid, carbohydrate, hormone, neurotransmitter, growth factors, toxin, biological cell, lipid, receptor binding drug, fluorescent proteins, organic polymer carrier material, inorganic polymeric carrier material, and combinations thereof.

15. A kit for labeling at least one biomolecule in a sample, the kit comprising the compound of claim 1 and instructions for use.

* * * * *

UNITED STATES PATENT AND TRADEMARK OFFICE
CERTIFICATE OF CORRECTION

| | |
|---|---|
| PATENT NO. | : 10,174,045 B2 |
| APPLICATION NO. | : 15/493208 |
| DATED | : January 8, 2019 |
| INVENTOR(S) | : Greg Hermanson et al. |

It is certified that error appears in the above-identified patent and that said Letters Patent is hereby corrected as shown below:

In the Claims

In Claim 1, Column 274, Line 40 should read "$NH_2$, -COO-, -COOH, -COSH, CO-NH-"

Signed and Sealed this
Fifth Day of March, 2019

Andrei Iancu
*Director of the United States Patent and Trademark Office*